US011702645B2

(12) United States Patent
Nureki et al.

(10) Patent No.: US 11,702,645 B2
(45) Date of Patent: Jul. 18, 2023

(54) POLYNUCLEOTIDE ENCODING MODIFIED CAS9 PROTEIN

(71) Applicant: The University of Tokyo, Tokyo (JP)

(72) Inventors: Osamu Nureki, Tokyo (JP); Hiroshi Nishimasu, Tokyo (JP); Hisato Hirano, Tokyo (JP)

(73) Assignee: The University of Tokyo, Tokyo (JP)

( * ) Notice: Subject to any disclaimer, the term of this patent is extended or adjusted under 35 U.S.C. 154(b) by 0 days.

(21) Appl. No.: 17/849,581

(22) Filed: Jun. 24, 2022

(65) Prior Publication Data

US 2022/0333090 A1    Oct. 20, 2022

Related U.S. Application Data

(62) Division of application No. 16/617,498, filed as application No. PCT/JP2018/021068 on May 31, 2018, now Pat. No. 11,371,030.

(30) Foreign Application Priority Data

May 31, 2017 (JP) ................................ 2017-108556

(51) Int. Cl.
C12N 9/22     (2006.01)
C12N 15/113   (2010.01)

(52) U.S. Cl.
CPC .............. *C12N 9/22* (2013.01); *C12N 15/113* (2013.01)

(58) Field of Classification Search
CPC ........ C12N 9/22; C12N 15/113; C12N 15/09; C07K 2319/21; C07K 2319/50
See application file for complete search history.

(56) References Cited

U.S. PATENT DOCUMENTS

| | | |
|---|---|---|
| 8,697,359 B1 | 4/2014 | Zhang |
| 8,771,945 B1 | 7/2014 | Zhang |
| 8,945,839 B2 | 2/2015 | Zhang |
| 9,637,739 B2 | 5/2017 | Siksnys et al. |
| 9,752,132 B2 | 9/2017 | Joung et al. |
| 9,926,545 B2 | 3/2018 | Joung et al. |
| 9,944,912 B2 | 4/2018 | Joung et al. |
| 10,202,589 B2 | 2/2019 | Joung et al. |
| 10,479,982 B2 | 11/2019 | Joung et al. |
| 2014/0170753 A1 | 6/2014 | Zhang |
| 2014/0227787 A1 | 8/2014 | Zhang |
| 2015/0045546 A1 | 2/2015 | Siksnys et al. |
| 2015/0050699 A1 | 2/2015 | Siksnys et al. |
| 2015/0184139 A1 | 7/2015 | Zhang et al. |
| 2015/0203872 A1 | 7/2015 | Zhang |
| 2015/0240261 A1 | 8/2015 | Siksnys et al. |
| 2015/0291961 A1 | 10/2015 | Siksnys et al. |
| 2016/0177278 A1 | 6/2016 | Wolfe et al. |
| 2016/0281072 A1 | 9/2016 | Zhang |
| 2016/0312198 A1 | 10/2016 | Joung et al. |
| 2016/0312199 A1 | 10/2016 | Joung et al. |
| 2016/0319260 A1 | 11/2016 | Joung et al. |
| 2016/0319261 A1 | 11/2016 | Joung et al. |
| 2017/0175142 A1 | 6/2017 | Zhang et al. |
| 2017/0327804 A9 | 11/2017 | Joung et al. |
| 2017/0327806 A1 | 11/2017 | Joung et al. |
| 2018/0002681 A9 | 1/2018 | Joung et al. |
| 2018/0187195 A1 | 7/2018 | Siksnys et al. |
| 2018/0201912 A1 | 7/2018 | Nureki et al. |
| 2018/0282714 A1 | 10/2018 | Joung et al. |
| 2019/0085329 A1 | 3/2019 | Siksnys et al. |
| 2019/0153476 A1 | 5/2019 | Zhang |
| 2020/0149023 A1 | 5/2020 | Joung et al. |

FOREIGN PATENT DOCUMENTS

| | | |
|---|---|---|
| JP | 2015-510778 A | 4/2015 |
| WO | WO 2014/093661 A2 | 6/2014 |
| WO | WO 2016/141224 A1 | 9/2016 |
| WO | WO 2017/010543 A1 | 1/2017 |
| WO | WO 2019/217944 A1 | 11/2019 |

OTHER PUBLICATIONS

Anders et al., "Structural basis of PAM-dependent target DNA recognition by the Cas9 endonuclease," *Nature*, 513(7519): 569-573 (2014).
Branden et al., "Prediction, Engineering, and Design of Protein Structures" in *Introduction to Protein Structure* (Garland Publishing Inc., New York, 1991), p. 247 (1991).
Hirano et al., "Structural Basis for the Altered PAM Specificities of Engineered CRISPR-Cas9," *Mol. Cell.*, 61(6): 886-894 (2016).
Kleinstiver et al., "Engineered CRISPR-Cas9 Nucleases with Altered PAM Specificities," *Nature*, 523(7561): 481-485 (2015).
Nishimasu et al., "Engineered CRISPR-Cas9 Nuclease with Expanded Targeting Space," *Science*, 361: 1259-1262 (2018).
Nureki et al., "Structure-based development of a CRISPR-Cas9 genome editing tool," *Bio Industry—Baiosaiensu-to-indasutori / Baioindusutori Kyōkai*, 75(2): 104-113(2017).
Ran et al., "Double Nicking by RNA-Guided CRISPR Cas9 for Enhanced Genome Editing Specificity," *Cell*, 154(6): 1380-1389 (2013).
Sadowski et al., "The Sequence-Structure Relationship and Protein Function Prediction," *Current Opinion in Structural Biology*, 19: 357-362 (2009).

(Continued)

*Primary Examiner* — Delia M Ramirez
(74) *Attorney, Agent, or Firm* — Leydig, Voit & Mayer, Ltd.

(57) ABSTRACT

The present invention aims to provide a modified Cas9 protein with relaxed restriction on target sequence while maintaining binding ability to guide RNA, and use thereof. A protein containing the amino acid sequence of SEQ ID NO: 1 in which the 1335-position arginine is mutated into alanine (R1335A), isoleucine (R1335I), methionine (R1335M), threonine (R1335T) or valine (R1335V), the 1111-position leucine is mutated into arginine (L1111R), the 1135-position aspartic acid is mutated into valine (D1135V), the 1218-position glycine is mutated into arginine (G1218R), the 1219-position glutamic acid is mutated into phenylalanine (E1219F), the 1322-position alanine is mutated into arginine (A1322R), and the 1337-position threonine is mutated into arginine (T1337R), and the like.

8 Claims, 6 Drawing Sheets

Specification includes a Sequence Listing.

(56) References Cited

OTHER PUBLICATIONS

Seffernick et al., "Melamine Deaminase and Atrazine Chlorohydrolase: 98 Percent Identical but Functionally Different," *J. Bacteriol.*, 183(8): 2405-2410 (2001).

Tang et al., "Identification of Dehalobacter Reductive Dehalogenases that Cataylse Dechlorination of Chloroform, 1,1,1-Trichloroethane and 1,1-Dichloroethane," *Phil. Trans. R. Soc. B*, 368: 20120318 (2013).

Witkowski et al., "Conversion of a β-Ketoacyl Synthase to a Malonyl Decarboxylase by Replacement of the Active-Site Cysteine with Glutamine," *Biochemistry*, 38: 11643-11650 (1999).

Japan Patent Office, International Search Report in International Patent Application No. PCT/JP2018/021068 (dated Aug. 21, 2018).

Japan Patent Office, International Preliminary Report on Patentability in International Patent Application No. PCT/JP2018/021068 (dated Dec. 3, 2019).

European Patent Office, Extended European Search Report in European Patent Application No. 18809170.6 (dated Feb. 19, 2021).

U.S. Appl. No. 16/617,498, filed May 4, 2020.

Cas9-sgRNA + 100 ng plasmid DNA
37C, 5 min, 1% agarose gel

R1335A/L1111R/D1135V/G1218R/A1322R/T1337R (ARVRRR)
R1335A/L1111R/D1135V/G1218R/E1219F/A1322R/T1337R (ARVRFRR)

ARVRFRR=m43

POLYNUCLEOTIDE ENCODING MODIFIED CAS9 PROTEIN

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 356,311 bytes ASCII (Text) file named "763017Sequence-Listing.txt," created May 16, 2022.

TECHNICAL FIELD

The present invention relates to a modified Cas9 protein with an expanded targetable region, and use thereof.

BACKGROUND ART

Clustered Regularly Interspaced Short Palindromic Repeats (CRISPR) are known to compose the adaptive immune system that provides acquired resistance against invasive foreign nucleic acids in bacteria and archaea together with Cas (CRISPR-associated) genes. CRISPR frequently originate from phage or plasmid DNA and are composed of 24 bp to 48 bp short, conserved repeat sequences having unique variable DNA sequences referred to as spacers of similar size inserted there between. In addition, a group of genes encoding the Cas protein family is present in the vicinity of the repeat and spacer sequences.

In the CRISPR-Cas system, foreign DNA is cleaved into fragments of about 30 bp by the Cas protein family and inserted into CRISPR. Cas1 and Cas2 proteins, which are among the Cas protein family, recognize a base sequence referred to as proto-spacer adjacent motif (PAM) of foreign DNA, cut the upstream, and insert same into the CRISPR sequence of the host, which creates immune memory of bacteria. RNA generated by transcription of a CRISPR sequence including immune memory (referred to as pre-crRNA) is paired with a partially complementary RNA (trans-activating crRNA: tracrRNA) and incorporated into Cas9 protein which is one of the Cas protein family. The pre-crRNA and tracrRNA incorporated into Cas9 are cleaved by RNaseIII to form small RNA fragments (CRISPR-RNAs: crRNAs) containing a foreign sequence (guide sequence), and a Cas9-crRNA-tracrRNA complex is thus formed. The Cas9-crRNA-tracrRNA complex binds to a foreign invasive DNA complementary to crRNA, and the Cas9 protein, which is an enzyme that cleaves the DNA (nuclease), cleaves the foreign invasive DNA, thereby suppressing and eliminating the function of the DNA that invaded from the outside.

Cas9 protein recognizes the PAM sequence in the foreign invasive DNA, and cleaves the double-stranded DNA at the upstream thereof to give a blunt end. The length and base sequence of the PAM sequence vary depending on the bacterial species, and *Streptococcus pyogenes* (*S. pyogenes*) recognizes 3 bases of "NGG". *Streptococcus thermophilus* (*S. thermophilus*) has two Cas9 and they respectively recognize 5-6 bases in the form of "NGGNG" or "NNAGAA" as PAM sequences. *Francisella novicida* (*F. novicida*) recognizes three bases of "NGR". The number of bps upstream at which the PAM sequence is cleaved varies depending on the bacterial species. Most Cas9 orthologs, including *S. pyogenes*, cleave 3 bases upstream of the PAM sequence.

In recent years, techniques for applying the CRISPR-Cas system in bacteria to genome editing have been actively developed. crRNA and tracrRNA are fused, expressed as a tracrRNA-crRNA chimera (hereinafter to be referred to as guide RNA: gRNA), and utilized. Using this, nuclease (RNA-guided nuclease: RGN) is then recruited to cleave genomic DNA at the target site.

The CRISPR-Cas system includes types I, II, and III, and type II CRISPR-Cas system is used nearly exclusively for genome editing, and Cas9 protein is used as RGN in type II. Since *S. pyogenes*-derived Cas9 protein recognizes three bases of NGG as a PAM sequence, it can be cleaved at the upstream as long as there is a sequence having consecutive two guanines.

A method using the CRISPR-Cas system only needs to synthesize a short gRNA homologous to the target DNA sequence, and can perform genome editing using the Cas9 protein which is a single protein. Therefore, it is not necessary to synthesize large proteins that differ for each DNA sequence in the manner of conventionally used zinc finger nuclease (ZFN) or transcription activator-like effector nuclease (TALEN), and genome editing can be performed easily and quickly.

Patent Document 1 discloses a genome editing technique that uses a CRISPR-Cas system derived from *S. pyogenes*.

Patent Document 2 discloses a genome editing technique that uses a CRISPR-Cas system derived from *S. thermophilus*. Moreover, Patent document 2 discloses that a Cas9 protein mutant D31A or N891A functions as a DNA nicking enzyme, nickase, that places a nick only in one of the DNA strands. Moreover, these mutants are also indicated as having homologous recombination efficiency comparable to that of wild-type Cas9 protein while retaining a low incidence of non-homologous end-joining susceptible to the occurrence of mutations such as insertions, deletions and the like in the repair mechanism following DNA cleavage.

Non-Patent Document 1 discloses a CRISPR-Cas system that uses *S. pyogenes*-derived Cas9, wherein the CRISPR-Cas system is a double nickase system that uses two Cas9 protein D10A mutants and a pair of target-specific guide RNA that form a complex with these D10A mutants. Each complex of Cas9 protein D10A mutant and target-specific guide RNA creates only one nick in DNA strand homologous to the guide DNA. The pair of guide RNA has about 20 bases of mismatch and only recognizes a target sequence located in the opposite strand of the target DNA. The two nicks created by each complex of Cas9 protein D10A mutant and target-specific guide RNA mimic a DNA double-strand break (DSB), and the use of the pair of guide RNA is indicated as being able to improve the specificity of Cas 9 protein-mediated genome editing while maintaining a high level of efficiency.

Patent document 3 discloses various Cas9 protein mutants derived from *S. pyogenes* and Patent Document 4 discloses various Cas9 protein mutants derived from *F. novicida*.

DOCUMENT LIST

Patent Documents patent document 1: WO2014/093661 patent document 2: National Publication of International Patent Application No. 2015-510778 patent document 3: WO2016/141224 patent document 4: WO2017/010543

Non-Patent Document non-patent document 1: Ran, F. A., et al., Double Nicking by RNA-Guided CRISPR Cas9 for Enhanced Genome Editing Specificity, Cell, vol. 154, p 1380-1389, 2013.

SUMMARY OF THE INVENTION

Problems to be Solved by the Invention

The PAM sequence able to be recognized by the *S. pyogenes*-derived Cas9 (to be also referred to as SpCas9 in the present specification) protein disclosed in patent document 1 consists of two bases of "NGG (N is any base)". In addition, the double nickase system disclosed in non-patent document 1 uses SpCas9 protein, and since recognizable PAM sequences are required at a total of two locations in the sense strand and antisense strand within a target sequence, there are further limitations on those target sequences that are able to be edited.

Since there are limitations on the PAM sequences that conventional Cas9 proteins can recognize, there is also a problem of limitation on the editable target sequences.

The present invention aims to provide a modified Cas9 protein with relaxed restriction on target sequence while maintaining binding ability to guide RNA, and use thereof.

Means of Solving the Problems

The present inventors have taken note of SpCas9 protein as Cas9 protein, and conducted intensive studies in an attempt to solve the above-mentioned problems. As a result, they have succeeded in converting a PAM sequence conventionally consisting of 2 bases of NGG (N is any base) to a 1 base sequence of NG while maintaining the binding ability to guide RNA, by substituting an amino acid at a predetermined position of the SpCas9 protein with a specific amino acid (introducing a mutation), which resulted in the completion of the present invention.

In the present specification, Cas9 protein before introduction of mutation is sometimes to be referred to as wild-type Cas9 protein, and Cas9 protein after introduction of mutation is sometimes to be referred to as modified Cas9 protein or mutant Cas9 protein.

That is, the present invention provides the following.

[1] A protein consisting of a sequence comprising the amino acid sequence shown in SEQ ID NO: 1 in which the 1335-position arginine is substituted by one amino acid selected from the group consisting of alanine, glycine, cysteine, isoleucine, leucine, methionine, phenylalanine, proline, valine, threonine, asparagine and aspartic acid, and having a binding ability to guide RNA.

[2] The protein of the above-mentioned [1], further having a mutation at the 1219-position of the amino acid sequence shown in SEQ ID NO: 1.

[3] The protein of the above-mentioned [1] or [2], further having a mutation at the 1322-position of the amino acid sequence shown in SEQ ID NO: 1.

[4] A protein consisting of a sequence comprising the amino acid sequence shown in SEQ ID NO: 1 in which the 1335-position arginine is substituted by one amino acid selected from the group consisting of alanine, glycine, cysteine, isoleucine, leucine, methionine, phenylalanine, proline, valine, threonine, asparagine and aspartic acid, and the 1219-position is further mutated, and having a binding ability to guide RNA.

[5] A protein consisting of a sequence comprising the amino acid sequence shown in SEQ ID NO: 1 in which the 1335-position arginine is substituted by one amino acid selected from the group consisting of alanine, glycine, cysteine, isoleucine, leucine, methionine, phenylalanine, proline, valine, threonine, asparagine and aspartic acid, and the 1322-position is further mutated, and having a binding ability to guide RNA.

[6] The protein of any of the above-mentioned [1] to [5], wherein the 1335-position arginine is substituted with alanine.

[7] The protein of any of the above-mentioned [1] to [5], wherein the 1335-position arginine is substituted with isoleucine, methionine, threonine or valine.

[8] The protein of the above-mentioned [2] or [4], wherein the mutation at 1219-position is a substitution of glutamic acid to phenylalanine.

[9] The protein of the above-mentioned [3] or [5], wherein the mutation at 1322-position is a substitution of alanine to arginine, histidine or lysine.

[10] The protein of the above-mentioned [9], wherein the mutation at 1322-position is a substitution of alanine to arginine.

[11] The protein of any of the above-mentioned [1] to [10], wherein the amino acid sequence shown in SEQ ID NO: 1 has further mutation at at least one position selected from the group consisting of the 1111-position, the 1135-position, the 1218-position and the 1337-position.

[12] The protein of the above-mentioned [11], wherein the amino acid sequence shown in SEQ ID NO: 1 has further mutation at at least two positions selected from the group consisting of the 1111-position, the 1135-position, the 1218-position and the 1337-position.

[13] The protein of the above-mentioned [11], wherein the amino acid sequence shown in SEQ ID NO: 1 has further mutation at at least three positions selected from the group consisting of the 1111-position, the 1135-position, the 1218-position and the 1337-position.

[14] The protein of the above-mentioned [11], wherein the amino acid sequence shown in SEQ ID NO: 1 has further mutation at the 1111-position, the 1135-position, the 1218-position and the 1337-position.

[15] The protein of any of the above-mentioned [11] to [14], wherein the mutation at 1111-position is a substitution of leucine to arginine, histidine or lysine;
the mutation at 1135-position is a substitution of aspartic acid to valine;
the mutation at 1218-position is a substitution of glycine to arginine, histidine or lysine; and
the mutation at 1337-position is a substitution of threonine to arginine, histidine or lysine.

[16] The protein of any of the above-mentioned [1] to [15], wherein the SEQ ID NO: 1 has identity of 80% or more at a site other than the mutated position(s).

[17] The protein of any of the above-mentioned [1] to [15], wherein the SEQ ID NO: 1 comprises one to several amino acids substituted, deleted, inserted and/or added at a site other than the mutated position(s).

[18] The protein of any of the above-mentioned [1] to [17], which has RNA-guided DNA endonuclease activity.

[19] The protein of any of the above-mentioned [1] to [16], wherein the amino acid sequence shown in SEQ ID NO: 1 further has a mutation that partly or entirely deletes nuclease activity.

[20] The protein of any of the above-mentioned [19], wherein the mutation that partly or entirely deletes nuclease activity is a mutation at, in the amino acid sequence shown in SEQ ID NO: 1, at least one site selected from the group consisting of (i) the 10-position, the 762-position, the 839-position, the 983-position and the 986-position or a position corresponding thereto, and/or (ii) a site selected from the group consisting of the 840-position and the 863-position or a position corresponding thereto.

[21] The protein of any of the above-mentioned [20], wherein the 10-position aspartic acid is substituted by alanine or asparagine; or
the 840-position histidine is substituted by alanine, asparagine or tyrosine.

[22] The protein of any of the above-mentioned [19] to [21], wherein a transcriptional regulator protein or domain is linked.

[23] The protein of the above-mentioned [22], wherein the transcriptional regulator is a transcription activation factor.

[24] The protein of the above-mentioned [22], wherein the transcriptional regulator is a transcription silencer or a transcription inhibitory factor.

[25] A nucleic acid encoding a protein of any of the above-mentioned [1] to [24].

[26] A protein-RNA complex provided with the protein of any of the above-mentioned [1] to [24] and a polynucleotide composed of a base sequence complementary to a base sequence located 1 to 20 to 24 bases upstream from a proto-spacer adjacent motif (PAM) sequence in a target double-stranded polynucleotide.

[27] A method for site-specifically modifying a target double-stranded polynucleotide, including:
a step for mixing and incubating a target double-stranded polynucleotide, a protein and a guide RNA, and
a step for having the aforementioned protein modify the aforementioned target double-stranded polynucleotide at a binding site located upstream of a PAM sequence; wherein,
the aforementioned target double-stranded polynucleotide has a PAM sequence composed of NG (wherein, N represents any base and G represents guanine),
the aforementioned protein is the protein of any of the above-mentioned [1] to [24], and
the aforementioned guide RNA contains a polynucleotide composed of a base sequence complementary to a base sequence located 1 to 20 to 24 bases upstream from the aforementioned PAM sequence in the aforementioned target double-stranded polynucleotide.

[28] The method of the above-mentioned [27], wherein the modification is site specific cleavage in the target double-stranded polynucleotide.

[29] The method of the above-mentioned [27], wherein the modification is site specific substitution, deletion and/or addition of one or more nucleotides in the target double-stranded polynucleotide.

[30] A method for increasing expression of a target gene in a cell, comprising expressing the protein of the above-mentioned
and one or multiple guide RNAs for the aforementioned target gene in the aforementioned cell.

[31] A method for decreasing expression of a target gene in a cell, comprising expressing the protein of the above-mentioned [24] and one or multiple guide RNAs for the aforementioned target gene in the aforementioned cell.

[32] The method of the above-mentioned [30] or [31], wherein the cell is a eukaryotic cell.

[33] The method of the above-mentioned [30] or [31], wherein the cell is a yeast cell, a plant cell or an animal cell.

Effect of the Invention

According to the present invention, a Cas9 protein can be obtained that recognizes a wide range of PAM sequences while retaining binding strength with a guide RNA. In addition, a simple and rapid site-specific genome editing technology for a target sequence can be provided that uses the aforementioned Cas9 protein.

DESCRIPTION OF EMBODIMENTS

Figure 1A:
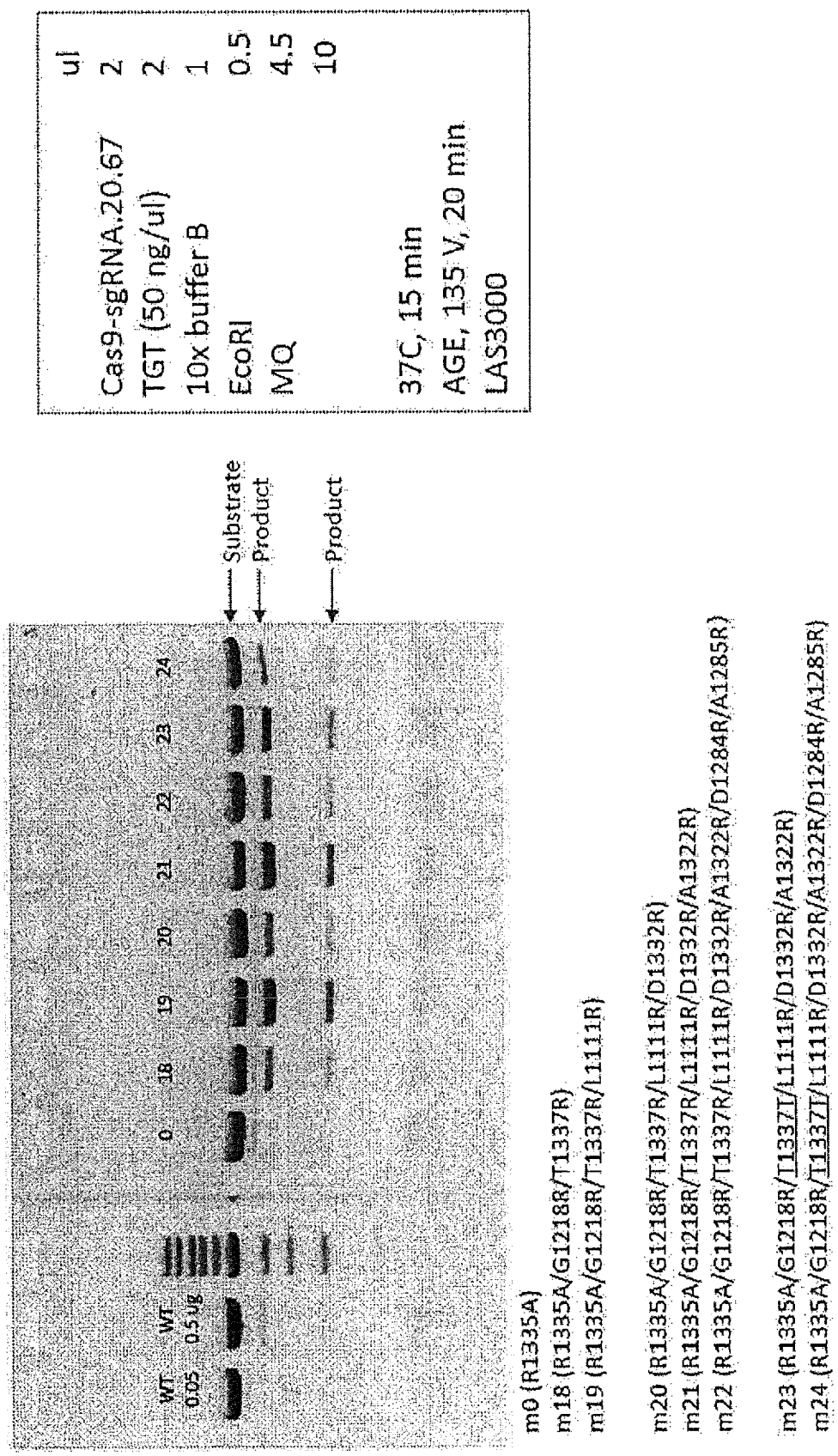
FIG. 1A shows an image representing the results of agarose gel electrophoresis in a DNA cleavage activity measurement test in Example 1. "TGT" was used as the PAM sequence and EcoRI was used as the restriction enzyme.
Figure 1B:
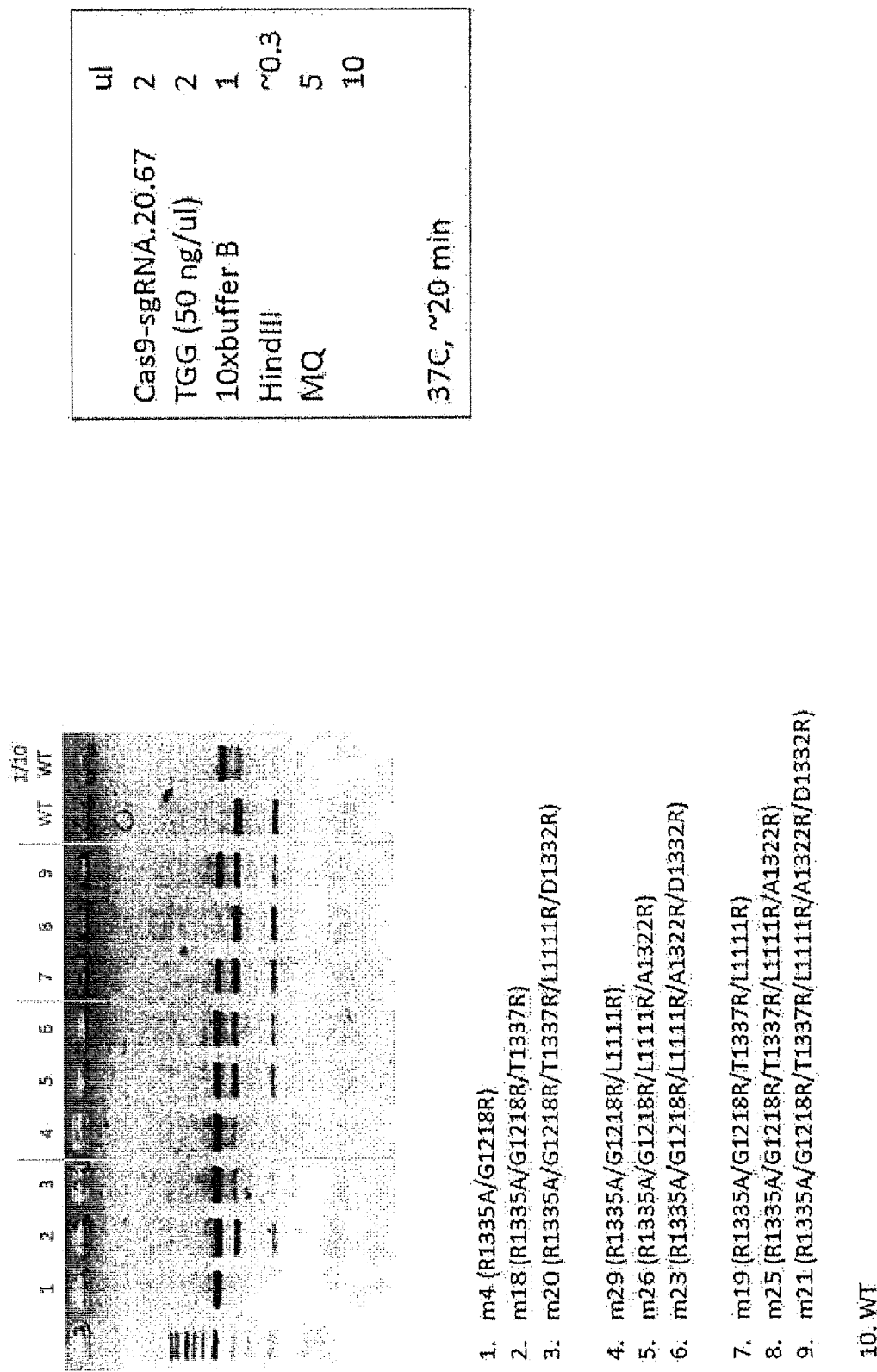
FIG. 1B shows an image representing the results of agarose gel electrophoresis in a DNA cleavage activity measurement test in Example 1. "TGG" was used as the PAM sequence and HindIII was used as the restriction enzyme.
Figure 1C:
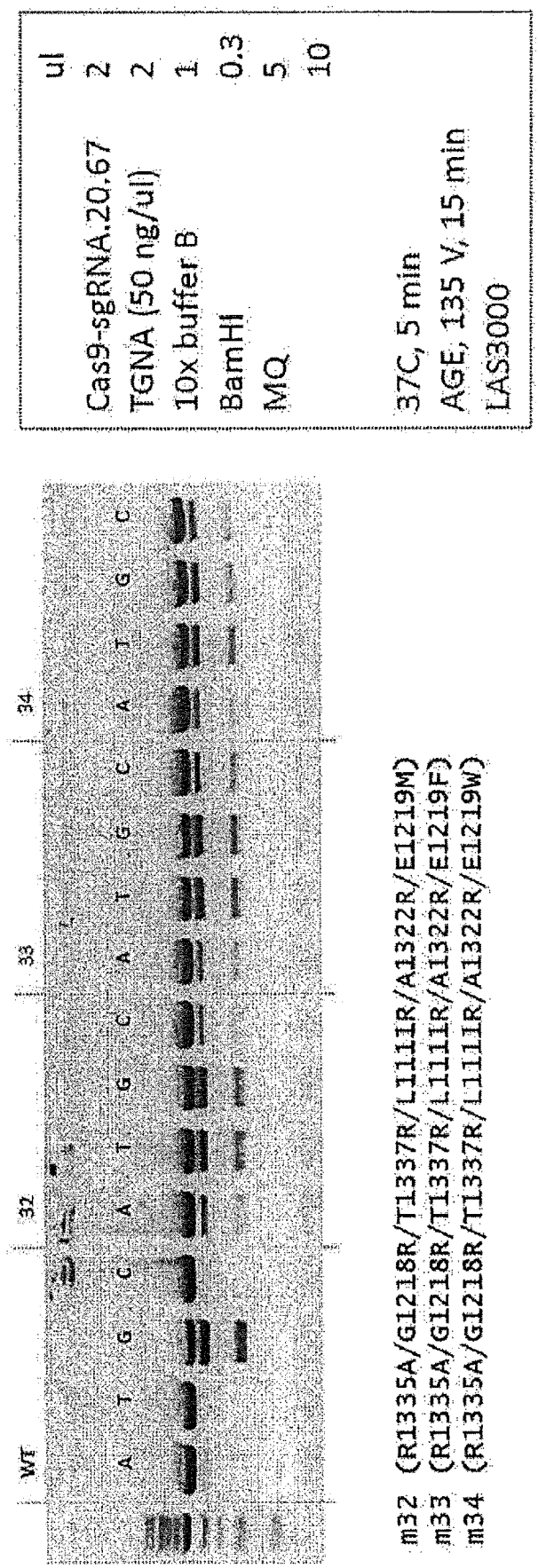
FIG. 1C shows an image representing the results of agarose gel electrophoresis in a DNA cleavage activity measurement test in Example 1. "TGNA" was used as the PAM sequence and BamHI was used as the restriction enzyme.
Figure 1D:
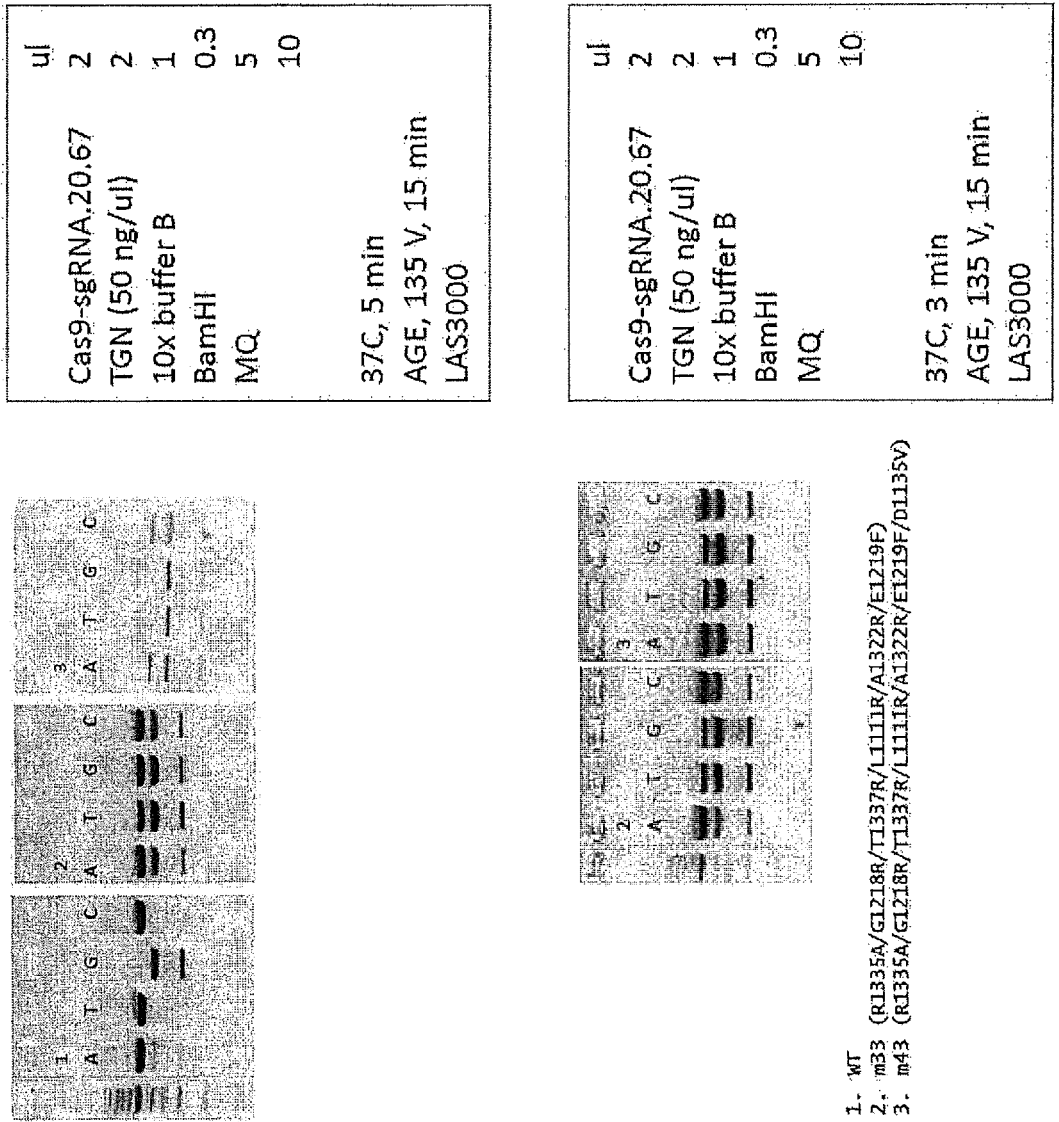
FIG. 1D shows an image representing the results of agarose gel electrophoresis in a DNA cleavage activity measurement test in Example 1. "TGN" was used as the PAM sequence and BamHI was used as the restriction enzyme.

The present invention is described below. Unless particularly indicated, the terms used in the present specification have meanings generally used in the pertinent so field.

<Cas9 Protein Recognizing Wide Range of PAM Sequences>

The protein of the present embodiment is a Cas9 protein that recognizes a wide range of PAM sequences while retaining binding strength with a guide RNA. According to the protein of the present embodiment, a simple and rapid technique can be provided for site-specific editing of the genome of a target sequence.

In the present description, "guide RNA" refers to that which mimics the hairpin structure of tracrRNA-crRNA, and contains in the 5'-terminal region thereof a polynucleotide composed of a base sequence complementary to a base sequence located from 1 to preferably 20 to 24 bases, and more preferably from 1 to preferably 22 to 24 bases, upstream from the PAM sequence in a target double-stranded polynucleotide. Moreover, guide RNA may contain one or more polynucleotides composed of a base sequence allowing the obtaining of a hairpin structure composed of base sequences non-complementary to a target double-stranded polynucleotide symmetrically arranged so as to form a complementary sequence having a single point as the axis thereof.

The guide RNA has a function of binding to the mutant Cas9 protein of the present invention and leading the protein to a target DNA. The guide RNA has a sequence at the 5'-terminal which is complementary to the target DNA, and binds to the target DNA via the complementary sequence, thereby leading the mutant Cas9 protein of the present invention to the target DNA. When the mutant Cas9 protein functions as a DNA endonuclease, the DNA can be cleaved at the site where the target DNA exists and, for example, the function of the target DNA can be specifically lost.

The guide RNA is designed and prepared based on the sequence information of the target DNA to be cleaved or modified. Specific examples include sequences such as those used in the Examples.

In the present description, an "endonuclease" refers to an enzyme that cleaves a nucleotide strand at an intermediate location. Accordingly, the Cas9 protein of the present embodiment that recognizes a wide range of PAM sequences and has endonuclease activity has enzyme activity guided by guide RNA that cleaves at an intermediate location of a DNA strand.

In the present description, the terms "polypeptide", "peptide" and "protein" refer to polymers of amino acid residues and are used interchangeably. In addition, these terms also refer to amino acid polymers in which one or a plurality of amino acid residues are in the form of a chemical analog or modified derivative of the corresponding amino acids present in nature.

In the present description, a "sequence" refers to a nucleotide sequence of an arbitrary length, is a deoxyribonucleotide or ribonucleotide, and may be linear or branched and single-stranded or double-stranded.

In the present description, a "PAM sequence" refers to a sequence present in a target double-stranded polynucleotide that can be recognized by Cas9 protein, and the length and base sequence of the PAM sequence differs according to the bacterial species. A sequence capable of being recognized by the Cas9 protein of the present embodiment capable of recognizing a wide range of PAM sequences can be represented by "5'-NG-3'".

Furthermore, in the present description, "N" refers to any one base selected from the group consisting of adenine, cytosine, thymine and guanine, "A" refers to adenine, "G" to guanine, "C" to cytosine, "T" to thymine, "R" to a base having a purine skeleton (adenine or guanine), and "Y" to a base having a pyrimidine skeleton (cytosine or thymine).

In the present description, a "polynucleotide" refers to a deoxyribonucleotide or ribonucleotide polymer having linear or cyclic coordination and may be single-stranded or double-stranded, and should not be interpreted as being restricted with respect to polymer length. In addition, polynucleotides include known analogs of naturally-occurring nucleotides as well as nucleotides in which at least one of the base moieties, sugar moieties and phosphate moieties thereof has been modified (such as a phosphorothioate backbone). In general, an analog of a specific nucleotide has the same base-pairing specificity, and for example, A analogs form base pairs with T.

In one embodiment, the present invention provides a protein (embodiment 1) consisting of an amino acid sequence having a mutation at the 1335-position in the amino acid sequence shown in SEQ ID NO: 1 and having a binding ability to guide RNA. In addition, the protein of embodiment 1 has RNA-guided DNA endonuclease activity.

SEQ ID NO: 1 is a full-length amino acid sequence of SpCas9 protein. The sequence of the PAM sequence recognition site in the SpCas9 protein is an amino acid sequence consisting of 271 residues from the 1097th to the 1368th of SEQ ID NO: 1.

The mutation at the 1335-position of SEQ ID NO: 1 is specifically substitution of the 1335-position arginine with one amino acid selected from the group consisting of alanine, glycine, cysteine, isoleucine, leucine, methionine, phenylalanine, proline, threonine, valine, asparagine and aspartic acid. It is preferably substitution with alanine. Another preferred mutation at the 1335-position is substitution with isoleucine, methionine, threonine or valine.

By the mutation at the 1335-position, a wider range of PAM sequence of the protein can be recognized since hydrogen bonding with the guanine at the third position in the PAM sequence (5'-NG[G]-3') no longer exists.

In another embodiment of the present invention, the present invention provides a protein further having a mutation at the 1219-position and having binding ability to guide RNA (embodiment 2) in addition to the mutation of the aforementioned embodiment 1. In addition, the protein of embodiment 2 has RNA-guided DNA endonuclease activity.

The mutation at the 1219-position is specifically substitution of the 1219-position glutamic acid with phenylalanine.

The mutation at the 1219-position can contribute to increase (maintenance) of the expression rate of the RNA-guided DNA endonuclease activity.

In another embodiment of the present invention, the present invention provides a protein further having a mutation at the 1322-position and having binding ability to guide RNA (embodiment 3) in addition to the mutation of the aforementioned embodiment 1 or 2.

The mutation at the 1322-position is specifically substitution of the 1322-position alanine with arginine, histidine or lysine. It is preferably substitution with arginine.

The mutation at the 1322-position can contribute to enhancement (activity maintenance) of the activity of the RNA-guided DNA endonuclease activity.

In another embodiment of the present invention, the present invention provides a protein having a mutation at at least one, preferably 2, more preferably 3, selected from the group consisting of the 1111-position, the 1135-position, the 1218-position and the 1337-position, particularly preferably all 4 positions, and having binding ability to guide RNA (embodiment 4) in addition to the mutation of the aforementioned embodiment 1, 2 or 3. The protein of embodiment 4 has RNA-guided DNA endonuclease activity.

The mutation at the 1111-position is specifically substitution of the 1111-position leucine with arginine, histidine or lysine. It is preferably substitution with arginine.

The mutation at the 1135-position is specifically substitution of the 1135-position aspartic acid with valine.

The mutation at the 1218-position is specifically substitution of the 1218-position glycine with arginine, histidine or lysine. It is preferably substitution with arginine.

The mutation at the 1337-position is specifically substitution of the 1337-position threonine with arginine, histidine or lysine. It is preferably substitution with arginine.

In another embodiment of the present invention, the present invention provides a protein having a mutation at (i) at least one site selected from the group consisting of (i) the 10-position, the 762-position, the 839-position, the 983-position and the 986-position, and/or (ii) a site selected from the group consisting of the 840-position and the 863-position, and having binding ability to guide (embodiment 5).

The mutation at the 10-position is specifically substitution of the 10-position aspartic acid with alanine or asparagine.

The mutation at the 762-position is specifically substitution of the 762-position glutamic acid with glutamine.

The mutation at the 839-position is specifically substitution of the 839-position aspartic acid with alanine or asparagine.

The mutation at the 983-position is specifically substitution of the 983-position histidine with asparagine or tyrosine.

The mutation at the 986-position is specifically substitution of the 986-position aspartic acid with asparagine.

The mutation at 840-position is specifically substitution of the 840-position histidine with alanine, asparagine or tyrosine.

The mutation at the 863-position is specifically substitution of the 863-position asparagine with aspartic acid, serine or histidine.

Preferred as embodiment 5 is a protein in which the 10-position aspartic acid is substituted with alanine or asparagine, or the 840-position histidine is substituted with alanine, asparagine or tyrosine.

A protein of embodiment 5 having mutation of (i) or mutation of (ii) has nickase activity.

A protein of embodiment 5 having mutation of (i) and mutation of (ii) binds to guide RNA and leaded to target DNA but the endonuclease activity is inactivated.

In another embodiment of the present invention, the present invention provides a protein (embodiment 6) that is functionally equivalent to the proteins of the aforementioned embodiments 1-5. To be functionally equivalent to the proteins of the aforementioned embodiments 1-5, the amino acid sequence shown in SEQ ID NO: 1 has identity of 80% or more at a site other than the position(s) where the mutation(s) has(have) been applied in the aforementioned embodiments 1-5 and has a binding ability to guide RNA. When amino acids are increased or decreased due to mutation, the "site other than the position(s) where the mutation(s) has(have) been applied" can be interpreted to mean a "site other than the position(s) corresponding to the position(s) where the mutation(s) has(have) been applied". This identity is preferably 80% or more, more preferably 85% or more, even more preferably 90% or more, particularly preferably 95% or more, and most preferably 99% or more. The amino acid sequence identity can be determined by a method known per se. For example, amino acid sequence identity (%) can be determined using a program conventionally used in the pertinent field (e.g., BLAST, FASTA, etc.) by default. In another aspect, identity (%) is determined by any algorithm known in the pertinent field, such as algorithms of Needleman et al. (1970) (J. Mol. Biol. 48: 444-453), Myers and Miller (CABIOS, 1988, 4: 11-17) and the like. The algorithm of Needleman et al. is incorporated into the GAP program in the GCG software package (available at gcg.com) and the identity (%) can be determined using, for example, any of BLOSUM 62 matrix and PAM250 matrix, as well as gap weight: 16, 14, 12, 10, 8, 6 or 4, and length weight: 1, 2, 3, 4, 5 or 6. The algorithm of Myers and Miller is incorporated into the ALIGN program that is a part of the GCG sequence alignment software package. When the ALIGN program is used to compare amino acid sequences, for example, PAM120 weight residue table, gap length penalty 12, and gap penalty 4 can be used.

As a protein functionally equivalent to the proteins of the aforementioned embodiments 1-5, a protein having the amino acid sequence shown in SEQ ID NO: 1 in which one to several amino acids are substituted, deleted, inserted and/or added at a site other than the position where the mutations of the aforementioned embodiment 1-5 have been applied and having the binding ability to guide RNA (embodiment 7) is provided. When amino acids are increased or decreased due to mutation, the "site other than the position(s) where the mutation(s) have been applied" can be interpreted to mean a "site other than the position(s) corresponding to the position(s) where the mutation(s) have been applied".

As a technique for artificially performing "substitution, deletion, insertion and/or addition of amino acid", for example, a method including applying conventional site specific mutation introduction to DNA encoding a predetermined amino acid sequence, and thereafter expressing the DNA by a conventional method can be mentioned. Examples of the site specific mutation introduction method include a method using amber mutation (gapped duplex method, Nucleic Acids Res., 12, 9441-9456 (1984)), a PCR method using a mutation introduction primer and the like.

The number of the amino acids modified above is at least one residue, specifically one or several, or more than that. Among the aforementioned substitution, deletion, insertion and addition, substitution of amino acid is particularly preferred. The substitution is more preferably substitution with an amino acid having similar properties such as hydrophobicity, charge, pK, and characteristic of steric structure and the like. Examples of the substitution include substitution within the groups of i) glycine, alanine; ii) valine, isoleucine, leucine; iii) aspartic acid, glutamic acid, asparagine, glutamine; iv) serine, threonine; v) lysine, arginine; vi) phenylalanine, tyrosine.

As the Cas9 protein that recognizes a wide range of PAM sequences of the present invention, preferably, a protein having the amino acid sequence (SEQ ID NO: 18) which is SEQ ID NO: 1 in which the 1335-position arginine is mutated into alanine (R1335A), the 1111-position leucine is mutated into arginine (L1111R), the 1135-position aspartic acid is mutated into valine (D1135V), the 1218-position glycine is mutated into arginine (G1218R), the 1219-position glutamic acid is mutated into phenylalanine (E1219F), the 1322-position alanine is mutated into arginine (A1322R), and the 1337-position threonine is mutated into arginine (T1337R) can be mentioned.

A protein containing the amino acid sequence of SEQ ID NO: 1 in which the 1335-position arginine is mutated into isoleucine (R1335I), methionine (R1335M), threonine (R1335T) or valine (R1335V) (more preferably R1335M and R1335V), the 1111-position leucine is mutated into arginine (L1111R), the 1135-position aspartic acid is mutated into valine (D1135V), the 1218-position glycine is mutated into arginine (G1218R), the 1219-position glutamic acid is mutated into phenylalanine (E1219F), the 1322-position alanine is mutated into arginine (A1322R), and the 1337-position threonine is mutated into arginine (T1337R) is also preferable as the Cas9 protein that recognizes a wide range of PAM sequences of the present invention. The protein corresponds to a protein containing the amino acid sequence of SEQ ID NO: 18 in which the 1335-position alanine is respectively mutated into isoleucine, methionine, threonine or valine.

In this specification, the alphabet displayed on the left side of the number indicating the number of amino acid so residues up to the substitution site indicates a single letter code of the amino acid before substitution, and the alphabet displayed on the right side indicates a single letter code of the amino acid after substitution.

The Cas9 protein recognizing a wide range of PAM sequences in the present embodiment can be produced according to, for example, the method indicated below. First, a host is transformed using a vector containing a nucleic acid that encodes the aforementioned Cas9 protein recognizing a wide range of PAM sequences. Then, the host is cultured to express the aforementioned protein. Conditions such as medium composition, culture temperature, duration of culturing or addition of inducing agents can be determined by a person with ordinary skill in the art in accordance with known methods so that the transformant grows and the aforementioned protein is efficiently produced. In addition, in the case of having incorporated a selection marker in the form of an antibiotic resistance gene in an expression vector, the transformant can be selected by adding antibiotic to the medium. Then, Cas9 protein recognizing a wide range of PAM sequences is obtained by purifying the aforementioned protein expressed by the host according to a method known per se.

There are no particular limitations on the host, and examples thereof include animal cells, plant cells, insect cells and microorganisms such as *Escherichia coli, Bacillus subtilis* or yeast.

<Complex of Cas9 Protein Recognizing Wide Range of PMA Sequences and Guide RNA>

In one embodiment thereof, the present invention provides a protein-RNA complex provided with the protein indicated in the previous section on <Cas9 Protein Recognizing Wide Range of PMA Sequences> and guide RNA containing a polynucleotide composed of a base sequence complementary to a base sequence located 1 to 20 to 24 bases upstream from a proto-spacer adjacent motif (PAM) sequence in a target double-stranded polynucleotide.

According to the protein-RNA complex of the present embodiment, a wide range of PMA sequences can be recognized and a target double-stranded polynucleotide can be easily and rapidly edited site-specifically for a target sequence.

The aforementioned protein and the aforementioned guide RNA are able to form a protein-RNA complex by mixing in vitro and in vivo under mild conditions. Mild conditions refer to a temperature and pH of a degree that does not cause protein decomposition or denaturation, and the temperature is preferably 4° C. to 40° C., while the pH is preferably 4 to 10.

In addition, the duration of mixing and incubating the aforementioned protein and the aforementioned guide RNA is preferably 0.5 hours to 1 hour. The complex formed by the aforementioned protein and the aforementioned guide RNA is stable and is able to maintain stability even if allowed to stand for several hours at room temperature.

<CRISPR-Cas Vector System>

In one embodiment thereof, the present invention provides a CRISPR-Cas vector system provided with a first vector containing a gene encoding a protein indicated in the previous section on <Cas9 Protein Recognizing Wide Range of PAM Sequences>, and a second vector containing a guide RNA containing a polynucleotide composed of a base sequence complementary to a base sequence located 1 to 20 to 24 bases upstream from PAM sequence in a target double-stranded polynucleotide.

According to the CRISPR-Cas vector system of the present embodiment, a wide range of PMA sequences can be recognized and a target double-stranded polynucleotide can be easily and rapidly edited site-specifically for a target sequence.

The guide RNA is suitably designed to contain in the 5'-terminal region thereof a polynucleotide composed of a base sequence complementary to a base sequence located from 1 to 20 to 24 bases, and preferably to 22 to 24 bases, upstream from a PAM sequence in a target double-stranded polynucleotide. Moreover, the guide RNA may also contain one or more polynucleotides composed of a base sequence allowing the obtaining of a hairpin structure composed of base sequences non-complementary to a target double-stranded polynucleotide symmetrically arranged so as to form a complementary sequence having a single point as the axis thereof.

The vector of the present embodiment is preferably an expression vector. There are no particular limitations on the expression vector, and examples thereof that can be used include *E. coli*-derived plasmids such as pBR322, pBR325, puC12 or puC13; *B. subtilis*-derived plasmids such as pUB110, pTP5 or pC194; yeast-derived plasmids such as pSH15; bacteriophages such as phages; viruses such as adenovirus, adeno-associated virus, lentivirus, vaccinia virus or baculovirus; and modified vectors thereof.

In the aforementioned expression vector, there are no particular limitations on the promoters for expression of the aforementioned Cas9 protein or the aforementioned guide RNA, and examples thereof that can be used include promoters for expression in animal cells such as EF1α promoter, SRα promoter, SV40 promoter, LTR promoter, cytomegalovirus (CMV) promoter or HSV-tk promoter, promoters for expression in plant cells such as the 35S promoter of cauliflower mosaic virus (CaMV) or rubber elongation factor (REF) promoter, and promoters for expression in insect cells such as polyhedrin promoter or p10 promoter. These promoters can be suitably selected according to the aforementioned Cas9 protein and the aforementioned guide RNA, or the type of cells expressing the aforementioned Cas9 protein and the aforementioned guide RNA.

The aforementioned expression vector may also further have a multi-cloning site, enhancer, splicing signal, polyadenylation signal, selection marker or replication origin and the like.

<Method for Site-Specifically Modifying Target Double-Stranded Polynucleotide>

First Embodiment

In one embodiment thereof, the present invention provides a method for site-specifically modifying a target double-stranded polynucleotide, provided with:

a step for mixing and incubating a target double-stranded polynucleotide, a protein and a guide RNA, and a step for having the aforementioned protein modify the aforementioned target double-stranded polynucleotide at a binding site located upstream of a PAM sequence; wherein, the aforementioned target double-stranded polynucleotide has a PAM sequence composed of NG (wherein, N represents any base and G represents guanine), the aforementioned protein is the protein indicated in the above-mentioned <Cas9 Protein Recognizing Wide Range of PMA Sequences>, and the aforementioned guide RNA contains a polynucleotide composed of a base sequence complementary to a base sequence located 1 to 20 to 24 bases upstream from the aforementioned PAM sequence in the aforementioned target double-stranded polynucleotide.

According to the method of the present embodiment, a target double-stranded polynucleotide can be modified easily, rapidly and site-specifically for a target sequence by using mutant Cas9 protein recognizing a wide range of PAM sequences.

In the present embodiment, there are no particular limitations on the target double-stranded polynucleotide provided it has a PAM sequence composed of NG (wherein, N represents any base and G represents guanine).

In the present embodiment, the protein and guide RNA are as indicated in the previous section on <Cas9 Protein Recognizing Wide Range of PMA Sequences>.

The following provides a detailed explanation of the method for site-specifically modifying a target double-stranded polynucleotide.

First, the aforementioned protein and the aforementioned guide RNA are mixed and incubated under mild conditions. Mild conditions are as previously described. The incubation time is preferably 0.5 hours to 1 hour. A complex formed by the aforementioned protein and the aforementioned guide RNA is stable and is able to maintain stability even if allowed to stand for several hours at room temperature.

Next, the aforementioned protein and the aforementioned guide RNA form a complex on the aforementioned target double-stranded polynucleotide. The aforementioned protein recognizes PAM sequences composed of "5'-NG-3'", and binds to the aforementioned target double-stranded polynucleotide at a binding site located upstream of the PAM sequence. When the aforementioned protein has an endonuclease activity, the polynucleotide is cleaved at this site. As a result of the Cas9 protein recognizing the PAM sequence, and the double helix structure of the target double-stranded polynucleotide being pulled apart starting at the PAM sequence and annealing with a base sequence complementary to the target double-stranded polynucleotide in the guide RNA, the double helix structure of the target double-stranded polynucleotide is partially unraveled. At this time, the aforementioned Cas9 protein cleaves phosphate diester bonds of the target double-stranded polynucleotide at a cleavage site located upstream of the PAM sequence and a cleavage site located upstream of a sequence complementary to the PAM sequence.

Second Embodiment

In the present embodiment, an expression step may be further provided prior to the incubation step in which the protein indicated in the previous section on <Cas9 Protein Recognizing Wide Range of PAM Sequences> and guide RNA are expressed using the previously described CRISPR-Cas vector system.

In the expression step of the present embodiment, Cas9 protein and guide RNA are first expressed using the aforementioned CRISPR-Cas vector system. A specific expression method consists of transforming a host using an expression vector containing a gene that encodes Cas9 protein and an expression vector containing guide RNA, respectively. Then, the host is cultured to express the Cas9 protein and guide RNA. Conditions such as medium composition, culture temperature, duration of culturing or addition of inducing agents can be determined by a person with ordinary skill in the art in accordance with known methods so that the transformant grows and the aforementioned protein is efficiently produced. In addition, in the case of having incorporated a selection marker in the form of an antibiotic resistance gene in the expression vector, the transformant can be selected by adding antibiotic to the medium. Then, the Cas9 protein and guide RNA are obtained by purifying the Cas9 protein and guide RNA expressed by the host according to a suitable method.

<Method for Site-Specifically Modifying Target Double-Stranded Polynucleotide>

First Embodiment

In one embodiment thereof, the present invention provides a method for site-specifically modifying a target double-stranded polynucleotide, provided with:

a step for mixing and incubating a target double-stranded polynucleotide, a protein and a guide RNA, a step for having the protein bind with the target double-stranded polynucleotide at a binding site located upstream of a PAM sequence, and a step for obtaining a modified target double-stranded polynucleotide in a region determined by complementary binding between the guide RNA and the target double-stranded polynucleotide; wherein, the aforementioned target double-stranded polynucleotide has a PAM sequence composed of NG (wherein, N represents any base and G represents guanine), the aforementioned protein is the protein indicated in the previous section on the aforementioned <Cas9 Protein Recognizing Wide Range of PAM Sequences>, and the aforementioned guide RNA contains a polynucleotide composed of a base sequence complementary to a base sequence located 1 to 20 to 24 bases upstream from the aforementioned PAM sequence in the aforementioned target double-stranded polynucleotide.

According to the method of the present embodiment, a target double-stranded polynucleotide can be modified easily, rapidly and site-specifically for a target sequence by using RNA-guided DNA endonuclease recognizing a wide range of PAM sequences.

In the present embodiment, the target double-stranded polynucleotide, protein and guide RNA are as indicated in the previous sections on <Cas9 Protein Recognizing Wide Range of PMA Sequences> and <Method for Site-Specifically Modifying Target Double-Stranded Polynucleotide>.

The following provides a detailed explanation of the method for site-specifically modifying a target double-stranded polynucleotide. The steps through site-specifically bind to a target double-stranded polynucleotide are the same as in the previous section on <Method for Site-Specifically Cleaving Target Double-Stranded Polynucleotide>. Then, a target double-stranded polynucleotide that has been modified as necessary in a region determined by complementary binding between the guide RNA and the target double-stranded polynucleotide is obtained.

In the present description, "modification" refers to a change in the base sequence of a target double-stranded polynucleotide. Examples thereof include cleavage of a target double-stranded polynucleotide, alteration of the base sequence of a target double-stranded polynucleotide by inserting an exogenous sequence following cleavage (by physical insertion or insertion by replicating through homology-directed repair), and alteration of the base sequence of a target double-stranded polynucleotide by non-homologous end-joining (NHEJ: rejoining the ends of DNA resulting from cleavage) following cleavage, as well as addition of functional protein or base sequence and the like.

Modification of a target double-stranded polynucleotide in the present embodiment makes it possible to introduce a mutation into the target double-stranded polynucleotide or disrupt or modify the function of the target double-stranded polynucleotide.

Second Embodiment

In the present embodiment, an expression step may be further provided prior to the incubation step in which the protein indicated in the previous section on <Cas9 Protein Recognizing Wide Range of PAM Sequences> and guide RNA are expressed using the previously described CRISPR-Cas vector system.

In the expression step of the present embodiment, Cas9 protein and guide RNA are first expressed using the aforementioned CRISPR-Cas vector system. The specific expression method is similar to the method exemplified in the second embodiment in the previous section on <Method for Site-Specifically Modifying Target Double-Stranded Polynucleotide>.

<Method for Site-Specifically Modifying Target Double-Stranded Polynucleotide in Cells>

In one embodiment thereof, the present invention provides a method for site-specifically modifying a target double-stranded polynucleotide in cells, provided with:

a step for introducing the previously described CRISPR-Cas9 vector system into a cell and expressing protein indicated in the previous section on <Cas9 Protein Recognizing Wide Range of PAM Sequences> and guide RNA, a step for having the aforementioned protein bind with the aforementioned target double-stranded polynucleotide at a binding site located upstream of a PAM sequence, and a step for obtaining a modified target double-stranded polynucleotide in a region determined by complementary binding between the aforementioned guide RNA and the aforementioned target double-stranded polynucleotide; wherein, the aforementioned target double-stranded polynucleotide has a PAM sequence composed of NG (wherein, N represents any base and G represents guanine), the aforementioned guide RNA contains a polynucleotide composed of a base sequence complementary to a base sequence located 1 to 20 to 24 bases upstream from the aforementioned PAM sequence in the aforementioned target double-stranded polynucleotide.

In the expression step of the present embodiment, first, Cas9 protein and guide RNA are expressed in a cell using the aforementioned CRISPR-Cas vector system.

Examples of organisms serving as the origin of the cells targeted for application of the method of the present embodiment include prokaryote, yeast, animal, plant, insect and the like. There are no particular limitations on the aforementioned animals, and examples thereof include, but are not limited to, human, monkey, dog, cat, rabbit, swine, bovine, mouse, rat and the like. In addition, the type of organism serving as the source of the cells can be arbitrarily selected according to the desired type or objective of the target double-stranded polynucleotide.

Examples of animal-derived cells targeted for application of the method of the present embodiment include, but are not limited to, germ cells (such as sperm or ova), somatic cells composing the body, stem cells, progenitor cells, cancer cells isolated from the body, cells isolated from the body that are stably maintained outside the body as a result of having become immortalized (cell line), and cells isolated from the body for which the nuclei have been artificially replaced.

Examples of somatic cells composing the body include, but are not limited to, cells harvested from arbitrary tissue such as the skin, kidneys, spleen, adrenals, liver, lungs, ovaries, pancreas, uterus, stomach, small intestine, large intestine, urinary bladder, prostate gland, testes, thymus, muscle, connective tissue, bone, cartilage, vascular tissue, blood, heart, eyes, brain or neural tissue. Specific examples of somatic cells include, but are not limited to, fibroblasts, bone marrow cells, immune cells (e.g., B lymphocytes, T lymphocytes, neutrophils, macrophages or monocytes etc.), erythrocytes, platelets, osteocytes, bone marrow cells, pericytes, dendritic cells, keratinocytes, adipocytes, mesenchymal cells, epithelial cells, epidermal cells, endothelial cells, intravascular endothelial cells, lymphatic endothelial cells, hepatocytes, pancreatic islet cells (e.g., α cells, β cells, δ cells, ε cells or PP cells etc.), chondrocytes, cumulus cells, glia cells, nerve cells (neurons), oligodendrocytes, microglia cells, astrocytes, cardiomyocytes, esophageal cells, muscle cells (e.g., smooth muscle cells or skeletal muscle cells etc.), melanocytes and mononuclear cells, and the like.

Stem cells refer to cells having both the ability to self-replicate as well as the ability to differentiate into a plurality of other cell lines. Examples of stem cells include, but are not limited to, embryonic stem cells (ES cells), embryonic tumor cells, embryonic germ stem cells, induced pluripotent stem cells (iPS cells), neural stem cells, hematopoietic stem cells, mesenchymal stem cells, hepatic stem cells, pancreatic stem cells, muscle stem cells, germ stem cells, intestinal stem cells, cancer stem cells and hair follicle stem cells, and the like.

Cancer cells are cells derived from somatic cells that have acquired reproductive integrity. Examples of the origins of cancer cells include, but are not limited to, breast cancer (e.g., invasive ductal carcinoma, non-invasive ductal carcinoma, inflammatory breast cancer etc.), prostate cancer (e.g., hormone-dependent prostate cancer or hormone-independent prostate cancer etc.), pancreatic cancer (e.g., pancreatic ductal carcinoma etc.), gastric cancer (e.g., papillary adenocarcinoma, mucinous carcinoma, adenosquamous carcinoma etc.), lung cancer (e.g., non-small cell lung cancer, small cell lung cancer, malignant mesothelioma etc.), colon cancer (e.g., gastrointestinal stromal tumor etc.), rectal cancer (e.g., gastrointestinal stromal tumor etc.), colorectal cancer (e.g., familial colorectal cancer, hereditary non-polyposis colon cancer, gastrointestinal stromal tumor etc.), small intestine cancer (e.g., non-Hodgkin's lymphoma, gastrointestinal stromal tumor etc.), esophageal cancer, duodenal cancer, tongue cancer, pharyngeal cancer (e.g., nasopharyngeal carcinoma, oropharyngeal carcinoma, hypopharyngeal carcinoma etc.), head and neck cancer, salivary gland cancer, brain tumor (e.g., pineal astrocytoma, pilocytic astrocytoma, diffuse astrocytoma, anaplastic astrocytoma etc.), schwannoma, liver cancer (e.g., primary liver cancer, extrahepatic bile duct cancer etc.), kidney cancer (e.g., renal cell carcinoma, transitional cell carcinoma of the renal pelvis and ureter etc.), gallbladder cancer, bile duct cancer, pancreatic cancer, endometrial carcinoma, cervical cancer, ovarian cancer (e.g., epithelial ovarian cancer, extragonadal germ cell tumor, ovarian germ cell tumor, ovarian low malignant potential tumor etc.), bladder cancer, urethral cancer, skin cancer (e.g., intraocular (ocular) melanoma, Merkel cell carcinoma etc.), hemangioma, malignant lymphoma (e.g., reticulum cell sarcoma, lymphosarcoma, Hodgkin's etc.), melanoma (malignant melanoma), thyroid cancer (e.g., medullary thyroid cancer etc.), parathyroid cancer, nasal cancer, paranasal cancer, bone tumor (e.g., osteosarcoma, Ewing's tumor, uterine sarcoma, soft tissue sarcoma etc.), metastatic medulloblastoma, angiofibroma, protuberant dermatofibrosarcoma, retinal sarcoma, penile cancer, testicular tumor, pediatric solid tumor (e.g., Wilms tumor or pediatric kidney tumor etc.), Kaposi's sarcoma, AIDS-induced Kaposi's sarcoma, maxillary sinus tumor, fibrous histiocytoma, leiomyosarcoma, rhabdomyosarcoma, chronic myeloproliferative disease and leukemia (e.g., acute myelogenous leukemia, acute lymphoblastic leukemia etc.).

Cell lines refer to cells that have acquired reproductive integrity through artificial manipulation ex vivo. Examples of cell lines include, but are not limited to, HCT116, Huh7, HEK293 (human embryonic kidney cells), HeLa (human cervical cancer cell line), HepG2 (human liver cancer cell line), UT7/TPO (human leukemia cell line), CHO (Chinese hamster ovary cell line), MDCK, MDBK, BHK, C-33A, HT-29, AE-1, 3D9, NsO/1, Jurkat, NIH3T3, PC12, S2, Sf9, Sf21, High Five and Vero.

Introduction of the CRISPR-Cas vector system into cells can be carried out using a method suitable for the viable cells used, and examples thereof include electroporation method, heat shock method, calcium phosphate method, lipofection method, DEAE dextran method, microinjection method, particle gun method, methods using viruses, and methods using commercially available transfection reagents such as FuGENE (registered trade mark) 6 Transfection Reagent (manufactured by Roche), Lipofectamine 2000 Reagent (manufactured by Invitrogen Corp.), Lipofectamine LTX Reagent (manufactured by Invitrogen Corp.) or Lipofectamine 3000 Reagent (manufactured by Invitrogen Corp.).

Then, the modification step is the same as the methods indicated in the first embodiment in the previous section on <Method for Site-Specifically Modifying Target Double-Stranded Polynucleotide>.

Modification of a target double-stranded polynucleotide in the present embodiment makes it possible to obtain cells in which a mutation has been introduced into the target double-stranded polynucleotide or the function of the target double-stranded polynucleotide has been disrupted and modified.

When an embodiment having no endonuclease activity (e.g., embodiment 5) is used as the mutant Cas9 protein of the present invention, the protein can bind to the aforementioned target double-stranded polynucleotide at a binding site located upstream of the PAM sequence but cannot remain there to cleave the double-stranded polynucleotide. Therefore, for example, when a labeled protein such as a fluorescent protein (e.g., GFP) is fused to the protein, the labeled protein can be bound to the target double-stranded polynucleotide via the guide RNA-mutant Cas9 protein. By appropriately selecting a substance to be bound to the mutant Cas9 protein, various functions can be imparted to the target double-stranded polynucleotide.

Furthermore, a transcriptional regulatory protein or domain can be linked to the N-terminal or C-terminal of the mutant Cas9 protein or a protein obtained by partly or entirely deleting cleavage enzyme activity from the mutant Cas9. Examples of the transcriptional regulator or domain thereof include transcriptional activator or domain thereof (e.g., VP64, NF-κB p65) and transcription silencer or domain thereof (e.g., heterochromatin protein 1 (HP1)) and transcription inhibitory factor or domain thereof (e.g., Kruppel associated box (KRAB), ERF repressor domain (ERD), mSin3A interacting domain (SID)).

Enzymes that modify the methylation state of DNA (e.g., DNA methyltransferase (DNMT), TET) and enzymes that modify histone subunits (e.g., histone acetyltransferase (HAT), histone deacetylase (HDAC), histone methyltransferase, histone demethylase) can also be linked.

<Gene Therapy>

In one embodiment thereof, the present invention provides a method and composition for gene therapy by carrying out genome editing. In contrast to previously known methods for targeted gene recombination, the method of the present embodiment can be carried out efficiently and inexpensively and can be applied to any cell or living organism. An arbitrary segment of a double-stranded nucleic acid of a cell or living organism can be modified by the gene therapy method of the present embodiment. The gene therapy method of the present embodiment utilizes both homologous and non-homologous recombination processes present in all cells.

In the present description, the term "genome editing" refers to a novel gene modification technology for carrying out a specific gene disruption or knock-in of a reporter gene by carrying out targeted recombination or targeted mutation using a technology such as the CRISPR/Cas9 system or transcription activator-like effector nucleases (TALEN).

In addition, in one embodiment thereof, the present invention provides a gene therapy method for carrying out targeted DNA insertion or targeted DNA deletion. This gene therapy method includes a step for transforming a cell using a nucleic acid construct containing donor DNA. The scheme relating to DNA insertion or DNA deletion after cleaving a target gene can be determined by a person with ordinary skill in the art in accordance with a known method.

In addition, in one embodiment thereof, the present invention provides a gene therapy method for carrying out gene manipulation at a specific genetic locus using both somatic cells and germ cells.

In addition, in one embodiment thereof, the present invention provides a gene therapy method for disrupting a gene in a somatic cell. Here, the gene expresses a product harmful to cells or living organisms by over-expressing a substance harmful to cells or living organisms. This type of gene is over-expressed in one or more cell types generated in a disease. Disruption of the aforementioned over-expressed gene by the gene therapy method of the present embodiment is able to bring about a more favorable state of health in an individual suffering from a disease attributable to the aforementioned over-expressed gene. Namely, therapeutic effects are manifested as a result of the gene being disrupted in only a very small proportion of cells, thereby leading to a reduction in the expression level thereof.

In addition, in one embodiment thereof, the present invention provides a gene therapy method for disrupting a gene in a germ cell. Cells in which a specific gene has been disrupted can be used to create living organisms that do not have the function of a specific gene. A gene can be completely knocked out in cells in which the aforementioned gene has been disrupted. This functional deficit in a specific cell can have a therapeutic effect.

In addition, in one embodiment thereof, the present invention provides a gene therapy method for inserting a donor DNA encoding a gene product. This gene product has a therapeutic effect in the case of having been constitutively expressed. An example of such a method consists of inserting donor DNA encoding an active promoter and insulin gene into an individual (patient) suffering from diabetes in order to induce insertion of the donor DNA in an individual group of pancreas cells. Next, the aforementioned individual group of pancreas cells containing the aforementioned donor DNA produces insulin making it possible to treat the diabetes patient. Moreover, a drug-related gene product can be made to be produced by inserting the aforementioned donor DNA into a plant. A gene of a protein product (such as insulin, lipase or hemoglobin) is inserted into the plant along with a control element (constitutively activated promoter or inducible promoter) to enable a large amount of a pharmaceutical to be produced in the plant. Next, this protein product is isolated from the plant.

Transgenic plants or transgenic animals can be produced by methods using nucleic acid transfer technology (McCreath, K. J. et al. (2000), Nature 405: 1066-1069; Polejaeva, I. A. et al. (2000), Nature 407: 86-90). A tissue type-specific vector or cell type-specific vector can be used to provide gene expression only in selected cells.

In addition, in the case of using the aforementioned method in germ cells, cells can be produced having a designed genetic alteration by inserting donor DNA into a target gene and allowing all of the subsequent cells to undergo cell division.

Examples of application targets of the gene therapy method of the present embodiment include, but are not limited to, any living organisms, cultured cells, cultured tissue, cultured nuclei (including cells, tissue or nuclei able to be used to regenerate a living organism in cultured cells, cultured tissue or intact cultured nuclei) and gametes (e.g., ova or sperm in various stages of development).

Examples of the origins of cells targeted for application of the gene therapy method of the present embodiment include, but are not limited to, any living organisms (such as insect, fungi, rodent, bovine, sheep, goat, chicken and other agriculturally important animal along with other mammals (e.g., dog, cat or human, although not limited thereto)).

Moreover, the gene therapy method of the present embodiment can be used in plants. There are no particular limitations on those plants targeted for application of the gene therapy method of the present embodiment, and the gene therapy method of the present embodiment can be applied to various arbitrary plant species (e.g., monocotyledons or dicotyledons etc.).

While the present invention is explained in more detail in the following by referring to Examples, they do not limit the scope of the present invention.

EXAMPLE

Example 1

1. Preparation of Wild-Type and Mutant SpCas9
(1) Construct Design

Wild-type or mutant SpCas9 gene in which codons had been optimized by gene synthesis was incorporated in pET vector (Novagen). Moreover, a TEV recognition sequence was added between His tag and the SpCas9 gene. The design of the construct was such that six consecutive histidine residues (His tag) were linked followed by the addition of the TEV protease recognition site to the N-terminal of the Cas9 expressed by the completed construct.

The base sequences of the SpCas9 genes used are as follows.
WT: base sequence of wild-type SpCas9: SEQ ID NO: 2
m0: base sequence of mutant SpCas9 gene (R1335A): SEQ ID NO: 3
m4: base sequence of mutant SpCas9 gene (R1335A/G1218R): SEQ ID NO: 4
m18: base sequence of mutant SpCas9 gene (R1335A/G1218R/T1337R): SEQ ID NO: 5
m19: base sequence of mutant SpCas9 gene (R1335A/G1218R/T1337R/L1111R): SEQ ID NO: 6
m20: base sequence of mutant SpCas9 gene (R1335A/G1218R/T1337R/L1111R/D1332R): SEQ ID NO: 7
m21: base sequence of mutant SpCas9 gene (R1335A/G1218R/T1337R/L1111R/D1332R/A1322R): SEQ ID NO: 8
m22: base sequence of mutant SpCas9 gene (R1335A/G1218R/T1337R/L1111R/D1332R/A1322R/D1284R/A1285R): SEQ ID NO: 9
m23: base sequence of mutant SpCas9 gene (R1335A/G1218R/L1111R/D1332R/A1322R): SEQ ID NO: 10
m24: base sequence of mutant SpCas9 gene (R1335A/G1218R/L1111R/D1332R/A1322R/D1284R/A1285R): SEQ ID NO: 11
m25: base sequence of mutant SpCas9 gene (R1335A/G1218R/T1337R/L1111R/A1322R): SEQ ID NO: 12
m26: base sequence of mutant SpCas9 gene (R1335A/G1218R/L1111R/A1322R): SEQ ID NO: 13
m29: base sequence of mutant SpCas9 gene (R1335A/G1218R/L1111R): SEQ ID NO: 14
m32: base sequence of mutant SpCas9 gene (R1335A/G1218R/T1337R/L1111R/A1322R/E1219M): SEQ ID NO: 15
m33: base sequence of mutant SpCas9 gene (R1335A/G1218R/T1337R/L1111R/A1322R/E1219F): SEQ ID NO: 16
m34: base sequence of mutant SpCas9 gene (R1335A/G1218R/T1337R/L1111R/A1322R/E1219W): SEQ ID NO: 17
m43: base sequence of mutant SpCas9 gene (R1335A/G1218R/T1337R/L1111R/A1322R/E1219F/D1135V): SEQ ID NO: 18
m61: base sequence of mutant SpCas9 gene (R1335I/G1218R/T1337R/L1111R/A1322R/E1219F/D1135V): base sequence of m43 (SEQ ID NO: 18) in which the 4003- to 4005-position gcc is converted to atc.
m62: base sequence of mutant SpCas9 gene (R1335L/G1218R/T1337R/L1111R/A1322R/E1219F/D1135V): base sequence of m43 (SEQ ID NO: 18) in which the 4003- to 4005-position gcc is converted to ctg.
m63: base sequence of mutant SpCas9 gene (R1335M/G1218R/T1337R/L1111R/A1322R/E1219F/D1135V): base sequence of m43 (SEQ ID NO: 18) in which the 4003- to 4005-position gcc is converted to atg.
m64: base sequence of mutant SpCas9 gene (R1335F/G1218R/T1337R/L1111R/A1322R/E1219F/D1135V): base sequence of m43 (SEQ ID NO: 18) in which the 4003- to 4005-position gcc is converted to ttt.
m65: base sequence of mutant SpCas9 gene (R1335T/G1218R/T1337R/L1111R/A1322R/E1219F/D1135V): base sequence of m43 (SEQ ID NO: 18) in which the 4003- to 4005-position gcc is converted to acc.
m66: base sequence of mutant SpCas9 gene (R1335V/G1218R/T1337R/L1111R/A1322R/E1219F/D1135V): base sequence of m43 (SEQ ID NO: 18) in which the 4003- to 4005-position gcc is converted to gtg.

(2) Expression in *Escherichia coli*

The resulting vectors were used to transform *Escherichia coli* strain rosetta 2 (DE3). Subsequently, the *E. coli* were cultured in LB medium containing 20 µg/ml of kanamycin and 20 µg/ml of chloramphenicol. After having cultured to OD=0.8, an expression inducing agent in the form of isopropyl-β-D-1-thiogalactopyranoside (IPTG) (final concentration: 1 mM) was added followed by culturing for 4 hours at 37° C. Following culturing, the *E. coli* were recovered by centrifugation (5,000 g, 10 minutes).

(3) Purification of Wild-Type and Mutant SpCas9

The bacterial cells recovered in (2) were suspended in a Buffer A and subjected to ultrasonication. Supernatant was recovered by centrifugation (25,000 g, 30 minutes) followed by mixing with Ni-NTA Superflow Resin (Qiagen Inc.) equilibrated with a Buffer A and gently inverting for 1 hour. After recovering the effluent fraction, the column was washed with the Buffer A in an amount equal to four times the column volume and a high salt concentration Buffer B in an amount equal to two times the column volume.

Then, after again washing with the Buffer A using an amount equal to twice the column volume, the target protein was eluted with a high imidazole concentration Buffer C in an amount equal to five times the column volume.

Then, the crudely purified sample was charged into HiTrapSP (GE Healthcare). After washing with a mixture of 92.5% Buffer D (0 M NaCl) and 7.5% Buffer F (2 M NaCl) in an amount equal to five times the column volume, the target protein was eluted by applying a linear gradient in which the concentration of Buffer E increased from 10% to 50% (NaCl concentration increased from 200 mM to 1 M).

The compositions of Buffers A to E are shown below.
Buffer A: 20 mM Tris-HCl, pH 8.0, 300 mM NaCl, 20 mM imidazole
Buffer B: 20 mM Tris-HCl, pH 8.0, 1000 mM NaCl, 20 mM imidazole
Buffer C: 20 mM Tris-HCl, pH 8.0, 300 mM NaCl, 300 mM imidazole
Buffer D: 20 mM Tris-HCl, pH 8.0
Buffer E: 20 mM Tris-HCl, pH 8.0, 2000 mM NaCl 2. Preparation of Guide RNA A vector inserted with the target guide RNA sequence (<u>ggaaauuaggugcgcuuggc</u>guuuuagagcuagaaauagcaaguuaaaa uaaggcuaguccguuaucaacuugaaaaagug; SEQ ID NO: 19)

was prepared. The underlined part shows a 20 base guide sequence and the rest corresponds to a scaffold part (stem-loop 2). A T7 promoter sequence was added upstream from the guide RNA sequence followed by incorporating a linearized pUC119 vector (Takara Corp.). Template DNA for an in vitro transcription reaction was produced using PCR based on the resulting vector. An in vitro transcription reaction was carried out by T7 RNA polymerase for 4 hours at 37° C. using this DNA template. After adding an equal volume of phenol-chloroform to the reaction solution containing the transcription product and mixing, the solution was centrifuged at 20° C. (10,000 g, 2 minutes) to recover the supernatant. 1/10th volume of 3 M sodium acetate and 2.5 volumes of 100% ethanol were added to the supernatant followed by centrifuging at 4° C. (10,000 g, 3 minutes) to precipitate the transcription product. The supernatant was discarded followed by adding 70% ethanol, centrifuging at 4° C. (10,000 g, 3 minutes) and again discarding the supernatant. After allowing the precipitate to air-dry, the precipitate was re-suspended in TBE buffer and purified by 7 M urea-denatured 10% PAGE. The band located at the molecular weight of the target RNA was cut out and the RNA was extracted with the Elutrap electroelution system (GE Healthcare Inc.). Subsequently, the eluted RNA was passed through a PD-10 column (GE Healthcare Inc.) and the buffer solution was replaced with Buffer H (10 mM Tris-HCl (pH 8.0), 150 mM NaCl).

3. Plasmid DNA Cleavage Activity Measurement Test

Vectors inserted with the target DNA sequence and PAM sequence were prepared for use in a DNA cleavage activity measurement test. PAM sequences 1 to 4 were each added to the target DNA sequence and incorporated in a linearized pUC119 vector. The target DNA sequence and PAM sequences 1 to 4 are shown in Table 1.

TABLE 1

|  | base sequence | SEQ ID NO: |
|---|---|---|
| target DNA | 5'-GGAAATTAGG TGCGCTTGGC-3' | SEQ ID NO: 20 |
| PAM sequence 1 | 5'-TGT-3' | |
| PAM sequence 2 | 5'-TGG-3' | |
| PAM sequence 3 | 5'-TGNA-3' | |
| PAM sequence 4 | 5'-TGN-3' | |

*Escherichia coli* strain Machi (Life Technologies) was transformed using the prepared vectors followed by culturing at 37° C. in LB medium containing 20 µg/ml of ampicillin.

Following culturing, the bacterial cells were recovered by centrifugation (8,000 g, 1 minute) and the plasmid DNA was purified using the QIAprep Spin Miniprep Kit (QIAGEN).

A cleavage experiment was carried out using the purified target plasmid DNA containing PAM sequence. The plasmid DNA was linearized into a single strand with restriction enzyme. When the wild-type or mutant SpCas9 was cleaved from the target DNA sequence in this linearized DNA, approximately 1000 bp and 2000 bp cleavage products were obtained. As the buffer for cleavage, cleavage buffer B with the following composition was used.

composition of B(×10)
200 mM HEPES 7.5
1000 mM KCl
50% glycerol
10 mM DTT
5 mM EDTA
20 mM $MgCl_2$ The samples were electrophoresed using agarose gel having a concentration of 1% following the reaction, and bands corresponding to the cleavage products were confirmed. The results are shown in FIGS. 1A to D. In the Figure, "Substrate" indicates the substrate while "Product" indicates the cleavage products. The PAM sequence and the reaction conditions are shown in the Figures.

In contrast to the target plasmid DNA having been cleaved as a result of recognizing only G for the third base of the PAM sequence in the case of the wild-type SpCas9, in the case of the mutant SpCas9, the target plasmid DNA could be cleaved as a result of recognizing PAM sequences in which the third base was other than G.

Accordingly, in contrast to recognizing "NGG" for the PAM sequence in the case of the wild-type SpCas9, the PAM sequence "NG" was confirmed to be recognized in the case of the mutant SpCas9.

Based on the above results, mutant SpCas9 was determined to be able to recognize a wide range of PAM sequences and site-specifically cleave a target double-stranded polynucleotide for a target sequence both easily and rapidly.

Example 2

Figure 2:
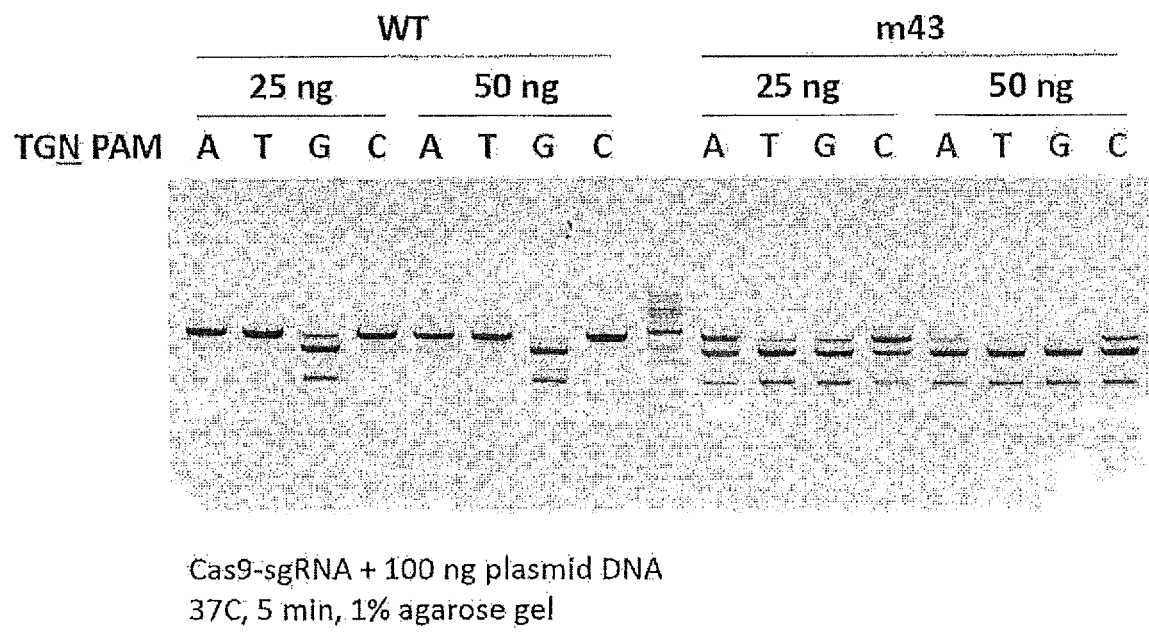
FIG. 2 shows an image representing the results of agarose gel electrophoresis in a DNA cleavage activity measurement test in Example 2.

Plasmid DNA Cleavage Activity Measurement Test was performed in the same manner as in Example 1 and using the mutant SpCas9(m43) prepared in Example 1. The results are shown in FIG. 2.

In contrast to the target plasmid having been cleaved as a result of recognizing only G for the third base of the PAM sequence in the case of the wild-type SpCas9, in the case of the mutant SpCas9, the target plasmid DNA could be cleaved as a result of recognizing PAM sequences in which the third base was other than G.

Accordingly, in contrast to recognizing "NGG" for the PAM sequence in the case of the wild-type SpCas9, the PAM sequence "NG" was confirmed to be recognized in the case of the mutant SpCas9.

Example 3

Figure 3:
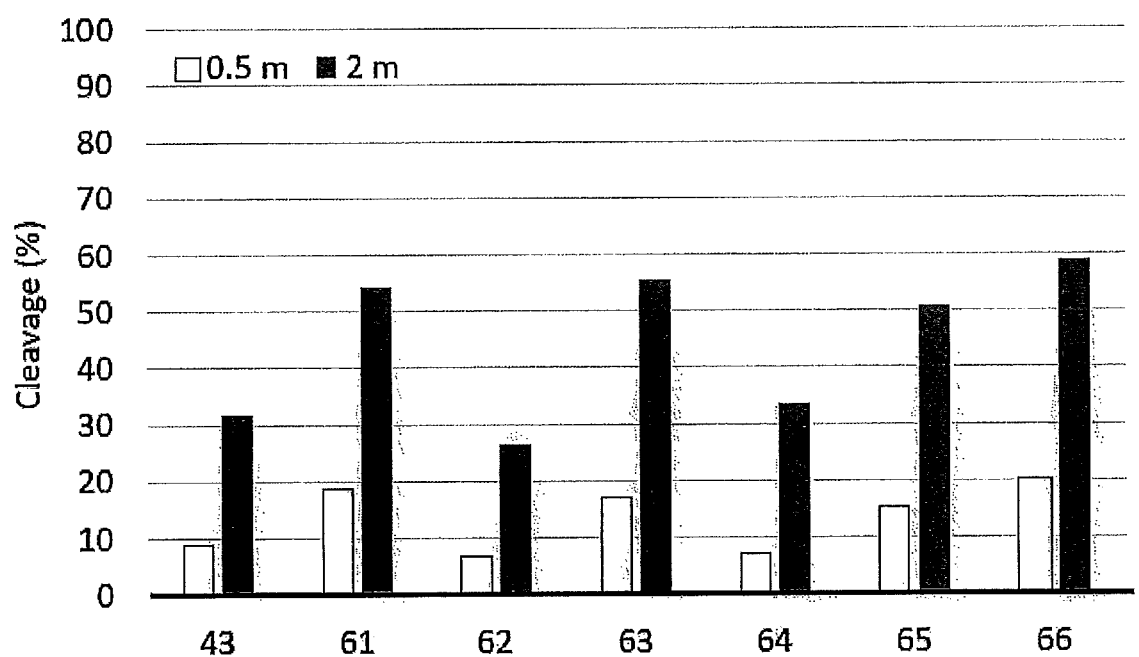
FIG. 3 shows a graph showing the results of a DNA cleavage activity measurement test in Example 3. "TGA" was used as the PAM sequence and BamHI was used as the restriction enzyme.

Plasmid DNA Cleavage Activity Measurement Test was performed in the same manner as in Example 1 and using the mutant SpCas9 (m43, m61-m66) prepared in Example 1. For detection of a cleavage product, MultiNA capillary electrophoresis apparatus (Shimadzu Corporation) was used. As the PAM sequence, 5'-TGC-3' (PAM sequence 4) was used. The cleavage experiment was performed for 0.5 minute (0.5 m) and 2 minutes (2 m). The results are shown in FIG. 3. Superior DNA cleavage activity was confirmed in m61, m63, m65 and m66.

Example 4

Figure 4:
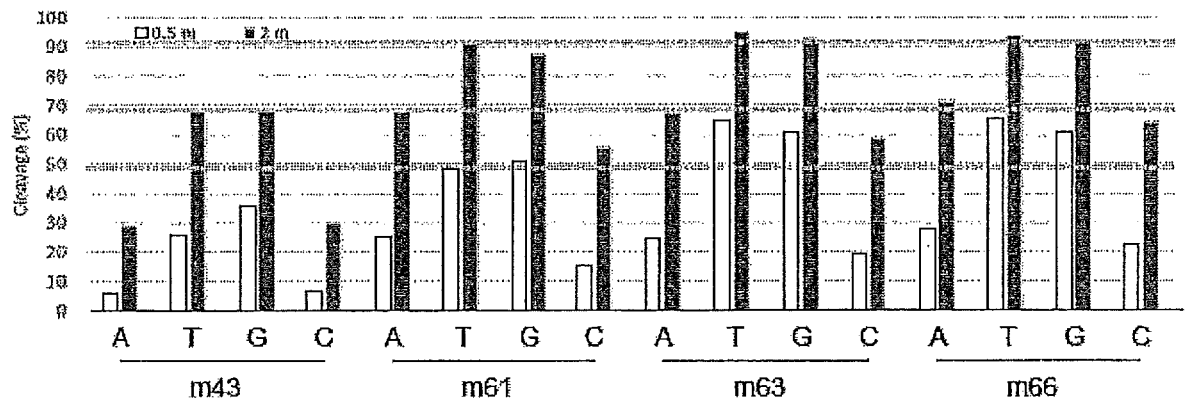
FIG. 4 is a graph showing the results of the DNA cleavage activity measurement test in Example 4.

Plasmid DNA Cleavage Activity Measurement Test was performed in the same manner as in Example 1 and using the mutant SpCas9 (m43, m61, m63 and m66) prepared in Example 1. The cleavage experiment was performed for 0.5 minute (0.5 m) and 2 minutes (2 m). The results are shown in FIG. 4.

In contrast to the target plasmid having been cleaved as a result of recognizing only G for the third base of the PAM sequence in the case of the wild-type SpCas9, in the case of the mutant SpCas9, the target plasmid DNA could be cleaved as a result of recognizing PAM sequences in which the third base was other than G. It was confirmed that m61, m63 and m66, particularly m63 and m66, could cleave DNA with high efficiency even when the PAM sequences of TGA and TGC, which showed low efficiency in m43, were used.

Example 5

Figure 5:
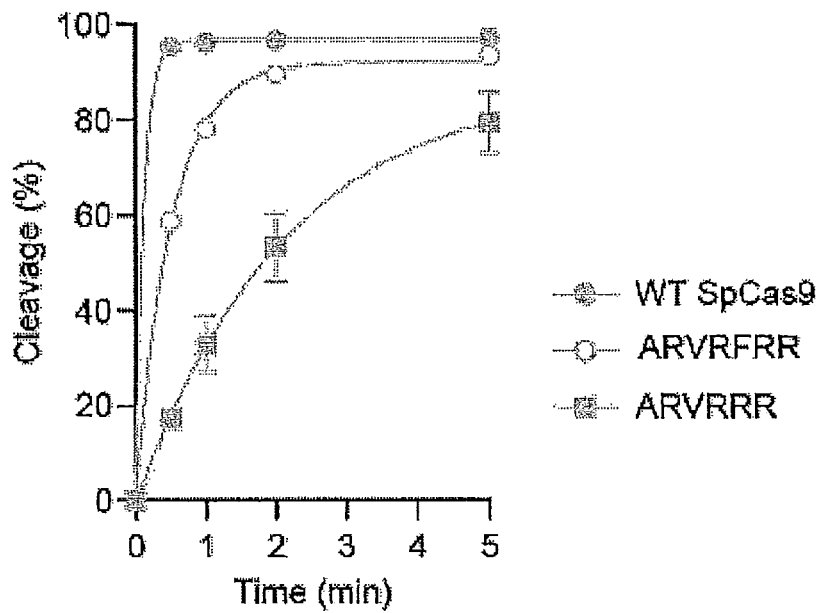
FIG. 5 is a graph showing the results of the DNA cleavage activity measurement test in Example 5.

Plasmid DNA Cleavage Activity Measurement Test was performed in the same manner as in Example 1 and using wild-type SpCas9 and mutant SpCas9(WT, m43) prepared in Example 1 and the following mutant SpCas9 prepared in the same manner as in Example 1. The cleavage experiment was performed over time (0, 0.5, 1, 2, 5 min). The results are shown in FIG. 5. In m43, rising of cleavage activity which is comparable to that in WT was confirmed.

base sequence of mutant SpCas9 gene (R1335A/G1218R/T1337R/L1111R/A1322R/D1135V): base sequence of m25 (SEQ ID NO: 12) in which the 3403- to 3405-position gac is converted to gtt.

INDUSTRIAL APPLICABILITY

According to the present invention, a Cas9 protein can be obtained that recognizes a wide range of PAM sequences while retaining binding strength with a target double-stranded polynucleotide and further retaining endonuclease activity. In addition, a simple and rapid site-specific genome editing technology for a target sequence can be provided that uses the aforementioned Cas9 protein.

This application is based on patent application No. 2017-108556 filed in Japan (filing date: May 31, 2017), the contents of which are encompassed in full herein.

---

The invention claimed is:

1. A polynucleotide encoding a polypeptide that binds a guide RNA wherein said polypeptide comprises all of SEQ ID NO:1 except for
   (a) the substitution of glutamic acid to phenylalanine, methionine, or tryptophan at the position corresponding to position 1219 of SEQ ID NO: 1, the substitution of alanine to arginine at the position corresponding to position 1322 of SEQ ID NO: 1, the substitution of arginine to alanine, isoleucine, leucine, methionine, phenylalanine, valine or threonine at the position corresponding to position 1335 of SEQ ID NO: 1, and three additional substitutions selected from the group consisting of the substitution of leucine to arginine at the position corresponding to position 1111 of SEQ ID NO: 1, the substitution of aspartic acid to valine at the position corresponding to position 1135 of SEQ ID NO: 1, the substitution of glycine to arginine at the position corresponding to position 1218 of SEQ ID NO: 1 and the substitution of threonine to arginine at the position corresponding to position 1337 of SEQ ID NO: 1, and optionally additional mutation(s) that adversely affect nuclease activity, or
   (b) the substitution of leucine to arginine at the position corresponding to position 1111 of SEQ ID NO: 1, the substitution of aspartic acid to valine at the position corresponding to position 1135 of SEQ ID NO: 1, the substitution of glycine to arginine at the position corresponding to position 1218 of SEQ ID NO: 1, the substitution of glutamic acid to phenylalanine at the position corresponding to position 1219 of the polypeptide of SEQ ID NO: 1, the substitution of alanine to arginine at the position corresponding to position 1322 of SEQ ID NO: 1, the substitution of arginine to valine at the position corresponding to position 1335 of SEQ ID NO: 1, and the substitution of threonine to arginine at the position corresponding to position 1337 of SEQ ID NO: 1, and optionally additional mutation(s) that adversely affect nuclease activity, wherein the mutation that adversely affects nuclease activity is (i) a mutation at at least one position corresponding to a position selected from positions 10, 762, 839, 983, and 986 of SEQ ID NO: 1, and/or (ii) a mutation at a position corresponding to a position selected from positions 840 and 863 of SEQ ID NO: 1.

2. The polynucleotide according to claim 1, wherein the arginine at the position corresponding to position 1335 of SEQ ID NO: 1 is substituted with alanine, isoleucine, methionine, threonine or valine.

3. The polynucleotide according to claim 1, wherein the glutamic acid at the position corresponding to position 1219 of SEQ ID NO: 1 is substituted with phenylalanine.

4. The polynucleotide according to claim 1, wherein the protein has RNA-guided DNA endonuclease activity.

5. The polynucleotide according to claim 1, wherein the mutation at the position corresponding to position 10 of SEQ ID NO: 1 is a substitution of aspartic acid to alanine or asparagine, or the mutation at the position corresponding to position 840 of SEQ ID NO: 1 is a substitution of histidine to alanine, asparagine or tyrosine.

6. The polynucleotide according to claim 1, which is linked to a polynucleotide that encodes a transcriptional regulator protein or a transcriptional regulator domain.

7. The polynucleotide according to claim 6, wherein the transcriptional regulator is a transcription activation factor.

8. The polynucleotide according to claim 6, wherein the transcriptional regulator is a transcription silencer or a transcription inhibitory factor.

* * * * *

SEQUENCE LISTING

```
<160> NUMBER OF SEQ ID NOS: 20

<210> SEQ ID NO 1
<211> LENGTH: 1368
<212> TYPE: PRT
<213> ORGANISM: Streptococcus pyogenes

<400> SEQUENCE: 1

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140
```

```
Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
            165                 170                 175

Asp Asn Ser Asp Val Asp Lys Leu Phe Ile Gln Leu Val Gln Thr Tyr
        180                 185                 190

Asn Gln Leu Phe Glu Glu Asn Pro Ile Asn Ala Ser Gly Val Asp Ala
    195                 200                 205

Lys Ala Ile Leu Ser Ala Arg Leu Ser Lys Ser Arg Arg Leu Glu Asn
210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
            245                 250                 255

Asp Leu Ala Glu Asp Ala Lys Leu Gln Leu Ser Lys Asp Thr Tyr Asp
        260                 265                 270

Asp Asp Leu Asp Asn Leu Leu Ala Gln Ile Gly Asp Gln Tyr Ala Asp
    275                 280                 285

Leu Phe Leu Ala Ala Lys Asn Leu Ser Asp Ala Ile Leu Leu Ser Asp
290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
            325                 330                 335

Ala Leu Val Arg Gln Gln Leu Pro Glu Lys Tyr Lys Glu Ile Phe Phe
        340                 345                 350

Asp Gln Ser Lys Asn Gly Tyr Ala Gly Tyr Ile Asp Gly Gly Ala Ser
    355                 360                 365

Gln Glu Glu Phe Tyr Lys Phe Ile Lys Pro Ile Leu Glu Lys Met Asp
370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
            405                 410                 415

Gly Glu Leu His Ala Ile Leu Arg Arg Gln Glu Asp Phe Tyr Pro Phe
        420                 425                 430

Leu Lys Asp Asn Arg Glu Lys Ile Glu Lys Ile Leu Thr Phe Arg Ile
    435                 440                 445

Pro Tyr Tyr Val Gly Pro Leu Ala Arg Gly Asn Ser Arg Phe Ala Trp
450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
            485                 490                 495

Asn Phe Asp Lys Asn Leu Pro Asn Glu Lys Val Leu Pro Lys His Ser
        500                 505                 510

Leu Leu Tyr Glu Tyr Phe Thr Val Tyr Asn Glu Leu Thr Lys Val Lys
    515                 520                 525

Tyr Val Thr Glu Gly Met Arg Lys Pro Ala Phe Leu Ser Gly Glu Gln
530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
```

```
                   565                 570                 575

Ser Val Glu Ile Ser Gly Val Glu Asp Arg Phe Asn Ala Ser Leu Gly
                         580                 585                 590

Thr Tyr His Asp Leu Leu Lys Ile Ile Lys Asp Lys Asp Phe Leu Asp
                         595                 600                 605

Asn Glu Glu Asn Glu Asp Ile Leu Glu Asp Ile Val Leu Thr Leu Thr
         610                 615                 620

Leu Phe Glu Asp Arg Glu Met Ile Glu Arg Leu Lys Thr Tyr Ala
         625                 630                 635                 640

His Leu Phe Asp Asp Lys Val Met Lys Gln Leu Lys Arg Arg Arg Tyr
                         645                 650                 655

Thr Gly Trp Gly Arg Leu Ser Arg Lys Leu Ile Asn Gly Ile Arg Asp
                         660                 665                 670

Lys Gln Ser Gly Lys Thr Ile Leu Asp Phe Leu Lys Ser Asp Gly Phe
                         675                 680                 685

Ala Asn Arg Asn Phe Met Gln Leu Ile His Asp Asp Ser Leu Thr Phe
                         690                 695                 700

Lys Glu Asp Ile Gln Lys Ala Gln Val Ser Gly Gln Gly Asp Ser Leu
         705                 710                 715                 720

His Glu His Ile Ala Asn Leu Ala Gly Ser Pro Ala Ile Lys Lys Gly
                         725                 730                 735

Ile Leu Gln Thr Val Lys Val Val Asp Glu Leu Val Lys Val Met Gly
                         740                 745                 750

Arg His Lys Pro Glu Asn Ile Val Ile Glu Met Ala Arg Glu Asn Gln
                         755                 760                 765

Thr Thr Gln Lys Gly Gln Lys Asn Ser Arg Glu Arg Met Lys Arg Ile
         770                 775                 780

Glu Glu Gly Ile Lys Glu Leu Gly Ser Gln Ile Leu Lys Glu His Pro
         785                 790                 795                 800

Val Glu Asn Thr Gln Leu Gln Asn Glu Lys Leu Tyr Leu Tyr Tyr Leu
                         805                 810                 815

Gln Asn Gly Arg Asp Met Tyr Val Asp Gln Glu Leu Asp Ile Asn Arg
                         820                 825                 830

Leu Ser Asp Tyr Asp Val Asp His Ile Val Pro Gln Ser Phe Leu Lys
                         835                 840                 845

Asp Asp Ser Ile Asp Asn Lys Val Leu Thr Arg Ser Asp Lys Asn Arg
         850                 855                 860

Gly Lys Ser Asp Asn Val Pro Ser Glu Glu Val Val Lys Lys Met Lys
         865                 870                 875                 880

Asn Tyr Trp Arg Gln Leu Leu Asn Ala Lys Leu Ile Thr Gln Arg Lys
                         885                 890                 895

Phe Asp Asn Leu Thr Lys Ala Glu Arg Gly Gly Leu Ser Glu Leu Asp
                         900                 905                 910

Lys Ala Gly Phe Ile Lys Arg Gln Leu Val Glu Thr Arg Gln Ile Thr
                         915                 920                 925

Lys His Val Ala Gln Ile Leu Asp Ser Arg Met Asn Thr Lys Tyr Asp
         930                 935                 940

Glu Asn Asp Lys Leu Ile Arg Glu Val Lys Val Ile Thr Leu Lys Ser
         945                 950                 955                 960

Lys Leu Val Ser Asp Phe Arg Lys Asp Phe Gln Phe Tyr Lys Val Arg
                         965                 970                 975

Glu Ile Asn Asn Tyr His His Ala His Asp Ala Tyr Leu Asn Ala Val
                         980                 985                 990
```

```
Val Gly Thr Ala Leu Ile Lys Lys  Tyr Pro Lys Leu Glu  Ser Glu Phe
        995                 1000                1005

Val Tyr  Gly Asp Tyr  Lys Val  Tyr Asp Val Arg  Lys Met Ile Ala
1010                 1015                    1020

Lys Ser  Glu Gln Glu  Ile Gly  Lys Ala Thr Ala  Lys Tyr Phe Phe
1025                 1030                    1035

Tyr Ser  Asn Ile Met  Asn Phe  Phe Lys Thr Glu  Ile Thr Leu Ala
1040                 1045                    1050

Asn Gly  Glu Ile Arg  Lys Arg  Pro Leu Ile Glu  Thr Asn Gly Glu
1055                 1060                    1065

Thr Gly  Glu Ile Val  Trp Asp  Lys Gly Arg Asp  Phe Ala Thr Val
1070                 1075                    1080

Arg Lys  Val Leu Ser  Met Pro  Gln Val Asn Ile  Val Lys Lys Thr
1085                 1090                    1095

Glu Val  Gln Thr Gly  Gly Phe  Ser Lys Glu Ser  Ile Leu Pro Lys
1100                 1105                    1110

Arg Asn  Ser Asp Lys  Leu Ile  Ala Arg Lys Lys  Asp Trp Asp Pro
1115                 1120                    1125

Lys Lys  Tyr Gly Gly  Phe Asp  Ser Pro Thr Val  Ala Tyr Ser Val
1130                 1135                    1140

Leu Val  Val Ala Lys  Val Glu  Lys Gly Lys Ser  Lys Lys Leu Lys
1145                 1150                    1155

Ser Val  Lys Glu Leu  Leu Gly  Ile Thr Ile Met  Glu Arg Ser Ser
1160                 1165                    1170

Phe Glu  Lys Asn Pro  Ile Asp  Phe Leu Glu Ala  Lys Gly Tyr Lys
1175                 1180                    1185

Glu Val  Lys Lys Asp  Leu Ile  Ile Lys Leu Pro  Lys Tyr Ser Leu
1190                 1195                    1200

Phe Glu  Leu Glu Asn  Gly Arg  Lys Arg Met Leu  Ala Ser Ala Gly
1205                 1210                    1215

Glu Leu  Gln Lys Gly  Asn Glu  Leu Ala Leu Pro  Ser Lys Tyr Val
1220                 1225                    1230

Asn Phe  Leu Tyr Leu  Ala Ser  His Tyr Glu Lys  Leu Lys Gly Ser
1235                 1240                    1245

Pro Glu  Asp Asn Glu  Gln Lys  Gln Leu Phe Val  Glu Gln His Lys
1250                 1255                    1260

His Tyr  Leu Asp Glu  Ile Ile  Glu Gln Ile Ser  Glu Phe Ser Lys
1265                 1270                    1275

Arg Val  Ile Leu Ala  Asp Ala  Asn Leu Asp Lys  Val Leu Ser Ala
1280                 1285                    1290

Tyr Asn  Lys His Arg  Asp Lys  Pro Ile Arg Glu  Gln Ala Glu Asn
1295                 1300                    1305

Ile Ile  His Leu Phe  Thr Leu  Thr Asn Leu Gly  Ala Pro Ala Ala
1310                 1315                    1320

Phe Lys  Tyr Phe Asp  Thr Thr  Ile Asp Arg Lys  Arg Tyr Thr Ser
1325                 1330                    1335

Thr Lys  Glu Val Leu  Asp Ala  Thr Leu Ile His  Gln Ser Ile Thr
1340                 1345                    1350

Gly Leu  Tyr Glu Thr  Arg Ile  Asp Leu Ser Gln  Leu Gly Gly Asp
1355                 1360                    1365

<210> SEQ ID NO 2
<211> LENGTH: 4107
```

```
<212> TYPE: DNA
<213> ORGANISM: Streptococcus pyogenes
<220> FEATURE:
<221> NAME/KEY: CDS
<222> LOCATION: (1)..(4107)

<400> SEQUENCE: 2 atg gac aag aag tac agc atc ggc ctg gac atc ggc acc aac tct gtg      48
Met Asp Lys Lys Tyr Ser Ile Gly Leu Asp Ile Gly Thr Asn Ser Val
1               5                   10                  15 ggc tgg gcc gtg atc acc gac gag tac aag gtg ccc agc aag aaa ttc      96
Gly Trp Ala Val Ile Thr Asp Glu Tyr Lys Val Pro Ser Lys Lys Phe
            20                  25                  30 aag gtg ctg ggc aac acc gac cgg cac agc atc aag aag aac ctg atc     144
Lys Val Leu Gly Asn Thr Asp Arg His Ser Ile Lys Lys Asn Leu Ile
        35                  40                  45 gga gcc ctg ctg ttc gac agc ggc gaa aca gcc gag gcc acc cgg ctg     192
Gly Ala Leu Leu Phe Asp Ser Gly Glu Thr Ala Glu Ala Thr Arg Leu
    50                  55                  60 aag aga acc gcc aga aga aga tac acc aga cgg aag aac cgg atc tgc     240
Lys Arg Thr Ala Arg Arg Arg Tyr Thr Arg Arg Lys Asn Arg Ile Cys
65                  70                  75                  80 tat ctg caa gag atc ttc agc aac gag atg gcc aag gtg gac gac agc     288
Tyr Leu Gln Glu Ile Phe Ser Asn Glu Met Ala Lys Val Asp Asp Ser
                85                  90                  95 ttc ttc cac aga ctg gaa gag tcc ttc ctg gtg gaa gag gat aag aag     336
Phe Phe His Arg Leu Glu Glu Ser Phe Leu Val Glu Glu Asp Lys Lys
            100                 105                 110 cac gag cgg cac ccc atc ttc ggc aac atc gtg gac gag gtg gcc tac     384
His Glu Arg His Pro Ile Phe Gly Asn Ile Val Asp Glu Val Ala Tyr
        115                 120                 125 cac gag aag tac ccc acc atc tac cac ctg aga aag aaa ctg gtg gac     432
His Glu Lys Tyr Pro Thr Ile Tyr His Leu Arg Lys Lys Leu Val Asp
    130                 135                 140 agc acc gac aag gcc gac ctg cgg ctg atc tat ctg gcc ctg gcc cac     480
Ser Thr Asp Lys Ala Asp Leu Arg Leu Ile Tyr Leu Ala Leu Ala His
145                 150                 155                 160 atg atc aag ttc cgg ggc cac ttc ctg atc gag ggc gac ctg aac ccc     528
Met Ile Lys Phe Arg Gly His Phe Leu Ile Glu Gly Asp Leu Asn Pro
                165                 170                 175 gac aac agc gac gtg gac aag ctg ttc atc cag ctg gtg cag acc tac     576
Asp Asn Ser Asp Val Asp Lys Leu Phe Ile Gln Leu Val Gln Thr Tyr
            180                 185                 190 aac cag ctg ttc gag gaa aac ccc atc aac gcc agc ggc gtg gac gcc     624
Asn Gln Leu Phe Glu Glu Asn Pro Ile Asn Ala Ser Gly Val Asp Ala
        195                 200                 205 aag gcc atc ctg tct gcc aga ctg agc aag agc aga cgg ctg gaa aat     672
Lys Ala Ile Leu Ser Ala Arg Leu Ser Lys Ser Arg Arg Leu Glu Asn
    210                 215                 220 ctg atc gcc cag ctg ccc ggc gag aag aag aat ggc ctg ttc ggc aac     720
Leu Ile Ala Gln Leu Pro Gly Glu Lys Lys Asn Gly Leu Phe Gly Asn
225                 230                 235                 240 ctg att gcc ctg agc ctg ggc ctg acc ccc aac ttc aag agc aac ttc     768
Leu Ile Ala Leu Ser Leu Gly Leu Thr Pro Asn Phe Lys Ser Asn Phe
                245                 250                 255 gac ctg gcc gag gat gcc aaa ctg cag ctg agc aag gac acc tac gac     816
Asp Leu Ala Glu Asp Ala Lys Leu Gln Leu Ser Lys Asp Thr Tyr Asp
            260                 265                 270 gac gac ctg gac aac ctg ctg gcc cag atc ggc gac cag tac gcc gac     864
Asp Asp Leu Asp Asn Leu Leu Ala Gln Ile Gly Asp Gln Tyr Ala Asp
        275                 280                 285
```

|  |  |  |  |  |  |  |  |  |  |  |  |  |  |  |  |
|---|---|---|---|---|---|---|---|---|---|---|---|---|---|---|---|
| ctg | ttt | ctg | gcc | gcc | aag | aac | ctg | tcc | gac | gcc | atc | ctg | ctg | agc | gac |
| Leu | Phe | Leu | Ala | Ala | Lys | Asn | Leu | Ser | Asp | Ala | Ile | Leu | Leu | Ser | Asp |
|  | 290 |  |  |  | 295 |  |  |  | 300 |  |  |  |  |  |  |

912 atc ctg aga gtg aac acc gag atc acc aag gcc ccc ctg agc gcc tct     960
Ile Leu Arg Val Asn Thr Glu Ile Thr Lys Ala Pro Leu Ser Ala Ser
305             310             315             320 atg atc aag aga tac gac gag cac cac cag gac ctg acc ctg ctg aaa    1008
Met Ile Lys Arg Tyr Asp Glu His His Gln Asp Leu Thr Leu Leu Lys
            325             330             335 gct ctc gtg cgg cag cag ctg cct gag aag tac aaa gag att ttc ttc    1056
Ala Leu Val Arg Gln Gln Leu Pro Glu Lys Tyr Lys Glu Ile Phe Phe
        340             345             350 gac cag agc aag aac ggc tac gcc ggc tac att gac ggc gga gcc agc    1104
Asp Gln Ser Lys Asn Gly Tyr Ala Gly Tyr Ile Asp Gly Gly Ala Ser
            355             360             365 cag gaa gag ttc tac aag ttc atc aag ccc atc ctg gaa aag atg gac    1152
Gln Glu Glu Phe Tyr Lys Phe Ile Lys Pro Ile Leu Glu Lys Met Asp
    370             375             380 ggc acc gag gaa ctg ctc gtg aag ctg aac aga gag gac ctg ctg cgg    1200
Gly Thr Glu Glu Leu Leu Val Lys Leu Asn Arg Glu Asp Leu Leu Arg
385             390             395             400 aag cag cgg acc ttc gac aac ggc agc atc ccc cac cag atc cac ctg    1248
Lys Gln Arg Thr Phe Asp Asn Gly Ser Ile Pro His Gln Ile His Leu
            405             410             415 gga gag ctg cac gcc att ctg cgg cgg cag gaa gat ttt tac cca ttc    1296
Gly Glu Leu His Ala Ile Leu Arg Arg Gln Glu Asp Phe Tyr Pro Phe
        420             425             430 ctg aag gac aac cgg gaa aag atc gag aag atc ctg acc ttc cgc atc    1344
Leu Lys Asp Asn Arg Glu Lys Ile Glu Lys Ile Leu Thr Phe Arg Ile
            435             440             445 ccc tac tac gtg ggc cct ctg gcc agg gga aac agc aga ttc gcc tgg    1392
Pro Tyr Tyr Val Gly Pro Leu Ala Arg Gly Asn Ser Arg Phe Ala Trp
    450             455             460 atg acc aga aag agc gag gaa acc atc acc ccc tgg aac ttc gag gaa    1440
Met Thr Arg Lys Ser Glu Glu Thr Ile Thr Pro Trp Asn Phe Glu Glu
465             470             475             480 gtg gtg gac aag ggc gct tcc gcc cag agc ttc atc gag cgg atg acc    1488
Val Val Asp Lys Gly Ala Ser Ala Gln Ser Phe Ile Glu Arg Met Thr
            485             490             495 aac ttc gat aag aac ctg ccc aac gag aag gtg ctg ccc aag cac agc    1536
Asn Phe Asp Lys Asn Leu Pro Asn Glu Lys Val Leu Pro Lys His Ser
        500             505             510 ctg ctg tac gag tac ttc acc gtg tat aac gag ctg acc aaa gtg aaa    1584
Leu Leu Tyr Glu Tyr Phe Thr Val Tyr Asn Glu Leu Thr Lys Val Lys
            515             520             525 tac gtg acc gag gga atg aga aag ccc gcc ttc ctg agc ggc gag cag    1632
Tyr Val Thr Glu Gly Met Arg Lys Pro Ala Phe Leu Ser Gly Glu Gln
    530             535             540 aaa aag gcc atc gtg gac ctg ctg ttc aag acc aac cgg aaa gtg acc    1680
Lys Lys Ala Ile Val Asp Leu Leu Phe Lys Thr Asn Arg Lys Val Thr
545             550             555             560 gtg aag cag ctg aaa gag gac tac ttc aag aaa atc gag tgc ttc gac    1728
Val Lys Gln Leu Lys Glu Asp Tyr Phe Lys Lys Ile Glu Cys Phe Asp
            565             570             575 tcc gtg gaa atc tcc ggc gtg gaa gat cgg ttc aac gcc tcc ctg ggc    1776
Ser Val Glu Ile Ser Gly Val Glu Asp Arg Phe Asn Ala Ser Leu Gly
        580             585             590 aca tac cac gat ctg ctg aaa att atc aag gac aag gac ttc ctg gac    1824
Thr Tyr His Asp Leu Leu Lys Ile Ile Lys Asp Lys Asp Phe Leu Asp

|                                                                                         |      |
|-----------------------------------------------------------------------------------------|------|
| 595                       600                       605                                 |      |
| aat gag gaa aac gag gac att ctg gaa gat atc gtg ctg acc ctg aca                         | 1872 |
| Asn Glu Glu Asn Glu Asp Ile Leu Glu Asp Ile Val Leu Thr Leu Thr                         |      |
| 610                       615                       620                                 |      |
| ctg ttt gag gac aga gag atg atc gag gaa cgg ctg aaa acc tat gcc                         | 1920 |
| Leu Phe Glu Asp Arg Glu Met Ile Glu Glu Arg Leu Lys Thr Tyr Ala                         |      |
| 625                       630                       635                       640       |      |
| cac ctg ttc gac gac aaa gtg atg aag cag ctg aag cgg cgg aga tac                         | 1968 |
| His Leu Phe Asp Asp Lys Val Met Lys Gln Leu Lys Arg Arg Arg Tyr                         |      |
|                           645                       650                       655       |      |
| acc ggc tgg ggc agg ctg agc cgg aag ctg atc aac ggc atc cgg gac                         | 2016 |
| Thr Gly Trp Gly Arg Leu Ser Arg Lys Leu Ile Asn Gly Ile Arg Asp                         |      |
|                 660                       665                       670                 |      |
| aag cag tcc ggc aag aca atc ctg gat ttc ctg aag tcc gac ggc ttc                         | 2064 |
| Lys Gln Ser Gly Lys Thr Ile Leu Asp Phe Leu Lys Ser Asp Gly Phe                         |      |
|                 675                       680                       685                 |      |
| gcc aac aga aac ttc atg cag ctg atc cac gac gac agc ctg acc ttt                         | 2112 |
| Ala Asn Arg Asn Phe Met Gln Leu Ile His Asp Asp Ser Leu Thr Phe                         |      |
|                 690                       695                       700                 |      |
| aaa gag gac atc cag aaa gcc cag gtg tcc ggc cag ggc gat agc ctg                         | 2160 |
| Lys Glu Asp Ile Gln Lys Ala Gln Val Ser Gly Gln Gly Asp Ser Leu                         |      |
| 705                       710                       715                       720       |      |
| cac gag cac att gcc aat ctg gcc ggc agc ccc gcc att aag aag ggc                         | 2208 |
| His Glu His Ile Ala Asn Leu Ala Gly Ser Pro Ala Ile Lys Lys Gly                         |      |
|                           725                       730                       735       |      |
| atc ctg cag aca gtg aag gtg gtg gac gag ctc gtg aaa gtg atg ggc                         | 2256 |
| Ile Leu Gln Thr Val Lys Val Val Asp Glu Leu Val Lys Val Met Gly                         |      |
|                 740                       745                       750                 |      |
| cgg cac aag ccc gag aac atc gtg atc gaa atg gcc aga gag aac cag                         | 2304 |
| Arg His Lys Pro Glu Asn Ile Val Ile Glu Met Ala Arg Glu Asn Gln                         |      |
|                 755                       760                       765                 |      |
| acc acc cag aag gga cag aag aac agc cgc gag aga atg aag cgg atc                         | 2352 |
| Thr Thr Gln Lys Gly Gln Lys Asn Ser Arg Glu Arg Met Lys Arg Ile                         |      |
|                 770                       775                       780                 |      |
| gaa gag ggc atc aaa gag ctg ggc agc cag atc ctg aaa gaa cac ccc                         | 2400 |
| Glu Glu Gly Ile Lys Glu Leu Gly Ser Gln Ile Leu Lys Glu His Pro                         |      |
| 785                       790                       795                       800       |      |
| gtg gaa aac acc cag ctg cag aac gag aag ctg tac ctg tac tac ctg                         | 2448 |
| Val Glu Asn Thr Gln Leu Gln Asn Glu Lys Leu Tyr Leu Tyr Tyr Leu                         |      |
|                           805                       810                       815       |      |
| cag aat ggg cgg gat atg tac gtg gac cag gaa ctg gac atc aac cgg                         | 2496 |
| Gln Asn Gly Arg Asp Met Tyr Val Asp Gln Glu Leu Asp Ile Asn Arg                         |      |
|                 820                       825                       830                 |      |
| ctg tcc gac tac gat gtg gac cat atc gtg cct cag agc ttt ctg aag                         | 2544 |
| Leu Ser Asp Tyr Asp Val Asp His Ile Val Pro Gln Ser Phe Leu Lys                         |      |
|                 835                       840                       845                 |      |
| gac gac tcc atc gac aac aag gtg ctg acc aga agc gac aag aac cgg                         | 2592 |
| Asp Asp Ser Ile Asp Asn Lys Val Leu Thr Arg Ser Asp Lys Asn Arg                         |      |
|                 850                       855                       860                 |      |
| ggc aag agc gac aac gtg ccc tcc gaa gag gtc gtg aag aag atg aag                         | 2640 |
| Gly Lys Ser Asp Asn Val Pro Ser Glu Glu Val Val Lys Lys Met Lys                         |      |
| 865                       870                       875                       880       |      |
| aac tac tgg cgg cag ctg ctg aac gcc aag ctg att acc cag aga aag                         | 2688 |
| Asn Tyr Trp Arg Gln Leu Leu Asn Ala Lys Leu Ile Thr Gln Arg Lys                         |      |
|                           885                       890                       895       |      |
| ttc gac aat ctg acc aag gcc gag aga ggc ggc ctg agc gaa ctg gat                         | 2736 |
| Phe Asp Asn Leu Thr Lys Ala Glu Arg Gly Gly Leu Ser Glu Leu Asp                         |      |
|                 900                       905                       910                 |      |
| aag gcc ggc ttc atc aag aga cag ctg gtg gaa acc cgg cag atc aca                         | 2784 |

-continued

|   |   |   |   |   |   |   |   |   |   |   |   |   |     |
|---|---|---|---|---|---|---|---|---|---|---|---|---|-----|
| Lys | Ala | Gly | Phe | Ile | Lys | Arg | Gln | Leu | Val | Glu | Thr | Arg | Gln | Ile | Thr |
|   |   |   | 915 |   |   |   | 920 |   |   |   | 925 |   |

```
aag cac gtg gca cag atc ctg gac tcc cgg atg aac act aag tac gac       2832
Lys His Val Ala Gln Ile Leu Asp Ser Arg Met Asn Thr Lys Tyr Asp
            930                 935                 940 gag aat gac aag ctg atc cgg gaa gtg aaa gtg atc acc ctg aag tcc       2880
Glu Asn Asp Lys Leu Ile Arg Glu Val Lys Val Ile Thr Leu Lys Ser
945                 950                 955                 960 aag ctg gtg tcc gat ttc cgg aag gat ttc cag ttt tac aaa gtg cgc       2928
Lys Leu Val Ser Asp Phe Arg Lys Asp Phe Gln Phe Tyr Lys Val Arg
                965                 970                 975 gag atc aac aac tac cac cac gcc cac gac gcc tac ctg aac gcc gtc       2976
Glu Ile Asn Asn Tyr His His Ala His Asp Ala Tyr Leu Asn Ala Val
            980                 985                 990 gtg gga acc gcc ctg atc aaa aag tac cct aag ctg gaa  agc gag ttc      3024
Val Gly Thr Ala Leu Ile Lys Lys Tyr Pro Lys Leu Glu  Ser Glu Phe
            995                 1000                1005 gtg tac  ggc gac tac aag gtg  tac gac gtg cgg aag  atg atc gcc        3069
Val Tyr  Gly Asp Tyr Lys Val  Tyr Asp Val Arg Lys  Met Ile Ala
1010                 1015                1020 aag agc gag cag gaa atc ggc  aag gct acc gcc aag  tac ttc ttc         3114
Lys Ser Glu Gln Glu Ile Gly  Lys Ala Thr Ala Lys  Tyr Phe Phe
1025                 1030                1035 tac agc aac atc atg aac ttt  ttc aag acc gag att  acc ctg gcc         3159
Tyr Ser Asn Ile Met Asn Phe  Phe Lys Thr Glu Ile  Thr Leu Ala
1040                 1045                1050 aac ggc gag atc cgg aag cgg  cct ctg atc gag aca  aac ggc gaa         3204
Asn Gly Glu Ile Arg Lys Arg  Pro Leu Ile Glu Thr  Asn Gly Glu
1055                 1060                1065 acc ggg gag atc gtg tgg gat  aag ggc cgg gat ttt  gcc acc gtg         3249
Thr Gly Glu Ile Val Trp Asp  Lys Gly Arg Asp Phe  Ala Thr Val
1070                 1075                1080 cgg aaa gtg ctg agc atg ccc  caa gtg aat atc gtg  aaa aag acc         3294
Arg Lys Val Leu Ser Met Pro  Gln Val Asn Ile Val  Lys Lys Thr
1085                 1090                1095 gag gtg cag aca ggc ggc ttc  agc aaa gag tct atc  ctg ccc aag         3339
Glu Val Gln Thr Gly Gly Phe  Ser Lys Glu Ser Ile  Leu Pro Lys
1100                 1105                1110 agg aac agc gat aag ctg atc  gcc aga aag aag gac  tgg gac cct         3384
Arg Asn Ser Asp Lys Leu Ile  Ala Arg Lys Lys Asp  Trp Asp Pro
1115                 1120                1125 aag aag tac ggc ggc ttc gac  agc ccc acc gtg gcc  tat tct gtg         3429
Lys Lys Tyr Gly Gly Phe Asp  Ser Pro Thr Val Ala  Tyr Ser Val
1130                 1135                1140 ctg gtg gtg gcc aaa gtg gaa  aag ggc aag tcc aag  aaa ctg aag         3474
Leu Val Val Ala Lys Val Glu  Lys Gly Lys Ser Lys  Lys Leu Lys
1145                 1150                1155 agt gtg aaa gag ctg ctg ggg  atc acc atc atg gaa  aga agc agc         3519
Ser Val Lys Glu Leu Leu Gly  Ile Thr Ile Met Glu  Arg Ser Ser
1160                 1165                1170 ttc gag aag aat ccc atc gac  ttt ctg gaa gcc aag  ggc tac aaa         3564
Phe Glu Lys Asn Pro Ile Asp  Phe Leu Glu Ala Lys  Gly Tyr Lys
1175                 1180                1185 gaa gtg aaa aag gac ctg atc  atc aag ctg cct aag  tac tcc ctg         3609
Glu Val Lys Lys Asp Leu Ile  Ile Lys Leu Pro Lys  Tyr Ser Leu
1190                 1195                1200 ttc gag ctg gaa aac ggc cgg  aag aga atg ctg gcc  tct gcc ggc         3654
Phe Glu Leu Glu Asn Gly Arg  Lys Arg Met Leu Ala  Ser Ala Gly
1205                 1210                1215
```

-continued

| | | |
|---|---|---|
| gaa ctg cag aag gga aac gaa ctg gcc ctg ccc tcc aaa tat gtg<br>Glu Leu Gln Lys Gly Asn Glu Leu Ala Leu Pro Ser Lys Tyr Val<br>1220                 1225                 1230 | | 3699 |
| aac ttc ctg tac ctg gcc agc cac tat gag aag ctg aag ggc tcc<br>Asn Phe Leu Tyr Leu Ala Ser His Tyr Glu Lys Leu Lys Gly Ser<br>1235                 1240                 1245 | | 3744 |
| ccc gag gat aat gag cag aaa cag ctg ttt gtg gaa cag cac aag<br>Pro Glu Asp Asn Glu Gln Lys Gln Leu Phe Val Glu Gln His Lys<br>1250                 1255                 1260 | | 3789 |
| cac tac ctg gac gag atc atc gag cag atc agc gag ttc tcc aag<br>His Tyr Leu Asp Glu Ile Ile Glu Gln Ile Ser Glu Phe Ser Lys<br>1265                 1270                 1275 | | 3834 |
| aga gtg atc ctg gcc gac gct aat ctg gac aaa gtg ctg tcc gcc<br>Arg Val Ile Leu Ala Asp Ala Asn Leu Asp Lys Val Leu Ser Ala<br>1280                 1285                 1290 | | 3879 |
| tac aac aag cac cgg gat aag ccc atc aga gag cag gcc gag aat<br>Tyr Asn Lys His Arg Asp Lys Pro Ile Arg Glu Gln Ala Glu Asn<br>1295                 1300                 1305 | | 3924 |
| atc atc cac ctg ttt acc ctg acc aat ctg gga gcc cct gcc gcc<br>Ile Ile His Leu Phe Thr Leu Thr Asn Leu Gly Ala Pro Ala Ala<br>1310                 1315                 1320 | | 3969 |
| ttc aag tac ttt gac acc acc atc gac cgg aag agg tac acc agc<br>Phe Lys Tyr Phe Asp Thr Thr Ile Asp Arg Lys Arg Tyr Thr Ser<br>1325                 1330                 1335 | | 4014 |
| acc aaa gag gtg ctg gac gcc acc ctg atc cac cag agc atc acc<br>Thr Lys Glu Val Leu Asp Ala Thr Leu Ile His Gln Ser Ile Thr<br>1340                 1345                 1350 | | 4059 |
| ggc ctg tac gag aca cgg atc gac ctg tct cag ctg gga ggc gac<br>Gly Leu Tyr Glu Thr Arg Ile Asp Leu Ser Gln Leu Gly Gly Asp<br>1355                 1360                 1365 | | 4104 |
| taa | | 4107 |

<210> SEQ ID NO 3
<211> LENGTH: 4107
<212> TYPE: DNA
<213> ORGANISM: Streptococcus pyogenes
<220> FEATURE:
<221> NAME/KEY: CDS
<222> LOCATION: (1)..(4107)

<400> SEQUENCE: 3

| | | |
|---|---|---|
| atg gac aag aag tac agc atc ggc ctg gac atc ggc acc aac tct gtg<br>Met Asp Lys Lys Tyr Ser Ile Gly Leu Asp Ile Gly Thr Asn Ser Val<br>1                  5                 10                 15 | | 48 |
| ggc tgg gcc gtg atc acc gac gag tac aag gtg ccc agc aag aaa ttc<br>Gly Trp Ala Val Ile Thr Asp Glu Tyr Lys Val Pro Ser Lys Lys Phe<br>                 20                 25                 30 | | 96 |
| aag gtg ctg ggc aac acc gac cgg cac agc atc aag aag aac ctg atc<br>Lys Val Leu Gly Asn Thr Asp Arg His Ser Ile Lys Lys Asn Leu Ile<br>35                 40                 45 | | 144 |
| gga gcc ctg ctg ttc gac agc ggc gaa aca gcc gag gcc acc cgg ctg<br>Gly Ala Leu Leu Phe Asp Ser Gly Glu Thr Ala Glu Ala Thr Arg Leu<br>50                 55                 60 | | 192 |
| aag aga acc gcc aga aga aga tac acc aga cgg aag aac cgg atc tgc<br>Lys Arg Thr Ala Arg Arg Arg Tyr Thr Arg Arg Lys Asn Arg Ile Cys<br>65                 70                 75                 80 | | 240 |
| tat ctg caa gag atc ttc agc aac gag atg gcc aag gtg gac gac agc<br>Tyr Leu Gln Glu Ile Phe Ser Asn Glu Met Ala Lys Val Asp Asp Ser<br>                 85                 90                 95 | | 288 |
| ttc ttc cac aga ctg gaa gag tcc ttc ctg gtg gaa gag gat aag aag<br>Phe Phe His Arg Leu Glu Glu Ser Phe Leu Val Glu Glu Asp Lys Lys | | 336 |

-continued

|     |     |     |     | 100 |     |     |     | 105 |     |     |     | 110 |     |     |      |
|-----|-----|-----|-----|-----|-----|-----|-----|-----|-----|-----|-----|-----|-----|-----|------|
| cac | gag | cgg | cac | ccc | atc | ttc | ggc | aac | atc | gtg | gac | gag | gtg | gcc | tac  | 384
| His | Glu | Arg | His | Pro | Ile | Phe | Gly | Asn | Ile | Val | Asp | Glu | Val | Ala | Tyr |
|     |     | 115 |     |     |     | 120 |     |     |     | 125 |     |     |     |     |     |

```
cac gag aag tac ccc acc atc tac cac ctg aga aag aaa ctg gtg gac      432
His Glu Lys Tyr Pro Thr Ile Tyr His Leu Arg Lys Lys Leu Val Asp
        130                 135                 140 agc acc gac aag gcc gac ctg cgg ctg atc tat ctg gcc ctg gcc cac      480
Ser Thr Asp Lys Ala Asp Leu Arg Leu Ile Tyr Leu Ala Leu Ala His
145                 150                 155                 160 atg atc aag ttc cgg ggc cac ttc ctg atc gag ggc gac ctg aac ccc      528
Met Ile Lys Phe Arg Gly His Phe Leu Ile Glu Gly Asp Leu Asn Pro
                165                 170                 175 gac aac agc gac gtg gac aag ctg ttc atc cag ctg gtg cag acc tac      576
Asp Asn Ser Asp Val Asp Lys Leu Phe Ile Gln Leu Val Gln Thr Tyr
            180                 185                 190 aac cag ctg ttc gag gaa aac ccc atc aac gcc agc ggc gtg gac gcc      624
Asn Gln Leu Phe Glu Glu Asn Pro Ile Asn Ala Ser Gly Val Asp Ala
        195                 200                 205 aag gcc atc ctg tct gcc aga ctg agc aag agc aga cgg ctg gaa aat      672
Lys Ala Ile Leu Ser Ala Arg Leu Ser Lys Ser Arg Arg Leu Glu Asn
210                 215                 220 ctg atc gcc cag ctg ccc ggc gag aag aag aat ggc ctg ttc ggc aac      720
Leu Ile Ala Gln Leu Pro Gly Glu Lys Lys Asn Gly Leu Phe Gly Asn
225                 230                 235                 240 ctg att gcc ctg agc ctg ggc ctg acc ccc aac ttc aag agc aac ttc      768
Leu Ile Ala Leu Ser Leu Gly Leu Thr Pro Asn Phe Lys Ser Asn Phe
                245                 250                 255 gac ctg gcc gag gat gcc aaa ctg cag ctg agc aag gac acc tac gac      816
Asp Leu Ala Glu Asp Ala Lys Leu Gln Leu Ser Lys Asp Thr Tyr Asp
        260                 265                 270 gac gac ctg gac aac ctg ctg gcc cag atc ggc gac cag tac gcc gac      864
Asp Asp Leu Asp Asn Leu Leu Ala Gln Ile Gly Asp Gln Tyr Ala Asp
            275                 280                 285 ctg ttt ctg gcc gcc aag aac ctg tcc gac gcc atc ctg ctg agc gac      912
Leu Phe Leu Ala Ala Lys Asn Leu Ser Asp Ala Ile Leu Leu Ser Asp
        290                 295                 300 atc ctg aga gtg aac acc gag atc acc aag gcc ccc ctg agc gcc tct     960
Ile Leu Arg Val Asn Thr Glu Ile Thr Lys Ala Pro Leu Ser Ala Ser
305                 310                 315                 320 atg atc aag aga tac gac gag cac cac cag gac ctg acc ctg ctg aaa    1008
Met Ile Lys Arg Tyr Asp Glu His His Gln Asp Leu Thr Leu Leu Lys
                325                 330                 335 gct ctc gtg cgg cag cag ctg cct gag aag tac aaa gag att ttc ttc    1056
Ala Leu Val Arg Gln Gln Leu Pro Glu Lys Tyr Lys Glu Ile Phe Phe
        340                 345                 350 gac cag agc aag aac ggc tac gcc ggc tac att gac ggc gga gcc agc    1104
Asp Gln Ser Lys Asn Gly Tyr Ala Gly Tyr Ile Asp Gly Gly Ala Ser
            355                 360                 365 cag gaa gag ttc tac aag ttc atc aag ccc atc ctg gaa aag atg gac    1152
Gln Glu Glu Phe Tyr Lys Phe Ile Lys Pro Ile Leu Glu Lys Met Asp
        370                 375                 380 ggc acc gag gaa ctg ctc gtg aag ctg aac aga gag gac ctg ctg cgg    1200
Gly Thr Glu Glu Leu Leu Val Lys Leu Asn Arg Glu Asp Leu Leu Arg
385                 390                 395                 400 aag cag cgg acc ttc gac aac ggc agc atc ccc cac cag atc cac ctg    1248
Lys Gln Arg Thr Phe Asp Asn Gly Ser Ile Pro His Gln Ile His Leu
                405                 410                 415 gga gag ctg cac gcc att ctg cgg cgg cag gaa gat ttt tac cca ttc    1296
```

```
                Gly Glu Leu His Ala Ile Leu Arg Arg Gln Glu Asp Phe Tyr Pro Phe
                            420                 425                 430 ctg aag gac aac cgg gaa aag atc gag aag atc ctg acc ttc cgc atc         1344
Leu Lys Asp Asn Arg Glu Lys Ile Glu Lys Ile Leu Thr Phe Arg Ile
            435                 440                 445 ccc tac tac gtg ggc cct ctg gcc agg gga aac agc aga ttc gcc tgg         1392
Pro Tyr Tyr Val Gly Pro Leu Ala Arg Gly Asn Ser Arg Phe Ala Trp
450                 455                 460 atg acc aga aag agc gag gaa acc atc acc ccc tgg aac ttc gag gaa         1440
Met Thr Arg Lys Ser Glu Glu Thr Ile Thr Pro Trp Asn Phe Glu Glu
465                 470                 475                 480 gtg gtg gac aag ggc gct tcc gcc cag agc ttc atc gag cgg atg acc         1488
Val Val Asp Lys Gly Ala Ser Ala Gln Ser Phe Ile Glu Arg Met Thr
                485                 490                 495 aac ttc gat aag aac ctg ccc aac gag aag gtg ctg ccc aag cac agc         1536
Asn Phe Asp Lys Asn Leu Pro Asn Glu Lys Val Leu Pro Lys His Ser
            500                 505                 510 ctg ctg tac gag tac ttc acc gtg tat aac gag ctg acc aaa gtg aaa         1584
Leu Leu Tyr Glu Tyr Phe Thr Val Tyr Asn Glu Leu Thr Lys Val Lys
            515                 520                 525 tac gtg acc gag gga atg aga aag ccc gcc ttc ctg agc ggc gag cag         1632
Tyr Val Thr Glu Gly Met Arg Lys Pro Ala Phe Leu Ser Gly Glu Gln
530                 535                 540 aaa aag gcc atc gtg gac ctg ctg ttc aag acc aac cgg aaa gtg acc         1680
Lys Lys Ala Ile Val Asp Leu Leu Phe Lys Thr Asn Arg Lys Val Thr
545                 550                 555                 560 gtg aag cag ctg aaa gag gac tac ttc aag aaa atc gag tgc ttc gac         1728
Val Lys Gln Leu Lys Glu Asp Tyr Phe Lys Lys Ile Glu Cys Phe Asp
                565                 570                 575 tcc gtg gaa atc tcc ggc gtg gaa gat cgg ttc aac gcc tcc ctg ggc         1776
Ser Val Glu Ile Ser Gly Val Glu Asp Arg Phe Asn Ala Ser Leu Gly
            580                 585                 590 aca tac cac gat ctg ctg aaa att atc aag gac aag gac ttc ctg gac         1824
Thr Tyr His Asp Leu Leu Lys Ile Ile Lys Asp Lys Asp Phe Leu Asp
            595                 600                 605 aat gag gaa aac gag gac att ctg gaa gat atc gtg ctg acc ctg aca         1872
Asn Glu Glu Asn Glu Asp Ile Leu Glu Asp Ile Val Leu Thr Leu Thr
610                 615                 620 ctg ttt gag gac aga gag atg atc gag gaa cgg ctg aaa acc tat gcc         1920
Leu Phe Glu Asp Arg Glu Met Ile Glu Glu Arg Leu Lys Thr Tyr Ala
625                 630                 635                 640 cac ctg ttc gac gac aaa gtg atg aag cag ctg aag cgg cgg aga tac         1968
His Leu Phe Asp Asp Lys Val Met Lys Gln Leu Lys Arg Arg Arg Tyr
                645                 650                 655 acc ggc tgg ggc agg ctg agc cgg aag ctg atc aac ggc atc cgg gac         2016
Thr Gly Trp Gly Arg Leu Ser Arg Lys Leu Ile Asn Gly Ile Arg Asp
            660                 665                 670 aag cag tcc ggc aag aca atc ctg gat ttc ctg aag tcc gac ggc ttc         2064
Lys Gln Ser Gly Lys Thr Ile Leu Asp Phe Leu Lys Ser Asp Gly Phe
            675                 680                 685 gcc aac aga aac ttc atg cag ctg atc cac gac gac agc ctg acc ttt         2112
Ala Asn Arg Asn Phe Met Gln Leu Ile His Asp Asp Ser Leu Thr Phe
690                 695                 700 aaa gag gac atc cag aaa gcc cag gtg tcc ggc cag ggc gat agc ctg         2160
Lys Glu Asp Ile Gln Lys Ala Gln Val Ser Gly Gln Gly Asp Ser Leu
705                 710                 715                 720 cac gag cac att gcc aat ctg gcc ggc agc ccc gcc att aag aag ggc         2208
His Glu His Ile Ala Asn Leu Ala Gly Ser Pro Ala Ile Lys Lys Gly
                725                 730                 735
```

|  |  |
|---|---|
| atc ctg cag aca gtg aag gtg gtg gac gag ctc gtg aaa gtg atg ggc<br>Ile Leu Gln Thr Val Lys Val Val Asp Glu Leu Val Lys Val Met Gly<br>740               745               750 | 2256 |
| cgg cac aag ccc gag aac atc gtg atc gaa atg gcc aga gag aac cag<br>Arg His Lys Pro Glu Asn Ile Val Ile Glu Met Ala Arg Glu Asn Gln<br>755               760               765 | 2304 |
| acc acc cag aag gga cag aag aac agc cgc gag aga atg aag cgg atc<br>Thr Thr Gln Lys Gly Gln Lys Asn Ser Arg Glu Arg Met Lys Arg Ile<br>770               775               780 | 2352 |
| gaa gag ggc atc aaa gag ctg ggc agc cag atc ctg aaa gaa cac ccc<br>Glu Glu Gly Ile Lys Glu Leu Gly Ser Gln Ile Leu Lys Glu His Pro<br>785               790               795               800 | 2400 |
| gtg gaa aac acc cag ctg cag aac gag aag ctg tac ctg tac tac ctg<br>Val Glu Asn Thr Gln Leu Gln Asn Glu Lys Leu Tyr Leu Tyr Tyr Leu<br>805             810               815 | 2448 |
| cag aat ggg cgg gat atg tac gtg gac cag gaa ctg gac atc aac cgg<br>Gln Asn Gly Arg Asp Met Tyr Val Asp Gln Glu Leu Asp Ile Asn Arg<br>820               825               830 | 2496 |
| ctg tcc gac tac gat gtg gac cat atc gtg cct cag agc ttt ctg aag<br>Leu Ser Asp Tyr Asp Val Asp His Ile Val Pro Gln Ser Phe Leu Lys<br>835               840               845 | 2544 |
| gac gac tcc atc gac aac aag gtg ctg acc aga agc gac aag aac cgg<br>Asp Asp Ser Ile Asp Asn Lys Val Leu Thr Arg Ser Asp Lys Asn Arg<br>850               855               860 | 2592 |
| ggc aag agc gac aac gtg ccc tcc gaa gag gtc gtg aag aag atg aag<br>Gly Lys Ser Asp Asn Val Pro Ser Glu Glu Val Val Lys Lys Met Lys<br>865               870               875               880 | 2640 |
| aac tac tgg cgg cag ctg ctg aac gcc aag ctg att acc cag aga aag<br>Asn Tyr Trp Arg Gln Leu Leu Asn Ala Lys Leu Ile Thr Gln Arg Lys<br>885               890               895 | 2688 |
| ttc gac aat ctg acc aag gcc gag aga ggc ggc ctg agc gaa ctg gat<br>Phe Asp Asn Leu Thr Lys Ala Glu Arg Gly Gly Leu Ser Glu Leu Asp<br>900             905               910 | 2736 |
| aag gcc ggc ttc atc aag aga cag ctg gtg gaa acc cgg cag atc aca<br>Lys Ala Gly Phe Ile Lys Arg Gln Leu Val Glu Thr Arg Gln Ile Thr<br>915             920               925 | 2784 |
| aag cac gtg gca cag atc ctg gac tcc cgg atg aac act aag tac gac<br>Lys His Val Ala Gln Ile Leu Asp Ser Arg Met Asn Thr Lys Tyr Asp<br>930             935               940 | 2832 |
| gag aat gac aag ctg atc cgg gaa gtg aaa gtg atc acc ctg aag tcc<br>Glu Asn Asp Lys Leu Ile Arg Glu Val Lys Val Ile Thr Leu Lys Ser<br>945             950               955               960 | 2880 |
| aag ctg gtg tcc gat ttc cgg aag gat ttc cag ttt tac aaa gtg cgc<br>Lys Leu Val Ser Asp Phe Arg Lys Asp Phe Gln Phe Tyr Lys Val Arg<br>965             970               975 | 2928 |
| gag atc aac aac tac cac cac gcc cac gac gcc tac ctg aac gcc gtc<br>Glu Ile Asn Asn Tyr His His Ala His Asp Ala Tyr Leu Asn Ala Val<br>980             985               990 | 2976 |
| gtg gga acc gcc ctg atc aaa aag tac cct aag ctg gaa agc gag ttc<br>Val Gly Thr Ala Leu Ile Lys Lys Tyr Pro Lys Leu Glu Ser Glu Phe<br>995             1000              1005 | 3024 |
| gtg tac ggc gac tac aag gtg tac gac gtg cgg aag atg atc gcc<br>Val Tyr Gly Asp Tyr Lys Val Tyr Asp Val Arg Lys Met Ile Ala<br>1010             1015             1020 | 3069 |
| aag agc gag cag gaa atc ggc aag gct acc gcc aag tac ttc ttc<br>Lys Ser Glu Gln Glu Ile Gly Lys Ala Thr Ala Lys Tyr Phe Phe<br>1025             1030             1035 | 3114 |
| tac agc aac atc atg aac ttt ttc aag acc gag att acc ctg gcc<br>Tyr Ser Asn Ile Met Asn Phe Phe Lys Thr Glu Ile Thr Leu Ala<br>1040             1045             1050 | 3159 |

```
aac ggc gag atc cgg aag cgg cct ctg atc gag aca aac ggc gaa     3204
Asn Gly Glu Ile Arg Lys Arg Pro Leu Ile Glu Thr Asn Gly Glu
    1055                1060                1065 acc ggg gag atc gtg tgg gat aag ggc cgg gat ttt gcc acc gtg     3249
Thr Gly Glu Ile Val Trp Asp Lys Gly Arg Asp Phe Ala Thr Val
    1070                1075                1080 cgg aaa gtg ctg agc atg ccc caa gtg aat atc gtg aaa aag acc     3294
Arg Lys Val Leu Ser Met Pro Gln Val Asn Ile Val Lys Lys Thr
    1085                1090                1095 gag gtg cag aca ggc ggc ttc agc aaa gag tct atc ctg ccc aag     3339
Glu Val Gln Thr Gly Gly Phe Ser Lys Glu Ser Ile Leu Pro Lys
    1100                1105                1110 agg aac agc gat aag ctg atc gcc aga aag aag gac tgg gac cct     3384
Arg Asn Ser Asp Lys Leu Ile Ala Arg Lys Lys Asp Trp Asp Pro
    1115                1120                1125 aag aag tac ggc ggc ttc gac agc ccc acc gtg gcc tat tct gtg     3429
Lys Lys Tyr Gly Gly Phe Asp Ser Pro Thr Val Ala Tyr Ser Val
    1130                1135                1140 ctg gtg gtg gcc aaa gtg gaa aag ggc aag tcc aag aaa ctg aag     3474
Leu Val Val Ala Lys Val Glu Lys Gly Lys Ser Lys Lys Leu Lys
    1145                1150                1155 agt gtg aaa gag ctg ctg ggg atc acc atc atg gaa aga agc agc     3519
Ser Val Lys Glu Leu Leu Gly Ile Thr Ile Met Glu Arg Ser Ser
    1160                1165                1170 ttc gag aag aat ccc atc gac ttt ctg gaa gcc aag ggc tac aaa     3564
Phe Glu Lys Asn Pro Ile Asp Phe Leu Glu Ala Lys Gly Tyr Lys
    1175                1180                1185 gaa gtg aaa aag gac ctg atc atc aag ctg cct aag tac tcc ctg     3609
Glu Val Lys Lys Asp Leu Ile Ile Lys Leu Pro Lys Tyr Ser Leu
    1190                1195                1200 ttc gag ctg gaa aac ggc cgg aag aga atg ctg gcc tct gcc ggc     3654
Phe Glu Leu Glu Asn Gly Arg Lys Arg Met Leu Ala Ser Ala Gly
    1205                1210                1215 gaa ctg cag aag gga aac gaa ctg gcc ctg ccc tcc aaa tat gtg     3699
Glu Leu Gln Lys Gly Asn Glu Leu Ala Leu Pro Ser Lys Tyr Val
    1220                1225                1230 aac ttc ctg tac ctg gcc agc cac tat gag aag ctg aag ggc tcc     3744
Asn Phe Leu Tyr Leu Ala Ser His Tyr Glu Lys Leu Lys Gly Ser
    1235                1240                1245 ccc gag gat aat gag cag aaa cag ctg ttt gtg gaa cag cac aag     3789
Pro Glu Asp Asn Glu Gln Lys Gln Leu Phe Val Glu Gln His Lys
    1250                1255                1260 cac tac ctg gac gag atc atc gag cag atc agc gag ttc tcc aag     3834
His Tyr Leu Asp Glu Ile Ile Glu Gln Ile Ser Glu Phe Ser Lys
    1265                1270                1275 aga gtg atc ctg gcc gac gct aat ctg gac aaa gtg ctg tcc gcc     3879
Arg Val Ile Leu Ala Asp Ala Asn Leu Asp Lys Val Leu Ser Ala
    1280                1285                1290 tac aac aag cac cgg gat aag ccc atc aga gag cag gcc gag aat     3924
Tyr Asn Lys His Arg Asp Lys Pro Ile Arg Glu Gln Ala Glu Asn
    1295                1300                1305 atc atc cac ctg ttt acc ctg acc aat ctg gga gcc cct gcc gcc     3969
Ile Ile His Leu Phe Thr Leu Thr Asn Leu Gly Ala Pro Ala Ala
    1310                1315                1320 ttc aag tac ttt gac acc acc atc gac cgg aag gcc tac acc agc     4014
Phe Lys Tyr Phe Asp Thr Thr Ile Asp Arg Lys Ala Tyr Thr Ser
    1325                1330                1335 acc aaa gag gtg ctg gac gcc acc ctg atc cac cag agc atc acc     4059
Thr Lys Glu Val Leu Asp Ala Thr Leu Ile His Gln Ser Ile Thr
```

-continued

```
         1340                1345                1350
ggc ctg  tac  gag  aca  cgg  atc  gac  ctg  tct  cag  ctg  gga  ggc gac         4104
Gly Leu  Tyr  Glu  Thr  Arg  Ile  Asp  Leu  Ser  Gln  Leu  Gly  Gly Asp
         1355                1360                1365 taa                                                                              4107

<210> SEQ ID NO 4
<211> LENGTH: 4107
<212> TYPE: DNA
<213> ORGANISM: Streptococcus pyogenes
<220> FEATURE:
<221> NAME/KEY: CDS
<222> LOCATION: (1)..(4107)

<400> SEQUENCE: 4 atg gac aag aag tac agc atc ggc ctg gac atc ggc acc aac tct gtg          48
Met Asp Lys Lys Tyr Ser Ile Gly Leu Asp Ile Gly Thr Asn Ser Val
1               5                   10                  15 ggc tgg gcc gtg atc acc gac gag tac aag gtg ccc agc aag aaa ttc          96
Gly Trp Ala Val Ile Thr Asp Glu Tyr Lys Val Pro Ser Lys Lys Phe
                20                  25                  30 aag gtg ctg ggc aac acc gac cgg cac agc atc aag aag aac ctg atc         144
Lys Val Leu Gly Asn Thr Asp Arg His Ser Ile Lys Lys Asn Leu Ile
            35                  40                  45 gga gcc ctg ctg ttc gac agc ggc gaa aca gcc gag gcc acc cgg ctg         192
Gly Ala Leu Leu Phe Asp Ser Gly Glu Thr Ala Glu Ala Thr Arg Leu
        50                  55                  60 aag aga acc gcc aga aga aga tac acc aga cgg aag aac cgg atc tgc         240
Lys Arg Thr Ala Arg Arg Arg Tyr Thr Arg Arg Lys Asn Arg Ile Cys
65                  70                  75                  80 tat ctg caa gag atc ttc agc aac gag atg gcc aag gtg gac gac agc         288
Tyr Leu Gln Glu Ile Phe Ser Asn Glu Met Ala Lys Val Asp Asp Ser
                85                  90                  95 ttc ttc cac aga ctg gaa gag tcc ttc ctg gtg gaa gag gat aag aag         336
Phe Phe His Arg Leu Glu Glu Ser Phe Leu Val Glu Glu Asp Lys Lys
                100                 105                 110 cac gag cgg cac ccc atc ttc ggc aac atc gtg gac gag gtg gcc tac         384
His Glu Arg His Pro Ile Phe Gly Asn Ile Val Asp Glu Val Ala Tyr
            115                 120                 125 cac gag aag tac ccc acc atc tac cac ctg aga aag aaa ctg gtg gac         432
His Glu Lys Tyr Pro Thr Ile Tyr His Leu Arg Lys Lys Leu Val Asp
        130                 135                 140 agc acc gac aag gcc gac ctg cgg ctg atc tat ctg gcc ctg gcc cac         480
Ser Thr Asp Lys Ala Asp Leu Arg Leu Ile Tyr Leu Ala Leu Ala His
145                 150                 155                 160 atg atc aag ttc cgg ggc cac ttc ctg atc gag ggc gac ctg aac ccc         528
Met Ile Lys Phe Arg Gly His Phe Leu Ile Glu Gly Asp Leu Asn Pro
                165                 170                 175 gac aac agc gac gtg gac aag ctg ttc atc cag ctg gtg cag acc tac         576
Asp Asn Ser Asp Val Asp Lys Leu Phe Ile Gln Leu Val Gln Thr Tyr
            180                 185                 190 aac cag ctg ttc gag gaa aac ccc atc aac gcc agc ggc gtg gac gcc         624
Asn Gln Leu Phe Glu Glu Asn Pro Ile Asn Ala Ser Gly Val Asp Ala
        195                 200                 205 aag gcc atc ctg tct gcc aga ctg agc aag agc aga cgg ctg gaa aat         672
Lys Ala Ile Leu Ser Ala Arg Leu Ser Lys Ser Arg Arg Leu Glu Asn
        210                 215                 220 ctg atc gcc cag ctg ccc ggc gag aag aag aat ggc ctg ttc ggc aac         720
Leu Ile Ala Gln Leu Pro Gly Glu Lys Lys Asn Gly Leu Phe Gly Asn
225                 230                 235                 240
```

```
ctg att gcc ctg agc ctg ggc ctg acc ccc aac ttc aag agc aac ttc      768
Leu Ile Ala Leu Ser Leu Gly Leu Thr Pro Asn Phe Lys Ser Asn Phe
            245                 250                 255 gac ctg gcc gag gat gcc aaa ctg cag ctg agc aag gac acc tac gac      816
Asp Leu Ala Glu Asp Ala Lys Leu Gln Leu Ser Lys Asp Thr Tyr Asp
            260                 265                 270 gac gac ctg gac aac ctg ctg gcc cag atc ggc gac cag tac gcc gac      864
Asp Asp Leu Asp Asn Leu Leu Ala Gln Ile Gly Asp Gln Tyr Ala Asp
            275                 280                 285 ctg ttt ctg gcc gcc aag aac ctg tcc gac gcc atc ctg ctg agc gac      912
Leu Phe Leu Ala Ala Lys Asn Leu Ser Asp Ala Ile Leu Leu Ser Asp
            290                 295                 300 atc ctg aga gtg aac acc gag atc acc aag gcc ccc ctg agc gcc tct      960
Ile Leu Arg Val Asn Thr Glu Ile Thr Lys Ala Pro Leu Ser Ala Ser
305             310                 315                 320 atg atc aag aga tac gac gag cac cac cag gac ctg acc ctg ctg aaa     1008
Met Ile Lys Arg Tyr Asp Glu His His Gln Asp Leu Thr Leu Leu Lys
            325                 330                 335 gct ctc gtg cgg cag cag ctg cct gag aag tac aaa gag att ttc ttc     1056
Ala Leu Val Arg Gln Gln Leu Pro Glu Lys Tyr Lys Glu Ile Phe Phe
            340                 345                 350 gac cag agc aag aac ggc tac gcc ggc tac att gac ggc gga gcc agc     1104
Asp Gln Ser Lys Asn Gly Tyr Ala Gly Tyr Ile Asp Gly Gly Ala Ser
            355                 360                 365 cag gaa gag ttc tac aag ttc atc aag ccc atc ctg gaa aag atg gac     1152
Gln Glu Glu Phe Tyr Lys Phe Ile Lys Pro Ile Leu Glu Lys Met Asp
            370                 375                 380 ggc acc gag gaa ctg ctc gtg aag ctg aac aga gag gac ctg ctg cgg     1200
Gly Thr Glu Glu Leu Leu Val Lys Leu Asn Arg Glu Asp Leu Leu Arg
385                 390                 395                 400 aag cag cgg acc ttc gac aac ggc agc atc ccc cac cag atc cac ctg     1248
Lys Gln Arg Thr Phe Asp Asn Gly Ser Ile Pro His Gln Ile His Leu
                405                 410                 415 gga gag ctg cac gcc att ctg cgg cgg cag gaa gat ttt tac cca ttc     1296
Gly Glu Leu His Ala Ile Leu Arg Arg Gln Glu Asp Phe Tyr Pro Phe
            420                 425                 430 ctg aag gac aac cgg gaa aag atc gag aag atc ctg acc ttc cgc atc     1344
Leu Lys Asp Asn Arg Glu Lys Ile Glu Lys Ile Leu Thr Phe Arg Ile
            435                 440                 445 ccc tac tac gtg ggc cct ctg gcc agg gga aac agc aga ttc gcc tgg     1392
Pro Tyr Tyr Val Gly Pro Leu Ala Arg Gly Asn Ser Arg Phe Ala Trp
            450                 455                 460 atg acc aga aag agc gag gaa acc atc acc ccc tgg aac ttc gag gaa     1440
Met Thr Arg Lys Ser Glu Glu Thr Ile Thr Pro Trp Asn Phe Glu Glu
465                 470                 475                 480 gtg gtg gac aag ggc gct tcc gcc cag agc ttc atc gag cgg atg acc     1488
Val Val Asp Lys Gly Ala Ser Ala Gln Ser Phe Ile Glu Arg Met Thr
                485                 490                 495 aac ttc gat aag aac ctg ccc aac gag aag gtg ctg ccc aag cac agc     1536
Asn Phe Asp Lys Asn Leu Pro Asn Glu Lys Val Leu Pro Lys His Ser
            500                 505                 510 ctg ctg tac gag tac ttc acc gtg tat aac gag ctg acc aaa gtg aaa     1584
Leu Leu Tyr Glu Tyr Phe Thr Val Tyr Asn Glu Leu Thr Lys Val Lys
            515                 520                 525 tac gtg acc gag gga atg aga aag ccc gcc ttc ctg agc ggc gag cag     1632
Tyr Val Thr Glu Gly Met Arg Lys Pro Ala Phe Leu Ser Gly Glu Gln
530                 535                 540 aaa aag gcc atc gtg gac ctg ctg ttc aag acc aac cgg aaa gtg acc     1680
Lys Lys Ala Ile Val Asp Leu Leu Phe Lys Thr Asn Arg Lys Val Thr
545                 550                 555                 560
```

-continued

```
gtg aag cag ctg aaa gag gac tac ttc aag aaa atc gag tgc ttc gac      1728
Val Lys Gln Leu Lys Glu Asp Tyr Phe Lys Lys Ile Glu Cys Phe Asp
            565                 570                 575 tcc gtg gaa atc tcc ggc gtg gaa gat cgg ttc aac gcc tcc ctg ggc      1776
Ser Val Glu Ile Ser Gly Val Glu Asp Arg Phe Asn Ala Ser Leu Gly
        580                 585                 590 aca tac cac gat ctg ctg aaa att atc aag gac aag gac ttc ctg gac      1824
Thr Tyr His Asp Leu Leu Lys Ile Ile Lys Asp Lys Asp Phe Leu Asp
    595                 600                 605 aat gag gaa aac gag gac att ctg gaa gat atc gtg ctg acc ctg aca      1872
Asn Glu Glu Asn Glu Asp Ile Leu Glu Asp Ile Val Leu Thr Leu Thr
610                 615                 620 ctg ttt gag gac aga gag atg atc gag gaa cgg ctg aaa acc tat gcc      1920
Leu Phe Glu Asp Arg Glu Met Ile Glu Glu Arg Leu Lys Thr Tyr Ala
625                 630                 635                 640 cac ctg ttc gac gac aaa gtg atg aag cag ctg aag cgg cgg aga tac      1968
His Leu Phe Asp Asp Lys Val Met Lys Gln Leu Lys Arg Arg Arg Tyr
                645                 650                 655 acc ggc tgg ggc agg ctg agc cgg aag ctg atc aac ggc atc cgg gac      2016
Thr Gly Trp Gly Arg Leu Ser Arg Lys Leu Ile Asn Gly Ile Arg Asp
            660                 665                 670 aag cag tcc ggc aag aca atc ctg gat ttc ctg aag tcc gac ggc ttc      2064
Lys Gln Ser Gly Lys Thr Ile Leu Asp Phe Leu Lys Ser Asp Gly Phe
        675                 680                 685 gcc aac aga aac ttc atg cag ctg atc cac gac gac agc ctg acc ttt      2112
Ala Asn Arg Asn Phe Met Gln Leu Ile His Asp Asp Ser Leu Thr Phe
    690                 695                 700 aaa gag gac atc cag aaa gcc cag gtg tcc ggc cag ggc gat agc ctg      2160
Lys Glu Asp Ile Gln Lys Ala Gln Val Ser Gly Gln Gly Asp Ser Leu
705                 710                 715                 720 cac gag cac att gcc aat ctg gcc ggc agc ccc gcc att aag aag ggc      2208
His Glu His Ile Ala Asn Leu Ala Gly Ser Pro Ala Ile Lys Lys Gly
                725                 730                 735 atc ctg cag aca gtg aag gtg gtg gac gag ctc gtg aaa gtg atg ggc      2256
Ile Leu Gln Thr Val Lys Val Val Asp Glu Leu Val Lys Val Met Gly
            740                 745                 750 cgg cac aag ccc gag aac atc gtg atc gaa atg gcc aga gag aac cag      2304
Arg His Lys Pro Glu Asn Ile Val Ile Glu Met Ala Arg Glu Asn Gln
        755                 760                 765 acc acc cag aag gga cag aag aac agc cgc gag aga atg aag cgg atc      2352
Thr Thr Gln Lys Gly Gln Lys Asn Ser Arg Glu Arg Met Lys Arg Ile
    770                 775                 780 gaa gag ggc atc aaa gag ctg ggc agc cag atc ctg aaa gaa cac ccc      2400
Glu Glu Gly Ile Lys Glu Leu Gly Ser Gln Ile Leu Lys Glu His Pro
785                 790                 795                 800 gtg gaa aac acc cag ctg cag aac gag aag ctg tac ctg tac tac ctg      2448
Val Glu Asn Thr Gln Leu Gln Asn Glu Lys Leu Tyr Leu Tyr Tyr Leu
                805                 810                 815 cag aat ggg cgg gat atg tac gtg gac cag gaa ctg gac atc aac cgg      2496
Gln Asn Gly Arg Asp Met Tyr Val Asp Gln Glu Leu Asp Ile Asn Arg
            820                 825                 830 ctg tcc gac tac gat gtg gac cat atc gtg cct cag agc ttt ctg aag      2544
Leu Ser Asp Tyr Asp Val Asp His Ile Val Pro Gln Ser Phe Leu Lys
        835                 840                 845 gac gac tcc atc gac aac aag gtg ctg acc aga agc gac aag aac cgg      2592
Asp Asp Ser Ile Asp Asn Lys Val Leu Thr Arg Ser Asp Lys Asn Arg
    850                 855                 860 ggc aag agc gac aac gtg ccc tcc gaa gag gtc gtg aag aag atg aag      2640
Gly Lys Ser Asp Asn Val Pro Ser Glu Glu Val Val Lys Lys Met Lys
```

```
                865                 870                 875                 880
aac tac tgg cgg cag ctg ctg aac gcc aag ctg att acc cag aga aag       2688
Asn Tyr Trp Arg Gln Leu Leu Asn Ala Lys Leu Ile Thr Gln Arg Lys
                    885                 890                 895 ttc gac aat ctg acc aag gcc gag aga ggc ggc ctg agc gaa ctg gat       2736
Phe Asp Asn Leu Thr Lys Ala Glu Arg Gly Gly Leu Ser Glu Leu Asp
            900                 905                 910 aag gcc ggc ttc atc aag aga cag ctg gtg gaa acc cgg cag atc aca       2784
Lys Ala Gly Phe Ile Lys Arg Gln Leu Val Glu Thr Arg Gln Ile Thr
        915                 920                 925 aag cac gtg gca cag atc ctg gac tcc cgg atg aac act aag tac gac       2832
Lys His Val Ala Gln Ile Leu Asp Ser Arg Met Asn Thr Lys Tyr Asp
    930                 935                 940 gag aat gac aag ctg atc cgg gaa gtg aaa gtg atc acc ctg aag tcc       2880
Glu Asn Asp Lys Leu Ile Arg Glu Val Lys Val Ile Thr Leu Lys Ser
945                 950                 955                 960 aag ctg gtg tcc gat ttc cgg aag gat ttc cag ttt tac aaa gtg cgc       2928
Lys Leu Val Ser Asp Phe Arg Lys Asp Phe Gln Phe Tyr Lys Val Arg
                965                 970                 975 gag atc aac aac tac cac cac gcc cac gac gcc tac ctg aac gcc gtc       2976
Glu Ile Asn Asn Tyr His His Ala His Asp Ala Tyr Leu Asn Ala Val
            980                 985                 990 gtg gga acc gcc ctg atc aaa aag tac cct aag ctg gaa agc gag ttc       3024
Val Gly Thr Ala Leu Ile Lys Lys Tyr Pro Lys Leu Glu Ser Glu Phe
        995                 1000                1005 gtg tac ggc gac tac aag gtg tac gac gtg cgg aag atg atc gcc          3069
Val Tyr Gly Asp Tyr Lys Val Tyr Asp Val Arg Lys Met Ile Ala
    1010                1015                1020 aag agc gag cag gaa atc ggc aag gct acc gcc aag tac ttc ttc          3114
Lys Ser Glu Gln Glu Ile Gly Lys Ala Thr Ala Lys Tyr Phe Phe
    1025                1030                1035 tac agc aac atc atg aac ttt ttc aag acc gag att acc ctg gcc          3159
Tyr Ser Asn Ile Met Asn Phe Phe Lys Thr Glu Ile Thr Leu Ala
    1040                1045                1050 aac ggc gag atc cgg aag cgg cct ctg atc gag aca aac ggc gaa          3204
Asn Gly Glu Ile Arg Lys Arg Pro Leu Ile Glu Thr Asn Gly Glu
    1055                1060                1065 acc ggg gag atc gtg tgg gat aag ggc cgg gat ttt gcc acc gtg          3249
Thr Gly Glu Ile Val Trp Asp Lys Gly Arg Asp Phe Ala Thr Val
    1070                1075                1080 cgg aaa gtg ctg agc atg ccc caa gtg aat atc gtg aaa aag acc          3294
Arg Lys Val Leu Ser Met Pro Gln Val Asn Ile Val Lys Lys Thr
    1085                1090                1095 gag gtg cag aca ggc ggc ttc agc aaa gag tct atc ctg ccc aag          3339
Glu Val Gln Thr Gly Gly Phe Ser Lys Glu Ser Ile Leu Pro Lys
    1100                1105                1110 agg aac agc gat aag ctg atc gcc aga aag aag gac tgg gac cct          3384
Arg Asn Ser Asp Lys Leu Ile Ala Arg Lys Lys Asp Trp Asp Pro
    1115                1120                1125 aag aag tac ggc ggc ttc gac agc ccc acc gtg gcc tat tct gtg          3429
Lys Lys Tyr Gly Gly Phe Asp Ser Pro Thr Val Ala Tyr Ser Val
    1130                1135                1140 ctg gtg gtg gcc aaa gtg gaa aag ggc aag tcc aag aaa ctg aag          3474
Leu Val Val Ala Lys Val Glu Lys Gly Lys Ser Lys Lys Leu Lys
    1145                1150                1155 agt gtg aaa gag ctg ctg ggg atc acc atc atg gaa aga agc agc          3519
Ser Val Lys Glu Leu Leu Gly Ile Thr Ile Met Glu Arg Ser Ser
    1160                1165                1170 ttc gag aag aat ccc atc gac ttt ctg gaa gcc aag ggc tac aaa          3564
```

|  |  |
|---|---:|
| Phe Glu Lys Asn Pro Ile Asp Phe Leu Glu Ala Lys Gly Tyr Lys<br>    1175                             1180                         1185 |  |
| gaa gtg aaa aag gac ctg atc atc aag ctg cct aag tac tcc ctg<br>Glu Val Lys Lys Asp Leu Ile Ile Lys Leu Pro Lys Tyr Ser Leu<br>    1190                           1195                       1200 | 3609 |
| ttc gag ctg gaa aac ggc cgg aag aga atg ctg gcc tct gcc cgg<br>Phe Glu Leu Glu Asn Gly Arg Lys Arg Met Leu Ala Ser Ala Arg<br>    1205                         1210                       1215 | 3654 |
| gaa ctg cag aag gga aac gaa ctg gcc ctg ccc tcc aaa tat gtg<br>Glu Leu Gln Lys Gly Asn Glu Leu Ala Leu Pro Ser Lys Tyr Val<br>    1220                       1225                       1230 | 3699 |
| aac ttc ctg tac ctg gcc agc cac tat gag aag ctg aag ggc tcc<br>Asn Phe Leu Tyr Leu Ala Ser His Tyr Glu Lys Leu Lys Gly Ser<br>    1235                       1240                       1245 | 3744 |
| ccc gag gat aat gag cag aaa cag ctg ttt gtg gaa cag cac aag<br>Pro Glu Asp Asn Glu Gln Lys Gln Leu Phe Val Glu Gln His Lys<br>    1250                       1255                       1260 | 3789 |
| cac tac ctg gac gag atc atc gag cag atc agc gag ttc tcc aag<br>His Tyr Leu Asp Glu Ile Ile Glu Gln Ile Ser Glu Phe Ser Lys<br>    1265                       1270                       1275 | 3834 |
| aga gtg atc ctg gcc gac gct aat ctg gac aaa gtg ctg tcc gcc<br>Arg Val Ile Leu Ala Asp Ala Asn Leu Asp Lys Val Leu Ser Ala<br>    1280                       1285                       1290 | 3879 |
| tac aac aag cac cgg gat aag ccc atc aga gag cag gcc gag aat<br>Tyr Asn Lys His Arg Asp Lys Pro Ile Arg Glu Gln Ala Glu Asn<br>    1295                       1300                       1305 | 3924 |
| atc atc cac ctg ttt acc ctg acc aat ctg gga gcc cct gcc gcc<br>Ile Ile His Leu Phe Thr Leu Thr Asn Leu Gly Ala Pro Ala Ala<br>    1310                       1315                       1320 | 3969 |
| ttc aag tac ttt gac acc acc atc gac cgg aag gcc tac acc agc<br>Phe Lys Tyr Phe Asp Thr Thr Ile Asp Arg Lys Ala Tyr Thr Ser<br>    1325                       1330                       1335 | 4014 |
| acc aaa gag gtg ctg gac gcc acc ctg atc cac cag agc atc acc<br>Thr Lys Glu Val Leu Asp Ala Thr Leu Ile His Gln Ser Ile Thr<br>    1340                       1345                       1350 | 4059 |
| ggc ctg tac gag aca cgg atc gac ctg tct cag ctg gga ggc gac<br>Gly Leu Tyr Glu Thr Arg Ile Asp Leu Ser Gln Leu Gly Gly Asp<br>    1355                       1360                       1365 | 4104 |
| taa | 4107 |

```
<210> SEQ ID NO 5
<211> LENGTH: 4107
<212> TYPE: DNA
<213> ORGANISM: Streptococcus pyogenes
<220> FEATURE:
<221> NAME/KEY: CDS
<222> LOCATION: (1)..(4107)

<400> SEQUENCE: 5
```

|  |  |
|---|---:|
| atg gac aag aag tac agc atc ggc ctg gac atc ggc acc aac tct gtg<br>Met Asp Lys Lys Tyr Ser Ile Gly Leu Asp Ile Gly Thr Asn Ser Val<br>1                 5                      10                      15 | 48 |
| ggc tgg gcc gtg atc acc gac gag tac aag gtg ccc agc aag aaa ttc<br>Gly Trp Ala Val Ile Thr Asp Glu Tyr Lys Val Pro Ser Lys Lys Phe<br>                 20                      25                      30 | 96 |
| aag gtg ctg ggc aac acc gac cgg cac agc atc aag aag aac ctg atc<br>Lys Val Leu Gly Asn Thr Asp Arg His Ser Ile Lys Lys Asn Leu Ile<br>        35                      40                      45 | 144 |
| gga gcc ctg ctg ttc gac agc ggc gaa aca gcc gag gcc acc cgg ctg<br>Gly Ala Leu Leu Phe Asp Ser Gly Glu Thr Ala Glu Ala Thr Arg Leu<br>   50                      55                      60 | 192 |

| | | | | | | | | | | | | | | | | |
|---|---|---|---|---|---|---|---|---|---|---|---|---|---|---|---|---|
| aag | aga | acc | gcc | aga | aga | aga | tac | acc | aga | cgg | aag | aac | cgg | atc | tgc | 240 |
| Lys | Arg | Thr | Ala | Arg | Arg | Arg | Tyr | Thr | Arg | Arg | Lys | Asn | Arg | Ile | Cys | |
| 65 | | | | 70 | | | | 75 | | | | 80 | | | | |

| tat | ctg | caa | gag | atc | ttc | agc | aac | gag | atg | gcc | aag | gtg | gac | gac | agc | 288 |
| Tyr | Leu | Gln | Glu | Ile | Phe | Ser | Asn | Glu | Met | Ala | Lys | Val | Asp | Asp | Ser | |
| | | | | 85 | | | | | 90 | | | | | 95 | | |

| ttc | ttc | cac | aga | ctg | gaa | gag | tcc | ttc | ctg | gtg | gaa | gag | gat | aag | aag | 336 |
| Phe | Phe | His | Arg | Leu | Glu | Glu | Ser | Phe | Leu | Val | Glu | Glu | Asp | Lys | Lys | |
| | | | 100 | | | | | 105 | | | | | 110 | | | |

| cac | gag | cgg | cac | ccc | atc | ttc | ggc | aac | atc | gtg | gac | gag | gtg | gcc | tac | 384 |
| His | Glu | Arg | His | Pro | Ile | Phe | Gly | Asn | Ile | Val | Asp | Glu | Val | Ala | Tyr | |
| | | 115 | | | | | 120 | | | | | 125 | | | | |

| cac | gag | aag | tac | ccc | acc | atc | tac | cac | ctg | aga | aag | aaa | ctg | gtg | gac | 432 |
| His | Glu | Lys | Tyr | Pro | Thr | Ile | Tyr | His | Leu | Arg | Lys | Lys | Leu | Val | Asp | |
| | 130 | | | | | 135 | | | | | 140 | | | | | |

| agc | acc | gac | aag | gcc | gac | ctg | cgg | ctg | atc | tat | ctg | gcc | ctg | gcc | cac | 480 |
| Ser | Thr | Asp | Lys | Ala | Asp | Leu | Arg | Leu | Ile | Tyr | Leu | Ala | Leu | Ala | His | |
| 145 | | | | 150 | | | | | 155 | | | | | 160 | | |

| atg | atc | aag | ttc | cgg | ggc | cac | ttc | ctg | atc | gag | ggc | gac | ctg | aac | ccc | 528 |
| Met | Ile | Lys | Phe | Arg | Gly | His | Phe | Leu | Ile | Glu | Gly | Asp | Leu | Asn | Pro | |
| | | | | 165 | | | | | 170 | | | | | 175 | | |

| gac | aac | agc | gac | gtg | gac | aag | ctg | ttc | atc | cag | ctg | gtg | cag | acc | tac | 576 |
| Asp | Asn | Ser | Asp | Val | Asp | Lys | Leu | Phe | Ile | Gln | Leu | Val | Gln | Thr | Tyr | |
| | | | 180 | | | | | 185 | | | | | 190 | | | |

| aac | cag | ctg | ttc | gag | gaa | aac | ccc | atc | aac | gcc | agc | ggc | gtg | gac | gcc | 624 |
| Asn | Gln | Leu | Phe | Glu | Glu | Asn | Pro | Ile | Asn | Ala | Ser | Gly | Val | Asp | Ala | |
| | | 195 | | | | | 200 | | | | | 205 | | | | |

| aag | gcc | atc | ctg | tct | gcc | aga | ctg | agc | aag | agc | aga | cgg | ctg | gaa | aat | 672 |
| Lys | Ala | Ile | Leu | Ser | Ala | Arg | Leu | Ser | Lys | Ser | Arg | Arg | Leu | Glu | Asn | |
| | 210 | | | | | 215 | | | | | 220 | | | | | |

| ctg | atc | gcc | cag | ctg | ccc | ggc | gag | aag | aag | aat | ggc | ctg | ttc | ggc | aac | 720 |
| Leu | Ile | Ala | Gln | Leu | Pro | Gly | Glu | Lys | Lys | Asn | Gly | Leu | Phe | Gly | Asn | |
| 225 | | | | 230 | | | | | 235 | | | | | 240 | | |

| ctg | att | gcc | ctg | agc | ctg | ggc | ctg | acc | ccc | aac | ttc | aag | agc | aac | ttc | 768 |
| Leu | Ile | Ala | Leu | Ser | Leu | Gly | Leu | Thr | Pro | Asn | Phe | Lys | Ser | Asn | Phe | |
| | | | | 245 | | | | | 250 | | | | | 255 | | |

| gac | ctg | gcc | gag | gat | gcc | aaa | ctg | cag | ctg | agc | aag | gac | acc | tac | gac | 816 |
| Asp | Leu | Ala | Glu | Asp | Ala | Lys | Leu | Gln | Leu | Ser | Lys | Asp | Thr | Tyr | Asp | |
| | | | 260 | | | | | 265 | | | | | 270 | | | |

| gac | gac | ctg | gac | aac | ctg | ctg | gcc | cag | atc | ggc | gac | cag | tac | gcc | gac | 864 |
| Asp | Asp | Leu | Asp | Asn | Leu | Leu | Ala | Gln | Ile | Gly | Asp | Gln | Tyr | Ala | Asp | |
| | | 275 | | | | | 280 | | | | | 285 | | | | |

| ctg | ttt | ctg | gcc | gcc | aag | aac | ctg | tcc | gac | gcc | atc | ctg | ctg | agc | gac | 912 |
| Leu | Phe | Leu | Ala | Ala | Lys | Asn | Leu | Ser | Asp | Ala | Ile | Leu | Leu | Ser | Asp | |
| | 290 | | | | | 295 | | | | | 300 | | | | | |

| atc | ctg | aga | gtg | aac | acc | gag | atc | acc | aag | gcc | ccc | ctg | agc | gcc | tct | 960 |
| Ile | Leu | Arg | Val | Asn | Thr | Glu | Ile | Thr | Lys | Ala | Pro | Leu | Ser | Ala | Ser | |
| 305 | | | | 310 | | | | | 315 | | | | | 320 | | |

| atg | atc | aag | aga | tac | gac | gag | cac | cac | cag | gac | ctg | acc | ctg | ctg | aaa | 1008 |
| Met | Ile | Lys | Arg | Tyr | Asp | Glu | His | His | Gln | Asp | Leu | Thr | Leu | Leu | Lys | |
| | | | | 325 | | | | | 330 | | | | | 335 | | |

| gct | ctc | gtg | cgg | cag | cag | ctg | cct | gag | aag | tac | aaa | gag | att | ttc | ttc | 1056 |
| Ala | Leu | Val | Arg | Gln | Gln | Leu | Pro | Glu | Lys | Tyr | Lys | Glu | Ile | Phe | Phe | |
| | | | 340 | | | | | 345 | | | | | 350 | | | |

| gac | cag | agc | aag | aac | ggc | tac | gcc | ggc | tac | att | gac | ggc | gga | gcc | agc | 1104 |
| Asp | Gln | Ser | Lys | Asn | Gly | Tyr | Ala | Gly | Tyr | Ile | Asp | Gly | Gly | Ala | Ser | |
| | | 355 | | | | | 360 | | | | | 365 | | | | |

| cag | gaa | gag | ttc | tac | aag | ttc | atc | aag | ccc | atc | ctg | gaa | aag | atg | gac | 1152 |
| Gln | Glu | Glu | Phe | Tyr | Lys | Phe | Ile | Lys | Pro | Ile | Leu | Glu | Lys | Met | Asp | |

```
                370             375             380
ggc acc gag gaa ctg ctc gtg aag ctg aac aga gag gac ctg ctg cgg    1200
Gly Thr Glu Glu Leu Leu Val Lys Leu Asn Arg Glu Asp Leu Leu Arg
385                 390                 395                 400 aag cag cgg acc ttc gac aac ggc agc atc ccc cac cag atc cac ctg    1248
Lys Gln Arg Thr Phe Asp Asn Gly Ser Ile Pro His Gln Ile His Leu
                405                 410                 415 gga gag ctg cac gcc att ctg cgg cgg cag gaa gat ttt tac cca ttc    1296
Gly Glu Leu His Ala Ile Leu Arg Arg Gln Glu Asp Phe Tyr Pro Phe
            420                 425                 430 ctg aag gac aac cgg gaa aag atc gag aag atc ctg acc ttc cgc atc    1344
Leu Lys Asp Asn Arg Glu Lys Ile Glu Lys Ile Leu Thr Phe Arg Ile
                435                 440                 445 ccc tac tac gtg ggc cct ctg gcc agg gga aac agc aga ttc gcc tgg    1392
Pro Tyr Tyr Val Gly Pro Leu Ala Arg Gly Asn Ser Arg Phe Ala Trp
            450                 455                 460 atg acc aga aag agc gag gaa acc atc acc ccc tgg aac ttc gag gaa    1440
Met Thr Arg Lys Ser Glu Glu Thr Ile Thr Pro Trp Asn Phe Glu Glu
465                 470                 475                 480 gtg gtg gac aag ggc gct tcc gcc cag agc ttc atc gag cgg atg acc    1488
Val Val Asp Lys Gly Ala Ser Ala Gln Ser Phe Ile Glu Arg Met Thr
                485                 490                 495 aac ttc gat aag aac ctg ccc aac gag aag gtg ctg ccc aag cac agc    1536
Asn Phe Asp Lys Asn Leu Pro Asn Glu Lys Val Leu Pro Lys His Ser
            500                 505                 510 ctg ctg tac gag tac ttc acc gtg tat aac gag ctg acc aaa gtg aaa    1584
Leu Leu Tyr Glu Tyr Phe Thr Val Tyr Asn Glu Leu Thr Lys Val Lys
                515                 520                 525 tac gtg acc gag gga atg aga aag ccc gcc ttc ctg agc ggc gag cag    1632
Tyr Val Thr Glu Gly Met Arg Lys Pro Ala Phe Leu Ser Gly Glu Gln
530                 535                 540 aaa aag gcc atc gtg gac ctg ctg ttc aag acc aac cgg aaa gtg acc    1680
Lys Lys Ala Ile Val Asp Leu Leu Phe Lys Thr Asn Arg Lys Val Thr
545                 550                 555                 560 gtg aag cag ctg aaa gag gac tac ttc aag aaa atc gag tgc ttc gac    1728
Val Lys Gln Leu Lys Glu Asp Tyr Phe Lys Lys Ile Glu Cys Phe Asp
                565                 570                 575 tcc gtg gaa atc tcc ggc gtg gaa gat cgg ttc aac gcc tcc ctg ggc    1776
Ser Val Glu Ile Ser Gly Val Glu Asp Arg Phe Asn Ala Ser Leu Gly
            580                 585                 590 aca tac cac gat ctg ctg aaa att atc aag gac aag gac ttc ctg gac    1824
Thr Tyr His Asp Leu Leu Lys Ile Ile Lys Asp Lys Asp Phe Leu Asp
                595                 600                 605 aat gag gaa aac gag gac att ctg gaa gat atc gtg ctg acc ctg aca    1872
Asn Glu Glu Asn Glu Asp Ile Leu Glu Asp Ile Val Leu Thr Leu Thr
            610                 615                 620 ctg ttt gag gac aga gag atg atc gag gaa cgg ctg aaa acc tat gcc    1920
Leu Phe Glu Asp Arg Glu Met Ile Glu Glu Arg Leu Lys Thr Tyr Ala
625                 630                 635                 640 cac ctg ttc gac gac aaa gtg atg aag cag ctg aag cgg cgg aga tac    1968
His Leu Phe Asp Asp Lys Val Met Lys Gln Leu Lys Arg Arg Arg Tyr
                645                 650                 655 acc ggc tgg ggc agg ctg agc cgg aag ctg atc aac ggc atc cgg gac    2016
Thr Gly Trp Gly Arg Leu Ser Arg Lys Leu Ile Asn Gly Ile Arg Asp
            660                 665                 670 aag cag tcc ggc aag aca atc ctg gat ttc ctg aag tcc gac ggc ttc    2064
Lys Gln Ser Gly Lys Thr Ile Leu Asp Phe Leu Lys Ser Asp Gly Phe
                675                 680                 685 gcc aac aga aac ttc atg cag ctg atc cac gac gac agc ctg acc ttt    2112
```

```
                Ala Asn Arg Asn Phe Met Gln Leu Ile His Asp Asp Ser Leu Thr Phe
                    690             695             700 aaa gag gac atc cag aaa gcc cag gtg tcc ggc cag ggc gat agc ctg            2160
Lys Glu Asp Ile Gln Lys Ala Gln Val Ser Gly Gln Gly Asp Ser Leu
705             710             715             720 cac gag cac att gcc aat ctg gcc ggc agc ccc gcc att aag aag ggc            2208
His Glu His Ile Ala Asn Leu Ala Gly Ser Pro Ala Ile Lys Lys Gly
                725             730             735 atc ctg cag aca gtg aag gtg gtg gac gag ctc gtg aaa gtg atg ggc            2256
Ile Leu Gln Thr Val Lys Val Val Asp Glu Leu Val Lys Val Met Gly
            740             745             750 cgg cac aag ccc gag aac atc gtg atc gaa atg gcc aga gag aac cag            2304
Arg His Lys Pro Glu Asn Ile Val Ile Glu Met Ala Arg Glu Asn Gln
        755             760             765 acc acc cag aag gga cag aag aac agc cgc gag aga atg aag cgg atc            2352
Thr Thr Gln Lys Gly Gln Lys Asn Ser Arg Glu Arg Met Lys Arg Ile
770             775             780 gaa gag ggc atc aaa gag ctg ggc agc cag atc ctg aaa gaa cac ccc            2400
Glu Glu Gly Ile Lys Glu Leu Gly Ser Gln Ile Leu Lys Glu His Pro
785             790             795             800 gtg gaa aac acc cag ctg cag aac gag aag ctg tac ctg tac tac ctg            2448
Val Glu Asn Thr Gln Leu Gln Asn Glu Lys Leu Tyr Leu Tyr Tyr Leu
                805             810             815 cag aat ggg cgg gat atg tac gtg gac cag gaa ctg gac atc aac cgg            2496
Gln Asn Gly Arg Asp Met Tyr Val Asp Gln Glu Leu Asp Ile Asn Arg
            820             825             830 ctg tcc gac tac gat gtg gac cat atc gtg cct cag agc ttt ctg aag            2544
Leu Ser Asp Tyr Asp Val Asp His Ile Val Pro Gln Ser Phe Leu Lys
        835             840             845 gac gac tcc atc gac aac aag gtg ctg acc aga agc gac aag aac cgg            2592
Asp Asp Ser Ile Asp Asn Lys Val Leu Thr Arg Ser Asp Lys Asn Arg
850             855             860 ggc aag agc gac aac gtg ccc tcc gaa gag gtc gtg aag aag atg aag            2640
Gly Lys Ser Asp Asn Val Pro Ser Glu Glu Val Val Lys Lys Met Lys
865             870             875             880 aac tac tgg cgg cag ctg ctg aac gcc aag ctg att acc cag aga aag            2688
Asn Tyr Trp Arg Gln Leu Leu Asn Ala Lys Leu Ile Thr Gln Arg Lys
                885             890             895 ttc gac aat ctg acc aag gcc gag aga ggc ggc ctg agc gaa ctg gat            2736
Phe Asp Asn Leu Thr Lys Ala Glu Arg Gly Gly Leu Ser Glu Leu Asp
            900             905             910 aag gcc ggc ttc atc aag aga cag ctg gtg gaa acc cgg cag atc aca            2784
Lys Ala Gly Phe Ile Lys Arg Gln Leu Val Glu Thr Arg Gln Ile Thr
        915             920             925 aag cac gtg gca cag atc ctg gac tcc cgg atg aac act aag tac gac            2832
Lys His Val Ala Gln Ile Leu Asp Ser Arg Met Asn Thr Lys Tyr Asp
930             935             940 gag aat gac aag ctg atc cgg gaa gtg aaa gtg atc acc ctg aag tcc            2880
Glu Asn Asp Lys Leu Ile Arg Glu Val Lys Val Ile Thr Leu Lys Ser
945             950             955             960 aag ctg gtg tcc gat ttc cgg aag gat ttc cag ttt tac aaa gtg cgc            2928
Lys Leu Val Ser Asp Phe Arg Lys Asp Phe Gln Phe Tyr Lys Val Arg
                965             970             975 gag atc aac aac tac cac cac gcc cac gac gcc tac ctg aac gcc gtc            2976
Glu Ile Asn Asn Tyr His His Ala His Asp Ala Tyr Leu Asn Ala Val
            980             985             990 gtg gga acc gcc ctg atc aaa aag tac cct aag ctg gaa agc gag ttc            3024
Val Gly Thr Ala Leu Ile Lys Lys Tyr Pro Lys Leu Glu Ser Glu Phe
        995             1000            1005
```

|  |  |  |  |  |  |  |  |  |  |  |
|---|---|---|---|---|---|---|---|---|---|---|
| gtg | tac | ggc | gac | tac | aag | gtg | tac | gac | gtg | cgg | aag | atg | atc | gcc | 3069 |
| Val | Tyr | Gly | Asp | Tyr | Lys | Val | Tyr | Asp | Val | Arg | Lys | Met | Ile | Ala | |
| 1010 | | | | 1015 | | | | | 1020 | | | | | | |

| aag | agc | gag | cag | gaa | atc | ggc | aag | gct | acc | gcc | aag | tac | ttc | ttc | 3114 |
| Lys | Ser | Glu | Gln | Glu | Ile | Gly | Lys | Ala | Thr | Ala | Lys | Tyr | Phe | Phe | |
| 1025 | | | | | 1030 | | | | | 1035 | | | | | |

| tac | agc | aac | atc | atg | aac | ttt | ttc | aag | acc | gag | att | acc | ctg | gcc | 3159 |
| Tyr | Ser | Asn | Ile | Met | Asn | Phe | Phe | Lys | Thr | Glu | Ile | Thr | Leu | Ala | |
| 1040 | | | | | 1045 | | | | | 1050 | | | | | |

| aac | ggc | gag | atc | cgg | aag | cgg | cct | ctg | atc | gag | aca | aac | ggc | gaa | 3204 |
| Asn | Gly | Glu | Ile | Arg | Lys | Arg | Pro | Leu | Ile | Glu | Thr | Asn | Gly | Glu | |
| 1055 | | | | | 1060 | | | | | 1065 | | | | | |

| acc | ggg | gag | atc | gtg | tgg | gat | aag | ggc | cgg | gat | ttt | gcc | acc | gtg | 3249 |
| Thr | Gly | Glu | Ile | Val | Trp | Asp | Lys | Gly | Arg | Asp | Phe | Ala | Thr | Val | |
| 1070 | | | | | 1075 | | | | | 1080 | | | | | |

| cgg | aaa | gtg | ctg | agc | atg | ccc | caa | gtg | aat | atc | gtg | aaa | aag | acc | 3294 |
| Arg | Lys | Val | Leu | Ser | Met | Pro | Gln | Val | Asn | Ile | Val | Lys | Lys | Thr | |
| 1085 | | | | | 1090 | | | | | 1095 | | | | | |

| gag | gtg | cag | aca | ggc | ggc | ttc | agc | aaa | gag | tct | atc | ctg | ccc | aag | 3339 |
| Glu | Val | Gln | Thr | Gly | Gly | Phe | Ser | Lys | Glu | Ser | Ile | Leu | Pro | Lys | |
| 1100 | | | | | 1105 | | | | | 1110 | | | | | |

| agg | aac | agc | gat | aag | ctg | atc | gcc | aga | aag | aag | gac | tgg | gac | cct | 3384 |
| Arg | Asn | Ser | Asp | Lys | Leu | Ile | Ala | Arg | Lys | Lys | Asp | Trp | Asp | Pro | |
| 1115 | | | | | 1120 | | | | | 1125 | | | | | |

| aag | aag | tac | ggc | ggc | ttc | gac | agc | ccc | acc | gtg | gcc | tat | tct | gtg | 3429 |
| Lys | Lys | Tyr | Gly | Gly | Phe | Asp | Ser | Pro | Thr | Val | Ala | Tyr | Ser | Val | |
| 1130 | | | | | 1135 | | | | | 1140 | | | | | |

| ctg | gtg | gtg | gcc | aaa | gtg | gaa | aag | ggc | aag | tcc | aag | aaa | ctg | aag | 3474 |
| Leu | Val | Val | Ala | Lys | Val | Glu | Lys | Gly | Lys | Ser | Lys | Lys | Leu | Lys | |
| 1145 | | | | | 1150 | | | | | 1155 | | | | | |

| agt | gtg | aaa | gag | ctg | ctg | ggg | atc | acc | atc | atg | gaa | aga | agc | agc | 3519 |
| Ser | Val | Lys | Glu | Leu | Leu | Gly | Ile | Thr | Ile | Met | Glu | Arg | Ser | Ser | |
| 1160 | | | | | 1165 | | | | | 1170 | | | | | |

| ttc | gag | aag | aat | ccc | atc | gac | ttt | ctg | gaa | gcc | aag | ggc | tac | aaa | 3564 |
| Phe | Glu | Lys | Asn | Pro | Ile | Asp | Phe | Leu | Glu | Ala | Lys | Gly | Tyr | Lys | |
| 1175 | | | | | 1180 | | | | | 1185 | | | | | |

| gaa | gtg | aaa | aag | gac | ctg | atc | atc | aag | ctg | cct | aag | tac | tcc | ctg | 3609 |
| Glu | Val | Lys | Lys | Asp | Leu | Ile | Ile | Lys | Leu | Pro | Lys | Tyr | Ser | Leu | |
| 1190 | | | | | 1195 | | | | | 1200 | | | | | |

| ttc | gag | ctg | gaa | aac | ggc | cgg | aag | aga | atg | ctg | gcc | tct | gcc | cgg | 3654 |
| Phe | Glu | Leu | Glu | Asn | Gly | Arg | Lys | Arg | Met | Leu | Ala | Ser | Ala | Arg | |
| 1205 | | | | | 1210 | | | | | 1215 | | | | | |

| gaa | ctg | cag | aag | gga | aac | gaa | ctg | gcc | ctg | ccc | tcc | aaa | tat | gtg | 3699 |
| Glu | Leu | Gln | Lys | Gly | Asn | Glu | Leu | Ala | Leu | Pro | Ser | Lys | Tyr | Val | |
| 1220 | | | | | 1225 | | | | | 1230 | | | | | |

| aac | ttc | ctg | tac | ctg | gcc | agc | cac | tat | gag | aag | ctg | aag | ggc | tcc | 3744 |
| Asn | Phe | Leu | Tyr | Leu | Ala | Ser | His | Tyr | Glu | Lys | Leu | Lys | Gly | Ser | |
| 1235 | | | | | 1240 | | | | | 1245 | | | | | |

| ccc | gag | gat | aat | gag | cag | aaa | cag | ctg | ttt | gtg | gaa | cag | cac | aag | 3789 |
| Pro | Glu | Asp | Asn | Glu | Gln | Lys | Gln | Leu | Phe | Val | Glu | Gln | His | Lys | |
| 1250 | | | | | 1255 | | | | | 1260 | | | | | |

| cac | tac | ctg | gac | gag | atc | atc | gag | cag | atc | agc | gag | ttc | tcc | aag | 3834 |
| His | Tyr | Leu | Asp | Glu | Ile | Ile | Glu | Gln | Ile | Ser | Glu | Phe | Ser | Lys | |
| 1265 | | | | | 1270 | | | | | 1275 | | | | | |

| aga | gtg | atc | ctg | gcc | gac | gct | aat | ctg | gac | aaa | gtg | ctg | tcc | gcc | 3879 |
| Arg | Val | Ile | Leu | Ala | Asp | Ala | Asn | Leu | Asp | Lys | Val | Leu | Ser | Ala | |
| 1280 | | | | | 1285 | | | | | 1290 | | | | | |

| tac | aac | aag | cac | cgg | gat | aag | ccc | atc | aga | gag | cag | gcc | gag | aat | 3924 |
| Tyr | Asn | Lys | His | Arg | Asp | Lys | Pro | Ile | Arg | Glu | Gln | Ala | Glu | Asn | |
| 1295 | | | | | 1300 | | | | | 1305 | | | | | |

```
atc atc cac ctg ttt acc ctg acc aat ctg gga gcc cct gcc gcc      3969
Ile Ile His Leu Phe Thr Leu Thr Asn Leu Gly Ala Pro Ala Ala
        1310                1315                1320 ttc aag tac ttt gac acc acc atc gac cgg aag gcc tac cgg agc      4014
Phe Lys Tyr Phe Asp Thr Thr Ile Asp Arg Lys Ala Tyr Arg Ser
1325                1330                1335 acc aaa gag gtg ctg gac gcc acc ctg atc cac cag agc atc acc      4059
Thr Lys Glu Val Leu Asp Ala Thr Leu Ile His Gln Ser Ile Thr
    1340                1345                1350 ggc ctg tac gag aca cgg atc gac ctg tct cag ctg gga ggc gac      4104
Gly Leu Tyr Glu Thr Arg Ile Asp Leu Ser Gln Leu Gly Gly Asp
                1355                1360                1365 taa                                                              4107

<210> SEQ ID NO 6
<211> LENGTH: 4107
<212> TYPE: DNA
<213> ORGANISM: Streptococcus pyogenes
<220> FEATURE:
<221> NAME/KEY: CDS
<222> LOCATION: (1)..(4107)

<400> SEQUENCE: 6 atg gac aag aag tac agc atc ggc ctg gac atc ggc acc aac tct gtg   48
Met Asp Lys Lys Tyr Ser Ile Gly Leu Asp Ile Gly Thr Asn Ser Val
1               5                   10                  15 ggc tgg gcc gtg atc acc gac gag tac aag gtg ccc agc aag aaa ttc   96
Gly Trp Ala Val Ile Thr Asp Glu Tyr Lys Val Pro Ser Lys Lys Phe
                20                  25                  30 aag gtg ctg ggc aac acc gac cgg cac agc atc aag aag aac ctg atc  144
Lys Val Leu Gly Asn Thr Asp Arg His Ser Ile Lys Lys Asn Leu Ile
            35                  40                  45 gga gcc ctg ctg ttc gac agc ggc gaa aca gcc gag gcc acc cgg ctg  192
Gly Ala Leu Leu Phe Asp Ser Gly Glu Thr Ala Glu Ala Thr Arg Leu
        50                  55                  60 aag aga acc gcc aga aga aga tac acc aga cgg aag aac cgg atc tgc  240
Lys Arg Thr Ala Arg Arg Arg Tyr Thr Arg Arg Lys Asn Arg Ile Cys
65                  70                  75                  80 tat ctg caa gag atc ttc agc aac gag atg gcc aag gtg gac gac agc  288
Tyr Leu Gln Glu Ile Phe Ser Asn Glu Met Ala Lys Val Asp Asp Ser
                85                  90                  95 ttc ttc cac aga ctg gaa gag tcc ttc ctg gtg gaa gag gat aag aag  336
Phe Phe His Arg Leu Glu Glu Ser Phe Leu Val Glu Glu Asp Lys Lys
                100                 105                 110 cac gag cgg cac ccc atc ttc ggc aac atc gtg gac gag gtg gcc tac  384
His Glu Arg His Pro Ile Phe Gly Asn Ile Val Asp Glu Val Ala Tyr
            115                 120                 125 cac gag aag tac ccc acc atc tac cac ctg aga aag aaa ctg gtg gac  432
His Glu Lys Tyr Pro Thr Ile Tyr His Leu Arg Lys Lys Leu Val Asp
        130                 135                 140 agc acc gac aag gcc gac ctg cgg ctg atc tat ctg gcc ctg gcc cac  480
Ser Thr Asp Lys Ala Asp Leu Arg Leu Ile Tyr Leu Ala Leu Ala His
145                 150                 155                 160 atg atc aag ttc cgg ggc cac ttc ctg atc gag ggc gac ctg aac ccc  528
Met Ile Lys Phe Arg Gly His Phe Leu Ile Glu Gly Asp Leu Asn Pro
                165                 170                 175 gac aac agc gac gtg gac aag ctg ttc atc cag ctg gtg cag acc tac  576
Asp Asn Ser Asp Val Asp Lys Leu Phe Ile Gln Leu Val Gln Thr Tyr
            180                 185                 190 aac cag ctg ttc gag gaa aac ccc atc aac gcc agc ggc gtg gac gcc  624
```

```
        Asn Gln Leu Phe Glu Glu Asn Pro Ile Asn Ala Ser Gly Val Asp Ala
                    195                 200                 205 aag gcc atc ctg tct gcc aga ctg agc aag agc aga cgg ctg gaa aat          672
Lys Ala Ile Leu Ser Ala Arg Leu Ser Lys Ser Arg Arg Leu Glu Asn
210                 215                 220 ctg atc gcc cag ctg ccc ggc gag aag aag aat ggc ctg ttc ggc aac          720
Leu Ile Ala Gln Leu Pro Gly Glu Lys Lys Asn Gly Leu Phe Gly Asn
225                 230                 235                 240 ctg att gcc ctg agc ctg ggc ctg acc ccc aac ttc aag agc aac ttc          768
Leu Ile Ala Leu Ser Leu Gly Leu Thr Pro Asn Phe Lys Ser Asn Phe
            245                 250                 255 gac ctg gcc gag gat gcc aaa ctg cag ctg agc aag gac acc tac gac          816
Asp Leu Ala Glu Asp Ala Lys Leu Gln Leu Ser Lys Asp Thr Tyr Asp
        260                 265                 270 gac gac ctg gac aac ctg ctg gcc cag atc ggc gac cag tac gcc gac          864
Asp Asp Leu Asp Asn Leu Leu Ala Gln Ile Gly Asp Gln Tyr Ala Asp
    275                 280                 285 ctg ttt ctg gcc gcc aag aac ctg tcc gac gcc atc ctg ctg agc gac          912
Leu Phe Leu Ala Ala Lys Asn Leu Ser Asp Ala Ile Leu Leu Ser Asp
290                 295                 300 atc ctg aga gtg aac acc gag atc acc aag gcc ccc ctg agc gcc tct          960
Ile Leu Arg Val Asn Thr Glu Ile Thr Lys Ala Pro Leu Ser Ala Ser
305                 310                 315                 320 atg atc aag aga tac gac gag cac cac cag gac ctg acc ctg ctg aaa         1008
Met Ile Lys Arg Tyr Asp Glu His His Gln Asp Leu Thr Leu Leu Lys
            325                 330                 335 gct ctc gtg cgg cag cag ctg cct gag aag tac aaa gag att ttc ttc         1056
Ala Leu Val Arg Gln Gln Leu Pro Glu Lys Tyr Lys Glu Ile Phe Phe
        340                 345                 350 gac cag agc aag aac ggc tac gcc ggc tac att gac ggc gga gcc agc         1104
Asp Gln Ser Lys Asn Gly Tyr Ala Gly Tyr Ile Asp Gly Gly Ala Ser
    355                 360                 365 cag gaa gag ttc tac aag ttc atc aag ccc atc ctg gaa aag atg gac         1152
Gln Glu Glu Phe Tyr Lys Phe Ile Lys Pro Ile Leu Glu Lys Met Asp
370                 375                 380 ggc acc gag gaa ctg ctc gtg aag ctg aac aga gag gac ctg ctg cgg         1200
Gly Thr Glu Glu Leu Leu Val Lys Leu Asn Arg Glu Asp Leu Leu Arg
385                 390                 395                 400 aag cag cgg acc ttc gac aac ggc agc atc ccc cac cag atc cac ctg         1248
Lys Gln Arg Thr Phe Asp Asn Gly Ser Ile Pro His Gln Ile His Leu
            405                 410                 415 gga gag ctg cac gcc att ctg cgg cgg cag gaa gat ttt tac cca ttc         1296
Gly Glu Leu His Ala Ile Leu Arg Arg Gln Glu Asp Phe Tyr Pro Phe
        420                 425                 430 ctg aag gac aac cgg gaa aag atc gag aag atc ctg acc ttc cgc atc         1344
Leu Lys Asp Asn Arg Glu Lys Ile Glu Lys Ile Leu Thr Phe Arg Ile
    435                 440                 445 ccc tac tac gtg ggc cct ctg gcc agg gga aac agc aga ttc gcc tgg         1392
Pro Tyr Tyr Val Gly Pro Leu Ala Arg Gly Asn Ser Arg Phe Ala Trp
450                 455                 460 atg acc aga aag agc gag gaa acc atc acc ccc tgg aac ttc gag gaa         1440
Met Thr Arg Lys Ser Glu Glu Thr Ile Thr Pro Trp Asn Phe Glu Glu
465                 470                 475                 480 gtg gtg gac aag ggc gct tcc gcc cag agc ttc atc gag cgg atg acc         1488
Val Val Asp Lys Gly Ala Ser Ala Gln Ser Phe Ile Glu Arg Met Thr
            485                 490                 495 aac ttc gat aag aac ctg ccc aac gag aag gtg ctg ccc aag cac agc         1536
Asn Phe Asp Lys Asn Leu Pro Asn Glu Lys Val Leu Pro Lys His Ser
        500                 505                 510
```

-continued

| | |
|---|---|
| ctg ctg tac gag tac ttc acc gtg tat aac gag ctg acc aaa gtg aaa<br>Leu Leu Tyr Glu Tyr Phe Thr Val Tyr Asn Glu Leu Thr Lys Val Lys<br>     515                   520                 525 | 1584 |
| tac gtg acc gag gga atg aga aag ccc gcc ttc ctg agc ggc gag cag<br>Tyr Val Thr Glu Gly Met Arg Lys Pro Ala Phe Leu Ser Gly Glu Gln<br>530                   535                 540 | 1632 |
| aaa aag gcc atc gtg gac ctg ctg ttc aag acc aac cgg aaa gtg acc<br>Lys Lys Ala Ile Val Asp Leu Leu Phe Lys Thr Asn Arg Lys Val Thr<br>545                550               555             560 | 1680 |
| gtg aag cag ctg aaa gag gac tac ttc aag aaa atc gag tgc ttc gac<br>Val Lys Gln Leu Lys Glu Asp Tyr Phe Lys Lys Ile Glu Cys Phe Asp<br>               565               570             575 | 1728 |
| tcc gtg gaa atc tcc ggc gtg gaa gat cgg ttc aac gcc tcc ctg ggc<br>Ser Val Glu Ile Ser Gly Val Glu Asp Arg Phe Asn Ala Ser Leu Gly<br>          580                 585             590 | 1776 |
| aca tac cac gat ctg ctg aaa att atc aag gac aag gac ttc ctg gac<br>Thr Tyr His Asp Leu Leu Lys Ile Ile Lys Asp Lys Asp Phe Leu Asp<br>               595               600             605 | 1824 |
| aat gag gaa aac gag gac att ctg gaa gat atc gtg ctg acc ctg aca<br>Asn Glu Glu Asn Glu Asp Ile Leu Glu Asp Ile Val Leu Thr Leu Thr<br>          610                 615             620 | 1872 |
| ctg ttt gag gac aga gag atg atc gag gaa cgg ctg aaa acc tat gcc<br>Leu Phe Glu Asp Arg Glu Met Ile Glu Glu Arg Leu Lys Thr Tyr Ala<br>625                   630                 635             640 | 1920 |
| cac ctg ttc gac gac aaa gtg atg aag cag ctg aag cgg cgg aga tac<br>His Leu Phe Asp Asp Lys Val Met Lys Gln Leu Lys Arg Arg Arg Tyr<br>               645               650             655 | 1968 |
| acc ggc tgg ggc agg ctg agc cgg aag ctg atc aac ggc atc cgg gac<br>Thr Gly Trp Gly Arg Leu Ser Arg Lys Leu Ile Asn Gly Ile Arg Asp<br>          660                 665             670 | 2016 |
| aag cag tcc ggc aag aca atc ctg gat ttc ctg aag tcc gac ggc ttc<br>Lys Gln Ser Gly Lys Thr Ile Leu Asp Phe Leu Lys Ser Asp Gly Phe<br>               675               680             685 | 2064 |
| gcc aac aga aac ttc atg cag ctg atc cac gac gac agc ctg acc ttt<br>Ala Asn Arg Asn Phe Met Gln Leu Ile His Asp Asp Ser Leu Thr Phe<br>          690                 695             700 | 2112 |
| aaa gag gac atc cag aaa gcc cag gtg tcc ggc cag ggc gat agc ctg<br>Lys Glu Asp Ile Gln Lys Ala Gln Val Ser Gly Gln Gly Asp Ser Leu<br>705                   710                 715             720 | 2160 |
| cac gag cac att gcc aat ctg gcc ggc agc ccc gcc att aag aag ggc<br>His Glu His Ile Ala Asn Leu Ala Gly Ser Pro Ala Ile Lys Lys Gly<br>               725               730             735 | 2208 |
| atc ctg cag aca gtg aag gtg gtg gac gag ctc gtg aaa gtg atg ggc<br>Ile Leu Gln Thr Val Lys Val Val Asp Glu Leu Val Lys Val Met Gly<br>          740                 745             750 | 2256 |
| cgg cac aag ccc gag aac atc gtg atc gaa atg gcc aga gag aac cag<br>Arg His Lys Pro Glu Asn Ile Val Ile Glu Met Ala Arg Glu Asn Gln<br>               755               760             765 | 2304 |
| acc acc cag aag gga cag aag aac agc cgc gag aga atg aag cgg atc<br>Thr Thr Gln Lys Gly Gln Lys Asn Ser Arg Glu Arg Met Lys Arg Ile<br>          770                 775             780 | 2352 |
| gaa gag ggc atc aaa gag ctg ggc agc cag atc ctg aaa gaa cac ccc<br>Glu Glu Gly Ile Lys Glu Leu Gly Ser Gln Ile Leu Lys Glu His Pro<br>785                   790                 795             800 | 2400 |
| gtg gaa aac acc cag ctg cag aac gag aag ctg tac ctg tac tac ctg<br>Val Glu Asn Thr Gln Leu Gln Asn Glu Lys Leu Tyr Leu Tyr Tyr Leu<br>               805               810             815 | 2448 |
| cag aat ggg cgg gat atg tac gtg gac cag gaa ctg gac atc aac cgg<br>Gln Asn Gly Arg Asp Met Tyr Val Asp Gln Glu Leu Asp Ile Asn Arg<br>          820                 825             830 | 2496 |

-continued

```
ctg tcc gac tac gat gtg gac cat atc gtg cct cag agc ttt ctg aag      2544
Leu Ser Asp Tyr Asp Val Asp His Ile Val Pro Gln Ser Phe Leu Lys
        835                 840                 845 gac gac tcc atc gac aac aag gtg ctg acc aga agc gac aag aac cgg      2592
Asp Asp Ser Ile Asp Asn Lys Val Leu Thr Arg Ser Asp Lys Asn Arg
850                 855                 860 ggc aag agc gac aac gtg ccc tcc gaa gag gtc gtg aag aag atg aag      2640
Gly Lys Ser Asp Asn Val Pro Ser Glu Glu Val Val Lys Lys Met Lys
865                 870                 875                 880 aac tac tgg cgg cag ctg ctg aac gcc aag ctg att acc cag aga aag      2688
Asn Tyr Trp Arg Gln Leu Leu Asn Ala Lys Leu Ile Thr Gln Arg Lys
                885                 890                 895 ttc gac aat ctg acc aag gcc gag aga ggc ggc ctg agc gaa ctg gat      2736
Phe Asp Asn Leu Thr Lys Ala Glu Arg Gly Gly Leu Ser Glu Leu Asp
            900                 905                 910 aag gcc ggc ttc atc aag aga cag ctg gtg gaa acc cgg cag atc aca      2784
Lys Ala Gly Phe Ile Lys Arg Gln Leu Val Glu Thr Arg Gln Ile Thr
        915                 920                 925 aag cac gtg gca cag atc ctg gac tcc cgg atg aac act aag tac gac      2832
Lys His Val Ala Gln Ile Leu Asp Ser Arg Met Asn Thr Lys Tyr Asp
    930                 935                 940 gag aat gac aag ctg atc cgg gaa gtg aaa gtg atc acc ctg aag tcc      2880
Glu Asn Asp Lys Leu Ile Arg Glu Val Lys Val Ile Thr Leu Lys Ser
945                 950                 955                 960 aag ctg gtg tcc gat ttc cgg aag gat ttc cag ttt tac aaa gtg cgc      2928
Lys Leu Val Ser Asp Phe Arg Lys Asp Phe Gln Phe Tyr Lys Val Arg
                965                 970                 975 gag atc aac aac tac cac cac gcc cac gac gcc tac ctg aac gcc gtc      2976
Glu Ile Asn Asn Tyr His His Ala His Asp Ala Tyr Leu Asn Ala Val
            980                 985                 990 gtg gga acc gcc ctg atc aaa aag tac cct aag ctg gaa agc gag ttc      3024
Val Gly Thr Ala Leu Ile Lys Lys Tyr Pro Lys Leu Glu Ser Glu Phe
        995                1000                1005 gtg tac ggc gac tac aag gtg tac gac gtg cgg aag atg atc gcc          3069
Val Tyr Gly Asp Tyr Lys Val Tyr Asp Val Arg Lys Met Ile Ala
   1010                1015                1020 aag agc gag cag gaa atc ggc aag gct acc gcc aag tac ttc ttc          3114
Lys Ser Glu Gln Glu Ile Gly Lys Ala Thr Ala Lys Tyr Phe Phe
   1025                1030                1035 tac agc aac atc atg aac ttt ttc aag acc gag att acc ctg gcc          3159
Tyr Ser Asn Ile Met Asn Phe Phe Lys Thr Glu Ile Thr Leu Ala
   1040                1045                1050 aac ggc gag atc cgg aag cgg cct ctg atc gag aca aac ggc gaa          3204
Asn Gly Glu Ile Arg Lys Arg Pro Leu Ile Glu Thr Asn Gly Glu
   1055                1060                1065 acc ggg gag atc gtg tgg gat aag ggc cgg gat ttt gcc acc gtg          3249
Thr Gly Glu Ile Val Trp Asp Lys Gly Arg Asp Phe Ala Thr Val
   1070                1075                1080 cgg aaa gtg ctg agc atg ccc caa gtg aat atc gtg aaa aag acc          3294
Arg Lys Val Leu Ser Met Pro Gln Val Asn Ile Val Lys Lys Thr
   1085                1090                1095 gag gtg cag aca ggc ggc ttc agc aaa gag tct atc cgg ccc aag          3339
Glu Val Gln Thr Gly Gly Phe Ser Lys Glu Ser Ile Arg Pro Lys
   1100                1105                1110 agg aac agc gat aag ctg atc gcc aga aag aag gac tgg gac cct          3384
Arg Asn Ser Asp Lys Leu Ile Ala Arg Lys Lys Asp Trp Asp Pro
   1115                1120                1125 aag aag tac ggc ggc ttc gac agc ccc acc gtg gcc tat tct gtg          3429
Lys Lys Tyr Gly Gly Phe Asp Ser Pro Thr Val Ala Tyr Ser Val
```

```
ctg gtg gtg gcc aaa gtg gaa aag ggc aag tcc aag aaa ctg aag      3474
Leu Val Val Ala Lys Val Glu Lys Gly Lys Ser Lys Lys Leu Lys
1145                1150                1155 agt gtg aaa gag ctg ctg ggg atc acc atc atg gaa aga agc agc      3519
Ser Val Lys Glu Leu Leu Gly Ile Thr Ile Met Glu Arg Ser Ser
    1160                1165                1170 ttc gag aag aat ccc atc gac ttt ctg gaa gcc aag ggc tac aaa      3564
Phe Glu Lys Asn Pro Ile Asp Phe Leu Glu Ala Lys Gly Tyr Lys
1175                1180                1185 gaa gtg aaa aag gac ctg atc atc aag ctg cct aag tac tcc ctg      3609
Glu Val Lys Lys Asp Leu Ile Ile Lys Leu Pro Lys Tyr Ser Leu
    1190                1195                1200 ttc gag ctg gaa aac ggc cgg aag aga atg ctg gcc tct gcc cgg      3654
Phe Glu Leu Glu Asn Gly Arg Lys Arg Met Leu Ala Ser Ala Arg
1205                1210                1215 gaa ctg cag aag gga aac gaa ctg gcc ctg ccc tcc aaa tat gtg      3699
Glu Leu Gln Lys Gly Asn Glu Leu Ala Leu Pro Ser Lys Tyr Val
    1220                1225                1230 aac ttc ctg tac ctg gcc agc cac tat gag aag ctg aag ggc tcc      3744
Asn Phe Leu Tyr Leu Ala Ser His Tyr Glu Lys Leu Lys Gly Ser
1235                1240                1245 ccc gag gat aat gag cag aaa cag ctg ttt gtg gaa cag cac aag      3789
Pro Glu Asp Asn Glu Gln Lys Gln Leu Phe Val Glu Gln His Lys
    1250                1255                1260 cac tac ctg gac gag atc atc gag cag atc agc gag ttc tcc aag      3834
His Tyr Leu Asp Glu Ile Ile Glu Gln Ile Ser Glu Phe Ser Lys
1265                1270                1275 aga gtg atc ctg gcc gac gct aat ctg gac aaa gtg ctg tcc gcc      3879
Arg Val Ile Leu Ala Asp Ala Asn Leu Asp Lys Val Leu Ser Ala
    1280                1285                1290 tac aac aag cac cgg gat aag ccc atc aga gag cag gcc gag aat      3924
Tyr Asn Lys His Arg Asp Lys Pro Ile Arg Glu Gln Ala Glu Asn
1295                1300                1305 atc atc cac ctg ttt acc ctg acc aat ctg gga gcc cct gcc gcc      3969
Ile Ile His Leu Phe Thr Leu Thr Asn Leu Gly Ala Pro Ala Ala
    1310                1315                1320 ttc aag tac ttt gac acc acc atc gac cgg aag gcc tac cgg agc      4014
Phe Lys Tyr Phe Asp Thr Thr Ile Asp Arg Lys Ala Tyr Arg Ser
1325                1330                1335 acc aaa gag gtg ctg gac gcc acc ctg atc cac cag agc atc acc      4059
Thr Lys Glu Val Leu Asp Ala Thr Leu Ile His Gln Ser Ile Thr
    1340                1345                1350 ggc ctg tac gag aca cgg atc gac ctg tct cag ctg gga ggc gac      4104
Gly Leu Tyr Glu Thr Arg Ile Asp Leu Ser Gln Leu Gly Gly Asp
1355                1360                1365 taa                                                              4107
```

<210> SEQ ID NO 7
<211> LENGTH: 4107
<212> TYPE: DNA
<213> ORGANISM: Streptococcus pyogenes
<220> FEATURE:
<221> NAME/KEY: CDS
<222> LOCATION: (1)..(4107)

<400> SEQUENCE: 7

```
atg gac aag aag tac agc atc ggc ctg gac atc ggc acc aac tct gtg     48
Met Asp Lys Lys Tyr Ser Ile Gly Leu Asp Ile Gly Thr Asn Ser Val
1               5                   10                  15
```

-continued

| | |
|---|---|
| ggc tgg gcc gtg atc acc gac gag tac aag gtg ccc agc aag aaa ttc<br>Gly Trp Ala Val Ile Thr Asp Glu Tyr Lys Val Pro Ser Lys Lys Phe<br>          20               25              30 | 96 |
| aag gtg ctg ggc aac acc gac cgg cac agc atc aag aag aac ctg atc<br>Lys Val Leu Gly Asn Thr Asp Arg His Ser Ile Lys Lys Asn Leu Ile<br>        35               40              45 | 144 |
| gga gcc ctg ctg ttc gac agc ggc gaa aca gcc gag gcc acc cgg ctg<br>Gly Ala Leu Leu Phe Asp Ser Gly Glu Thr Ala Glu Ala Thr Arg Leu<br>50               55              60 | 192 |
| aag aga acc gcc aga aga aga tac acc aga cgg aag aac cgg atc tgc<br>Lys Arg Thr Ala Arg Arg Arg Tyr Thr Arg Arg Lys Asn Arg Ile Cys<br>65               70              75              80 | 240 |
| tat ctg caa gag atc ttc agc aac gag atg gcc aag gtg gac gac agc<br>Tyr Leu Gln Glu Ile Phe Ser Asn Glu Met Ala Lys Val Asp Asp Ser<br>               85              90              95 | 288 |
| ttc ttc cac aga ctg gaa gag tcc ttc ctg gtg gaa gag gat aag aag<br>Phe Phe His Arg Leu Glu Glu Ser Phe Leu Val Glu Glu Asp Lys Lys<br>           100              105            110 | 336 |
| cac gag cgg cac ccc atc ttc ggc aac atc gtg gac gag gtg gcc tac<br>His Glu Arg His Pro Ile Phe Gly Asn Ile Val Asp Glu Val Ala Tyr<br>           115              120            125 | 384 |
| cac gag aag tac ccc acc atc tac cac ctg aga aag aaa ctg gtg gac<br>His Glu Lys Tyr Pro Thr Ile Tyr His Leu Arg Lys Lys Leu Val Asp<br>130               135              140 | 432 |
| agc acc gac aag gcc gac ctg cgg ctg atc tat ctg gcc ctg gcc cac<br>Ser Thr Asp Lys Ala Asp Leu Arg Leu Ile Tyr Leu Ala Leu Ala His<br>145               150              155              160 | 480 |
| atg atc aag ttc cgg ggc cac ttc ctg atc gag ggc gac ctg aac ccc<br>Met Ile Lys Phe Arg Gly His Phe Leu Ile Glu Gly Asp Leu Asn Pro<br>               165              170            175 | 528 |
| gac aac agc gac gtg gac aag ctg ttc atc cag ctg gtg cag acc tac<br>Asp Asn Ser Asp Val Asp Lys Leu Phe Ile Gln Leu Val Gln Thr Tyr<br>           180              185            190 | 576 |
| aac cag ctg ttc gag gaa aac ccc atc aac gcc agc ggc gtg gac gcc<br>Asn Gln Leu Phe Glu Glu Asn Pro Ile Asn Ala Ser Gly Val Asp Ala<br>             195              200            205 | 624 |
| aag gcc atc ctg tct gcc aga ctg agc aag agc aga cgg ctg gaa aat<br>Lys Ala Ile Leu Ser Ala Arg Leu Ser Lys Ser Arg Arg Leu Glu Asn<br>210               215              220 | 672 |
| ctg atc gcc cag ctg ccc ggc gag aag aag aat ggc ctg ttc ggc aac<br>Leu Ile Ala Gln Leu Pro Gly Glu Lys Lys Asn Gly Leu Phe Gly Asn<br>225               230              235              240 | 720 |
| ctg att gcc ctg agc ctg ggc ctg acc ccc aac ttc aag agc aac ttc<br>Leu Ile Ala Leu Ser Leu Gly Leu Thr Pro Asn Phe Lys Ser Asn Phe<br>           245              250            255 | 768 |
| gac ctg gcc gag gat gcc aaa ctg cag ctg agc aag gac acc tac gac<br>Asp Leu Ala Glu Asp Ala Lys Leu Gln Leu Ser Lys Asp Thr Tyr Asp<br>             260              265            270 | 816 |
| gac gac ctg gac aac ctg ctg gcc cag atc ggc gac cag tac gcc gac<br>Asp Asp Leu Asp Asn Leu Leu Ala Gln Ile Gly Asp Gln Tyr Ala Asp<br>        275               280              285 | 864 |
| ctg ttt ctg gcc gcc aag aac ctg tcc gac gcc atc ctg ctg agc gac<br>Leu Phe Leu Ala Ala Lys Asn Leu Ser Asp Ala Ile Leu Leu Ser Asp<br>290               295              300 | 912 |
| atc ctg aga gtg aac acc gag atc acc aag gcc ccc ctg agc gcc tct<br>Ile Leu Arg Val Asn Thr Glu Ile Thr Lys Ala Pro Leu Ser Ala Ser<br>305               310              315              320 | 960 |
| atg atc aag aga tac gac gag cac cac cag gac ctg acc ctg ctg aaa<br>Met Ile Lys Arg Tyr Asp Glu His His Gln Asp Leu Thr Leu Leu Lys<br>             325              330            335 | 1008 |

```
gct ctc gtg cgg cag cag ctg cct gag aag tac aaa gag att ttc ttc    1056
Ala Leu Val Arg Gln Gln Leu Pro Glu Lys Tyr Lys Glu Ile Phe Phe
         340                 345                 350 gac cag agc aag aac ggc tac gcc ggc tac att gac ggc gga gcc agc    1104
Asp Gln Ser Lys Asn Gly Tyr Ala Gly Tyr Ile Asp Gly Gly Ala Ser
             355                 360                 365 cag gaa gag ttc tac aag ttc atc aag ccc atc ctg gaa aag atg gac    1152
Gln Glu Glu Phe Tyr Lys Phe Ile Lys Pro Ile Leu Glu Lys Met Asp
370                 375                 380 ggc acc gag gaa ctg ctc gtg aag ctg aac aga gag gac ctg ctg cgg    1200
Gly Thr Glu Glu Leu Leu Val Lys Leu Asn Arg Glu Asp Leu Leu Arg
385                 390                 395                 400 aag cag cgg acc ttc gac aac ggc agc atc ccc cac cag atc cac ctg    1248
Lys Gln Arg Thr Phe Asp Asn Gly Ser Ile Pro His Gln Ile His Leu
             405                 410                 415 gga gag ctg cac gcc att ctg cgg cgg cag gaa gat ttt tac cca ttc    1296
Gly Glu Leu His Ala Ile Leu Arg Arg Gln Glu Asp Phe Tyr Pro Phe
         420                 425                 430 ctg aag gac aac cgg gaa aag atc gag aag atc ctg acc ttc cgc atc    1344
Leu Lys Asp Asn Arg Glu Lys Ile Glu Lys Ile Leu Thr Phe Arg Ile
             435                 440                 445 ccc tac tac gtg ggc cct ctg gcc agg gga aac agc aga ttc gcc tgg    1392
Pro Tyr Tyr Val Gly Pro Leu Ala Arg Gly Asn Ser Arg Phe Ala Trp
         450                 455                 460 atg acc aga aag agc gag gaa acc atc acc ccc tgg aac ttc gag gaa    1440
Met Thr Arg Lys Ser Glu Glu Thr Ile Thr Pro Trp Asn Phe Glu Glu
465                 470                 475                 480 gtg gtg gac aag ggc gct tcc gcc cag agc ttc atc gag cgg atg acc    1488
Val Val Asp Lys Gly Ala Ser Ala Gln Ser Phe Ile Glu Arg Met Thr
             485                 490                 495 aac ttc gat aag aac ctg ccc aac gag aag gtg ctg ccc aag cac agc    1536
Asn Phe Asp Lys Asn Leu Pro Asn Glu Lys Val Leu Pro Lys His Ser
         500                 505                 510 ctg ctg tac gag tac ttc acc gtg tat aac gag ctg acc aaa gtg aaa    1584
Leu Leu Tyr Glu Tyr Phe Thr Val Tyr Asn Glu Leu Thr Lys Val Lys
             515                 520                 525 tac gtg acc gag gga atg aga aag ccc gcc ttc ctg agc ggc gag cag    1632
Tyr Val Thr Glu Gly Met Arg Lys Pro Ala Phe Leu Ser Gly Glu Gln
530                 535                 540 aaa aag gcc atc gtg gac ctg ctg ttc aag acc aac cgg aaa gtg acc    1680
Lys Lys Ala Ile Val Asp Leu Leu Phe Lys Thr Asn Arg Lys Val Thr
545                 550                 555                 560 gtg aag cag ctg aaa gag gac tac ttc aag aaa atc gag tgc ttc gac    1728
Val Lys Gln Leu Lys Glu Asp Tyr Phe Lys Lys Ile Glu Cys Phe Asp
             565                 570                 575 tcc gtg gaa atc tcc ggc gtg gaa gat cgg ttc aac gcc tcc ctg ggc    1776
Ser Val Glu Ile Ser Gly Val Glu Asp Arg Phe Asn Ala Ser Leu Gly
         580                 585                 590 aca tac cac gat ctg ctg aaa att atc aag gac aag gac ttc ctg gac    1824
Thr Tyr His Asp Leu Leu Lys Ile Ile Lys Asp Lys Asp Phe Leu Asp
             595                 600                 605 aat gag gaa aac gag gac att ctg gaa gat atc gtg ctg acc ctg aca    1872
Asn Glu Glu Asn Glu Asp Ile Leu Glu Asp Ile Val Leu Thr Leu Thr
         610                 615                 620 ctg ttt gag gac aga gag atg atc gag gaa cgg ctg aaa acc tat gcc    1920
Leu Phe Glu Asp Arg Glu Met Ile Glu Glu Arg Leu Lys Thr Tyr Ala
625                 630                 635                 640 cac ctg ttc gac gac aaa gtg atg aag cag ctg aag cgg cgg aga tac    1968
His Leu Phe Asp Asp Lys Val Met Lys Gln Leu Lys Arg Arg Arg Tyr
```

-continued

```
                    645                 650                 655
acc ggc tgg ggc agg ctg agc cgg aag ctg atc aac ggc atc cgg gac    2016
Thr Gly Trp Gly Arg Leu Ser Arg Lys Leu Ile Asn Gly Ile Arg Asp
            660                 665                 670 aag cag tcc ggc aag aca atc ctg gat ttc ctg aag tcc gac ggc ttc    2064
Lys Gln Ser Gly Lys Thr Ile Leu Asp Phe Leu Lys Ser Asp Gly Phe
            675                 680                 685 gcc aac aga aac ttc atg cag ctg atc cac gac gac agc ctg acc ttt    2112
Ala Asn Arg Asn Phe Met Gln Leu Ile His Asp Asp Ser Leu Thr Phe
690                 695                 700 aaa gag gac atc cag aaa gcc cag gtg tcc ggc cag ggc gat agc ctg    2160
Lys Glu Asp Ile Gln Lys Ala Gln Val Ser Gly Gln Gly Asp Ser Leu
705                 710                 715                 720 cac gag cac att gcc aat ctg gcc ggc agc ccc gcc att aag aag ggc    2208
His Glu His Ile Ala Asn Leu Ala Gly Ser Pro Ala Ile Lys Lys Gly
                725                 730                 735 atc ctg cag aca gtg aag gtg gtg gac gag ctc gtg aaa gtg atg ggc    2256
Ile Leu Gln Thr Val Lys Val Val Asp Glu Leu Val Lys Val Met Gly
                740                 745                 750 cgg cac aag ccc gag aac atc gtg atc gaa atg gcc aga gag aac cag    2304
Arg His Lys Pro Glu Asn Ile Val Ile Glu Met Ala Arg Glu Asn Gln
            755                 760                 765 acc acc cag aag gga cag aag aac agc cgc gag aga atg aag cgg atc    2352
Thr Thr Gln Lys Gly Gln Lys Asn Ser Arg Glu Arg Met Lys Arg Ile
            770                 775                 780 gaa gag ggc atc aaa gag ctg ggc agc cag atc ctg aaa gaa cac ccc    2400
Glu Glu Gly Ile Lys Glu Leu Gly Ser Gln Ile Leu Lys Glu His Pro
785                 790                 795                 800 gtg gaa aac acc cag ctg cag aac gag aag ctg tac ctg tac tac ctg    2448
Val Glu Asn Thr Gln Leu Gln Asn Glu Lys Leu Tyr Leu Tyr Tyr Leu
                805                 810                 815 cag aat ggg cgg gat atg tac gtg gac cag gaa ctg gac atc aac cgg    2496
Gln Asn Gly Arg Asp Met Tyr Val Asp Gln Glu Leu Asp Ile Asn Arg
            820                 825                 830 ctg tcc gac tac gat gtg gac cat atc gtg cct cag agc ttt ctg aag    2544
Leu Ser Asp Tyr Asp Val Asp His Ile Val Pro Gln Ser Phe Leu Lys
            835                 840                 845 gac gac tcc atc gac aac aag gtg ctg acc aga agc gac aag aac cgg    2592
Asp Asp Ser Ile Asp Asn Lys Val Leu Thr Arg Ser Asp Lys Asn Arg
850                 855                 860 ggc aag agc gac aac gtg ccc tcc gaa gag gtc gtg aag aag atg aag    2640
Gly Lys Ser Asp Asn Val Pro Ser Glu Glu Val Val Lys Lys Met Lys
865                 870                 875                 880 aac tac tgg cgg cag ctg ctg aac gcc aag ctg att acc cag aga aag    2688
Asn Tyr Trp Arg Gln Leu Leu Asn Ala Lys Leu Ile Thr Gln Arg Lys
                885                 890                 895 ttc gac aat ctg acc aag gcc gag aga ggc ggc ctg agc gaa ctg gat    2736
Phe Asp Asn Leu Thr Lys Ala Glu Arg Gly Gly Leu Ser Glu Leu Asp
            900                 905                 910 aag gcc ggc ttc atc aag aga cag ctg gtg gaa acc cgg cag atc aca    2784
Lys Ala Gly Phe Ile Lys Arg Gln Leu Val Glu Thr Arg Gln Ile Thr
            915                 920                 925 aag cac gtg gca cag atc ctg gac tcc cgg atg aac act aag tac gac    2832
Lys His Val Ala Gln Ile Leu Asp Ser Arg Met Asn Thr Lys Tyr Asp
            930                 935                 940 gag aat gac aag ctg atc cgg gaa gtg aaa gtg atc acc ctg aag tcc    2880
Glu Asn Asp Lys Leu Ile Arg Glu Val Lys Val Ile Thr Leu Lys Ser
945                 950                 955                 960 aag ctg gtg tcc gat ttc cgg aag gat ttc cag ttt tac aaa gtg cgc    2928
```

-continued

```
                    Lys Leu Val Ser Asp Phe Arg Lys Asp Phe Gln Phe Tyr Lys Val Arg
                                    965                 970                 975 gag atc aac aac tac cac cac gcc cac gac gcc tac ctg aac gcc gtc                    2976
Glu Ile Asn Asn Tyr His His Ala His Asp Ala Tyr Leu Asn Ala Val
            980                 985                 990 gtg gga acc gcc ctg atc aaa aag tac cct aag ctg gaa agc gag ttc                    3024
Val Gly Thr Ala Leu Ile Lys Lys Tyr Pro Lys Leu Glu Ser Glu Phe
        995                 1000                1005 gtg tac ggc gac tac aag gtg tac gac gtg cgg aag atg atc gcc                        3069
Val Tyr Gly Asp Tyr Lys Val Tyr Asp Val Arg Lys Met Ile Ala
    1010                1015                1020 aag agc gag cag gaa atc ggc aag gct acc gcc aag tac ttc ttc                        3114
Lys Ser Glu Gln Glu Ile Gly Lys Ala Thr Ala Lys Tyr Phe Phe
    1025                1030                1035 tac agc aac atc atg aac ttt ttc aag acc gag att acc ctg gcc                        3159
Tyr Ser Asn Ile Met Asn Phe Phe Lys Thr Glu Ile Thr Leu Ala
    1040                1045                1050 aac ggc gag atc cgg aag cgg cct ctg atc gag aca aac ggc gaa                        3204
Asn Gly Glu Ile Arg Lys Arg Pro Leu Ile Glu Thr Asn Gly Glu
    1055                1060                1065 acc ggg gag atc gtg tgg gat aag ggc cgg gat ttt gcc acc gtg                        3249
Thr Gly Glu Ile Val Trp Asp Lys Gly Arg Asp Phe Ala Thr Val
    1070                1075                1080 cgg aaa gtg ctg agc atg ccc caa gtg aat atc gtg aaa aag acc                        3294
Arg Lys Val Leu Ser Met Pro Gln Val Asn Ile Val Lys Lys Thr
    1085                1090                1095 gag gtg cag aca ggc ggc ttc agc aaa gag tct atc cgg ccc aag                        3339
Glu Val Gln Thr Gly Gly Phe Ser Lys Glu Ser Ile Arg Pro Lys
    1100                1105                1110 agg aac agc gat aag ctg atc gcc aga aag aag gac tgg gac cct                        3384
Arg Asn Ser Asp Lys Leu Ile Ala Arg Lys Lys Asp Trp Asp Pro
    1115                1120                1125 aag aag tac ggc ggc ttc gac agc ccc acc gtg gcc tat tct gtg                        3429
Lys Lys Tyr Gly Gly Phe Asp Ser Pro Thr Val Ala Tyr Ser Val
    1130                1135                1140 ctg gtg gtg gcc aaa gtg gaa aag ggc aag tcc aag aaa ctg aag                        3474
Leu Val Val Ala Lys Val Glu Lys Gly Lys Ser Lys Lys Leu Lys
    1145                1150                1155 agt gtg aaa gag ctg ctg ggg atc acc atc atg gaa aga agc agc                        3519
Ser Val Lys Glu Leu Leu Gly Ile Thr Ile Met Glu Arg Ser Ser
    1160                1165                1170 ttc gag aag aat ccc atc gac ttt ctg gaa gcc aag ggc tac aaa                        3564
Phe Glu Lys Asn Pro Ile Asp Phe Leu Glu Ala Lys Gly Tyr Lys
    1175                1180                1185 gaa gtg aaa aag gac ctg atc atc aag ctg cct aag tac tcc ctg                        3609
Glu Val Lys Lys Asp Leu Ile Ile Lys Leu Pro Lys Tyr Ser Leu
    1190                1195                1200 ttc gag ctg gaa aac ggc cgg aag aga atg ctg gcc tct gcc cgg                        3654
Phe Glu Leu Glu Asn Gly Arg Lys Arg Met Leu Ala Ser Ala Arg
    1205                1210                1215 gaa ctg cag aag gga aac gaa ctg gcc ctg ccc tcc aaa tat gtg                        3699
Glu Leu Gln Lys Gly Asn Glu Leu Ala Leu Pro Ser Lys Tyr Val
    1220                1225                1230 aac ttc ctg tac ctg gcc agc cac tat gag aag ctg aag ggc tcc                        3744
Asn Phe Leu Tyr Leu Ala Ser His Tyr Glu Lys Leu Lys Gly Ser
    1235                1240                1245 ccc gag gat aat gag cag aaa cag ctg ttt gtg gaa cag cac aag                        3789
Pro Glu Asp Asn Glu Gln Lys Gln Leu Phe Val Glu Gln His Lys
    1250                1255                1260
```

-continued

| | |
|---|---|
| cac tac ctg gac gag atc atc gag cag atc agc gag ttc tcc aag<br>His Tyr Leu Asp Glu Ile Ile Glu Gln Ile Ser Glu Phe Ser Lys<br>1265                   1270                     1275 | 3834 |
| aga gtg atc ctg gcc gac gct aat ctg gac aaa gtg ctg tcc gcc<br>Arg Val Ile Leu Ala Asp Ala Asn Leu Asp Lys Val Leu Ser Ala<br>1280                     1285                     1290 | 3879 |
| tac aac aag cac cgg gat aag ccc atc aga gag cag gcc gag aat<br>Tyr Asn Lys His Arg Asp Lys Pro Ile Arg Glu Gln Ala Glu Asn<br>1295                   1300                     1305 | 3924 |
| atc atc cac ctg ttt acc ctg acc aat ctg gga gcc cct gcc gcc<br>Ile Ile His Leu Phe Thr Leu Thr Asn Leu Gly Ala Pro Ala Ala<br>1310                     1315                     1320 | 3969 |
| ttc aag tac ttt gac acc acc atc cgg cgg aag gcc tac cgg agc<br>Phe Lys Tyr Phe Asp Thr Thr Ile Arg Arg Lys Ala Tyr Arg Ser<br>1325                     1330                     1335 | 4014 |
| acc aaa gag gtg ctg gac gcc acc ctg atc cac cag agc atc acc<br>Thr Lys Glu Val Leu Asp Ala Thr Leu Ile His Gln Ser Ile Thr<br>1340                     1345                     1350 | 4059 |
| ggc ctg tac gag aca cgg atc gac ctg tct cag ctg gga ggc gac<br>Gly Leu Tyr Glu Thr Arg Ile Asp Leu Ser Gln Leu Gly Gly Asp<br>1355                     1360                     1365 | 4104 |
| taa | 4107 |

```
<210> SEQ ID NO 8
<211> LENGTH: 4107
<212> TYPE: DNA
<213> ORGANISM: Streptococcus pyogenes
<220> FEATURE:
<221> NAME/KEY: CDS
<222> LOCATION: (1)..(4107)

<400> SEQUENCE: 8
```

| | |
|---|---|
| atg gac aag aag tac agc atc ggc ctg gac atc ggc acc aac tct gtg<br>Met Asp Lys Lys Tyr Ser Ile Gly Leu Asp Ile Gly Thr Asn Ser Val<br>1                     5                     10                  15 | 48 |
| ggc tgg gcc gtg atc acc gac gag tac aag gtg ccc agc aag aaa ttc<br>Gly Trp Ala Val Ile Thr Asp Glu Tyr Lys Val Pro Ser Lys Lys Phe<br>                   20                     25                     30 | 96 |
| aag gtg ctg ggc aac acc gac cgg cac agc atc aag aag aac ctg atc<br>Lys Val Leu Gly Asn Thr Asp Arg His Ser Ile Lys Lys Asn Leu Ile<br>             35                     40                     45 | 144 |
| gga gcc ctg ctg ttc gac agc ggc gaa aca gcc gag gcc acc cgg ctg<br>Gly Ala Leu Leu Phe Asp Ser Gly Glu Thr Ala Glu Ala Thr Arg Leu<br>50                     55                     60 | 192 |
| aag aga acc gcc aga aga aga tac acc aga cgg aag aac cgg atc tgc<br>Lys Arg Thr Ala Arg Arg Arg Tyr Thr Arg Arg Lys Asn Arg Ile Cys<br>65                     70                     75                  80 | 240 |
| tat ctg caa gag atc ttc agc aac gag atg gcc aag gtg gac gac agc<br>Tyr Leu Gln Glu Ile Phe Ser Asn Glu Met Ala Lys Val Asp Asp Ser<br>                     85                     90                     95 | 288 |
| ttc ttc cac aga ctg gaa gag tcc ttc ctg gtg gaa gag gat aag aag<br>Phe Phe His Arg Leu Glu Glu Ser Phe Leu Val Glu Glu Asp Lys Lys<br>             100                     105                     110 | 336 |
| cac gag cgg cac ccc atc ttc ggc aac atc gtg gac gag gtg gcc tac<br>His Glu Arg His Pro Ile Phe Gly Asn Ile Val Asp Glu Val Ala Tyr<br>             115                     120                     125 | 384 |
| cac gag aag tac ccc acc atc tac cac ctg aga aag aaa ctg gtg gac<br>His Glu Lys Tyr Pro Thr Ile Tyr His Leu Arg Lys Lys Leu Val Asp<br>130                     135                     140 | 432 |
| agc acc gac aag gcc gac ctg cgg ctg atc tat ctg gcc ctg gcc cac<br>Ser Thr Asp Lys Ala Asp Leu Arg Leu Ile Tyr Leu Ala Leu Ala His | 480 |

-continued

| | | |
|---|---|---|
| atg atc aag ttc cgg ggc cac ttc ctg atc gag ggc gac ctg aac ccc<br>Met Ile Lys Phe Arg Gly His Phe Leu Ile Glu Gly Asp Leu Asn Pro<br>145                        150                        155                        160 | 528 |
| gac aac agc gac gtg gac aag ctg ttc atc cag ctg gtg cag acc tac<br>Asp Asn Ser Asp Val Asp Lys Leu Phe Ile Gln Leu Val Gln Thr Tyr<br>     165                      180                      185                      190 | 576 |
| aac cag ctg ttc gag gaa aac ccc atc aac gcc agc ggc gtg gac gcc<br>Asn Gln Leu Phe Glu Glu Asn Pro Ile Asn Ala Ser Gly Val Asp Ala<br>           195                      200                      205 | 624 |
| aag gcc atc ctg tct gcc aga ctg agc aag agc aga cgg ctg gaa aat<br>Lys Ala Ile Leu Ser Ala Arg Leu Ser Lys Ser Arg Arg Leu Glu Asn<br>210                        215                        220 | 672 |
| ctg atc gcc cag ctg ccc ggc gag aag aag aat ggc ctg ttc ggc aac<br>Leu Ile Ala Gln Leu Pro Gly Glu Lys Lys Asn Gly Leu Phe Gly Asn<br>225                        230                        235                      240 | 720 |
| ctg att gcc ctg agc ctg ggc ctg acc ccc aac ttc aag agc aac ttc<br>Leu Ile Ala Leu Ser Leu Gly Leu Thr Pro Asn Phe Lys Ser Asn Phe<br>           245                      250                      255 | 768 |
| gac ctg gcc gag gat gcc aaa ctg cag ctg agc aag gac acc tac gac<br>Asp Leu Ala Glu Asp Ala Lys Leu Gln Leu Ser Lys Asp Thr Tyr Asp<br>                260                      265                      270 | 816 |
| gac gac ctg gac aac ctg ctg gcc cag atc ggc gac cag tac gcc gac<br>Asp Asp Leu Asp Asn Leu Leu Ala Gln Ile Gly Asp Gln Tyr Ala Asp<br>275                        280                        285 | 864 |
| ctg ttt ctg gcc gcc aag aac ctg tcc gac gcc atc ctg ctg agc gac<br>Leu Phe Leu Ala Ala Lys Asn Leu Ser Asp Ala Ile Leu Leu Ser Asp<br>     290                      295                      300 | 912 |
| atc ctg aga gtg aac acc gag atc acc aag gcc ccc ctg agc gcc tct<br>Ile Leu Arg Val Asn Thr Glu Ile Thr Lys Ala Pro Leu Ser Ala Ser<br>305                        310                        315                      320 | 960 |
| atg atc aag aga tac gac gag cac cac cag gac ctg acc ctg ctg aaa<br>Met Ile Lys Arg Tyr Asp Glu His His Gln Asp Leu Thr Leu Leu Lys<br>                325                      330                      335 | 1008 |
| gct ctc gtg cgg cag cag ctg cct gag aag tac aaa gag att ttc ttc<br>Ala Leu Val Arg Gln Gln Leu Pro Glu Lys Tyr Lys Glu Ile Phe Phe<br>                    340                      345                      350 | 1056 |
| gac cag agc aag aac ggc tac gcc ggc tac att gac ggc gga gcc agc<br>Asp Gln Ser Lys Asn Gly Tyr Ala Gly Tyr Ile Asp Gly Gly Ala Ser<br>                        355                      360                      365 | 1104 |
| cag gaa gag ttc tac aag ttc atc aag ccc atc ctg gaa aag atg gac<br>Gln Glu Glu Phe Tyr Lys Phe Ile Lys Pro Ile Leu Glu Lys Met Asp<br>370                        375                        380 | 1152 |
| ggc acc gag gaa ctg ctc gtg aag ctg aac aga gag gac ctg ctg cgg<br>Gly Thr Glu Glu Leu Leu Val Lys Leu Asn Arg Glu Asp Leu Leu Arg<br>385                        390                        395                      400 | 1200 |
| aag cag cgg acc ttc gac aac ggc agc atc ccc cac cag atc cac ctg<br>Lys Gln Arg Thr Phe Asp Asn Gly Ser Ile Pro His Gln Ile His Leu<br>                    405                      410                      415 | 1248 |
| gga gag ctg cac gcc att ctg cgg cgg cag gaa gat ttt tac cca ttc<br>Gly Glu Leu His Ala Ile Leu Arg Arg Gln Glu Asp Phe Tyr Pro Phe<br>                420                      425                      430 | 1296 |
| ctg aag gac aac cgg gaa aag atc gag aag atc ctg acc ttc cgc atc<br>Leu Lys Asp Asn Arg Glu Lys Ile Glu Lys Ile Leu Thr Phe Arg Ile<br>                        435                      440                      445 | 1344 |
| ccc tac tac gtg ggc cct ctg gcc agg gga aac agc aga ttc gcc tgg<br>Pro Tyr Tyr Val Gly Pro Leu Ala Arg Gly Asn Ser Arg Phe Ala Trp<br>450                        455                        460 | 1392 |
| atg acc aga aag agc gag gaa acc atc acc ccc tgg aac ttc gag gaa | 1440 |

-continued

```
                Met Thr Arg Lys Ser Glu Glu Thr Ile Thr Pro Trp Asn Phe Glu
                465                 470                 475                 480 gtg gtg gac aag ggc gct tcc gcc cag agc ttc atc gag cgg atg acc         1488
Val Val Asp Lys Gly Ala Ser Ala Gln Ser Phe Ile Glu Arg Met Thr
                    485                 490                 495 aac ttc gat aag aac ctg ccc aac gag aag gtg ctg ccc aag cac agc         1536
Asn Phe Asp Lys Asn Leu Pro Asn Glu Lys Val Leu Pro Lys His Ser
                500                 505                 510 ctg ctg tac gag tac ttc acc gtg tat aac gag ctg acc aaa gtg aaa         1584
Leu Leu Tyr Glu Tyr Phe Thr Val Tyr Asn Glu Leu Thr Lys Val Lys
            515                 520                 525 tac gtg acc gag gga atg aga aag ccc gcc ttc ctg agc ggc gag cag         1632
Tyr Val Thr Glu Gly Met Arg Lys Pro Ala Phe Leu Ser Gly Glu Gln
        530                 535                 540 aaa aag gcc atc gtg gac ctg ctg ttc aag acc aac cgg aaa gtg acc         1680
Lys Lys Ala Ile Val Asp Leu Leu Phe Lys Thr Asn Arg Lys Val Thr
545                 550                 555                 560 gtg aag cag ctg aaa gag gac tac ttc aag aaa atc gag tgc ttc gac         1728
Val Lys Gln Leu Lys Glu Asp Tyr Phe Lys Lys Ile Glu Cys Phe Asp
                    565                 570                 575 tcc gtg gaa atc tcc ggc gtg gaa gat cgg ttc aac gcc tcc ctg ggc         1776
Ser Val Glu Ile Ser Gly Val Glu Asp Arg Phe Asn Ala Ser Leu Gly
                580                 585                 590 aca tac cac gat ctg ctg aaa att atc aag gac aag gac ttc ctg gac         1824
Thr Tyr His Asp Leu Leu Lys Ile Ile Lys Asp Lys Asp Phe Leu Asp
            595                 600                 605 aat gag gaa aac gag gac att ctg gaa gat atc gtg ctg acc ctg aca         1872
Asn Glu Glu Asn Glu Asp Ile Leu Glu Asp Ile Val Leu Thr Leu Thr
        610                 615                 620 ctg ttt gag gac aga gag atg atc gag gaa cgg ctg aaa acc tat gcc         1920
Leu Phe Glu Asp Arg Glu Met Ile Glu Glu Arg Leu Lys Thr Tyr Ala
625                 630                 635                 640 cac ctg ttc gac gac aaa gtg atg aag cag ctg aag cgg cgg aga tac         1968
His Leu Phe Asp Asp Lys Val Met Lys Gln Leu Lys Arg Arg Arg Tyr
                    645                 650                 655 acc ggc tgg ggc agg ctg agc cgg aag ctg atc aac ggc atc cgg gac         2016
Thr Gly Trp Gly Arg Leu Ser Arg Lys Leu Ile Asn Gly Ile Arg Asp
                660                 665                 670 aag cag tcc ggc aag aca atc ctg gat ttc ctg aag tcc gac ggc ttc         2064
Lys Gln Ser Gly Lys Thr Ile Leu Asp Phe Leu Lys Ser Asp Gly Phe
            675                 680                 685 gcc aac aga aac ttc atg cag ctg atc cac gac gac agc ctg acc ttt         2112
Ala Asn Arg Asn Phe Met Gln Leu Ile His Asp Asp Ser Leu Thr Phe
        690                 695                 700 aaa gag gac atc cag aaa gcc cag gtg tcc ggc cag ggc gat agc ctg         2160
Lys Glu Asp Ile Gln Lys Ala Gln Val Ser Gly Gln Gly Asp Ser Leu
705                 710                 715                 720 cac gag cac att gcc aat ctg gcc ggc agc ccc gcc att aag aag ggc         2208
His Glu His Ile Ala Asn Leu Ala Gly Ser Pro Ala Ile Lys Lys Gly
                    725                 730                 735 atc ctg cag aca gtg aag gtg gtg gac gag ctc gtg aaa gtg atg ggc         2256
Ile Leu Gln Thr Val Lys Val Val Asp Glu Leu Val Lys Val Met Gly
                740                 745                 750 cgg cac aag ccc gag aac atc gtg atc gaa atg gcc aga gag aac cag         2304
Arg His Lys Pro Glu Asn Ile Val Ile Glu Met Ala Arg Glu Asn Gln
            755                 760                 765 acc acc cag aag gga cag aag aac agc cgc gag aga atg aag cgg atc         2352
Thr Thr Gln Lys Gly Gln Lys Asn Ser Arg Glu Arg Met Lys Arg Ile
        770                 775                 780
```

-continued

| | |
|---|---|
| gaa gag ggc atc aaa gag ctg ggc agc cag atc ctg aaa gaa cac ccc<br>Glu Glu Gly Ile Lys Glu Leu Gly Ser Gln Ile Leu Lys Glu His Pro<br>785                    790                  795                  800 | 2400 |
| gtg gaa aac acc cag ctg cag aac gag aag ctg tac ctg tac tac ctg<br>Val Glu Asn Thr Gln Leu Gln Asn Glu Lys Leu Tyr Leu Tyr Tyr Leu<br>            805                  810                  815 | 2448 |
| cag aat ggg cgg gat atg tac gtg gac cag gaa ctg gac atc aac cgg<br>Gln Asn Gly Arg Asp Met Tyr Val Asp Gln Glu Leu Asp Ile Asn Arg<br>820                    825                  830 | 2496 |
| ctg tcc gac tac gat gtg gac cat atc gtg cct cag agc ttt ctg aag<br>Leu Ser Asp Tyr Asp Val Asp His Ile Val Pro Gln Ser Phe Leu Lys<br>            835                  840                  845 | 2544 |
| gac gac tcc atc gac aac aag gtg ctg acc aga agc gac aag aac cgg<br>Asp Asp Ser Ile Asp Asn Lys Val Leu Thr Arg Ser Asp Lys Asn Arg<br>850                    855                  860 | 2592 |
| ggc aag agc gac aac gtg ccc tcc gaa gag gtc gtg aag aag atg aag<br>Gly Lys Ser Asp Asn Val Pro Ser Glu Glu Val Val Lys Lys Met Lys<br>865                    870                  875                  880 | 2640 |
| aac tac tgg cgg cag ctg ctg aac gcc aag ctg att acc cag aga aag<br>Asn Tyr Trp Arg Gln Leu Leu Asn Ala Lys Leu Ile Thr Gln Arg Lys<br>                  885                  890                  895 | 2688 |
| ttc gac aat ctg acc aag gcc gag aga ggc ggc ctg agc gaa ctg gat<br>Phe Asp Asn Leu Thr Lys Ala Glu Arg Gly Gly Leu Ser Glu Leu Asp<br>            900                  905                  910 | 2736 |
| aag gcc ggc ttc atc aag aga cag ctg gtg gaa acc cgg cag atc aca<br>Lys Ala Gly Phe Ile Lys Arg Gln Leu Val Glu Thr Arg Gln Ile Thr<br>915                    920                  925 | 2784 |
| aag cac gtg gca cag atc ctg gac tcc cgg atg aac act aag tac gac<br>Lys His Val Ala Gln Ile Leu Asp Ser Arg Met Asn Thr Lys Tyr Asp<br>930                    935                  940 | 2832 |
| gag aat gac aag ctg atc cgg gaa gtg aaa gtg atc acc ctg aag tcc<br>Glu Asn Asp Lys Leu Ile Arg Glu Val Lys Val Ile Thr Leu Lys Ser<br>945                    950                  955                  960 | 2880 |
| aag ctg gtg tcc gat ttc cgg aag gat ttc cag ttt tac aaa gtg cgc<br>Lys Leu Val Ser Asp Phe Arg Lys Asp Phe Gln Phe Tyr Lys Val Arg<br>                  965                  970                  975 | 2928 |
| gag atc aac aac tac cac cac gcc cac gac gcc tac ctg aac gcc gtc<br>Glu Ile Asn Asn Tyr His His Ala His Asp Ala Tyr Leu Asn Ala Val<br>            980                  985                  990 | 2976 |
| gtg gga acc gcc ctg atc aaa aag tac cct aag ctg gaa agc gag ttc<br>Val Gly Thr Ala Leu Ile Lys Lys Tyr Pro Lys Leu Glu Ser Glu Phe<br>        995                  1000                  1005 | 3024 |
| gtg tac ggc gac tac aag gtg tac gac gtg cgg aag atg atc gcc<br>Val Tyr Gly Asp Tyr Lys Val Tyr Asp Val Arg Lys Met Ile Ala<br>1010                    1015                  1020 | 3069 |
| aag agc gag cag gaa atc ggc aag gct acc gcc aag tac ttc ttc<br>Lys Ser Glu Gln Glu Ile Gly Lys Ala Thr Ala Lys Tyr Phe Phe<br>1025                    1030                  1035 | 3114 |
| tac agc aac atc atg aac ttt ttc aag acc gag att acc ctg gcc<br>Tyr Ser Asn Ile Met Asn Phe Phe Lys Thr Glu Ile Thr Leu Ala<br>1040                    1045                  1050 | 3159 |
| aac ggc gag atc cgg aag cgg cct ctg atc gag aca aac ggc gaa<br>Asn Gly Glu Ile Arg Lys Arg Pro Leu Ile Glu Thr Asn Gly Glu<br>1055                    1060                  1065 | 3204 |
| acc ggg gag atc gtg tgg gat aag ggc cgg gat ttt gcc acc gtg<br>Thr Gly Glu Ile Val Trp Asp Lys Gly Arg Asp Phe Ala Thr Val<br>1070                    1075                  1080 | 3249 |
| cgg aaa gtg ctg agc atg ccc caa gtg aat atc gtg aaa aag acc<br>Arg Lys Val Leu Ser Met Pro Gln Val Asn Ile Val Lys Lys Thr<br>1085                    1090                  1095 | 3294 |

-continued

| | | |
|---|---|---|
| gag gtg cag aca ggc ggc ttc agc aaa gag tct atc cgg ccc aag<br>Glu Val Gln Thr Gly Gly Phe Ser Lys Glu Ser Ile Arg Pro Lys<br>1100                     1105                    1110 | 3339 |
| agg aac agc gat aag ctg atc gcc aga aag aag gac tgg gac cct<br>Arg Asn Ser Asp Lys Leu Ile Ala Arg Lys Lys Asp Trp Asp Pro<br>1115                   1120                  1125 | 3384 |
| aag aag tac ggc ggc ttc gac agc ccc acc gtg gcc tat tct gtg<br>Lys Lys Tyr Gly Gly Phe Asp Ser Pro Thr Val Ala Tyr Ser Val<br>1130                   1135                  1140 | 3429 |
| ctg gtg gtg gcc aaa gtg gaa aag ggc aag tcc aag aaa ctg aag<br>Leu Val Val Ala Lys Val Glu Lys Gly Lys Ser Lys Lys Leu Lys<br>1145                   1150                  1155 | 3474 |
| agt gtg aaa gag ctg ctg ggg atc acc atc atg gaa aga agc agc<br>Ser Val Lys Glu Leu Leu Gly Ile Thr Ile Met Glu Arg Ser Ser<br>1160                   1165                  1170 | 3519 |
| ttc gag aag aat ccc atc gac ttt ctg gaa gcc aag ggc tac aaa<br>Phe Glu Lys Asn Pro Ile Asp Phe Leu Glu Ala Lys Gly Tyr Lys<br>1175                   1180                  1185 | 3564 |
| gaa gtg aaa aag gac ctg atc atc aag ctg cct aag tac tcc ctg<br>Glu Val Lys Lys Asp Leu Ile Ile Lys Leu Pro Lys Tyr Ser Leu<br>1190                   1195                  1200 | 3609 |
| ttc gag ctg gaa aac ggc cgg aag aga atg ctg gcc tct gcc cgg<br>Phe Glu Leu Glu Asn Gly Arg Lys Arg Met Leu Ala Ser Ala Arg<br>1205                   1210                  1215 | 3654 |
| gaa ctg cag aag gga aac gaa ctg gcc ctg ccc tcc aaa tat gtg<br>Glu Leu Gln Lys Gly Asn Glu Leu Ala Leu Pro Ser Lys Tyr Val<br>1220                   1225                  1230 | 3699 |
| aac ttc ctg tac ctg gcc agc cac tat gag aag ctg aag ggc tcc<br>Asn Phe Leu Tyr Leu Ala Ser His Tyr Glu Lys Leu Lys Gly Ser<br>1235                   1240                  1245 | 3744 |
| ccc gag gat aat gag cag aaa cag ctg ttt gtg gaa cag cac aag<br>Pro Glu Asp Asn Glu Gln Lys Gln Leu Phe Val Glu Gln His Lys<br>1250                   1255                  1260 | 3789 |
| cac tac ctg gac gag atc atc gag cag atc agc gag ttc tcc aag<br>His Tyr Leu Asp Glu Ile Ile Glu Gln Ile Ser Glu Phe Ser Lys<br>1265                   1270                  1275 | 3834 |
| aga gtg atc ctg gcc gac gct aat ctg gac aaa gtg ctg tcc gcc<br>Arg Val Ile Leu Ala Asp Ala Asn Leu Asp Lys Val Leu Ser Ala<br>1280                   1285                  1290 | 3879 |
| tac aac aag cac cgg gat aag ccc atc aga gag cag gcc gag aat<br>Tyr Asn Lys His Arg Asp Lys Pro Ile Arg Glu Gln Ala Glu Asn<br>1295                   1300                  1305 | 3924 |
| atc atc cac ctg ttt acc ctg acc aat ctg gga gcc cct cgg gcc<br>Ile Ile His Leu Phe Thr Leu Thr Asn Leu Gly Ala Pro Arg Ala<br>1310                   1315                  1320 | 3969 |
| ttc aag tac ttt gac acc acc atc cgg cgg aag gcc tac cgg agc<br>Phe Lys Tyr Phe Asp Thr Thr Ile Arg Arg Lys Ala Tyr Arg Ser<br>1325                   1330                  1335 | 4014 |
| acc aaa gag gtg ctg gac gcc acc ctg atc cac cag agc atc acc<br>Thr Lys Glu Val Leu Asp Ala Thr Leu Ile His Gln Ser Ile Thr<br>1340                   1345                  1350 | 4059 |
| ggc ctg tac gag aca cgg atc gac ctg tct cag ctg gga ggc gac<br>Gly Leu Tyr Glu Thr Arg Ile Asp Leu Ser Gln Leu Gly Gly Asp<br>1355                   1360                  1365 | 4104 |
| taa | 4107 |

<210> SEQ ID NO 9
<211> LENGTH: 4107
<212> TYPE: DNA

```
<213> ORGANISM: Streptococcus pyogenes
<220> FEATURE:
<221> NAME/KEY: CDS
<222> LOCATION: (1)..(4107)

<400> SEQUENCE: 9 atg gac aag aag tac agc atc ggc ctg gac atc ggc acc aac tct gtg      48
Met Asp Lys Lys Tyr Ser Ile Gly Leu Asp Ile Gly Thr Asn Ser Val
1               5                   10                  15 ggc tgg gcc gtg atc acc gac gag tac aag gtg ccc agc aag aaa ttc      96
Gly Trp Ala Val Ile Thr Asp Glu Tyr Lys Val Pro Ser Lys Lys Phe
                20                  25                  30 aag gtg ctg ggc aac acc gac cgg cac agc atc aag aag aac ctg atc     144
Lys Val Leu Gly Asn Thr Asp Arg His Ser Ile Lys Lys Asn Leu Ile
        35                  40                  45 gga gcc ctg ctg ttc gac agc ggc gaa aca gcc gag gcc acc cgg ctg     192
Gly Ala Leu Leu Phe Asp Ser Gly Glu Thr Ala Glu Ala Thr Arg Leu
    50                  55                  60 aag aga acc gcc aga aga aga tac acc aga cgg aag aac cgg atc tgc     240
Lys Arg Thr Ala Arg Arg Arg Tyr Thr Arg Arg Lys Asn Arg Ile Cys
65                  70                  75                  80 tat ctg caa gag atc ttc agc aac gag atg gcc aag gtg gac gac agc     288
Tyr Leu Gln Glu Ile Phe Ser Asn Glu Met Ala Lys Val Asp Asp Ser
                85                  90                  95 ttc ttc cac aga ctg gaa gag tcc ttc ctg gtg gaa gag gat aag aag     336
Phe Phe His Arg Leu Glu Glu Ser Phe Leu Val Glu Glu Asp Lys Lys
                100                 105                 110 cac gag cgg cac ccc atc ttc ggc aac atc gtg gac gag gtg gcc tac     384
His Glu Arg His Pro Ile Phe Gly Asn Ile Val Asp Glu Val Ala Tyr
        115                 120                 125 cac gag aag tac ccc acc atc tac cac ctg aga aag aaa ctg gtg gac     432
His Glu Lys Tyr Pro Thr Ile Tyr His Leu Arg Lys Lys Leu Val Asp
    130                 135                 140 agc acc gac aag gcc gac ctg cgg ctg atc tat ctg gcc ctg gcc cac     480
Ser Thr Asp Lys Ala Asp Leu Arg Leu Ile Tyr Leu Ala Leu Ala His
145                 150                 155                 160 atg atc aag ttc cgg ggc cac ttc ctg atc gag ggc gac ctg aac ccc     528
Met Ile Lys Phe Arg Gly His Phe Leu Ile Glu Gly Asp Leu Asn Pro
                165                 170                 175 gac aac agc gac gtg gac aag ctg ttc atc cag ctg gtg cag acc tac     576
Asp Asn Ser Asp Val Asp Lys Leu Phe Ile Gln Leu Val Gln Thr Tyr
                180                 185                 190 aac cag ctg ttc gag gaa aac ccc atc aac gcc agc ggc gtg gac gcc     624
Asn Gln Leu Phe Glu Glu Asn Pro Ile Asn Ala Ser Gly Val Asp Ala
        195                 200                 205 aag gcc atc ctg tct gcc aga ctg agc aag agc aga cgg ctg gaa aat     672
Lys Ala Ile Leu Ser Ala Arg Leu Ser Lys Ser Arg Arg Leu Glu Asn
    210                 215                 220 ctg atc gcc cag ctg ccc ggc gag aag aag aat ggc ctg ttc ggc aac     720
Leu Ile Ala Gln Leu Pro Gly Glu Lys Lys Asn Gly Leu Phe Gly Asn
225                 230                 235                 240 ctg att gcc ctg agc ctg ggc ctg acc ccc aac ttc aag agc aac ttc     768
Leu Ile Ala Leu Ser Leu Gly Leu Thr Pro Asn Phe Lys Ser Asn Phe
                245                 250                 255 gac ctg gcc gag gat gcc aaa ctg cag ctg agc aag gac acc tac gac     816
Asp Leu Ala Glu Asp Ala Lys Leu Gln Leu Ser Lys Asp Thr Tyr Asp
                260                 265                 270 gac gac ctg gac aac ctg ctg gcc cag atc ggc gac cag tac gcc gac     864
Asp Asp Leu Asp Asn Leu Leu Ala Gln Ile Gly Asp Gln Tyr Ala Asp
        275                 280                 285
```

```
ctg ttt ctg gcc gcc aag aac ctg tcc gac gcc atc ctg ctg agc gac         912
Leu Phe Leu Ala Ala Lys Asn Leu Ser Asp Ala Ile Leu Leu Ser Asp
    290             295                 300 atc ctg aga gtg aac acc gag atc acc aag gcc ccc ctg agc gcc tct         960
Ile Leu Arg Val Asn Thr Glu Ile Thr Lys Ala Pro Leu Ser Ala Ser
305                 310                 315                 320 atg atc aag aga tac gac gag cac cac cag gac ctg acc ctg ctg aaa        1008
Met Ile Lys Arg Tyr Asp Glu His His Gln Asp Leu Thr Leu Leu Lys
                325                 330                 335 gct ctc gtg cgg cag cag ctg cct gag aag tac aaa gag att ttc ttc        1056
Ala Leu Val Arg Gln Gln Leu Pro Glu Lys Tyr Lys Glu Ile Phe Phe
            340                 345                 350 gac cag agc aag aac ggc tac gcc ggc tac att gac ggc gga gcc agc        1104
Asp Gln Ser Lys Asn Gly Tyr Ala Gly Tyr Ile Asp Gly Gly Ala Ser
        355                 360                 365 cag gaa gag ttc tac aag ttc atc aag ccc atc ctg gaa aag atg gac        1152
Gln Glu Glu Phe Tyr Lys Phe Ile Lys Pro Ile Leu Glu Lys Met Asp
    370                 375                 380 ggc acc gag gaa ctg ctc gtg aag ctg aac aga gag gac ctg ctg cgg        1200
Gly Thr Glu Glu Leu Leu Val Lys Leu Asn Arg Glu Asp Leu Leu Arg
385                 390                 395                 400 aag cag cgg acc ttc gac aac ggc agc atc ccc cac cag atc cac ctg        1248
Lys Gln Arg Thr Phe Asp Asn Gly Ser Ile Pro His Gln Ile His Leu
                405                 410                 415 gga gag ctg cac gcc att ctg cgg cgg cag gaa gat ttt tac cca ttc        1296
Gly Glu Leu His Ala Ile Leu Arg Arg Gln Glu Asp Phe Tyr Pro Phe
            420                 425                 430 ctg aag gac aac cgg gaa aag atc gag aag atc ctg acc ttc cgc atc        1344
Leu Lys Asp Asn Arg Glu Lys Ile Glu Lys Ile Leu Thr Phe Arg Ile
        435                 440                 445 ccc tac tac gtg ggc cct ctg gcc agg gga aac agc aga ttc gcc tgg        1392
Pro Tyr Tyr Val Gly Pro Leu Ala Arg Gly Asn Ser Arg Phe Ala Trp
    450                 455                 460 atg acc aga aag agc gag gaa acc atc acc ccc tgg aac ttc gag gaa        1440
Met Thr Arg Lys Ser Glu Glu Thr Ile Thr Pro Trp Asn Phe Glu Glu
465                 470                 475                 480 gtg gtg gac aag ggc gct tcc gcc cag agc ttc atc gag cgg atg acc        1488
Val Val Asp Lys Gly Ala Ser Ala Gln Ser Phe Ile Glu Arg Met Thr
                485                 490                 495 aac ttc gat aag aac ctg ccc aac gag aag gtg ctg ccc aag cac agc        1536
Asn Phe Asp Lys Asn Leu Pro Asn Glu Lys Val Leu Pro Lys His Ser
            500                 505                 510 ctg ctg tac gag tac ttc acc gtg tat aac gag ctg acc aaa gtg aaa        1584
Leu Leu Tyr Glu Tyr Phe Thr Val Tyr Asn Glu Leu Thr Lys Val Lys
        515                 520                 525 tac gtg acc gag gga atg aga aag ccc gcc ttc ctg agc ggc gag cag        1632
Tyr Val Thr Glu Gly Met Arg Lys Pro Ala Phe Leu Ser Gly Glu Gln
    530                 535                 540 aaa aag gcc atc gtg gac ctg ctg ttc aag acc aac cgg aaa gtg acc        1680
Lys Lys Ala Ile Val Asp Leu Leu Phe Lys Thr Asn Arg Lys Val Thr
545                 550                 555                 560 gtg aag cag ctg aaa gag gac tac ttc aag aaa atc gag tgc ttc gac        1728
Val Lys Gln Leu Lys Glu Asp Tyr Phe Lys Lys Ile Glu Cys Phe Asp
                565                 570                 575 tcc gtg gaa atc tcc ggc gtg gaa gat cgg ttc aac gcc tcc ctg ggc        1776
Ser Val Glu Ile Ser Gly Val Glu Asp Arg Phe Asn Ala Ser Leu Gly
            580                 585                 590 aca tac cac gat ctg ctg aaa att atc aag gac aag gac ttc ctg gac        1824
Thr Tyr His Asp Leu Leu Lys Ile Ile Lys Asp Lys Asp Phe Leu Asp
        595                 600                 605
```

```
aat gag gaa aac gag gac att ctg gaa gat atc gtg ctg acc ctg aca      1872
Asn Glu Glu Asn Glu Asp Ile Leu Glu Asp Ile Val Leu Thr Leu Thr
    610                 615                 620 ctg ttt gag gac aga gag atg atc gag gaa cgg ctg aaa acc tat gcc      1920
Leu Phe Glu Asp Arg Glu Met Ile Glu Glu Arg Leu Lys Thr Tyr Ala
625                 630                 635                 640 cac ctg ttc gac gac aaa gtg atg aag cag ctg aag cgg cgg aga tac      1968
His Leu Phe Asp Asp Lys Val Met Lys Gln Leu Lys Arg Arg Arg Tyr
                645                 650                 655 acc ggc tgg ggc agg ctg agc cgg aag ctg atc aac ggc atc cgg gac      2016
Thr Gly Trp Gly Arg Leu Ser Arg Lys Leu Ile Asn Gly Ile Arg Asp
            660                 665                 670 aag cag tcc ggc aag aca atc ctg gat ttc ctg aag tcc gac ggc ttc      2064
Lys Gln Ser Gly Lys Thr Ile Leu Asp Phe Leu Lys Ser Asp Gly Phe
        675                 680                 685 gcc aac aga aac ttc atg cag ctg atc cac gac gac agc ctg acc ttt      2112
Ala Asn Arg Asn Phe Met Gln Leu Ile His Asp Asp Ser Leu Thr Phe
    690                 695                 700 aaa gag gac atc cag aaa gcc cag gtg tcc ggc cag ggc gat agc ctg      2160
Lys Glu Asp Ile Gln Lys Ala Gln Val Ser Gly Gln Gly Asp Ser Leu
705                 710                 715                 720 cac gag cac att gcc aat ctg gcc ggc agc ccc gcc att aag aag ggc      2208
His Glu His Ile Ala Asn Leu Ala Gly Ser Pro Ala Ile Lys Lys Gly
                725                 730                 735 atc ctg cag aca gtg aag gtg gtg gac gag ctc gtg aaa gtg atg ggc      2256
Ile Leu Gln Thr Val Lys Val Val Asp Glu Leu Val Lys Val Met Gly
            740                 745                 750 cgg cac aag ccc gag aac atc gtg atc gaa atg gcc aga gag aac cag      2304
Arg His Lys Pro Glu Asn Ile Val Ile Glu Met Ala Arg Glu Asn Gln
        755                 760                 765 acc acc cag aag gga cag aag aac agc cgc gag aga atg aag cgg atc      2352
Thr Thr Gln Lys Gly Gln Lys Asn Ser Arg Glu Arg Met Lys Arg Ile
    770                 775                 780 gaa gag ggc atc aaa gag ctg ggc agc cag atc ctg aaa gaa cac ccc      2400
Glu Glu Gly Ile Lys Glu Leu Gly Ser Gln Ile Leu Lys Glu His Pro
785                 790                 795                 800 gtg gaa aac acc cag ctg cag aac gag aag ctg tac ctg tac tac ctg      2448
Val Glu Asn Thr Gln Leu Gln Asn Glu Lys Leu Tyr Leu Tyr Tyr Leu
                805                 810                 815 cag aat ggg cgg gat atg tac gtg gac cag gaa ctg gac atc aac cgg      2496
Gln Asn Gly Arg Asp Met Tyr Val Asp Gln Glu Leu Asp Ile Asn Arg
            820                 825                 830 ctg tcc gac tac gat gtg gac cat atc gtg cct cag agc ttt ctg aag      2544
Leu Ser Asp Tyr Asp Val Asp His Ile Val Pro Gln Ser Phe Leu Lys
        835                 840                 845 gac gac tcc atc gac aac aag gtg ctg acc aga agc gac aag aac cgg      2592
Asp Asp Ser Ile Asp Asn Lys Val Leu Thr Arg Ser Asp Lys Asn Arg
    850                 855                 860 ggc aag agc gac aac gtg ccc tcc gaa gag gtc gtg aag aag atg aag      2640
Gly Lys Ser Asp Asn Val Pro Ser Glu Glu Val Val Lys Lys Met Lys
865                 870                 875                 880 aac tac tgg cgg cag ctg ctg aac gcc aag ctg att acc cag aga aag      2688
Asn Tyr Trp Arg Gln Leu Leu Asn Ala Lys Leu Ile Thr Gln Arg Lys
                885                 890                 895 ttc gac aat ctg acc aag gcc gag aga ggc ggc ctg agc gaa ctg gat      2736
Phe Asp Asn Leu Thr Lys Ala Glu Arg Gly Gly Leu Ser Glu Leu Asp
            900                 905                 910 aag gcc ggc ttc atc aag aga cag ctg gtg gaa acc cgg cag atc aca      2784
Lys Ala Gly Phe Ile Lys Arg Gln Leu Val Glu Thr Arg Gln Ile Thr
```

-continued

```
                915                 920                 925 aag  cac  gtg  gca  cag  atc  ctg  gac  tcc  cgg  atg  aac  act  aag  tac  gac      2832
Lys  His  Val  Ala  Gln  Ile  Leu  Asp  Ser  Arg  Met  Asn  Thr  Lys  Tyr  Asp
     930                      935                      940 gag  aat  gac  aag  ctg  atc  cgg  gaa  gtg  aaa  gtg  atc  acc  ctg  aag  tcc      2880
Glu  Asn  Asp  Lys  Leu  Ile  Arg  Glu  Val  Lys  Val  Ile  Thr  Leu  Lys  Ser
945                      950                      955                      960 aag  ctg  gtg  tcc  gat  ttc  cgg  aag  gat  ttc  cag  ttt  tac  aaa  gtg  cgc      2928
Lys  Leu  Val  Ser  Asp  Phe  Arg  Lys  Asp  Phe  Gln  Phe  Tyr  Lys  Val  Arg
                    965                      970                      975 gag  atc  aac  aac  tac  cac  cac  gcc  cac  gac  gcc  tac  ctg  aac  gcc  gtc      2976
Glu  Ile  Asn  Asn  Tyr  His  His  Ala  His  Asp  Ala  Tyr  Leu  Asn  Ala  Val
                         980                      985                      990 gtg  gga  acc  gcc  ctg  atc  aaa  aag   tac  cct  aag  ctg  gaa   agc  gag  ttc     3024
Val  Gly  Thr  Ala  Leu  Ile  Lys  Lys   Tyr  Pro  Lys  Leu  Glu   Ser  Glu  Phe
                              995                      1000                     1005 gtg  tac  ggc  gac  tac  aag  gtg   tac  gac  gtg  cgg  aag   atg  atc  gcc           3069
Val  Tyr  Gly  Asp  Tyr  Lys  Val   Tyr  Asp  Val  Arg  Lys   Met  Ile  Ala
               1010                     1015                     1020 aag  agc  gag  cag  gaa  atc  ggc   aag  gct  acc  gcc  aag   tac  ttc  ttc           3114
Lys  Ser  Glu  Gln  Glu  Ile  Gly   Lys  Ala  Thr  Ala  Lys   Tyr  Phe  Phe
     1025                     1030                     1035 tac  agc  aac  atc  atg  aac  ttt   ttc  aag  acc  gag  att   acc  ctg  gcc           3159
Tyr  Ser  Asn  Ile  Met  Asn  Phe   Phe  Lys  Thr  Glu  Ile   Thr  Leu  Ala
     1040                     1045                     1050 aac  ggc  gag  atc  cgg  aag  cgg   cct  ctg  atc  gag  aca   aac  ggc  gaa           3204
Asn  Gly  Glu  Ile  Arg  Lys  Arg   Pro  Leu  Ile  Glu  Thr   Asn  Gly  Glu
     1055                     1060                     1065 acc  ggg  gag  atc  gtg  tgg  gat   aag  ggc  cgg  gat  ttt   gcc  acc  gtg           3249
Thr  Gly  Glu  Ile  Val  Trp  Asp   Lys  Gly  Arg  Asp  Phe   Ala  Thr  Val
     1070                     1075                     1080 cgg  aaa  gtg  ctg  agc  atg  ccc   caa  gtg  aat  atc  gtg   aaa  aag  acc           3294
Arg  Lys  Val  Leu  Ser  Met  Pro   Gln  Val  Asn  Ile  Val   Lys  Lys  Thr
     1085                     1090                     1095 gag  gtg  cag  aca  ggc  ggc  ttc   agc  aaa  gag  tct  atc   cgg  ccc  aag           3339
Glu  Val  Gln  Thr  Gly  Gly  Phe   Ser  Lys  Glu  Ser  Ile   Arg  Pro  Lys
     1100                     1105                     1110 agg  aac  agc  gat  aag  ctg  atc   gcc  aga  aag  aag  gac   tgg  gac  cct           3384
Arg  Asn  Ser  Asp  Lys  Leu  Ile   Ala  Arg  Lys  Lys  Asp   Trp  Asp  Pro
     1115                     1120                     1125 aag  aag  tac  ggc  ggc  ttc  gac   agc  ccc  acc  gtg  gcc   tat  tct  gtg           3429
Lys  Lys  Tyr  Gly  Gly  Phe  Asp   Ser  Pro  Thr  Val  Ala   Tyr  Ser  Val
     1130                     1135                     1140 ctg  gtg  gtg  gcc  aaa  gtg  gaa   aag  ggc  aag  tcc  aag   aaa  ctg  aag           3474
Leu  Val  Val  Ala  Lys  Val  Glu   Lys  Gly  Lys  Ser  Lys   Lys  Leu  Lys
     1145                     1150                     1155 agt  gtg  aaa  gag  ctg  ctg  ggg   atc  acc  atc  atg  gaa   aga  agc  agc           3519
Ser  Val  Lys  Glu  Leu  Leu  Gly   Ile  Thr  Ile  Met  Glu   Arg  Ser  Ser
     1160                     1165                     1170 ttc  gag  aag  aat  ccc  atc  gac   ttt  ctg  gaa  gcc  aag   ggc  tac  aaa           3564
Phe  Glu  Lys  Asn  Pro  Ile  Asp   Phe  Leu  Glu  Ala  Lys   Gly  Tyr  Lys
     1175                     1180                     1185 gaa  gtg  aaa  aag  gac  ctg  atc   atc  aag  ctg  cct  aag   tac  tcc  ctg           3609
Glu  Val  Lys  Lys  Asp  Leu  Ile   Ile  Lys  Leu  Pro  Lys   Tyr  Ser  Leu
     1190                     1195                     1200 ttc  gag  ctg  gaa  aac  ggc  cgg   aag  aga  atg  ctg  gcc   tct  gcc  cgg           3654
Phe  Glu  Leu  Glu  Asn  Gly  Arg   Lys  Arg  Met  Leu  Ala   Ser  Ala  Arg
     1205                     1210                     1215 gaa  ctg  cag  aag  gga  aac  gaa   ctg  gcc  ctg  ccc  tcc   aaa  tat  gtg           3699
```

-continued

```
          Glu Leu Gln Lys Gly Asn Glu Leu Ala Leu Pro Ser Lys Tyr Val
              1220                1225                1230 aac ttc ctg tac ctg gcc agc cac tat gag aag ctg aag ggc tcc         3744
Asn Phe Leu Tyr Leu Ala Ser His Tyr Glu Lys Leu Lys Gly Ser
    1235                1240                1245 ccc gag gat aat gag cag aaa cag ctg ttt gtg gaa cag cac aag         3789
Pro Glu Asp Asn Glu Gln Lys Gln Leu Phe Val Glu Gln His Lys
1250                1255                1260 cac tac ctg gac gag atc atc gag cag atc agc gag ttc tcc aag         3834
His Tyr Leu Asp Glu Ile Ile Glu Gln Ile Ser Glu Phe Ser Lys
    1265                1270                1275 aga gtg atc ctg gcc cgg cgg aat ctg gac aaa gtg ctg tcc gcc         3879
Arg Val Ile Leu Ala Arg Arg Asn Leu Asp Lys Val Leu Ser Ala
    1280                1285                1290 tac aac aag cac cgg gat aag ccc atc aga gag cag gcc gag aat         3924
Tyr Asn Lys His Arg Asp Lys Pro Ile Arg Glu Gln Ala Glu Asn
    1295                1300                1305 atc atc cac ctg ttt acc ctg acc aat ctg gga gcc cct cgg gcc         3969
Ile Ile His Leu Phe Thr Leu Thr Asn Leu Gly Ala Pro Arg Ala
    1310                1315                1320 ttc aag tac ttt gac acc acc atc cgg cgg aag gcc tac cgg agc         4014
Phe Lys Tyr Phe Asp Thr Thr Ile Arg Arg Lys Ala Tyr Arg Ser
    1325                1330                1335 acc aaa gag gtg ctg gac gcc acc ctg atc cac cag agc atc acc         4059
Thr Lys Glu Val Leu Asp Ala Thr Leu Ile His Gln Ser Ile Thr
    1340                1345                1350 ggc ctg tac gag aca cgg atc gac ctg tct cag ctg gga ggc gac         4104
Gly Leu Tyr Glu Thr Arg Ile Asp Leu Ser Gln Leu Gly Gly Asp
    1355                1360                1365 taa                                                                 4107
```

```
<210> SEQ ID NO 10
<211> LENGTH: 4107
<212> TYPE: DNA
<213> ORGANISM: Streptococcus pyogenes
<220> FEATURE:
<221> NAME/KEY: CDS
<222> LOCATION: (1)..(4107)

<400> SEQUENCE: 10 atg gac aag aag tac agc atc ggc ctg gac atc ggc acc aac tct gtg     48
Met Asp Lys Lys Tyr Ser Ile Gly Leu Asp Ile Gly Thr Asn Ser Val
1               5                   10                  15 ggc tgg gcc gtg atc acc gac gag tac aag gtg ccc agc aag aaa ttc     96
Gly Trp Ala Val Ile Thr Asp Glu Tyr Lys Val Pro Ser Lys Lys Phe
            20                  25                  30 aag gtg ctg ggc aac acc gac cgg cac agc atc aag aag aac ctg atc    144
Lys Val Leu Gly Asn Thr Asp Arg His Ser Ile Lys Lys Asn Leu Ile
        35                  40                  45 gga gcc ctg ctg ttc gac agc ggc gaa aca gcc gag gcc acc cgg ctg    192
Gly Ala Leu Leu Phe Asp Ser Gly Glu Thr Ala Glu Ala Thr Arg Leu
    50                  55                  60 aag aga acc gcc aga aga aga tac acc aga cgg aag aac cgg atc tgc    240
Lys Arg Thr Ala Arg Arg Arg Tyr Thr Arg Arg Lys Asn Arg Ile Cys
65                  70                  75                  80 tat ctg caa gag atc ttc agc aac gag atg gcc aag gtg gac gac agc    288
Tyr Leu Gln Glu Ile Phe Ser Asn Glu Met Ala Lys Val Asp Asp Ser
                85                  90                  95 ttc ttc cac aga ctg gaa gag tcc ttc ctg gtg gaa gag gat aag aag    336
Phe Phe His Arg Leu Glu Glu Ser Phe Leu Val Glu Glu Asp Lys Lys
            100                 105                 110
```

```
cac gag cgg cac ccc atc ttc ggc aac atc gtg gac gag gtg gcc tac      384
His Glu Arg His Pro Ile Phe Gly Asn Ile Val Asp Glu Val Ala Tyr
            115                 120                 125 cac gag aag tac ccc acc atc tac cac ctg aga aag aaa ctg gtg gac      432
His Glu Lys Tyr Pro Thr Ile Tyr His Leu Arg Lys Lys Leu Val Asp
            130                 135                 140 agc acc gac aag gcc gac ctg cgg ctg atc tat ctg gcc ctg gcc cac      480
Ser Thr Asp Lys Ala Asp Leu Arg Leu Ile Tyr Leu Ala Leu Ala His
145                 150                 155                 160 atg atc aag ttc cgg ggc cac ttc ctg atc gag ggc gac ctg aac ccc      528
Met Ile Lys Phe Arg Gly His Phe Leu Ile Glu Gly Asp Leu Asn Pro
                165                 170                 175 gac aac agc gac gtg gac aag ctg ttc atc cag ctg gtg cag acc tac      576
Asp Asn Ser Asp Val Asp Lys Leu Phe Ile Gln Leu Val Gln Thr Tyr
            180                 185                 190 aac cag ctg ttc gag gaa aac ccc atc aac gcc agc ggc gtg gac gcc      624
Asn Gln Leu Phe Glu Glu Asn Pro Ile Asn Ala Ser Gly Val Asp Ala
            195                 200                 205 aag gcc atc ctg tct gcc aga ctg agc aag agc aga cgg ctg gaa aat      672
Lys Ala Ile Leu Ser Ala Arg Leu Ser Lys Ser Arg Arg Leu Glu Asn
        210                 215                 220 ctg atc gcc cag ctg ccc ggc gag aag aag aat ggc ctg ttc ggc aac      720
Leu Ile Ala Gln Leu Pro Gly Glu Lys Lys Asn Gly Leu Phe Gly Asn
225                 230                 235                 240 ctg att gcc ctg agc ctg ggc ctg acc ccc aac ttc aag agc aac ttc      768
Leu Ile Ala Leu Ser Leu Gly Leu Thr Pro Asn Phe Lys Ser Asn Phe
                245                 250                 255 gac ctg gcc gag gat gcc aaa ctg cag ctg agc aag gac acc tac gac      816
Asp Leu Ala Glu Asp Ala Lys Leu Gln Leu Ser Lys Asp Thr Tyr Asp
            260                 265                 270 gac gac ctg gac aac ctg ctg gcc cag atc ggc gac cag tac gcc gac      864
Asp Asp Leu Asp Asn Leu Leu Ala Gln Ile Gly Asp Gln Tyr Ala Asp
            275                 280                 285 ctg ttt ctg gcc gcc aag aac ctg tcc gac gcc atc ctg ctg agc gac      912
Leu Phe Leu Ala Ala Lys Asn Leu Ser Asp Ala Ile Leu Leu Ser Asp
        290                 295                 300 atc ctg aga gtg aac acc gag atc acc aag gcc ccc ctg agc gcc tct      960
Ile Leu Arg Val Asn Thr Glu Ile Thr Lys Ala Pro Leu Ser Ala Ser
305                 310                 315                 320 atg atc aag aga tac gac gag cac cac cag gac ctg acc ctg ctg aaa     1008
Met Ile Lys Arg Tyr Asp Glu His His Gln Asp Leu Thr Leu Leu Lys
                325                 330                 335 gct ctc gtg cgg cag cag ctg cct gag aag tac aaa gag att ttc ttc     1056
Ala Leu Val Arg Gln Gln Leu Pro Glu Lys Tyr Lys Glu Ile Phe Phe
            340                 345                 350 gac cag agc aag aac ggc tac gcc ggc tac att gac ggc gga gcc agc     1104
Asp Gln Ser Lys Asn Gly Tyr Ala Gly Tyr Ile Asp Gly Gly Ala Ser
            355                 360                 365 cag gaa gag ttc tac aag ttc atc aag ccc atc ctg gaa aag atg gac     1152
Gln Glu Glu Phe Tyr Lys Phe Ile Lys Pro Ile Leu Glu Lys Met Asp
        370                 375                 380 ggc acc gag gaa ctg ctc gtg aag ctg aac aga gag gac ctg ctg cgg     1200
Gly Thr Glu Glu Leu Leu Val Lys Leu Asn Arg Glu Asp Leu Leu Arg
385                 390                 395                 400 aag cag cgg acc ttc gac aac ggc agc atc ccc cac cag atc cac ctg     1248
Lys Gln Arg Thr Phe Asp Asn Gly Ser Ile Pro His Gln Ile His Leu
                405                 410                 415 gga gag ctg cac gcc att ctg cgg cgg cag gaa gat ttt tac cca ttc     1296
Gly Glu Leu His Ala Ile Leu Arg Arg Gln Glu Asp Phe Tyr Pro Phe
```

-continued

```
                420               425               430
ctg aag gac aac cgg gaa aag atc gag aag atc ctg acc ttc cgc atc      1344
Leu Lys Asp Asn Arg Glu Lys Ile Glu Lys Ile Leu Thr Phe Arg Ile
            435               440               445 ccc tac tac gtg ggc cct ctg gcc agg gga aac agc aga ttc gcc tgg      1392
Pro Tyr Tyr Val Gly Pro Leu Ala Arg Gly Asn Ser Arg Phe Ala Trp
450               455               460 atg acc aga aag agc gag gaa acc atc acc ccc tgg aac ttc gag gaa      1440
Met Thr Arg Lys Ser Glu Glu Thr Ile Thr Pro Trp Asn Phe Glu Glu
465               470               475               480 gtg gtg gac aag ggc gct tcc gcc cag agc ttc atc gag cgg atg acc      1488
Val Val Asp Lys Gly Ala Ser Ala Gln Ser Phe Ile Glu Arg Met Thr
            485               490               495 aac ttc gat aag aac ctg ccc aac gag aag gtg ctg ccc aag cac agc      1536
Asn Phe Asp Lys Asn Leu Pro Asn Glu Lys Val Leu Pro Lys His Ser
        500               505               510 ctg ctg tac gag tac ttc acc gtg tat aac gag ctg acc aaa gtg aaa      1584
Leu Leu Tyr Glu Tyr Phe Thr Val Tyr Asn Glu Leu Thr Lys Val Lys
            515               520               525 tac gtg acc gag gga atg aga aag ccc gcc ttc ctg agc ggc gag cag      1632
Tyr Val Thr Glu Gly Met Arg Lys Pro Ala Phe Leu Ser Gly Glu Gln
530               535               540 aaa aag gcc atc gtg gac ctg ctg ttc aag acc aac cgg aaa gtg acc      1680
Lys Lys Ala Ile Val Asp Leu Leu Phe Lys Thr Asn Arg Lys Val Thr
545               550               555               560 gtg aag cag ctg aaa gag gac tac ttc aag aaa atc gag tgc ttc gac      1728
Val Lys Gln Leu Lys Glu Asp Tyr Phe Lys Lys Ile Glu Cys Phe Asp
            565               570               575 tcc gtg gaa atc tcc ggc gtg gaa gat cgg ttc aac gcc tcc ctg ggc      1776
Ser Val Glu Ile Ser Gly Val Glu Asp Arg Phe Asn Ala Ser Leu Gly
        580               585               590 aca tac cac gat ctg ctg aaa att atc aag gac aag gac ttc ctg gac      1824
Thr Tyr His Asp Leu Leu Lys Ile Ile Lys Asp Lys Asp Phe Leu Asp
            595               600               605 aat gag gaa aac gag gac att ctg gaa gat atc gtg ctg acc ctg aca      1872
Asn Glu Glu Asn Glu Asp Ile Leu Glu Asp Ile Val Leu Thr Leu Thr
610               615               620 ctg ttt gag gac aga gag atg atc gag gaa cgg ctg aaa acc tat gcc      1920
Leu Phe Glu Asp Arg Glu Met Ile Glu Glu Arg Leu Lys Thr Tyr Ala
625               630               635               640 cac ctg ttc gac gac aaa gtg atg aag cag ctg aag cgg cgg aga tac      1968
His Leu Phe Asp Asp Lys Val Met Lys Gln Leu Lys Arg Arg Arg Tyr
            645               650               655 acc ggc tgg ggc agg ctg agc cgg aag ctg atc aac ggc atc cgg gac      2016
Thr Gly Trp Gly Arg Leu Ser Arg Lys Leu Ile Asn Gly Ile Arg Asp
        660               665               670 aag cag tcc ggc aag aca atc ctg gat ttc ctg aag tcc gac ggc ttc      2064
Lys Gln Ser Gly Lys Thr Ile Leu Asp Phe Leu Lys Ser Asp Gly Phe
            675               680               685 gcc aac aga aac ttc atg cag ctg atc cac gac gac agc ctg acc ttt      2112
Ala Asn Arg Asn Phe Met Gln Leu Ile His Asp Asp Ser Leu Thr Phe
        690               695               700 aaa gag gac atc cag aaa gcc cag gtg tcc ggc cag ggc gat agc ctg      2160
Lys Glu Asp Ile Gln Lys Ala Gln Val Ser Gly Gln Gly Asp Ser Leu
705               710               715               720 cac gag cac att gcc aat ctg gcc ggc agc ccc gcc att aag aag ggc      2208
His Glu His Ile Ala Asn Leu Ala Gly Ser Pro Ala Ile Lys Lys Gly
            725               730               735 atc ctg cag aca gtg aag gtg gtg gac gag ctc gtg aaa gtg atg ggc      2256
```

```
        Ile Leu Gln Thr Val Lys Val Val Asp Glu Leu Val Lys Val Met Gly
                    740                 745                 750 cgg cac aag ccc gag aac atc gtg atc gaa atg gcc aga gag aac cag       2304
Arg His Lys Pro Glu Asn Ile Val Ile Glu Met Ala Arg Glu Asn Gln
            755                 760                 765 acc acc cag aag gga cag aag aac agc cgc gag aga atg aag cgg atc       2352
Thr Thr Gln Lys Gly Gln Lys Asn Ser Arg Glu Arg Met Lys Arg Ile
770                 775                 780 gaa gag ggc atc aaa gag ctg ggc agc cag atc ctg aaa gaa cac ccc       2400
Glu Glu Gly Ile Lys Glu Leu Gly Ser Gln Ile Leu Lys Glu His Pro
785                 790                 795                 800 gtg gaa aac acc cag ctg cag aac gag aag ctg tac ctg tac tac ctg       2448
Val Glu Asn Thr Gln Leu Gln Asn Glu Lys Leu Tyr Leu Tyr Tyr Leu
                805                 810                 815 cag aat ggg cgg gat atg tac gtg gac cag gaa ctg gac atc aac cgg       2496
Gln Asn Gly Arg Asp Met Tyr Val Asp Gln Glu Leu Asp Ile Asn Arg
            820                 825                 830 ctg tcc gac tac gat gtg gac cat atc gtg cct cag agc ttt ctg aag       2544
Leu Ser Asp Tyr Asp Val Asp His Ile Val Pro Gln Ser Phe Leu Lys
        835                 840                 845 gac gac tcc atc gac aac aag gtg ctg acc aga agc gac aag aac cgg       2592
Asp Asp Ser Ile Asp Asn Lys Val Leu Thr Arg Ser Asp Lys Asn Arg
850                 855                 860 ggc aag agc gac aac gtg ccc tcc gaa gag gtc gtg aag aag atg aag       2640
Gly Lys Ser Asp Asn Val Pro Ser Glu Glu Val Val Lys Lys Met Lys
865                 870                 875                 880 aac tac tgg cgg cag ctg ctg aac gcc aag ctg att acc cag aga aag       2688
Asn Tyr Trp Arg Gln Leu Leu Asn Ala Lys Leu Ile Thr Gln Arg Lys
                885                 890                 895 ttc gac aat ctg acc aag gcc gag aga ggc ggc ctg agc gaa ctg gat       2736
Phe Asp Asn Leu Thr Lys Ala Glu Arg Gly Gly Leu Ser Glu Leu Asp
            900                 905                 910 aag gcc ggc ttc atc aag aga cag ctg gtg gaa acc cgg cag atc aca       2784
Lys Ala Gly Phe Ile Lys Arg Gln Leu Val Glu Thr Arg Gln Ile Thr
        915                 920                 925 aag cac gtg gca cag atc ctg gac tcc cgg atg aac act aag tac gac       2832
Lys His Val Ala Gln Ile Leu Asp Ser Arg Met Asn Thr Lys Tyr Asp
930                 935                 940 gag aat gac aag ctg atc cgg gaa gtg aaa gtg atc acc ctg aag tcc       2880
Glu Asn Asp Lys Leu Ile Arg Glu Val Lys Val Ile Thr Leu Lys Ser
945                 950                 955                 960 aag ctg gtg tcc gat ttc cgg aag gat ttc cag ttt tac aaa gtg cgc       2928
Lys Leu Val Ser Asp Phe Arg Lys Asp Phe Gln Phe Tyr Lys Val Arg
                965                 970                 975 gag atc aac aac tac cac cac gcc cac gac gcc tac ctg aac gcc gtc       2976
Glu Ile Asn Asn Tyr His His Ala His Asp Ala Tyr Leu Asn Ala Val
            980                 985                 990 gtg gga acc gcc ctg atc aaa aag tac cct aag ctg gaa agc gag ttc       3024
Val Gly Thr Ala Leu Ile Lys Lys Tyr Pro Lys Leu Glu Ser Glu Phe
        995                 1000                1005 gtg tac ggc gac tac aag gtg tac gac gtg cgg aag atg atc gcc          3069
Val Tyr Gly Asp Tyr Lys Val Tyr Asp Val Arg Lys Met Ile Ala
        1010                1015                1020 aag agc gag cag gaa atc ggc aag gct acc gcc aag tac ttc ttc          3114
Lys Ser Glu Gln Glu Ile Gly Lys Ala Thr Ala Lys Tyr Phe Phe
        1025                1030                1035 tac agc aac atc atg aac ttt ttc aag acc gag att acc ctg gcc          3159
Tyr Ser Asn Ile Met Asn Phe Phe Lys Thr Glu Ile Thr Leu Ala
        1040                1045                1050
```

```
aac  ggc  gag  atc  cgg  aag  cgg  cct  ctg  atc  gag  aca  aac  ggc  gaa        3204
Asn  Gly  Glu  Ile  Arg  Lys  Arg  Pro  Leu  Ile  Glu  Thr  Asn  Gly  Glu
1055           1060                     1065 acc  ggg  gag  atc  gtg  tgg  gat  aag  ggc  cgg  gat  ttt  gcc  acc  gtg        3249
Thr  Gly  Glu  Ile  Val  Trp  Asp  Lys  Gly  Arg  Asp  Phe  Ala  Thr  Val
1070                     1075                     1080 cgg  aaa  gtg  ctg  agc  atg  ccc  caa  gtg  aat  atc  gtg  aaa  aag  acc        3294
Arg  Lys  Val  Leu  Ser  Met  Pro  Gln  Val  Asn  Ile  Val  Lys  Lys  Thr
     1085                     1090                     1095 gag  gtg  cag  aca  ggc  ggc  ttc  agc  aaa  gag  tct  atc  cgg  ccc  aag        3339
Glu  Val  Gln  Thr  Gly  Gly  Phe  Ser  Lys  Glu  Ser  Ile  Arg  Pro  Lys
1100                     1105                     1110 agg  aac  agc  gat  aag  ctg  atc  gcc  aga  aag  aag  gac  tgg  gac  cct        3384
Arg  Asn  Ser  Asp  Lys  Leu  Ile  Ala  Arg  Lys  Lys  Asp  Trp  Asp  Pro
1115                     1120                     1125 aag  aag  tac  ggc  ggc  ttc  gac  agc  ccc  acc  gtg  gcc  tat  tct  gtg        3429
Lys  Lys  Tyr  Gly  Gly  Phe  Asp  Ser  Pro  Thr  Val  Ala  Tyr  Ser  Val
     1130                     1135                     1140 ctg  gtg  gtg  gcc  aaa  gtg  gaa  aag  ggc  aag  tcc  aag  aaa  ctg  aag        3474
Leu  Val  Val  Ala  Lys  Val  Glu  Lys  Gly  Lys  Ser  Lys  Lys  Leu  Lys
1145                     1150                     1155 agt  gtg  aaa  gag  ctg  ctg  ggg  atc  acc  atc  atg  gaa  aga  agc  agc        3519
Ser  Val  Lys  Glu  Leu  Leu  Gly  Ile  Thr  Ile  Met  Glu  Arg  Ser  Ser
1160                     1165                     1170 ttc  gag  aag  aat  ccc  atc  gac  ttt  ctg  gaa  gcc  aag  ggc  tac  aaa        3564
Phe  Glu  Lys  Asn  Pro  Ile  Asp  Phe  Leu  Glu  Ala  Lys  Gly  Tyr  Lys
     1175                     1180                     1185 gaa  gtg  aaa  aag  gac  ctg  atc  atc  aag  ctg  cct  aag  tac  tcc  ctg        3609
Glu  Val  Lys  Lys  Asp  Leu  Ile  Ile  Lys  Leu  Pro  Lys  Tyr  Ser  Leu
1190                     1195                     1200 ttc  gag  ctg  gaa  aac  ggc  cgg  aag  aga  atg  ctg  gcc  tct  gcc  cgg        3654
Phe  Glu  Leu  Glu  Asn  Gly  Arg  Lys  Arg  Met  Leu  Ala  Ser  Ala  Arg
1205                     1210                     1215 gaa  ctg  cag  aag  gga  aac  gaa  ctg  gcc  ctg  ccc  tcc  aaa  tat  gtg        3699
Glu  Leu  Gln  Lys  Gly  Asn  Glu  Leu  Ala  Leu  Pro  Ser  Lys  Tyr  Val
     1220                     1225                     1230 aac  ttc  ctg  tac  ctg  gcc  agc  cac  tat  gag  aag  ctg  aag  ggc  tcc        3744
Asn  Phe  Leu  Tyr  Leu  Ala  Ser  His  Tyr  Glu  Lys  Leu  Lys  Gly  Ser
1235                     1240                     1245 ccc  gag  gat  aat  gag  cag  aaa  cag  ctg  ttt  gtg  gaa  cag  cac  aag        3789
Pro  Glu  Asp  Asn  Glu  Gln  Lys  Gln  Leu  Phe  Val  Glu  Gln  His  Lys
     1250                     1255                     1260 cac  tac  ctg  gac  gag  atc  atc  gag  cag  atc  agc  gag  ttc  tcc  aag        3834
His  Tyr  Leu  Asp  Glu  Ile  Ile  Glu  Gln  Ile  Ser  Glu  Phe  Ser  Lys
1265                     1270                     1275 aga  gtg  atc  ctg  gcc  gac  gct  aat  ctg  gac  aaa  gtg  ctg  tcc  gcc        3879
Arg  Val  Ile  Leu  Ala  Asp  Ala  Asn  Leu  Asp  Lys  Val  Leu  Ser  Ala
     1280                     1285                     1290 tac  aac  aag  cac  cgg  gat  aag  ccc  atc  aga  gag  cag  gcc  gag  aat        3924
Tyr  Asn  Lys  His  Arg  Asp  Lys  Pro  Ile  Arg  Glu  Gln  Ala  Glu  Asn
1295                     1300                     1305 atc  atc  cac  ctg  ttt  acc  ctg  acc  aat  ctg  gga  gcc  cct  cgg  gcc        3969
Ile  Ile  His  Leu  Phe  Thr  Leu  Thr  Asn  Leu  Gly  Ala  Pro  Arg  Ala
     1310                     1315                     1320 ttc  aag  tac  ttt  gac  acc  acc  atc  cgg  cgg  aag  gcc  tac  acc  agc        4014
Phe  Lys  Tyr  Phe  Asp  Thr  Thr  Ile  Arg  Arg  Lys  Ala  Tyr  Thr  Ser
1325                     1330                     1335 acc  aaa  gag  gtg  ctg  gac  gcc  acc  ctg  atc  cac  cag  agc  atc  acc        4059
Thr  Lys  Glu  Val  Leu  Asp  Ala  Thr  Leu  Ile  His  Gln  Ser  Ile  Thr
     1340                     1345                     1350
```

-continued

```
ggc ctg tac gag aca cgg atc gac ctg tct cag ctg gga ggc gac      4104
Gly Leu Tyr Glu Thr Arg Ile Asp Leu Ser Gln Leu Gly Gly Asp
    1355                1360                1365 taa                                                              4107

<210> SEQ ID NO 11
<211> LENGTH: 4107
<212> TYPE: DNA
<213> ORGANISM: Streptococcus pyogenes
<220> FEATURE:
<221> NAME/KEY: CDS
<222> LOCATION: (1)..(4107)

<400> SEQUENCE: 11 atg gac aag aag tac agc atc ggc ctg gac atc ggc acc aac tct gtg   48
Met Asp Lys Lys Tyr Ser Ile Gly Leu Asp Ile Gly Thr Asn Ser Val
1               5                   10                  15 ggc tgg gcc gtg atc acc gac gag tac aag gtg ccc agc aag aaa ttc   96
Gly Trp Ala Val Ile Thr Asp Glu Tyr Lys Val Pro Ser Lys Lys Phe
            20                  25                  30 aag gtg ctg ggc aac acc gac cgg cac agc atc aag aag aac ctg atc  144
Lys Val Leu Gly Asn Thr Asp Arg His Ser Ile Lys Lys Asn Leu Ile
        35                  40                  45 gga gcc ctg ctg ttc gac agc ggc gaa aca gcc gag gcc acc cgg ctg  192
Gly Ala Leu Leu Phe Asp Ser Gly Glu Thr Ala Glu Ala Thr Arg Leu
    50                  55                  60 aag aga acc gcc aga aga aga tac acc aga cgg aag aac cgg atc tgc  240
Lys Arg Thr Ala Arg Arg Arg Tyr Thr Arg Arg Lys Asn Arg Ile Cys
65                  70                  75                  80 tat ctg caa gag atc ttc agc aac gag atg gcc aag gtg gac gac agc  288
Tyr Leu Gln Glu Ile Phe Ser Asn Glu Met Ala Lys Val Asp Asp Ser
                85                  90                  95 ttc ttc cac aga ctg gaa gag tcc ttc ctg gtg gaa gag gat aag aag  336
Phe Phe His Arg Leu Glu Glu Ser Phe Leu Val Glu Glu Asp Lys Lys
            100                 105                 110 cac gag cgg cac ccc atc ttc ggc aac atc gtg gac gag gtg gcc tac  384
His Glu Arg His Pro Ile Phe Gly Asn Ile Val Asp Glu Val Ala Tyr
        115                 120                 125 cac gag aag tac ccc acc atc tac cac ctg aga aag aaa ctg gtg gac  432
His Glu Lys Tyr Pro Thr Ile Tyr His Leu Arg Lys Lys Leu Val Asp
    130                 135                 140 agc acc gac aag gcc gac ctg cgg ctg atc tat ctg gcc ctg gcc cac  480
Ser Thr Asp Lys Ala Asp Leu Arg Leu Ile Tyr Leu Ala Leu Ala His
145                 150                 155                 160 atg atc aag ttc cgg ggc cac ttc ctg atc gag ggc gac ctg aac ccc  528
Met Ile Lys Phe Arg Gly His Phe Leu Ile Glu Gly Asp Leu Asn Pro
                165                 170                 175 gac aac agc gac gtg gac aag ctg ttc atc cag ctg gtg cag acc tac  576
Asp Asn Ser Asp Val Asp Lys Leu Phe Ile Gln Leu Val Gln Thr Tyr
            180                 185                 190 aac cag ctg ttc gag gaa aac ccc atc aac gcc agc ggc gtg gac gcc  624
Asn Gln Leu Phe Glu Glu Asn Pro Ile Asn Ala Ser Gly Val Asp Ala
        195                 200                 205 aag gcc atc ctg tct gcc aga ctg agc aag agc aga cgg ctg gaa aat  672
Lys Ala Ile Leu Ser Ala Arg Leu Ser Lys Ser Arg Arg Leu Glu Asn
    210                 215                 220 ctg atc gcc cag ctg ccc ggc gag aag aag aat ggc ctg ttc ggc aac  720
Leu Ile Ala Gln Leu Pro Gly Glu Lys Lys Asn Gly Leu Phe Gly Asn
225                 230                 235                 240 ctg att gcc ctg agc ctg ggc ctg acc ccc aac ttc aag agc aac ttc  768
```

```
                    Leu Ile Ala Leu Ser Leu Gly Leu Thr Pro Asn Phe Lys Ser Asn Phe
                                245                 250                 255 gac ctg gcc gag gat gcc aaa ctg cag ctg agc aag gac acc tac gac           816
Asp Leu Ala Glu Asp Ala Lys Leu Gln Leu Ser Lys Asp Thr Tyr Asp
            260                 265                 270 gac gac ctg gac aac ctg ctg gcc cag atc ggc gac cag tac gcc gac           864
Asp Asp Leu Asp Asn Leu Leu Ala Gln Ile Gly Asp Gln Tyr Ala Asp
                275                 280                 285 ctg ttt ctg gcc gcc aag aac ctg tcc gac gcc atc ctg ctg agc gac           912
Leu Phe Leu Ala Ala Lys Asn Leu Ser Asp Ala Ile Leu Leu Ser Asp
290                 295                 300 atc ctg aga gtg aac acc gag atc acc aag gcc ccc ctg agc gcc tct           960
Ile Leu Arg Val Asn Thr Glu Ile Thr Lys Ala Pro Leu Ser Ala Ser
305                 310                 315                 320 atg atc aag aga tac gac gag cac cac cag gac ctg acc ctg ctg aaa          1008
Met Ile Lys Arg Tyr Asp Glu His His Gln Asp Leu Thr Leu Leu Lys
            325                 330                 335 gct ctc gtg cgg cag cag ctg cct gag aag tac aaa gag att ttc ttc          1056
Ala Leu Val Arg Gln Gln Leu Pro Glu Lys Tyr Lys Glu Ile Phe Phe
                340                 345                 350 gac cag agc aag aac ggc tac gcc ggc tac att gac ggc gga gcc agc          1104
Asp Gln Ser Lys Asn Gly Tyr Ala Gly Tyr Ile Asp Gly Gly Ala Ser
                    355                 360                 365 cag gaa gag ttc tac aag ttc atc aag ccc atc ctg gaa aag atg gac          1152
Gln Glu Glu Phe Tyr Lys Phe Ile Lys Pro Ile Leu Glu Lys Met Asp
370                 375                 380 ggc acc gag gaa ctg ctc gtg aag ctg aac aga gag gac ctg ctg cgg          1200
Gly Thr Glu Glu Leu Leu Val Lys Leu Asn Arg Glu Asp Leu Leu Arg
385                 390                 395                 400 aag cag cgg acc ttc gac aac ggc agc atc ccc cac cag atc cac ctg          1248
Lys Gln Arg Thr Phe Asp Asn Gly Ser Ile Pro His Gln Ile His Leu
            405                 410                 415 gga gag ctg cac gcc att ctg cgg cgg cag gaa gat ttt tac cca ttc          1296
Gly Glu Leu His Ala Ile Leu Arg Arg Gln Glu Asp Phe Tyr Pro Phe
                420                 425                 430 ctg aag gac aac cgg gaa aag atc gag aag atc ctg acc ttc cgc atc          1344
Leu Lys Asp Asn Arg Glu Lys Ile Glu Lys Ile Leu Thr Phe Arg Ile
                    435                 440                 445 ccc tac tac gtg ggc cct ctg gcc agg gga aac agc aga ttc gcc tgg          1392
Pro Tyr Tyr Val Gly Pro Leu Ala Arg Gly Asn Ser Arg Phe Ala Trp
450                 455                 460 atg acc aga aag agc gag gaa acc atc acc ccc tgg aac ttc gag gaa          1440
Met Thr Arg Lys Ser Glu Glu Thr Ile Thr Pro Trp Asn Phe Glu Glu
465                 470                 475                 480 gtg gtg gac aag ggc gct tcc gcc cag agc ttc atc gag cgg atg acc          1488
Val Val Asp Lys Gly Ala Ser Ala Gln Ser Phe Ile Glu Arg Met Thr
            485                 490                 495 aac ttc gat aag aac ctg ccc aac gag aag gtg ctg ccc aag cac agc          1536
Asn Phe Asp Lys Asn Leu Pro Asn Glu Lys Val Leu Pro Lys His Ser
                500                 505                 510 ctg ctg tac gag tac ttc acc gtg tat aac gag ctg acc aaa gtg aaa          1584
Leu Leu Tyr Glu Tyr Phe Thr Val Tyr Asn Glu Leu Thr Lys Val Lys
                    515                 520                 525 tac gtg acc gag gga atg aga aag ccc gcc ttc ctg agc ggc gag cag          1632
Tyr Val Thr Glu Gly Met Arg Lys Pro Ala Phe Leu Ser Gly Glu Gln
530                 535                 540 aaa aag gcc atc gtg gac ctg ctg ttc aag acc aac cgg aaa gtg acc          1680
Lys Lys Ala Ile Val Asp Leu Leu Phe Lys Thr Asn Arg Lys Val Thr
545                 550                 555                 560
```

-continued

| | | |
|---|---|---|
| gtg aag cag ctg aaa gag gac tac ttc aag aaa atc gag tgc ttc gac<br>Val Lys Gln Leu Lys Glu Asp Tyr Phe Lys Lys Ile Glu Cys Phe Asp<br>               565                     570                   575 | | 1728 |
| tcc gtg gaa atc tcc ggc gtg gaa gat cgg ttc aac gcc tcc ctg ggc<br>Ser Val Glu Ile Ser Gly Val Glu Asp Arg Phe Asn Ala Ser Leu Gly<br>580                     585                     590 | | 1776 |
| aca tac cac gat ctg ctg aaa att atc aag gac aag gac ttc ctg gac<br>Thr Tyr His Asp Leu Leu Lys Ile Ile Lys Asp Lys Asp Phe Leu Asp<br>        595                     600                     605 | | 1824 |
| aat gag gaa aac gag gac att ctg gaa gat atc gtg ctg acc ctg aca<br>Asn Glu Glu Asn Glu Asp Ile Leu Glu Asp Ile Val Leu Thr Leu Thr<br>610                     615                     620 | | 1872 |
| ctg ttt gag gac aga gag atg atc gag gaa cgg ctg aaa acc tat gcc<br>Leu Phe Glu Asp Arg Glu Met Ile Glu Glu Arg Leu Lys Thr Tyr Ala<br>625                  630                   635                   640 | | 1920 |
| cac ctg ttc gac gac aaa gtg atg aag cag ctg aag cgg cgg aga tac<br>His Leu Phe Asp Asp Lys Val Met Lys Gln Leu Lys Arg Arg Arg Tyr<br>                     645                     650                   655 | | 1968 |
| acc ggc tgg ggc agg ctg agc cgg aag ctg atc aac ggc atc cgg gac<br>Thr Gly Trp Gly Arg Leu Ser Arg Lys Leu Ile Asn Gly Ile Arg Asp<br>660                     665                     670 | | 2016 |
| aag cag tcc ggc aag aca atc ctg gat ttc ctg aag tcc gac ggc ttc<br>Lys Gln Ser Gly Lys Thr Ile Leu Asp Phe Leu Lys Ser Asp Gly Phe<br>        675                     680                     685 | | 2064 |
| gcc aac aga aac ttc atg cag ctg atc cac gac gac agc ctg acc ttt<br>Ala Asn Arg Asn Phe Met Gln Leu Ile His Asp Asp Ser Leu Thr Phe<br>690                     695                     700 | | 2112 |
| aaa gag gac atc cag aaa gcc cag gtg tcc ggc cag ggc gat agc ctg<br>Lys Glu Asp Ile Gln Lys Ala Gln Val Ser Gly Gln Gly Asp Ser Leu<br>705                     710                     715                   720 | | 2160 |
| cac gag cac att gcc aat ctg gcc ggc agc ccc gcc att aag aag ggc<br>His Glu His Ile Ala Asn Leu Ala Gly Ser Pro Ala Ile Lys Lys Gly<br>                     725                     730                   735 | | 2208 |
| atc ctg cag aca gtg aag gtg gtg gac gag ctc gtg aaa gtg atg ggc<br>Ile Leu Gln Thr Val Lys Val Val Asp Glu Leu Val Lys Val Met Gly<br>740                     745                     750 | | 2256 |
| cgg cac aag ccc gag aac atc gtg atc gaa atg gcc aga gag aac cag<br>Arg His Lys Pro Glu Asn Ile Val Ile Glu Met Ala Arg Glu Asn Gln<br>        755                     760                   765 | | 2304 |
| acc acc cag aag gga cag aag aac agc cgc gag aga atg aag cgg atc<br>Thr Thr Gln Lys Gly Gln Lys Asn Ser Arg Glu Arg Met Lys Arg Ile<br>770                     775                     780 | | 2352 |
| gaa gag ggc atc aaa gag ctg ggc agc cag atc ctg aaa gaa cac ccc<br>Glu Glu Gly Ile Lys Glu Leu Gly Ser Gln Ile Leu Lys Glu His Pro<br>785                     790                     795                   800 | | 2400 |
| gtg gaa aac acc cag ctg cag aac gag aag ctg tac ctg tac tac ctg<br>Val Glu Asn Thr Gln Leu Gln Asn Glu Lys Leu Tyr Leu Tyr Tyr Leu<br>                     805                     810                   815 | | 2448 |
| cag aat ggg cgg gat atg tac gtg gac cag gaa ctg gac atc aac cgg<br>Gln Asn Gly Arg Asp Met Tyr Val Asp Gln Glu Leu Asp Ile Asn Arg<br>820                     825                     830 | | 2496 |
| ctg tcc gac tac gat gtg gac cat atc gtg cct cag agc ttt ctg aag<br>Leu Ser Asp Tyr Asp Val Asp His Ile Val Pro Gln Ser Phe Leu Lys<br>        835                     840                     845 | | 2544 |
| gac gac tcc atc gac aac aag gtg ctg acc aga agc gac aag aac cgg<br>Asp Asp Ser Ile Asp Asn Lys Val Leu Thr Arg Ser Asp Lys Asn Arg<br>850                     855                     860 | | 2592 |
| ggc aag agc gac aac gtg ccc tcc gaa gag gtc gtg aag aag atg aag<br>Gly Lys Ser Asp Asn Val Pro Ser Glu Glu Val Val Lys Lys Met Lys<br>865                     870                     875                   880 | | 2640 |

```
aac tac tgg cgg cag ctg ctg aac gcc aag ctg att acc cag aga aag    2688
Asn Tyr Trp Arg Gln Leu Leu Asn Ala Lys Leu Ile Thr Gln Arg Lys
            885                 890                 895 ttc gac aat ctg acc aag gcc gag aga ggc ggc ctg agc gaa ctg gat    2736
Phe Asp Asn Leu Thr Lys Ala Glu Arg Gly Gly Leu Ser Glu Leu Asp
        900                 905                 910 aag gcc ggc ttc atc aag aga cag ctg gtg gaa acc cgg cag atc aca    2784
Lys Ala Gly Phe Ile Lys Arg Gln Leu Val Glu Thr Arg Gln Ile Thr
        915                 920                 925 aag cac gtg gca cag atc ctg gac tcc cgg atg aac act aag tac gac    2832
Lys His Val Ala Gln Ile Leu Asp Ser Arg Met Asn Thr Lys Tyr Asp
        930                 935                 940 gag aat gac aag ctg atc cgg gaa gtg aaa gtg atc acc ctg aag tcc    2880
Glu Asn Asp Lys Leu Ile Arg Glu Val Lys Val Ile Thr Leu Lys Ser
945                 950                 955                 960 aag ctg gtg tcc gat ttc cgg aag gat ttc cag ttt tac aaa gtg cgc    2928
Lys Leu Val Ser Asp Phe Arg Lys Asp Phe Gln Phe Tyr Lys Val Arg
                965                 970                 975 gag atc aac aac tac cac cac gcc cac gac gcc tac ctg aac gcc gtc    2976
Glu Ile Asn Asn Tyr His His Ala His Asp Ala Tyr Leu Asn Ala Val
            980                 985                 990 gtg gga acc gcc ctg atc aaa aag tac cct aag ctg gaa agc gag ttc    3024
Val Gly Thr Ala Leu Ile Lys Lys Tyr Pro Lys Leu Glu Ser Glu Phe
        995                 1000                1005 gtg tac ggc gac tac aag gtg tac gac gtg cgg aag atg atc gcc       3069
Val Tyr Gly Asp Tyr Lys Val Tyr Asp Val Arg Lys Met Ile Ala
        1010                1015                1020 aag agc gag cag gaa atc ggc aag gct acc gcc aag tac ttc ttc       3114
Lys Ser Glu Gln Glu Ile Gly Lys Ala Thr Ala Lys Tyr Phe Phe
        1025                1030                1035 tac agc aac atc atg aac ttt ttc aag acc gag att acc ctg gcc       3159
Tyr Ser Asn Ile Met Asn Phe Phe Lys Thr Glu Ile Thr Leu Ala
        1040                1045                1050 aac ggc gag atc cgg aag cgg cct ctg atc gag aca aac ggc gaa       3204
Asn Gly Glu Ile Arg Lys Arg Pro Leu Ile Glu Thr Asn Gly Glu
        1055                1060                1065 acc ggg gag atc gtg tgg gat aag ggc cgg gat ttt gcc acc gtg       3249
Thr Gly Glu Ile Val Trp Asp Lys Gly Arg Asp Phe Ala Thr Val
        1070                1075                1080 cgg aaa gtg ctg agc atg ccc caa gtg aat atc gtg aaa aag acc       3294
Arg Lys Val Leu Ser Met Pro Gln Val Asn Ile Val Lys Lys Thr
        1085                1090                1095 gag gtg cag aca ggc ggc ttc agc aaa gag tct atc cgg ccc aag       3339
Glu Val Gln Thr Gly Gly Phe Ser Lys Glu Ser Ile Arg Pro Lys
        1100                1105                1110 agg aac agc gat aag ctg atc gcc aga aag aag gac tgg gac cct       3384
Arg Asn Ser Asp Lys Leu Ile Ala Arg Lys Lys Asp Trp Asp Pro
        1115                1120                1125 aag aag tac ggc ggc ttc gac agc ccc acc gtg gcc tat tct gtg       3429
Lys Lys Tyr Gly Gly Phe Asp Ser Pro Thr Val Ala Tyr Ser Val
        1130                1135                1140 ctg gtg gtg gcc aaa gtg gaa aag ggc aag tcc aag aaa ctg aag       3474
Leu Val Val Ala Lys Val Glu Lys Gly Lys Ser Lys Lys Leu Lys
        1145                1150                1155 agt gtg aaa gag ctg ctg ggg atc acc atc atg gaa aga agc agc       3519
Ser Val Lys Glu Leu Leu Gly Ile Thr Ile Met Glu Arg Ser Ser
        1160                1165                1170 ttc gag aag aat ccc atc gac ttt ctg gaa gcc aag ggc tac aaa       3564
Phe Glu Lys Asn Pro Ile Asp Phe Leu Glu Ala Lys Gly Tyr Lys
```

```
       1175                1180               1185 gaa gtg aaa aag gac ctg atc atc aag ctg cct aag tac tcc ctg      3609
Glu Val Lys Lys Asp Leu Ile Ile Lys Leu Pro Lys Tyr Ser Leu
        1190                1195                1200 ttc gag ctg gaa aac ggc cgg aag aga atg ctg gcc tct gcc cgg      3654
Phe Glu Leu Glu Asn Gly Arg Lys Arg Met Leu Ala Ser Ala Arg
    1205                1210                1215 gaa ctg cag aag gga aac gaa ctg gcc ctg ccc tcc aaa tat gtg      3699
Glu Leu Gln Lys Gly Asn Glu Leu Ala Leu Pro Ser Lys Tyr Val
1220                1225                1230 aac ttc ctg tac ctg gcc agc cac tat gag aag ctg aag ggc tcc      3744
Asn Phe Leu Tyr Leu Ala Ser His Tyr Glu Lys Leu Lys Gly Ser
        1235                1240                1245 ccc gag gat aat gag cag aaa cag ctg ttt gtg gaa cag cac aag      3789
Pro Glu Asp Asn Glu Gln Lys Gln Leu Phe Val Glu Gln His Lys
    1250                1255                1260 cac tac ctg gac gag atc atc gag cag atc agc gag ttc tcc aag      3834
His Tyr Leu Asp Glu Ile Ile Glu Gln Ile Ser Glu Phe Ser Lys
1265                1270                1275 aga gtg atc ctg gcc cgg cgg aat ctg gac aaa gtg ctg tcc gcc      3879
Arg Val Ile Leu Ala Arg Arg Asn Leu Asp Lys Val Leu Ser Ala
        1280                1285                1290 tac aac aag cac cgg gat aag ccc atc aga gag cag gcc gag aat      3924
Tyr Asn Lys His Arg Asp Lys Pro Ile Arg Glu Gln Ala Glu Asn
    1295                1300                1305 atc atc cac ctg ttt acc ctg acc aat ctg gga gcc cct cgg gcc      3969
Ile Ile His Leu Phe Thr Leu Thr Asn Leu Gly Ala Pro Arg Ala
1310                1315                1320 ttc aag tac ttt gac acc acc atc cgg cgg aag gcc tac acc agc      4014
Phe Lys Tyr Phe Asp Thr Thr Ile Arg Arg Lys Ala Tyr Thr Ser
        1325                1330                1335 acc aaa gag gtg ctg gac gcc acc ctg atc cac cag agc atc acc      4059
Thr Lys Glu Val Leu Asp Ala Thr Leu Ile His Gln Ser Ile Thr
    1340                1345                1350 ggc ctg tac gag aca cgg atc gac ctg tct cag ctg gga ggc gac      4104
Gly Leu Tyr Glu Thr Arg Ile Asp Leu Ser Gln Leu Gly Gly Asp
1355                1360                1365 taa                                                               4107

<210> SEQ ID NO 12
<211> LENGTH: 4107
<212> TYPE: DNA
<213> ORGANISM: Streptococcus pyogenes
<220> FEATURE:
<221> NAME/KEY: CDS
<222> LOCATION: (1)..(4107)

<400> SEQUENCE: 12 atg gac aag aag tac agc atc ggc ctg gac atc ggc acc aac tct gtg    48
Met Asp Lys Lys Tyr Ser Ile Gly Leu Asp Ile Gly Thr Asn Ser Val
1               5                  10                  15 ggc tgg gcc gtg atc acc gac gag tac aag gtg ccc agc aag aaa ttc    96
Gly Trp Ala Val Ile Thr Asp Glu Tyr Lys Val Pro Ser Lys Lys Phe
            20                  25                  30 aag gtg ctg ggc aac acc gac cgg cac agc atc aag aag aac ctg atc   144
Lys Val Leu Gly Asn Thr Asp Arg His Ser Ile Lys Lys Asn Leu Ile
        35                  40                  45 gga gcc ctg ctg ttc gac agc ggc gaa aca gcc gag gcc acc cgg ctg   192
Gly Ala Leu Leu Phe Asp Ser Gly Glu Thr Ala Glu Ala Thr Arg Leu
    50                  55                  60
```

```
                                            -continued aag aga acc gcc aga aga aga tac acc aga cgg aag aac cgg atc tgc     240
Lys Arg Thr Ala Arg Arg Arg Tyr Thr Arg Arg Lys Asn Arg Ile Cys
 65                  70                  75                  80 tat ctg caa gag atc ttc agc aac gag atg gcc aag gtg gac gac agc     288
Tyr Leu Gln Glu Ile Phe Ser Asn Glu Met Ala Lys Val Asp Asp Ser
                     85                  90                  95 ttc ttc cac aga ctg gaa gag tcc ttc ctg gtg gaa gag gat aag aag     336
Phe Phe His Arg Leu Glu Glu Ser Phe Leu Val Glu Glu Asp Lys Lys
                100                 105                 110 cac gag cgg cac ccc atc ttc ggc aac atc gtg gac gag gtg gcc tac     384
His Glu Arg His Pro Ile Phe Gly Asn Ile Val Asp Glu Val Ala Tyr
            115                 120                 125 cac gag aag tac ccc acc atc tac cac ctg aga aag aaa ctg gtg gac     432
His Glu Lys Tyr Pro Thr Ile Tyr His Leu Arg Lys Lys Leu Val Asp
        130                 135                 140 agc acc gac aag gcc gac ctg cgg ctg atc tat ctg gcc ctg gcc cac     480
Ser Thr Asp Lys Ala Asp Leu Arg Leu Ile Tyr Leu Ala Leu Ala His
145                 150                 155                 160 atg atc aag ttc cgg ggc cac ttc ctg atc gag ggc gac ctg aac ccc     528
Met Ile Lys Phe Arg Gly His Phe Leu Ile Glu Gly Asp Leu Asn Pro
                165                 170                 175 gac aac agc gac gtg gac aag ctg ttc atc cag ctg gtg cag acc tac     576
Asp Asn Ser Asp Val Asp Lys Leu Phe Ile Gln Leu Val Gln Thr Tyr
            180                 185                 190 aac cag ctg ttc gag gaa aac ccc atc aac gcc agc ggc gtg gac gcc     624
Asn Gln Leu Phe Glu Glu Asn Pro Ile Asn Ala Ser Gly Val Asp Ala
        195                 200                 205 aag gcc atc ctg tct gcc aga ctg agc aag agc aga cgg ctg gaa aat     672
Lys Ala Ile Leu Ser Ala Arg Leu Ser Lys Ser Arg Arg Leu Glu Asn
    210                 215                 220 ctg atc gcc cag ctg ccc ggc gag aag aag aat ggc ctg ttc ggc aac     720
Leu Ile Ala Gln Leu Pro Gly Glu Lys Lys Asn Gly Leu Phe Gly Asn
225                 230                 235                 240 ctg att gcc ctg agc ctg ggc ctg acc ccc aac ttc aag agc aac ttc     768
Leu Ile Ala Leu Ser Leu Gly Leu Thr Pro Asn Phe Lys Ser Asn Phe
                245                 250                 255 gac ctg gcc gag gat gcc aaa ctg cag ctg agc aag gac acc tac gac     816
Asp Leu Ala Glu Asp Ala Lys Leu Gln Leu Ser Lys Asp Thr Tyr Asp
            260                 265                 270 gac gac ctg gac aac ctg ctg gcc cag atc ggc gac cag tac gcc gac     864
Asp Asp Leu Asp Asn Leu Leu Ala Gln Ile Gly Asp Gln Tyr Ala Asp
        275                 280                 285 ctg ttt ctg gcc gcc aag aac ctg tcc gac gcc atc ctg ctg agc gac     912
Leu Phe Leu Ala Ala Lys Asn Leu Ser Asp Ala Ile Leu Leu Ser Asp
    290                 295                 300 atc ctg aga gtg aac acc gag atc acc aag gcc ccc ctg agc gcc tct     960
Ile Leu Arg Val Asn Thr Glu Ile Thr Lys Ala Pro Leu Ser Ala Ser
305                 310                 315                 320 atg atc aag aga tac gac gag cac cac cag gac ctg acc ctg ctg aaa    1008
Met Ile Lys Arg Tyr Asp Glu His His Gln Asp Leu Thr Leu Leu Lys
                325                 330                 335 gct ctc gtg cgg cag cag ctg cct gag aag tac aaa gag att ttc ttc    1056
Ala Leu Val Arg Gln Gln Leu Pro Glu Lys Tyr Lys Glu Ile Phe Phe
            340                 345                 350 gac cag agc aag aac ggc tac gcc ggc tac att gac ggc gga gcc agc    1104
Asp Gln Ser Lys Asn Gly Tyr Ala Gly Tyr Ile Asp Gly Gly Ala Ser
        355                 360                 365 cag gaa gag ttc tac aag ttc atc aag ccc atc ctg gaa aag atg gac    1152
Gln Glu Glu Phe Tyr Lys Phe Ile Lys Pro Ile Leu Glu Lys Met Asp
    370                 375                 380
```

```
ggc acc gag gaa ctg ctc gtg aag ctg aac aga gag gac ctg ctg cgg      1200
Gly Thr Glu Glu Leu Leu Val Lys Leu Asn Arg Glu Asp Leu Leu Arg
385                 390                 395                 400 aag cag cgg acc ttc gac aac ggc agc atc ccc cac cag atc cac ctg      1248
Lys Gln Arg Thr Phe Asp Asn Gly Ser Ile Pro His Gln Ile His Leu
                405                 410                 415 gga gag ctg cac gcc att ctg cgg cgg cag gaa gat ttt tac cca ttc      1296
Gly Glu Leu His Ala Ile Leu Arg Arg Gln Glu Asp Phe Tyr Pro Phe
            420                 425                 430 ctg aag gac aac cgg gaa aag atc gag aag atc ctg acc ttc cgc atc      1344
Leu Lys Asp Asn Arg Glu Lys Ile Glu Lys Ile Leu Thr Phe Arg Ile
        435                 440                 445 ccc tac tac gtg ggc cct ctg gcc agg gga aac agc aga ttc gcc tgg      1392
Pro Tyr Tyr Val Gly Pro Leu Ala Arg Gly Asn Ser Arg Phe Ala Trp
    450                 455                 460 atg acc aga aag agc gag gaa acc atc acc ccc tgg aac ttc gag gaa      1440
Met Thr Arg Lys Ser Glu Glu Thr Ile Thr Pro Trp Asn Phe Glu Glu
465                 470                 475                 480 gtg gtg gac aag ggc gct tcc gcc cag agc ttc atc gag cgg atg acc      1488
Val Val Asp Lys Gly Ala Ser Ala Gln Ser Phe Ile Glu Arg Met Thr
                485                 490                 495 aac ttc gat aag aac ctg ccc aac gag aag gtg ctg ccc aag cac agc      1536
Asn Phe Asp Lys Asn Leu Pro Asn Glu Lys Val Leu Pro Lys His Ser
                500                 505                 510 ctg ctg tac gag tac ttc acc gtg tat aac gag ctg acc aaa gtg aaa      1584
Leu Leu Tyr Glu Tyr Phe Thr Val Tyr Asn Glu Leu Thr Lys Val Lys
            515                 520                 525 tac gtg acc gag gga atg aga aag ccc gcc ttc ctg agc ggc gag cag      1632
Tyr Val Thr Glu Gly Met Arg Lys Pro Ala Phe Leu Ser Gly Glu Gln
        530                 535                 540 aaa aag gcc atc gtg gac ctg ctg ttc aag acc aac cgg aaa gtg acc      1680
Lys Lys Ala Ile Val Asp Leu Leu Phe Lys Thr Asn Arg Lys Val Thr
545                 550                 555                 560 gtg aag cag ctg aaa gag gac tac ttc aag aaa atc gag tgc ttc gac      1728
Val Lys Gln Leu Lys Glu Asp Tyr Phe Lys Lys Ile Glu Cys Phe Asp
                565                 570                 575 tcc gtg gaa atc tcc ggc gtg gaa gat cgg ttc aac gcc tcc ctg ggc      1776
Ser Val Glu Ile Ser Gly Val Glu Asp Arg Phe Asn Ala Ser Leu Gly
                580                 585                 590 aca tac cac gat ctg ctg aaa att atc aag gac aag gac ttc ctg gac      1824
Thr Tyr His Asp Leu Leu Lys Ile Ile Lys Asp Lys Asp Phe Leu Asp
            595                 600                 605 aat gag gaa aac gag gac att ctg gaa gat atc gtg ctg acc ctg aca      1872
Asn Glu Glu Asn Glu Asp Ile Leu Glu Asp Ile Val Leu Thr Leu Thr
        610                 615                 620 ctg ttt gag gac aga gag atg atc gag gaa cgg ctg aaa acc tat gcc      1920
Leu Phe Glu Asp Arg Glu Met Ile Glu Glu Arg Leu Lys Thr Tyr Ala
625                 630                 635                 640 cac ctg ttc gac gac aaa gtg atg aag cag ctg aag cgg cgg aga tac      1968
His Leu Phe Asp Asp Lys Val Met Lys Gln Leu Lys Arg Arg Arg Tyr
                645                 650                 655 acc ggc tgg ggc agg ctg agc cgg aag ctg atc aac ggc atc cgg gac      2016
Thr Gly Trp Gly Arg Leu Ser Arg Lys Leu Ile Asn Gly Ile Arg Asp
                660                 665                 670 aag cag tcc ggc aag aca atc ctg gat ttc ctg aag tcc gac ggc ttc      2064
Lys Gln Ser Gly Lys Thr Ile Leu Asp Phe Leu Lys Ser Asp Gly Phe
            675                 680                 685 gcc aac aga aac ttc atg cag ctg atc cac gac gac agc ctg acc ttt      2112
Ala Asn Arg Asn Phe Met Gln Leu Ile His Asp Asp Ser Leu Thr Phe
```

|     |     |     |     |     |     |     |     |     |     |     |     |     |     |     |     |      |
|---|---|---|---|---|---|---|---|---|---|---|---|---|---|---|---|---|
| | 690 | | | | 695 | | | | | 700 | | | | | | |
| aaa | gag | gac | atc | cag | aaa | gcc | cag | gtg | tcc | ggc | cag | ggc | gat | agc | ctg | 2160 |
| Lys | Glu | Asp | Ile | Gln | Lys | Ala | Gln | Val | Ser | Gly | Gln | Gly | Asp | Ser | Leu | |
| 705 | | | | 710 | | | | | 715 | | | | | 720 | | |
| cac | gag | cac | att | gcc | aat | ctg | gcc | ggc | agc | ccc | gcc | att | aag | aag | ggc | 2208 |
| His | Glu | His | Ile | Ala | Asn | Leu | Ala | Gly | Ser | Pro | Ala | Ile | Lys | Lys | Gly | |
| | | | | | 725 | | | | | 730 | | | | | 735 | |
| atc | ctg | cag | aca | gtg | aag | gtg | gtg | gac | gag | ctc | gtg | aaa | gtg | atg | ggc | 2256 |
| Ile | Leu | Gln | Thr | Val | Lys | Val | Val | Asp | Glu | Leu | Val | Lys | Val | Met | Gly | |
| | | | 740 | | | | | 745 | | | | | 750 | | | |
| cgg | cac | aag | ccc | gag | aac | atc | gtg | atc | gaa | atg | gcc | aga | gag | aac | cag | 2304 |
| Arg | His | Lys | Pro | Glu | Asn | Ile | Val | Ile | Glu | Met | Ala | Arg | Glu | Asn | Gln | |
| | | 755 | | | | | 760 | | | | | 765 | | | | |
| acc | acc | cag | aag | gga | cag | aag | aac | agc | cgc | gag | aga | atg | aag | cgg | atc | 2352 |
| Thr | Thr | Gln | Lys | Gly | Gln | Lys | Asn | Ser | Arg | Glu | Arg | Met | Lys | Arg | Ile | |
| | 770 | | | | | 775 | | | | | 780 | | | | | |
| gaa | gag | ggc | atc | aaa | gag | ctg | ggc | agc | cag | atc | ctg | aaa | gaa | cac | ccc | 2400 |
| Glu | Glu | Gly | Ile | Lys | Glu | Leu | Gly | Ser | Gln | Ile | Leu | Lys | Glu | His | Pro | |
| 785 | | | | | 790 | | | | | 795 | | | | | 800 | |
| gtg | gaa | aac | acc | cag | ctg | cag | aac | gag | aag | ctg | tac | ctg | tac | tac | ctg | 2448 |
| Val | Glu | Asn | Thr | Gln | Leu | Gln | Asn | Glu | Lys | Leu | Tyr | Leu | Tyr | Tyr | Leu | |
| | | | | 805 | | | | | 810 | | | | | 815 | | |
| cag | aat | ggg | cgg | gat | atg | tac | gtg | gac | cag | gaa | ctg | gac | atc | aac | cgg | 2496 |
| Gln | Asn | Gly | Arg | Asp | Met | Tyr | Val | Asp | Gln | Glu | Leu | Asp | Ile | Asn | Arg | |
| | | | 820 | | | | | 825 | | | | | 830 | | | |
| ctg | tcc | gac | tac | gat | gtg | gac | cat | atc | gtg | cct | cag | agc | ttt | ctg | aag | 2544 |
| Leu | Ser | Asp | Tyr | Asp | Val | Asp | His | Ile | Val | Pro | Gln | Ser | Phe | Leu | Lys | |
| | | 835 | | | | | 840 | | | | | 845 | | | | |
| gac | gac | tcc | atc | gac | aac | aag | gtg | ctg | acc | aga | agc | gac | aag | aac | cgg | 2592 |
| Asp | Asp | Ser | Ile | Asp | Asn | Lys | Val | Leu | Thr | Arg | Ser | Asp | Lys | Asn | Arg | |
| | 850 | | | | | 855 | | | | | 860 | | | | | |
| ggc | aag | agc | gac | aac | gtg | ccc | tcc | gaa | gag | gtc | gtg | aag | aag | atg | aag | 2640 |
| Gly | Lys | Ser | Asp | Asn | Val | Pro | Ser | Glu | Glu | Val | Val | Lys | Lys | Met | Lys | |
| 865 | | | | | 870 | | | | | 875 | | | | | 880 | |
| aac | tac | tgg | cgg | cag | ctg | ctg | aac | gcc | aag | ctg | att | acc | cag | aga | aag | 2688 |
| Asn | Tyr | Trp | Arg | Gln | Leu | Leu | Asn | Ala | Lys | Leu | Ile | Thr | Gln | Arg | Lys | |
| | | | | 885 | | | | | 890 | | | | | 895 | | |
| ttc | gac | aat | ctg | acc | aag | gcc | gag | aga | ggc | ggc | ctg | agc | gaa | ctg | gat | 2736 |
| Phe | Asp | Asn | Leu | Thr | Lys | Ala | Glu | Arg | Gly | Gly | Leu | Ser | Glu | Leu | Asp | |
| | | | 900 | | | | | 905 | | | | | 910 | | | |
| aag | gcc | ggc | ttc | atc | aag | aga | cag | ctg | gtg | gaa | acc | cgg | cag | atc | aca | 2784 |
| Lys | Ala | Gly | Phe | Ile | Lys | Arg | Gln | Leu | Val | Glu | Thr | Arg | Gln | Ile | Thr | |
| | | 915 | | | | | 920 | | | | | 925 | | | | |
| aag | cac | gtg | gca | cag | atc | ctg | gac | tcc | cgg | atg | aac | act | aag | tac | gac | 2832 |
| Lys | His | Val | Ala | Gln | Ile | Leu | Asp | Ser | Arg | Met | Asn | Thr | Lys | Tyr | Asp | |
| | 930 | | | | | 935 | | | | | 940 | | | | | |
| gag | aat | gac | aag | ctg | atc | cgg | gaa | gtg | aaa | gtg | atc | acc | ctg | aag | tcc | 2880 |
| Glu | Asn | Asp | Lys | Leu | Ile | Arg | Glu | Val | Lys | Val | Ile | Thr | Leu | Lys | Ser | |
| 945 | | | | | 950 | | | | | 955 | | | | | 960 | |
| aag | ctg | gtg | tcc | gat | ttc | cgg | aag | gat | ttc | cag | ttt | tac | aaa | gtg | cgc | 2928 |
| Lys | Leu | Val | Ser | Asp | Phe | Arg | Lys | Asp | Phe | Gln | Phe | Tyr | Lys | Val | Arg | |
| | | | | 965 | | | | | 970 | | | | | 975 | | |
| gag | atc | aac | aac | tac | cac | cac | gcc | cac | gac | gcc | tac | ctg | aac | gcc | gtc | 2976 |
| Glu | Ile | Asn | Asn | Tyr | His | His | Ala | His | Asp | Ala | Tyr | Leu | Asn | Ala | Val | |
| | | | 980 | | | | | 985 | | | | | 990 | | | |
| gtg | gga | acc | gcc | ctg | atc | aaa | aag | tac | cct | aag | ctg | gaa | agc | gag | ttc | 3024 |
| Val | Gly | Thr | Ala | Leu | Ile | Lys | Lys | Tyr | Pro | Lys | Leu | Glu | Ser | Glu | Phe | |
| | | 995 | | | | | 1000 | | | | | 1005 | | | | |
| gtg | tac | ggc | gac | tac | aag | gtg | tac | gac | gtg | cgg | aag | atg | atc | gcc | | 3069 |

|     |     |     |     |     |     |     |     |     |     |     |     |     |     |     |      |
|-----|-----|-----|-----|-----|-----|-----|-----|-----|-----|-----|-----|-----|-----|-----|------|
| Val | Tyr | Gly | Asp | Tyr | Lys | Val | Tyr | Asp | Val | Arg | Lys | Met | Ile | Ala |      |
|     | 1010 |    |     |     | 1015|     |     |     | 1020|     |     |     |     |     |      |

```
aag agc gag cag gaa atc ggc aag gct acc gcc aag tac ttc ttc      3114
Lys Ser Glu Gln Glu Ile Gly Lys Ala Thr Ala Lys Tyr Phe Phe
    1025            1030            1035 tac agc aac atc atg aac ttt ttc aag acc gag att acc ctg gcc      3159
Tyr Ser Asn Ile Met Asn Phe Phe Lys Thr Glu Ile Thr Leu Ala
    1040            1045            1050 aac ggc gag atc cgg aag cgg cct ctg atc gag aca aac ggc gaa      3204
Asn Gly Glu Ile Arg Lys Arg Pro Leu Ile Glu Thr Asn Gly Glu
    1055            1060            1065 acc ggg gag atc gtg tgg gat aag ggc cgg gat ttt gcc acc gtg      3249
Thr Gly Glu Ile Val Trp Asp Lys Gly Arg Asp Phe Ala Thr Val
    1070            1075            1080 cgg aaa gtg ctg agc atg ccc caa gtg aat atc gtg aaa aag acc      3294
Arg Lys Val Leu Ser Met Pro Gln Val Asn Ile Val Lys Lys Thr
    1085            1090            1095 gag gtg cag aca ggc ggc ttc agc aaa gag tct atc cgg ccc aag      3339
Glu Val Gln Thr Gly Gly Phe Ser Lys Glu Ser Ile Arg Pro Lys
    1100            1105            1110 agg aac agc gat aag ctg atc gcc aga aag aag gac tgg gac cct      3384
Arg Asn Ser Asp Lys Leu Ile Ala Arg Lys Lys Asp Trp Asp Pro
    1115            1120            1125 aag aag tac ggc ggc ttc gac agc ccc acc gtg gcc tat tct gtg      3429
Lys Lys Tyr Gly Gly Phe Asp Ser Pro Thr Val Ala Tyr Ser Val
    1130            1135            1140 ctg gtg gtg gcc aaa gtg gaa aag ggc aag tcc aag aaa ctg aag      3474
Leu Val Val Ala Lys Val Glu Lys Gly Lys Ser Lys Lys Leu Lys
    1145            1150            1155 agt gtg aaa gag ctg ctg ggg atc acc atc atg gaa aga agc agc      3519
Ser Val Lys Glu Leu Leu Gly Ile Thr Ile Met Glu Arg Ser Ser
    1160            1165            1170 ttc gag aag aat ccc atc gac ttt ctg gaa gcc aag ggc tac aaa      3564
Phe Glu Lys Asn Pro Ile Asp Phe Leu Glu Ala Lys Gly Tyr Lys
    1175            1180            1185 gaa gtg aaa aag gac ctg atc atc aag ctg cct aag tac tcc ctg      3609
Glu Val Lys Lys Asp Leu Ile Ile Lys Leu Pro Lys Tyr Ser Leu
    1190            1195            1200 ttc gag ctg gaa aac ggc cgg aag aga atg ctg gcc tct gcc cgg      3654
Phe Glu Leu Glu Asn Gly Arg Lys Arg Met Leu Ala Ser Ala Arg
    1205            1210            1215 gaa ctg cag aag gga aac gaa ctg gcc ctg ccc tcc aaa tat gtg      3699
Glu Leu Gln Lys Gly Asn Glu Leu Ala Leu Pro Ser Lys Tyr Val
    1220            1225            1230 aac ttc ctg tac ctg gcc agc cac tat gag aag ctg aag ggc tcc      3744
Asn Phe Leu Tyr Leu Ala Ser His Tyr Glu Lys Leu Lys Gly Ser
    1235            1240            1245 ccc gag gat aat gag cag aaa cag ctg ttt gtg gaa cag cac aag      3789
Pro Glu Asp Asn Glu Gln Lys Gln Leu Phe Val Glu Gln His Lys
    1250            1255            1260 cac tac ctg gac gag atc atc gag cag atc agc gag ttc tcc aag      3834
His Tyr Leu Asp Glu Ile Ile Glu Gln Ile Ser Glu Phe Ser Lys
    1265            1270            1275 aga gtg atc ctg gcc gac gct aat ctg gac aaa gtg ctg tcc gcc      3879
Arg Val Ile Leu Ala Asp Ala Asn Leu Asp Lys Val Leu Ser Ala
    1280            1285            1290 tac aac aag cac cgg gat aag ccc atc aga gag cag gcc gag aat      3924
Tyr Asn Lys His Arg Asp Lys Pro Ile Arg Glu Gln Ala Glu Asn
    1295            1300            1305
```

-continued

| | | |
|---|---|---|
| atc atc cac ctg ttt acc ctg acc aat ctg gga gcc cct cgg gcc<br>Ile Ile His Leu Phe Thr Leu Thr Asn Leu Gly Ala Pro Arg Ala<br>1310                     1315                    1320 | | 3969 |
| ttc aag tac ttt gac acc acc atc gac cgg aag gcc tac cgg agc<br>Phe Lys Tyr Phe Asp Thr Thr Ile Asp Arg Lys Ala Tyr Arg Ser<br>1325                     1330                    1335 | | 4014 |
| acc aaa gag gtg ctg gac gcc acc ctg atc cac cag agc atc acc<br>Thr Lys Glu Val Leu Asp Ala Thr Leu Ile His Gln Ser Ile Thr<br>1340                     1345                    1350 | | 4059 |
| ggc ctg tac gag aca cgg atc gac ctg tct cag ctg gga ggc gac<br>Gly Leu Tyr Glu Thr Arg Ile Asp Leu Ser Gln Leu Gly Gly Asp<br>1355                     1360                    1365 | | 4104 |
| taa | | 4107 |

<210> SEQ ID NO 13
<211> LENGTH: 4107
<212> TYPE: DNA
<213> ORGANISM: Streptococcus pyogenes
<220> FEATURE:
<221> NAME/KEY: CDS
<222> LOCATION: (1)..(4107)

<400> SEQUENCE: 13

| | | |
|---|---|---|
| atg gac aag aag tac agc atc ggc ctg gac atc ggc acc aac tct gtg<br>Met Asp Lys Lys Tyr Ser Ile Gly Leu Asp Ile Gly Thr Asn Ser Val<br>1                   5                   10                 15 | | 48 |
| ggc tgg gcc gtg atc acc gac gag tac aag gtg ccc agc aag aaa ttc<br>Gly Trp Ala Val Ile Thr Asp Glu Tyr Lys Val Pro Ser Lys Lys Phe<br>                  20                   25                   30 | | 96 |
| aag gtg ctg ggc aac acc gac cgg cac agc atc aag aag aac ctg atc<br>Lys Val Leu Gly Asn Thr Asp Arg His Ser Ile Lys Lys Asn Leu Ile<br>      35                   40                   45 | | 144 |
| gga gcc ctg ctg ttc gac agc ggc gaa aca gcc gag gcc acc cgg ctg<br>Gly Ala Leu Leu Phe Asp Ser Gly Glu Thr Ala Glu Ala Thr Arg Leu<br>50                     55                   60 | | 192 |
| aag aga acc gcc aga aga aga tac acc aga cgg aag aac cgg atc tgc<br>Lys Arg Thr Ala Arg Arg Arg Tyr Thr Arg Arg Lys Asn Arg Ile Cys<br>65                     70                   75                   80 | | 240 |
| tat ctg caa gag atc ttc agc aac gag atg gcc aag gtg gac gac agc<br>Tyr Leu Gln Glu Ile Phe Ser Asn Glu Met Ala Lys Val Asp Asp Ser<br>                         85                   90                   95 | | 288 |
| ttc ttc cac aga ctg gaa gag tcc ttc ctg gtg gaa gag gat aag aag<br>Phe Phe His Arg Leu Glu Glu Ser Phe Leu Val Glu Glu Asp Lys Lys<br>                100                 105                110 | | 336 |
| cac gag cgg cac ccc atc ttc ggc aac atc gtg gac gag gtg gcc tac<br>His Glu Arg His Pro Ile Phe Gly Asn Ile Val Asp Glu Val Ala Tyr<br>           115                 120                125 | | 384 |
| cac gag aag tac ccc acc atc tac cac ctg aga aag aaa ctg gtg gac<br>His Glu Lys Tyr Pro Thr Ile Tyr His Leu Arg Lys Lys Leu Val Asp<br>130                    135                  140 | | 432 |
| agc acc gac aag gcc gac ctg cgg ctg atc tat ctg gcc ctg gcc cac<br>Ser Thr Asp Lys Ala Asp Leu Arg Leu Ile Tyr Leu Ala Leu Ala His<br>145                    150                  155                160 | | 480 |
| atg atc aag ttc cgg ggc cac ttc ctg atc gag ggc gac ctg aac ccc<br>Met Ile Lys Phe Arg Gly His Phe Leu Ile Glu Gly Asp Leu Asn Pro<br>                165                 170                175 | | 528 |
| gac aac agc gac gtg gac aag ctg ttc atc cag ctg gtg cag acc tac<br>Asp Asn Ser Asp Val Asp Lys Leu Phe Ile Gln Leu Val Gln Thr Tyr<br>           180                 185                190 | | 576 |
| aac cag ctg ttc gag gaa aac ccc atc aac gcc agc ggc gtg gac gcc<br>Asn Gln Leu Phe Glu Glu Asn Pro Ile Asn Ala Ser Gly Val Asp Ala | | 624 |

-continued

```
              195                 200                 205
aag gcc atc ctg tct gcc aga ctg agc aag agc aga cgg ctg gaa aat       672
Lys Ala Ile Leu Ser Ala Arg Leu Ser Lys Ser Arg Arg Leu Glu Asn
    210                 215                 220 ctg atc gcc cag ctg ccc ggc gag aag aag aat ggc ctg ttc ggc aac       720
Leu Ile Ala Gln Leu Pro Gly Glu Lys Lys Asn Gly Leu Phe Gly Asn
225                 230                 235                 240 ctg att gcc ctg agc ctg ggc ctg acc ccc aac ttc aag agc aac ttc       768
Leu Ile Ala Leu Ser Leu Gly Leu Thr Pro Asn Phe Lys Ser Asn Phe
                245                 250                 255 gac ctg gcc gag gat gcc aaa ctg cag ctg agc aag gac acc tac gac       816
Asp Leu Ala Glu Asp Ala Lys Leu Gln Leu Ser Lys Asp Thr Tyr Asp
        260                 265                 270 gac gac ctg gac aac ctg ctg gcc cag atc ggc gac cag tac gcc gac       864
Asp Asp Leu Asp Asn Leu Leu Ala Gln Ile Gly Asp Gln Tyr Ala Asp
            275                 280                 285 ctg ttt ctg gcc gcc aag aac ctg tcc gac gcc atc ctg ctg agc gac       912
Leu Phe Leu Ala Ala Lys Asn Leu Ser Asp Ala Ile Leu Leu Ser Asp
    290                 295                 300 atc ctg aga gtg aac acc gag atc acc aag gcc ccc ctg agc gcc tct       960
Ile Leu Arg Val Asn Thr Glu Ile Thr Lys Ala Pro Leu Ser Ala Ser
305                 310                 315                 320 atg atc aag aga tac gac gag cac cac cag gac ctg acc ctg ctg aaa      1008
Met Ile Lys Arg Tyr Asp Glu His His Gln Asp Leu Thr Leu Leu Lys
                325                 330                 335 gct ctc gtg cgg cag cag ctg cct gag aag tac aaa gag att ttc ttc      1056
Ala Leu Val Arg Gln Gln Leu Pro Glu Lys Tyr Lys Glu Ile Phe Phe
        340                 345                 350 gac cag agc aag aac ggc tac gcc ggc tac att gac ggc gga gcc agc      1104
Asp Gln Ser Lys Asn Gly Tyr Ala Gly Tyr Ile Asp Gly Gly Ala Ser
            355                 360                 365 cag gaa gag ttc tac aag ttc atc aag ccc atc ctg gaa aag atg gac      1152
Gln Glu Glu Phe Tyr Lys Phe Ile Lys Pro Ile Leu Glu Lys Met Asp
    370                 375                 380 ggc acc gag gaa ctg ctc gtg aag ctg aac aga gag gac ctg ctg cgg      1200
Gly Thr Glu Glu Leu Leu Val Lys Leu Asn Arg Glu Asp Leu Leu Arg
385                 390                 395                 400 aag cag cgg acc ttc gac aac ggc agc atc ccc cac cag atc cac ctg      1248
Lys Gln Arg Thr Phe Asp Asn Gly Ser Ile Pro His Gln Ile His Leu
                405                 410                 415 gga gag ctg cac gcc att ctg cgg cgg cag gaa gat ttt tac cca ttc      1296
Gly Glu Leu His Ala Ile Leu Arg Arg Gln Glu Asp Phe Tyr Pro Phe
        420                 425                 430 ctg aag gac aac cgg gaa aag atc gag aag atc ctg acc ttc cgc atc      1344
Leu Lys Asp Asn Arg Glu Lys Ile Glu Lys Ile Leu Thr Phe Arg Ile
            435                 440                 445 ccc tac tac gtg ggc cct ctg gcc agg gga aac agc aga ttc gcc tgg      1392
Pro Tyr Tyr Val Gly Pro Leu Ala Arg Gly Asn Ser Arg Phe Ala Trp
    450                 455                 460 atg acc aga aag agc gag gaa acc atc acc ccc tgg aac ttc gag gaa      1440
Met Thr Arg Lys Ser Glu Glu Thr Ile Thr Pro Trp Asn Phe Glu Glu
465                 470                 475                 480 gtg gtg gac aag ggc gct tcc gcc cag agc ttc atc gag cgg atg acc      1488
Val Val Asp Lys Gly Ala Ser Ala Gln Ser Phe Ile Glu Arg Met Thr
                485                 490                 495 aac ttc gat aag aac ctg ccc aac gag aag gtg ctg ccc aag cac agc      1536
Asn Phe Asp Lys Asn Leu Pro Asn Glu Lys Val Leu Pro Lys His Ser
        500                 505                 510 ctg ctg tac gag tac ttc acc gtg tat aac gag ctg acc aaa gtg aaa      1584
```

```
                    Leu Leu Tyr Glu Tyr Phe Thr Val Tyr Asn Glu Leu Thr Lys Val Lys
                            515                 520                 525 tac gtg acc gag gga atg aga aag ccc gcc ttc ctg agc ggc gag cag          1632
Tyr Val Thr Glu Gly Met Arg Lys Pro Ala Phe Leu Ser Gly Glu Gln
530                 535                 540 aaa aag gcc atc gtg gac ctg ctg ttc aag acc aac cgg aaa gtg acc          1680
Lys Lys Ala Ile Val Asp Leu Leu Phe Lys Thr Asn Arg Lys Val Thr
545                 550                 555                 560 gtg aag cag ctg aaa gag gac tac ttc aag aaa atc gag tgc ttc gac          1728
Val Lys Gln Leu Lys Glu Asp Tyr Phe Lys Lys Ile Glu Cys Phe Asp
                565                 570                 575 tcc gtg gaa atc tcc ggc gtg gaa gat cgg ttc aac gcc tcc ctg ggc          1776
Ser Val Glu Ile Ser Gly Val Glu Asp Arg Phe Asn Ala Ser Leu Gly
                580                 585                 590 aca tac cac gat ctg ctg aaa att atc aag gac aag gac ttc ctg gac          1824
Thr Tyr His Asp Leu Leu Lys Ile Ile Lys Asp Lys Asp Phe Leu Asp
                595                 600                 605 aat gag gaa aac gag gac att ctg gaa gat atc gtg ctg acc ctg aca          1872
Asn Glu Glu Asn Glu Asp Ile Leu Glu Asp Ile Val Leu Thr Leu Thr
610                 615                 620 ctg ttt gag gac aga gag atg atc gag gaa cgg ctg aaa acc tat gcc          1920
Leu Phe Glu Asp Arg Glu Met Ile Glu Glu Arg Leu Lys Thr Tyr Ala
625                 630                 635                 640 cac ctg ttc gac gac aaa gtg atg aag cag ctg aag cgg cgg aga tac          1968
His Leu Phe Asp Asp Lys Val Met Lys Gln Leu Lys Arg Arg Arg Tyr
                645                 650                 655 acc ggc tgg ggc agg ctg agc cgg aag ctg atc aac ggc atc cgg gac          2016
Thr Gly Trp Gly Arg Leu Ser Arg Lys Leu Ile Asn Gly Ile Arg Asp
                660                 665                 670 aag cag tcc ggc aag aca atc ctg gat ttc ctg aag tcc gac ggc ttc          2064
Lys Gln Ser Gly Lys Thr Ile Leu Asp Phe Leu Lys Ser Asp Gly Phe
                675                 680                 685 gcc aac aga aac ttc atg cag ctg atc cac gac gac agc ctg acc ttt          2112
Ala Asn Arg Asn Phe Met Gln Leu Ile His Asp Asp Ser Leu Thr Phe
690                 695                 700 aaa gag gac atc cag aaa gcc cag gtg tcc ggc cag ggc gat agc ctg          2160
Lys Glu Asp Ile Gln Lys Ala Gln Val Ser Gly Gln Gly Asp Ser Leu
705                 710                 715                 720 cac gag cac att gcc aat ctg gcc ggc agc ccc gcc att aag aag ggc          2208
His Glu His Ile Ala Asn Leu Ala Gly Ser Pro Ala Ile Lys Lys Gly
                725                 730                 735 atc ctg cag aca gtg aag gtg gtg gac gag ctc gtg aaa gtg atg ggc          2256
Ile Leu Gln Thr Val Lys Val Val Asp Glu Leu Val Lys Val Met Gly
                740                 745                 750 cgg cac aag ccc gag aac atc gtg atc gaa atg gcc aga gag aac cag          2304
Arg His Lys Pro Glu Asn Ile Val Ile Glu Met Ala Arg Glu Asn Gln
                755                 760                 765 acc acc cag aag gga cag aag aac agc cgc gag aga atg aag cgg atc          2352
Thr Thr Gln Lys Gly Gln Lys Asn Ser Arg Glu Arg Met Lys Arg Ile
770                 775                 780 gaa gag ggc atc aaa gag ctg ggc agc cag atc ctg aaa gaa cac ccc          2400
Glu Glu Gly Ile Lys Glu Leu Gly Ser Gln Ile Leu Lys Glu His Pro
785                 790                 795                 800 gtg gaa aac acc cag ctg cag aac gag aag ctg tac ctg tac tac ctg          2448
Val Glu Asn Thr Gln Leu Gln Asn Glu Lys Leu Tyr Leu Tyr Tyr Leu
                805                 810                 815 cag aat ggg cgg gat atg tac gtg gac cag gaa ctg gac atc aac cgg          2496
Gln Asn Gly Arg Asp Met Tyr Val Asp Gln Glu Leu Asp Ile Asn Arg
                820                 825                 830
```

| | |
|---|---|
| ctg tcc gac tac gat gtg gac cat atc gtg cct cag agc ttt ctg aag<br>Leu Ser Asp Tyr Asp Val Asp His Ile Val Pro Gln Ser Phe Leu Lys<br>835                     840                     845 | 2544 |
| gac gac tcc atc gac aac aag gtg ctg acc aga agc gac aag aac cgg<br>Asp Asp Ser Ile Asp Asn Lys Val Leu Thr Arg Ser Asp Lys Asn Arg<br>850                     855                     860 | 2592 |
| ggc aag agc gac aac gtg ccc tcc gaa gag gtc gtg aag aag atg aag<br>Gly Lys Ser Asp Asn Val Pro Ser Glu Glu Val Val Lys Lys Met Lys<br>865                   870                   875                   880 | 2640 |
| aac tac tgg cgg cag ctg ctg aac gcc aag ctg att acc cag aga aag<br>Asn Tyr Trp Arg Gln Leu Leu Asn Ala Lys Leu Ile Thr Gln Arg Lys<br>                   885                     890                   895 | 2688 |
| ttc gac aat ctg acc aag gcc gag aga ggc ggc ctg agc gaa ctg gat<br>Phe Asp Asn Leu Thr Lys Ala Glu Arg Gly Gly Leu Ser Glu Leu Asp<br>900                     905                     910 | 2736 |
| aag gcc ggc ttc atc aag aga cag ctg gtg gaa acc cgg cag atc aca<br>Lys Ala Gly Phe Ile Lys Arg Gln Leu Val Glu Thr Arg Gln Ile Thr<br>                   915                     920                   925 | 2784 |
| aag cac gtg gca cag atc ctg gac tcc cgg atg aac act aag tac gac<br>Lys His Val Ala Gln Ile Leu Asp Ser Arg Met Asn Thr Lys Tyr Asp<br>930                     935                     940 | 2832 |
| gag aat gac aag ctg atc cgg gaa gtg aaa gtg atc acc ctg aag tcc<br>Glu Asn Asp Lys Leu Ile Arg Glu Val Lys Val Ile Thr Leu Lys Ser<br>945                   950                   955                   960 | 2880 |
| aag ctg gtg tcc gat ttc cgg aag gat ttc cag ttt tac aaa gtg cgc<br>Lys Leu Val Ser Asp Phe Arg Lys Asp Phe Gln Phe Tyr Lys Val Arg<br>                   965                     970                   975 | 2928 |
| gag atc aac aac tac cac cac gcc cac gac gcc tac ctg aac gcc gtc<br>Glu Ile Asn Asn Tyr His His Ala His Asp Ala Tyr Leu Asn Ala Val<br>980                     985                     990 | 2976 |
| gtg gga acc gcc ctg atc aaa aag tac cct aag ctg gaa agc gag ttc<br>Val Gly Thr Ala Leu Ile Lys Lys Tyr Pro Lys Leu Glu Ser Glu Phe<br>                   995                   1000                 1005 | 3024 |
| gtg tac ggc gac tac aag gtg tac gac gtg cgg aag atg atc gcc<br>Val Tyr Gly Asp Tyr Lys Val Tyr Asp Val Arg Lys Met Ile Ala<br>1010                     1015                     1020 | 3069 |
| aag agc gag cag gaa atc ggc aag gct acc gcc aag tac ttc ttc<br>Lys Ser Glu Gln Glu Ile Gly Lys Ala Thr Ala Lys Tyr Phe Phe<br>1025                     1030                     1035 | 3114 |
| tac agc aac atc atg aac ttt ttc aag acc gag att acc ctg gcc<br>Tyr Ser Asn Ile Met Asn Phe Phe Lys Thr Glu Ile Thr Leu Ala<br>1040                     1045                     1050 | 3159 |
| aac ggc gag atc cgg aag cgg cct ctg atc gag aca aac ggc gaa<br>Asn Gly Glu Ile Arg Lys Arg Pro Leu Ile Glu Thr Asn Gly Glu<br>1055                     1060                     1065 | 3204 |
| acc ggg gag atc gtg tgg gat aag ggc cgg gat ttt gcc acc gtg<br>Thr Gly Glu Ile Val Trp Asp Lys Gly Arg Asp Phe Ala Thr Val<br>1070                     1075                     1080 | 3249 |
| cgg aaa gtg ctg agc atg ccc caa gtg aat atc gtg aaa aag acc<br>Arg Lys Val Leu Ser Met Pro Gln Val Asn Ile Val Lys Lys Thr<br>1085                     1090                     1095 | 3294 |
| gag gtg cag aca ggc ggc ttc agc aaa gag tct atc cgg ccc aag<br>Glu Val Gln Thr Gly Gly Phe Ser Lys Glu Ser Ile Arg Pro Lys<br>1100                     1105                     1110 | 3339 |
| agg aac agc gat aag ctg atc gcc aga aag aag gac tgg gac cct<br>Arg Asn Ser Asp Lys Leu Ile Ala Arg Lys Lys Asp Trp Asp Pro<br>1115                     1120                     1125 | 3384 |
| aag aag tac ggc ggc ttc gac agc ccc acc gtg gcc tat tct gtg<br>Lys Lys Tyr Gly Gly Phe Asp Ser Pro Thr Val Ala Tyr Ser Val<br>1130                     1135                     1140 | 3429 |

```
ctg gtg gtg gcc aaa gtg gaa aag ggc aag tcc aag aaa ctg aag      3474
Leu Val Val Ala Lys Val Glu Lys Gly Lys Ser Lys Lys Leu Lys
    1145            1150                1155 agt gtg aaa gag ctg ctg ggg atc acc atc atg gaa aga agc agc      3519
Ser Val Lys Glu Leu Leu Gly Ile Thr Ile Met Glu Arg Ser Ser
    1160            1165                1170 ttc gag aag aat ccc atc gac ttt ctg gaa gcc aag ggc tac aaa      3564
Phe Glu Lys Asn Pro Ile Asp Phe Leu Glu Ala Lys Gly Tyr Lys
    1175            1180                1185 gaa gtg aaa aag gac ctg atc atc aag ctg cct aag tac tcc ctg      3609
Glu Val Lys Lys Asp Leu Ile Ile Lys Leu Pro Lys Tyr Ser Leu
    1190            1195                1200 ttc gag ctg gaa aac ggc cgg aag aga atg ctg gcc tct gcc cgg      3654
Phe Glu Leu Glu Asn Gly Arg Lys Arg Met Leu Ala Ser Ala Arg
    1205            1210                1215 gaa ctg cag aag gga aac gaa ctg gcc ctg ccc tcc aaa tat gtg      3699
Glu Leu Gln Lys Gly Asn Glu Leu Ala Leu Pro Ser Lys Tyr Val
    1220            1225                1230 aac ttc ctg tac ctg gcc agc cac tat gag aag ctg aag ggc tcc      3744
Asn Phe Leu Tyr Leu Ala Ser His Tyr Glu Lys Leu Lys Gly Ser
    1235            1240                1245 ccc gag gat aat gag cag aaa cag ctg ttt gtg gaa cag cac aag      3789
Pro Glu Asp Asn Glu Gln Lys Gln Leu Phe Val Glu Gln His Lys
    1250            1255                1260 cac tac ctg gac gag atc atc gag cag atc agc gag ttc tcc aag      3834
His Tyr Leu Asp Glu Ile Ile Glu Gln Ile Ser Glu Phe Ser Lys
    1265            1270                1275 aga gtg atc ctg gcc gac gct aat ctg gac aaa gtg ctg tcc gcc      3879
Arg Val Ile Leu Ala Asp Ala Asn Leu Asp Lys Val Leu Ser Ala
    1280            1285                1290 tac aac aag cac cgg gat aag ccc atc aga gag cag gcc gag aat      3924
Tyr Asn Lys His Arg Asp Lys Pro Ile Arg Glu Gln Ala Glu Asn
    1295            1300                1305 atc atc cac ctg ttt acc ctg acc aat ctg gga gcc cct cgg gcc      3969
Ile Ile His Leu Phe Thr Leu Thr Asn Leu Gly Ala Pro Arg Ala
    1310            1315                1320 ttc aag tac ttt gac acc acc atc gac cgg aag gcc tac acc agc      4014
Phe Lys Tyr Phe Asp Thr Thr Ile Asp Arg Lys Ala Tyr Thr Ser
    1325            1330                1335 acc aaa gag gtg ctg gac gcc acc ctg atc cac cag agc atc acc      4059
Thr Lys Glu Val Leu Asp Ala Thr Leu Ile His Gln Ser Ile Thr
    1340            1345                1350 ggc ctg tac gag aca cgg atc gac ctg tct cag ctg gga ggc gac      4104
Gly Leu Tyr Glu Thr Arg Ile Asp Leu Ser Gln Leu Gly Gly Asp
    1355            1360                1365 taa                                                               4107

<210> SEQ ID NO 14
<211> LENGTH: 4107
<212> TYPE: DNA
<213> ORGANISM: Streptococcus pyogenes
<220> FEATURE:
<221> NAME/KEY: CDS
<222> LOCATION: (1)..(4107)

<400> SEQUENCE: 14 atg gac aag aag tac agc atc ggc ctg gac atc ggc acc aac tct gtg      48
Met Asp Lys Lys Tyr Ser Ile Gly Leu Asp Ile Gly Thr Asn Ser Val
1               5                   10                  15 ggc tgg gcc gtg atc acc gac gag tac aag gtg ccc agc aag aaa ttc      96
```

-continued

```
                Gly Trp Ala Val Ile Thr Asp Glu Tyr Lys Val Pro Ser Lys Lys Phe
                         20                  25                  30 aag gtg ctg ggc aac acc gac cgg cac agc atc aag aag aac ctg atc         144
Lys Val Leu Gly Asn Thr Asp Arg His Ser Ile Lys Lys Asn Leu Ile
             35                  40                  45 gga gcc ctg ctg ttc gac agc ggc gaa aca gcc gag gcc acc cgg ctg         192
Gly Ala Leu Leu Phe Asp Ser Gly Glu Thr Ala Glu Ala Thr Arg Leu
 50                  55                  60 aag aga acc gcc aga aga aga tac acc aga cgg aag aac cgg atc tgc         240
Lys Arg Thr Ala Arg Arg Arg Tyr Thr Arg Arg Lys Asn Arg Ile Cys
 65                  70                  75                  80 tat ctg caa gag atc ttc agc aac gag atg gcc aag gtg gac gac agc         288
Tyr Leu Gln Glu Ile Phe Ser Asn Glu Met Ala Lys Val Asp Asp Ser
                 85                  90                  95 ttc ttc cac aga ctg gaa gag tcc ttc ctg gtg gaa gag gat aag aag         336
Phe Phe His Arg Leu Glu Glu Ser Phe Leu Val Glu Glu Asp Lys Lys
            100                 105                 110 cac gag cgg cac ccc atc ttc ggc aac atc gtg gac gag gtg gcc tac         384
His Glu Arg His Pro Ile Phe Gly Asn Ile Val Asp Glu Val Ala Tyr
        115                 120                 125 cac gag aag tac ccc acc atc tac cac ctg aga aag aaa ctg gtg gac         432
His Glu Lys Tyr Pro Thr Ile Tyr His Leu Arg Lys Lys Leu Val Asp
    130                 135                 140 agc acc gac aag gcc gac ctg cgg ctg atc tat ctg gcc ctg gcc cac         480
Ser Thr Asp Lys Ala Asp Leu Arg Leu Ile Tyr Leu Ala Leu Ala His
145                 150                 155                 160 atg atc aag ttc cgg ggc cac ttc ctg atc gag ggc gac ctg aac ccc         528
Met Ile Lys Phe Arg Gly His Phe Leu Ile Glu Gly Asp Leu Asn Pro
                165                 170                 175 gac aac agc gac gtg gac aag ctg ttc atc cag ctg gtg cag acc tac         576
Asp Asn Ser Asp Val Asp Lys Leu Phe Ile Gln Leu Val Gln Thr Tyr
            180                 185                 190 aac cag ctg ttc gag gaa aac ccc atc aac gcc agc ggc gtg gac gcc         624
Asn Gln Leu Phe Glu Glu Asn Pro Ile Asn Ala Ser Gly Val Asp Ala
        195                 200                 205 aag gcc atc ctg tct gcc aga ctg agc aag agc aga cgg ctg gaa aat         672
Lys Ala Ile Leu Ser Ala Arg Leu Ser Lys Ser Arg Arg Leu Glu Asn
    210                 215                 220 ctg atc gcc cag ctg ccc ggc gag aag aag aat ggc ctg ttc ggc aac         720
Leu Ile Ala Gln Leu Pro Gly Glu Lys Lys Asn Gly Leu Phe Gly Asn
225                 230                 235                 240 ctg att gcc ctg agc ctg ggc ctg acc ccc aac ttc aag agc aac ttc         768
Leu Ile Ala Leu Ser Leu Gly Leu Thr Pro Asn Phe Lys Ser Asn Phe
                245                 250                 255 gac ctg gcc gag gat gcc aaa ctg cag ctg agc aag gac acc tac gac         816
Asp Leu Ala Glu Asp Ala Lys Leu Gln Leu Ser Lys Asp Thr Tyr Asp
            260                 265                 270 gac gac ctg gac aac ctg ctg gcc cag atc ggc gac cag tac gcc gac         864
Asp Asp Leu Asp Asn Leu Leu Ala Gln Ile Gly Asp Gln Tyr Ala Asp
        275                 280                 285 ctg ttt ctg gcc gcc aag aac ctg tcc gac gcc atc ctg ctg agc gac         912
Leu Phe Leu Ala Ala Lys Asn Leu Ser Asp Ala Ile Leu Leu Ser Asp
    290                 295                 300 atc ctg aga gtg aac acc gag atc acc aag gcc ccc ctg agc gcc tct         960
Ile Leu Arg Val Asn Thr Glu Ile Thr Lys Ala Pro Leu Ser Ala Ser
305                 310                 315                 320 atg atc aag aga tac gac gag cac cac cag gac ctg acc ctg ctg aaa        1008
Met Ile Lys Arg Tyr Asp Glu His His Gln Asp Leu Thr Leu Leu Lys
                325                 330                 335
```

-continued

| | | |
|---|---|---|
| gct ctc gtg cgg cag cag ctg cct gag aag tac aaa gag att ttc ttc<br>Ala Leu Val Arg Gln Gln Leu Pro Glu Lys Tyr Lys Glu Ile Phe Phe<br>340 345 350 | 1056 |
| gac cag agc aag aac ggc tac gcc ggc tac att gac ggc gga gcc agc<br>Asp Gln Ser Lys Asn Gly Tyr Ala Gly Tyr Ile Asp Gly Gly Ala Ser<br>355 360 365 | 1104 |
| cag gaa gag ttc tac aag ttc atc aag ccc atc ctg gaa aag atg gac<br>Gln Glu Glu Phe Tyr Lys Phe Ile Lys Pro Ile Leu Glu Lys Met Asp<br>370 375 380 | 1152 |
| ggc acc gag gaa ctg ctc gtg aag ctg aac aga gag gac ctg ctg cgg<br>Gly Thr Glu Glu Leu Leu Val Lys Leu Asn Arg Glu Asp Leu Leu Arg<br>385 390 395 400 | 1200 |
| aag cag cgg acc ttc gac aac ggc agc atc ccc cac cag atc cac ctg<br>Lys Gln Arg Thr Phe Asp Asn Gly Ser Ile Pro His Gln Ile His Leu<br>405 410 415 | 1248 |
| gga gag ctg cac gcc att ctg cgg cgg cag gaa gat ttt tac cca ttc<br>Gly Glu Leu His Ala Ile Leu Arg Arg Gln Glu Asp Phe Tyr Pro Phe<br>420 425 430 | 1296 |
| ctg aag gac aac cgg gaa aag atc gag aag atc ctg acc ttc cgc atc<br>Leu Lys Asp Asn Arg Glu Lys Ile Glu Lys Ile Leu Thr Phe Arg Ile<br>435 440 445 | 1344 |
| ccc tac tac gtg ggc cct ctg gcc agg gga aac agc aga ttc gcc tgg<br>Pro Tyr Tyr Val Gly Pro Leu Ala Arg Gly Asn Ser Arg Phe Ala Trp<br>450 455 460 | 1392 |
| atg acc aga aag agc gag gaa acc atc acc ccc tgg aac ttc gag gaa<br>Met Thr Arg Lys Ser Glu Glu Thr Ile Thr Pro Trp Asn Phe Glu Glu<br>465 470 475 480 | 1440 |
| gtg gtg gac aag ggc gct tcc gcc cag agc ttc atc gag cgg atg acc<br>Val Val Asp Lys Gly Ala Ser Ala Gln Ser Phe Ile Glu Arg Met Thr<br>485 490 495 | 1488 |
| aac ttc gat aag aac ctg ccc aac gag aag gtg ctg ccc aag cac agc<br>Asn Phe Asp Lys Asn Leu Pro Asn Glu Lys Val Leu Pro Lys His Ser<br>500 505 510 | 1536 |
| ctg ctg tac gag tac ttc acc gtg tat aac gag ctg acc aaa gtg aaa<br>Leu Leu Tyr Glu Tyr Phe Thr Val Tyr Asn Glu Leu Thr Lys Val Lys<br>515 520 525 | 1584 |
| tac gtg acc gag gga atg aga aag ccc gcc ttc ctg agc ggc gag cag<br>Tyr Val Thr Glu Gly Met Arg Lys Pro Ala Phe Leu Ser Gly Glu Gln<br>530 535 540 | 1632 |
| aaa aag gcc atc gtg gac ctg ctg ttc aag acc aac cgg aaa gtg acc<br>Lys Lys Ala Ile Val Asp Leu Leu Phe Lys Thr Asn Arg Lys Val Thr<br>545 550 555 560 | 1680 |
| gtg aag cag ctg aaa gag gac tac ttc aag aaa atc gag tgc ttc gac<br>Val Lys Gln Leu Lys Glu Asp Tyr Phe Lys Lys Ile Glu Cys Phe Asp<br>565 570 575 | 1728 |
| tcc gtg gaa atc tcc ggc gtg gaa gat cgg ttc aac gcc tcc ctg ggc<br>Ser Val Glu Ile Ser Gly Val Glu Asp Arg Phe Asn Ala Ser Leu Gly<br>580 585 590 | 1776 |
| aca tac cac gat ctg ctg aaa att atc aag gac aag gac ttc ctg gac<br>Thr Tyr His Asp Leu Leu Lys Ile Ile Lys Asp Lys Asp Phe Leu Asp<br>595 600 605 | 1824 |
| aat gag gaa aac gag gac att ctg gaa gat atc gtg ctg acc ctg aca<br>Asn Glu Glu Asn Glu Asp Ile Leu Glu Asp Ile Val Leu Thr Leu Thr<br>610 615 620 | 1872 |
| ctg ttt gag gac aga gag atg atc gag gaa cgg ctg aaa acc tat gcc<br>Leu Phe Glu Asp Arg Glu Met Ile Glu Glu Arg Leu Lys Thr Tyr Ala<br>625 630 635 640 | 1920 |
| cac ctg ttc gac gac aaa gtg atg aag cag ctg aag cgg cgg aga tac<br>His Leu Phe Asp Asp Lys Val Met Lys Gln Leu Lys Arg Arg Arg Tyr<br>645 650 655 | 1968 |

```
acc ggc tgg ggc agg ctg agc cgg aag ctg atc aac ggc atc cgg gac    2016
Thr Gly Trp Gly Arg Leu Ser Arg Lys Leu Ile Asn Gly Ile Arg Asp
            660                 665                 670 aag cag tcc ggc aag aca atc ctg gat ttc ctg aag tcc gac ggc ttc    2064
Lys Gln Ser Gly Lys Thr Ile Leu Asp Phe Leu Lys Ser Asp Gly Phe
675                 680                 685 gcc aac aga aac ttc atg cag ctg atc cac gac gac agc ctg acc ttt    2112
Ala Asn Arg Asn Phe Met Gln Leu Ile His Asp Asp Ser Leu Thr Phe
690                 695                 700 aaa gag gac atc cag aaa gcc cag gtg tcc ggc cag ggc gat agc ctg    2160
Lys Glu Asp Ile Gln Lys Ala Gln Val Ser Gly Gln Gly Asp Ser Leu
705                 710                 715                 720 cac gag cac att gcc aat ctg gcc ggc agc ccc gcc att aag aag ggc    2208
His Glu His Ile Ala Asn Leu Ala Gly Ser Pro Ala Ile Lys Lys Gly
            725                 730                 735 atc ctg cag aca gtg aag gtg gtg gac gag ctc gtg aaa gtg atg ggc    2256
Ile Leu Gln Thr Val Lys Val Val Asp Glu Leu Val Lys Val Met Gly
            740                 745                 750 cgg cac aag ccc gag aac atc gtg atc gaa atg gcc aga gag aac cag    2304
Arg His Lys Pro Glu Asn Ile Val Ile Glu Met Ala Arg Glu Asn Gln
            755                 760                 765 acc acc cag aag gga cag aag aac agc cgc gag aga atg aag cgg atc    2352
Thr Thr Gln Lys Gly Gln Lys Asn Ser Arg Glu Arg Met Lys Arg Ile
770                 775                 780 gaa gag ggc atc aaa gag ctg ggc agc cag atc ctg aaa gaa cac ccc    2400
Glu Glu Gly Ile Lys Glu Leu Gly Ser Gln Ile Leu Lys Glu His Pro
785                 790                 795                 800 gtg gaa aac acc cag ctg cag aac gag aag ctg tac ctg tac tac ctg    2448
Val Glu Asn Thr Gln Leu Gln Asn Glu Lys Leu Tyr Leu Tyr Tyr Leu
            805                 810                 815 cag aat ggg cgg gat atg tac gtg gac cag gaa ctg gac atc aac cgg    2496
Gln Asn Gly Arg Asp Met Tyr Val Asp Gln Glu Leu Asp Ile Asn Arg
            820                 825                 830 ctg tcc gac tac gat gtg gac cat atc gtg cct cag agc ttt ctg aag    2544
Leu Ser Asp Tyr Asp Val Asp His Ile Val Pro Gln Ser Phe Leu Lys
            835                 840                 845 gac gac tcc atc gac aac aag gtg ctg acc aga agc gac aag aac cgg    2592
Asp Asp Ser Ile Asp Asn Lys Val Leu Thr Arg Ser Asp Lys Asn Arg
850                 855                 860 ggc aag agc gac aac gtg ccc tcc gaa gag gtc gtg aag aag atg aag    2640
Gly Lys Ser Asp Asn Val Pro Ser Glu Glu Val Val Lys Lys Met Lys
865                 870                 875                 880 aac tac tgg cgg cag ctg ctg aac gcc aag ctg att acc cag aga aag    2688
Asn Tyr Trp Arg Gln Leu Leu Asn Ala Lys Leu Ile Thr Gln Arg Lys
            885                 890                 895 ttc gac aat ctg acc aag gcc gag aga ggc ggc ctg agc gaa ctg gat    2736
Phe Asp Asn Leu Thr Lys Ala Glu Arg Gly Gly Leu Ser Glu Leu Asp
            900                 905                 910 aag gcc ggc ttc atc aag aga cag ctg gtg gaa acc cgg cag atc aca    2784
Lys Ala Gly Phe Ile Lys Arg Gln Leu Val Glu Thr Arg Gln Ile Thr
            915                 920                 925 aag cac gtg gca cag atc ctg gac tcc cgg atg aac act aag tac gac    2832
Lys His Val Ala Gln Ile Leu Asp Ser Arg Met Asn Thr Lys Tyr Asp
930                 935                 940 gag aat gac aag ctg atc cgg gaa gtg aaa gtg atc acc ctg aag tcc    2880
Glu Asn Asp Lys Leu Ile Arg Glu Val Lys Val Ile Thr Leu Lys Ser
945                 950                 955                 960 aag ctg gtg tcc gat ttc cgg aag gat ttc cag ttt tac aaa gtg cgc    2928
Lys Leu Val Ser Asp Phe Arg Lys Asp Phe Gln Phe Tyr Lys Val Arg
```

-continued

```
                 965                 970                 975
gag atc aac aac tac cac cac gcc cac gac gcc tac ctg aac gcc gtc        2976
Glu Ile Asn Asn Tyr His His Ala His Asp Ala Tyr Leu Asn Ala Val
                 980                 985                 990 gtg gga acc gcc ctg atc aaa aag tac cct aag ctg gaa agc gag ttc        3024
Val Gly Thr Ala Leu Ile Lys Lys Tyr Pro Lys Leu Glu Ser Glu Phe
             995                1000                1005 gtg tac ggc gac tac aag gtg tac gac gtg cgg aag atg atc gcc            3069
Val Tyr Gly Asp Tyr Lys Val Tyr Asp Val Arg Lys Met Ile Ala
        1010                1015                1020 aag agc gag cag gaa atc ggc aag gct acc gcc aag tac ttc ttc            3114
Lys Ser Glu Gln Glu Ile Gly Lys Ala Thr Ala Lys Tyr Phe Phe
        1025                1030                1035 tac agc aac atc atg aac ttt ttc aag acc gag att acc ctg gcc            3159
Tyr Ser Asn Ile Met Asn Phe Phe Lys Thr Glu Ile Thr Leu Ala
        1040                1045                1050 aac ggc gag atc cgg aag cgg cct ctg atc gag aca aac ggc gaa            3204
Asn Gly Glu Ile Arg Lys Arg Pro Leu Ile Glu Thr Asn Gly Glu
        1055                1060                1065 acc ggg gag atc gtg tgg gat aag ggc cgg gat ttt gcc acc gtg            3249
Thr Gly Glu Ile Val Trp Asp Lys Gly Arg Asp Phe Ala Thr Val
        1070                1075                1080 cgg aaa gtg ctg agc atg ccc caa gtg aat atc gtg aaa aag acc            3294
Arg Lys Val Leu Ser Met Pro Gln Val Asn Ile Val Lys Lys Thr
        1085                1090                1095 gag gtg cag aca ggc ggc ttc agc aaa gag tct atc cgg ccc aag            3339
Glu Val Gln Thr Gly Gly Phe Ser Lys Glu Ser Ile Arg Pro Lys
        1100                1105                1110 agg aac agc gat aag ctg atc gcc aga aag aag gac tgg gac cct            3384
Arg Asn Ser Asp Lys Leu Ile Ala Arg Lys Lys Asp Trp Asp Pro
        1115                1120                1125 aag aag tac ggc ggc ttc gac agc ccc acc gtg gcc tat tct gtg            3429
Lys Lys Tyr Gly Gly Phe Asp Ser Pro Thr Val Ala Tyr Ser Val
        1130                1135                1140 ctg gtg gtg gcc aaa gtg gaa aag ggc aag tcc aag aaa ctg aag            3474
Leu Val Val Ala Lys Val Glu Lys Gly Lys Ser Lys Lys Leu Lys
        1145                1150                1155 agt gtg aaa gag ctg ctg ggg atc acc atc atg gaa aga agc agc            3519
Ser Val Lys Glu Leu Leu Gly Ile Thr Ile Met Glu Arg Ser Ser
        1160                1165                1170 ttc gag aag aat ccc atc gac ttt ctg gaa gcc aag ggc tac aaa            3564
Phe Glu Lys Asn Pro Ile Asp Phe Leu Glu Ala Lys Gly Tyr Lys
        1175                1180                1185 gaa gtg aaa aag gac ctg atc atc aag ctg cct aag tac tcc ctg            3609
Glu Val Lys Lys Asp Leu Ile Ile Lys Leu Pro Lys Tyr Ser Leu
        1190                1195                1200 ttc gag ctg gaa aac ggc cgg aag aga atg ctg gcc tct gcc cgg            3654
Phe Glu Leu Glu Asn Gly Arg Lys Arg Met Leu Ala Ser Ala Arg
        1205                1210                1215 gaa ctg cag aag gga aac gaa ctg gcc ctg ccc tcc aaa tat gtg            3699
Glu Leu Gln Lys Gly Asn Glu Leu Ala Leu Pro Ser Lys Tyr Val
        1220                1225                1230 aac ttc ctg tac ctg gcc agc cac tat gag aag ctg aag ggc tcc            3744
Asn Phe Leu Tyr Leu Ala Ser His Tyr Glu Lys Leu Lys Gly Ser
        1235                1240                1245 ccc gag gat aat gag cag aaa cag ctg ttt gtg gaa cag cac aag            3789
Pro Glu Asp Asn Glu Gln Lys Gln Leu Phe Val Glu Gln His Lys
        1250                1255                1260 cac tac ctg gac gag atc atc gag cag atc agc gag ttc tcc aag            3834
```

-continued

```
His Tyr Leu Asp Glu Ile Ile Glu Gln Ile Ser Glu Phe Ser Lys
    1265                1270                1275 aga gtg atc ctg gcc gac gct aat ctg gac aaa gtg ctg tcc gcc      3879
Arg Val Ile Leu Ala Asp Ala Asn Leu Asp Lys Val Leu Ser Ala
    1280                1285                1290 tac aac aag cac cgg gat aag ccc atc aga gag cag gcc gag aat      3924
Tyr Asn Lys His Arg Asp Lys Pro Ile Arg Glu Gln Ala Glu Asn
    1295                1300                1305 atc atc cac ctg ttt acc ctg acc aat ctg gga gcc cct gcc gcc      3969
Ile Ile His Leu Phe Thr Leu Thr Asn Leu Gly Ala Pro Ala Ala
    1310                1315                1320 ttc aag tac ttt gac acc acc atc gac cgg aag gcc tac acc agc      4014
Phe Lys Tyr Phe Asp Thr Thr Ile Asp Arg Lys Ala Tyr Thr Ser
    1325                1330                1335 acc aaa gag gtg ctg gac gcc acc ctg atc cac cag agc atc acc      4059
Thr Lys Glu Val Leu Asp Ala Thr Leu Ile His Gln Ser Ile Thr
    1340                1345                1350 ggc ctg tac gag aca cgg atc gac ctg tct cag ctg gga ggc gac      4104
Gly Leu Tyr Glu Thr Arg Ile Asp Leu Ser Gln Leu Gly Gly Asp
    1355                1360                1365 taa                                                              4107
```

<210> SEQ ID NO 15
<211> LENGTH: 4107
<212> TYPE: DNA
<213> ORGANISM: Streptococcus pyogenes
<220> FEATURE:
<221> NAME/KEY: CDS
<222> LOCATION: (1)..(4107)

<400> SEQUENCE: 15

```
atg gac aag aag tac agc atc ggc ctg gac atc ggc acc aac tct gtg    48
Met Asp Lys Lys Tyr Ser Ile Gly Leu Asp Ile Gly Thr Asn Ser Val
1               5                   10                  15 ggc tgg gcc gtg atc acc gac gag tac aag gtg ccc agc aag aaa ttc    96
Gly Trp Ala Val Ile Thr Asp Glu Tyr Lys Val Pro Ser Lys Lys Phe
                20                  25                  30 aag gtg ctg ggc aac acc gac cgg cac agc atc aag aag aac ctg atc   144
Lys Val Leu Gly Asn Thr Asp Arg His Ser Ile Lys Lys Asn Leu Ile
            35                  40                  45 gga gcc ctg ctg ttc gac agc ggc gaa aca gcc gag gcc acc cgg ctg   192
Gly Ala Leu Leu Phe Asp Ser Gly Glu Thr Ala Glu Ala Thr Arg Leu
        50                  55                  60 aag aga acc gcc aga aga aga tac acc aga cgg aag aac cgg atc tgc   240
Lys Arg Thr Ala Arg Arg Arg Tyr Thr Arg Arg Lys Asn Arg Ile Cys
65                  70                  75                  80 tat ctg caa gag atc ttc agc aac gag atg gcc aag gtg gac gac agc   288
Tyr Leu Gln Glu Ile Phe Ser Asn Glu Met Ala Lys Val Asp Asp Ser
                85                  90                  95 ttc ttc cac aga ctg gaa gag tcc ttc ctg gtg gaa gag gat aag aag   336
Phe Phe His Arg Leu Glu Glu Ser Phe Leu Val Glu Glu Asp Lys Lys
                100                 105                 110 cac gag cgg cac ccc atc ttc ggc aac atc gtg gac gag gtg gcc tac   384
His Glu Arg His Pro Ile Phe Gly Asn Ile Val Asp Glu Val Ala Tyr
            115                 120                 125 cac gag aag tac ccc acc atc tac cac ctg aga aag aaa ctg gtg gac   432
His Glu Lys Tyr Pro Thr Ile Tyr His Leu Arg Lys Lys Leu Val Asp
        130                 135                 140 agc acc gac aag gcc gac ctg cgg ctg atc tat ctg gcc ctg gcc cac   480
Ser Thr Asp Lys Ala Asp Leu Arg Leu Ile Tyr Leu Ala Leu Ala His
145                 150                 155                 160
```

-continued

| | |
|---|---|
| atg atc aag ttc cgg ggc cac ttc ctg atc gag ggc gac ctg aac ccc<br>Met Ile Lys Phe Arg Gly His Phe Leu Ile Glu Gly Asp Leu Asn Pro<br>165                    170                        175 | 528 |
| gac aac agc gac gtg gac aag ctg ttc atc cag ctg gtg cag acc tac<br>Asp Asn Ser Asp Val Asp Lys Leu Phe Ile Gln Leu Val Gln Thr Tyr<br>180                    185                       190 | 576 |
| aac cag ctg ttc gag gaa aac ccc atc aac gcc agc ggc gtg gac gcc<br>Asn Gln Leu Phe Glu Glu Asn Pro Ile Asn Ala Ser Gly Val Asp Ala<br>195                    200                       205 | 624 |
| aag gcc atc ctg tct gcc aga ctg agc aag agc aga cgg ctg gaa aat<br>Lys Ala Ile Leu Ser Ala Arg Leu Ser Lys Ser Arg Arg Leu Glu Asn<br>210                    215                       220 | 672 |
| ctg atc gcc cag ctg ccc ggc gag aag aag aat ggc ctg ttc gga aac<br>Leu Ile Ala Gln Leu Pro Gly Glu Lys Lys Asn Gly Leu Phe Gly Asn<br>225                       230                   235                   240 | 720 |
| ctg att gcc ctg agc ctg ggc ctg acc ccc aac ttc aag agc aac ttc<br>Leu Ile Ala Leu Ser Leu Gly Leu Thr Pro Asn Phe Lys Ser Asn Phe<br>                    245                   250                   255 | 768 |
| gac ctg gcc gag gat gcc aaa ctg cag ctg agc aag gac acc tac gac<br>Asp Leu Ala Glu Asp Ala Lys Leu Gln Leu Ser Lys Asp Thr Tyr Asp<br>                       260                   265                  270 | 816 |
| gac gac ctg gac aac ctg ctg gcc cag atc ggc gac cag tac gcc gac<br>Asp Asp Leu Asp Asn Leu Leu Ala Gln Ile Gly Asp Gln Tyr Ala Asp<br>275                    280                    285 | 864 |
| ctg ttt ctg gcc gcc aag aac ctg tcc gac gcc atc ctg ctg agc gac<br>Leu Phe Leu Ala Ala Lys Asn Leu Ser Asp Ala Ile Leu Leu Ser Asp<br>290                    295                   300 | 912 |
| atc ctg aga gtg aac acc gag atc acc aag gcc ccc ctg agc gcc tct<br>Ile Leu Arg Val Asn Thr Glu Ile Thr Lys Ala Pro Leu Ser Ala Ser<br>305                     310                   315                   320 | 960 |
| atg atc aag aga tac gac gag cac cac cag gac ctg acc ctg ctg aaa<br>Met Ile Lys Arg Tyr Asp Glu His His Gln Asp Leu Thr Leu Leu Lys<br>                    325                   330                  335 | 1008 |
| gct ctc gtg cgg cag cag ctg cct gag aag tac aaa gag att ttc ttc<br>Ala Leu Val Arg Gln Gln Leu Pro Glu Lys Tyr Lys Glu Ile Phe Phe<br>                    340                   345                  350 | 1056 |
| gac cag agc aag aac ggc tac gcc ggc tac att gac ggc gga gcc agc<br>Asp Gln Ser Lys Asn Gly Tyr Ala Gly Tyr Ile Asp Gly Gly Ala Ser<br>355                    360                    365 | 1104 |
| cag gaa gag ttc tac aag ttc atc aag ccc atc ctg gaa aag atg gac<br>Gln Glu Glu Phe Tyr Lys Phe Ile Lys Pro Ile Leu Glu Lys Met Asp<br>370                    375                   380 | 1152 |
| ggc acc gag gaa ctg ctc gtg aag ctg aac aga gag gac ctg ctg cgg<br>Gly Thr Glu Glu Leu Leu Val Lys Leu Asn Arg Glu Asp Leu Leu Arg<br>385                     390                   395                   400 | 1200 |
| aag cag cgg acc ttc gac aac ggc agc atc ccc cac cag atc cac ctg<br>Lys Gln Arg Thr Phe Asp Asn Gly Ser Ile Pro His Gln Ile His Leu<br>                    405                   410                  415 | 1248 |
| gga gag ctg cac gcc att ctg cgg cgg cag gaa gat ttt tac cca ttc<br>Gly Glu Leu His Ala Ile Leu Arg Arg Gln Glu Asp Phe Tyr Pro Phe<br>                      420                   425                  430 | 1296 |
| ctg aag gac aac cgg gaa aag atc gag aag atc ctg acc ttc cgc atc<br>Leu Lys Asp Asn Arg Glu Lys Ile Glu Lys Ile Leu Thr Phe Arg Ile<br>435                    440                    445 | 1344 |
| ccc tac tac gtg ggc cct ctg gcc agg gga aac agc aga ttc gcc tgg<br>Pro Tyr Tyr Val Gly Pro Leu Ala Arg Gly Asn Ser Arg Phe Ala Trp<br>450                    455                   460 | 1392 |
| atg acc aga aag agc gag gaa acc atc acc ccc tgg aac ttc gag gaa<br>Met Thr Arg Lys Ser Glu Glu Thr Ile Thr Pro Trp Asn Phe Glu Glu | 1440 |

| | |
|---|---|
| gtg gtg gac aag ggc gct tcc gcc cag agc ttc atc gag cgg atg acc<br>Val Val Asp Lys Gly Ala Ser Ala Gln Ser Phe Ile Glu Arg Met Thr<br>                485                    490                    495 | 1488 |
| aac ttc gat aag aac ctg ccc aac gag aag gtg ctg ccc aag cac agc<br>Asn Phe Asp Lys Asn Leu Pro Asn Glu Lys Val Leu Pro Lys His Ser<br>                500                    505                    510 | 1536 |
| ctg ctg tac gag tac ttc acc gtg tat aac gag ctg acc aaa gtg aaa<br>Leu Leu Tyr Glu Tyr Phe Thr Val Tyr Asn Glu Leu Thr Lys Val Lys<br>            515                    520                    525 | 1584 |
| tac gtg acc gag gga atg aga aag ccc gcc ttc ctg agc ggc gag cag<br>Tyr Val Thr Glu Gly Met Arg Lys Pro Ala Phe Leu Ser Gly Glu Gln<br>530                    535                    540 | 1632 |
| aaa aag gcc atc gtg gac ctg ctg ttc aag acc aac cgg aaa gtg acc<br>Lys Lys Ala Ile Val Asp Leu Leu Phe Lys Thr Asn Arg Lys Val Thr<br>545                    550                    555                    560 | 1680 |
| gtg aag cag ctg aaa gag gac tac ttc aag aaa atc gag tgc ttc gac<br>Val Lys Gln Leu Lys Glu Asp Tyr Phe Lys Lys Ile Glu Cys Phe Asp<br>                565                    570                    575 | 1728 |
| tcc gtg gaa atc tcc ggc gtg gaa gat cgg ttc aac gcc tcc ctg ggc<br>Ser Val Glu Ile Ser Gly Val Glu Asp Arg Phe Asn Ala Ser Leu Gly<br>            580                    585                    590 | 1776 |
| aca tac cac gat ctg ctg aaa att atc aag gac aag gac ttc ctg gac<br>Thr Tyr His Asp Leu Leu Lys Ile Ile Lys Asp Lys Asp Phe Leu Asp<br>                595                    600                    605 | 1824 |
| aat gag gaa aac gag gac att ctg gaa gat atc gtg ctg acc ctg aca<br>Asn Glu Glu Asn Glu Asp Ile Leu Glu Asp Ile Val Leu Thr Leu Thr<br>            610                    615                    620 | 1872 |
| ctg ttt gag gac aga gag atg atc gag gaa cgg ctg aaa acc tat gcc<br>Leu Phe Glu Asp Arg Glu Met Ile Glu Glu Arg Leu Lys Thr Tyr Ala<br>625                    630                    635                    640 | 1920 |
| cac ctg ttc gac gac aaa gtg atg aag cag ctg aag cgg cgg aga tac<br>His Leu Phe Asp Asp Lys Val Met Lys Gln Leu Lys Arg Arg Arg Tyr<br>                645                    650                    655 | 1968 |
| acc ggc tgg ggc agg ctg agc cgg aag ctg atc aac ggc atc cgg gac<br>Thr Gly Trp Gly Arg Leu Ser Arg Lys Leu Ile Asn Gly Ile Arg Asp<br>            660                    665                    670 | 2016 |
| aag cag tcc ggc aag aca atc ctg gat ttc ctg aag tcc gac ggc ttc<br>Lys Gln Ser Gly Lys Thr Ile Leu Asp Phe Leu Lys Ser Asp Gly Phe<br>                675                    680                    685 | 2064 |
| gcc aac aga aac ttc atg cag ctg atc cac gac gac agc ctg acc ttt<br>Ala Asn Arg Asn Phe Met Gln Leu Ile His Asp Asp Ser Leu Thr Phe<br>            690                    695                    700 | 2112 |
| aaa gag gac atc cag aaa gcc cag gtg tcc ggc cag ggc gat agc ctg<br>Lys Glu Asp Ile Gln Lys Ala Gln Val Ser Gly Gln Gly Asp Ser Leu<br>705                    710                    715                    720 | 2160 |
| cac gag cac att gcc aat ctg gcc ggc agc ccc gcc att aag aag ggc<br>His Glu His Ile Ala Asn Leu Ala Gly Ser Pro Ala Ile Lys Lys Gly<br>                725                    730                    735 | 2208 |
| atc ctg cag aca gtg aag gtg gtg gac gag ctc gtg aaa gtg atg ggc<br>Ile Leu Gln Thr Val Lys Val Val Asp Glu Leu Val Lys Val Met Gly<br>            740                    745                    750 | 2256 |
| cgg cac aag ccc gag aac atc gtg atc gaa atg gcc aga gag aac cag<br>Arg His Lys Pro Glu Asn Ile Val Ile Glu Met Ala Arg Glu Asn Gln<br>                755                    760                    765 | 2304 |
| acc acc cag aag gga cag aag aac agc cgc gag aga atg aag cgg atc<br>Thr Thr Gln Lys Gly Gln Lys Asn Ser Arg Glu Arg Met Lys Arg Ile<br>            770                    775                    780 | 2352 |
| gaa gag ggc atc aaa gag ctg ggc agc cag atc ctg aaa gaa cac ccc | 2400 |

```
                Glu Glu Gly Ile Lys Glu Leu Gly Ser Gln Ile Leu Lys Glu His Pro
                785                 790                 795                 800 gtg gaa aac acc cag ctg cag aac gag aag ctg tac ctg tac tac ctg              2448
Val Glu Asn Thr Gln Leu Gln Asn Glu Lys Leu Tyr Leu Tyr Tyr Leu
                    805                 810                 815 cag aat ggg cgg gat atg tac gtg gac cag gaa ctg gac atc aac cgg              2496
Gln Asn Gly Arg Asp Met Tyr Val Asp Gln Glu Leu Asp Ile Asn Arg
                820                 825                 830 ctg tcc gac tac gat gtg gac cat atc gtg cct cag agc ttt ctg aag              2544
Leu Ser Asp Tyr Asp Val Asp His Ile Val Pro Gln Ser Phe Leu Lys
            835                 840                 845 gac gac tcc atc gac aac aag gtg ctg acc aga agc gac aag aac cgg              2592
Asp Asp Ser Ile Asp Asn Lys Val Leu Thr Arg Ser Asp Lys Asn Arg
850                 855                 860 ggc aag agc gac aac gtg ccc tcc gaa gag gtc gtg aag aag atg aag              2640
Gly Lys Ser Asp Asn Val Pro Ser Glu Glu Val Val Lys Lys Met Lys
865                 870                 875                 880 aac tac tgg cgg cag ctg ctg aac gcc aag ctg att acc cag aga aag              2688
Asn Tyr Trp Arg Gln Leu Leu Asn Ala Lys Leu Ile Thr Gln Arg Lys
                885                 890                 895 ttc gac aat ctg acc aag gcc gag aga ggc ggc ctg agc gaa ctg gat              2736
Phe Asp Asn Leu Thr Lys Ala Glu Arg Gly Gly Leu Ser Glu Leu Asp
            900                 905                 910 aag gcc ggc ttc atc aag aga cag ctg gtg gaa acc cgg cag atc aca              2784
Lys Ala Gly Phe Ile Lys Arg Gln Leu Val Glu Thr Arg Gln Ile Thr
        915                 920                 925 aag cac gtg gca cag atc ctg gac tcc cgg atg aac act aag tac gac              2832
Lys His Val Ala Gln Ile Leu Asp Ser Arg Met Asn Thr Lys Tyr Asp
930                 935                 940 gag aat gac aag ctg atc cgg gaa gtg aaa gtg atc acc ctg aag tcc              2880
Glu Asn Asp Lys Leu Ile Arg Glu Val Lys Val Ile Thr Leu Lys Ser
945                 950                 955                 960 aag ctg gtg tcc gat ttc cgg aag gat ttc cag ttt tac aaa gtg cgc              2928
Lys Leu Val Ser Asp Phe Arg Lys Asp Phe Gln Phe Tyr Lys Val Arg
                965                 970                 975 gag atc aac aac tac cac cac gcc cac gac gcc tac ctg aac gcc gtc              2976
Glu Ile Asn Asn Tyr His His Ala His Asp Ala Tyr Leu Asn Ala Val
            980                 985                 990 gtg gga acc gcc ctg atc aaa aag tac cct aag ctg gaa agc gag ttc              3024
Val Gly Thr Ala Leu Ile Lys Lys Tyr Pro Lys Leu Glu Ser Glu Phe
        995                 1000                1005 gtg tac ggc gac tac aag gtg tac gac gtg cgg aag atg atc gcc              3069
Val Tyr Gly Asp Tyr Lys Val Tyr Asp Val Arg Lys Met Ile Ala
    1010                1015                1020 aag agc gag cag gaa atc ggc aag gct acc gcc aag tac ttc ttc              3114
Lys Ser Glu Gln Glu Ile Gly Lys Ala Thr Ala Lys Tyr Phe Phe
    1025                1030                1035 tac agc aac atc atg aac ttt ttc aag acc gag att acc ctg gcc              3159
Tyr Ser Asn Ile Met Asn Phe Phe Lys Thr Glu Ile Thr Leu Ala
    1040                1045                1050 aac ggc gag atc cgg aag cgg cct ctg atc gag aca aac ggc gaa              3204
Asn Gly Glu Ile Arg Lys Arg Pro Leu Ile Glu Thr Asn Gly Glu
    1055                1060                1065 acc ggg gag atc gtg tgg gat aag ggc cgg gat ttt gcc acc gtg              3249
Thr Gly Glu Ile Val Trp Asp Lys Gly Arg Asp Phe Ala Thr Val
    1070                1075                1080 cgg aaa gtg ctg agc atg ccc caa gtg aat atc gtg aaa aag acc              3294
Arg Lys Val Leu Ser Met Pro Gln Val Asn Ile Val Lys Lys Thr
    1085                1090                1095
```

-continued

| | |
|---|---|
| gag gtg cag aca ggc ggc ttc agc aaa gag tct atc cgg ccc aag<br>Glu Val Gln Thr Gly Gly Phe Ser Lys Glu Ser Ile Arg Pro Lys<br>1100                         1105                      1110 | 3339 |
| agg aac agc gat aag ctg atc gcc aga aag aag gac tgg gac cct<br>Arg Asn Ser Asp Lys Leu Ile Ala Arg Lys Lys Asp Trp Asp Pro<br>1115                         1120                      1125 | 3384 |
| aag aag tac ggc ggc ttc gtt agc ccc acc gtg gcc tat tct gtg<br>Lys Lys Tyr Gly Gly Phe Val Ser Pro Thr Val Ala Tyr Ser Val<br>1130                         1135                      1140 | 3429 |
| ctg gtg gtg gcc aaa gtg gaa aag ggc aag tcc aag aaa ctg aag<br>Leu Val Val Ala Lys Val Glu Lys Gly Lys Ser Lys Lys Leu Lys<br>1145                         1150                      1155 | 3474 |
| agt gtg aaa gag ctg ctg ggg atc acc atc atg gaa aga agc agc<br>Ser Val Lys Glu Leu Leu Gly Ile Thr Ile Met Glu Arg Ser Ser<br>1160                         1165                      1170 | 3519 |
| ttc gag aag aat ccc atc gac ttt ctg gaa gcc aag ggc tac aaa<br>Phe Glu Lys Asn Pro Ile Asp Phe Leu Glu Ala Lys Gly Tyr Lys<br>1175                         1180                      1185 | 3564 |
| gaa gtg aaa aag gac ctg atc atc aag ctg cct aag tac tcc ctg<br>Glu Val Lys Lys Asp Leu Ile Ile Lys Leu Pro Lys Tyr Ser Leu<br>1190                         1195                      1200 | 3609 |
| ttc gag ctg gaa aac ggc cgg aag aga atg ctg gcc tct gcc cgg<br>Phe Glu Leu Glu Asn Gly Arg Lys Arg Met Leu Ala Ser Ala Arg<br>1205                         1210                      1215 | 3654 |
| atg ctg cag aag gga aac gaa ctg gcc ctg ccc tcc aaa tat gtg<br>Met Leu Gln Lys Gly Asn Glu Leu Ala Leu Pro Ser Lys Tyr Val<br>1220                         1225                      1230 | 3699 |
| aac ttc ctg tac ctg gcc agc cac tat gag aag ctg aag ggc tcc<br>Asn Phe Leu Tyr Leu Ala Ser His Tyr Glu Lys Leu Lys Gly Ser<br>1235                         1240                      1245 | 3744 |
| ccc gag gat aat gag cag aaa cag ctg ttt gtg gaa cag cac aag<br>Pro Glu Asp Asn Glu Gln Lys Gln Leu Phe Val Glu Gln His Lys<br>1250                         1255                      1260 | 3789 |
| cac tac ctg gac gag atc atc gag cag atc agc gag ttc tcc aag<br>His Tyr Leu Asp Glu Ile Ile Glu Gln Ile Ser Glu Phe Ser Lys<br>1265                         1270                      1275 | 3834 |
| aga gtg atc ctg gcc gac gct aat ctg gac aaa gtg ctg tcc gcc<br>Arg Val Ile Leu Ala Asp Ala Asn Leu Asp Lys Val Leu Ser Ala<br>1280                         1285                      1290 | 3879 |
| tac aac aag cac cgg gat aag ccc atc aga gag cag gcc gag aat<br>Tyr Asn Lys His Arg Asp Lys Pro Ile Arg Glu Gln Ala Glu Asn<br>1295                         1300                      1305 | 3924 |
| atc atc cac ctg ttt acc ctg acc aat ctg gga gcc cct cgg gcc<br>Ile Ile His Leu Phe Thr Leu Thr Asn Leu Gly Ala Pro Arg Ala<br>1310                         1315                      1320 | 3969 |
| ttc aag tac ttt gac acc acc atc gac cgg aag gcc tac cgg agc<br>Phe Lys Tyr Phe Asp Thr Thr Ile Asp Arg Lys Ala Tyr Arg Ser<br>1325                         1330                      1335 | 4014 |
| acc aaa gag gtg ctg gac gcc acc ctg atc cac cag agc atc acc<br>Thr Lys Glu Val Leu Asp Ala Thr Leu Ile His Gln Ser Ile Thr<br>1340                         1345                      1350 | 4059 |
| ggc ctg tac gag aca cgg atc gac ctg tct cag ctg gga ggc gac<br>Gly Leu Tyr Glu Thr Arg Ile Asp Leu Ser Gln Leu Gly Gly Asp<br>1355                         1360                      1365 | 4104 |
| taa | 4107 |

<210> SEQ ID NO 16
<211> LENGTH: 4107
<212> TYPE: DNA
<213> ORGANISM: Streptococcus pyogenes

```
<220> FEATURE:
<221> NAME/KEY: CDS
<222> LOCATION: (1)..(4107)

<400> SEQUENCE: 16 atg gac aag aag tac agc atc ggc ctg gac atc ggc acc aac tct gtg     48
Met Asp Lys Lys Tyr Ser Ile Gly Leu Asp Ile Gly Thr Asn Ser Val
1               5                   10                  15 ggc tgg gcc gtg atc acc gac gag tac aag gtg ccc agc aag aaa ttc     96
Gly Trp Ala Val Ile Thr Asp Glu Tyr Lys Val Pro Ser Lys Lys Phe
            20                  25                  30 aag gtg ctg ggc aac acc gac cgg cac agc atc aag aag aac ctg atc    144
Lys Val Leu Gly Asn Thr Asp Arg His Ser Ile Lys Lys Asn Leu Ile
        35                  40                  45 gga gcc ctg ctg ttc gac agc ggc gaa aca gcc gag gcc acc cgg ctg    192
Gly Ala Leu Leu Phe Asp Ser Gly Glu Thr Ala Glu Ala Thr Arg Leu
    50                  55                  60 aag aga acc gcc aga aga aga tac acc aga cgg aag aac cgg atc tgc    240
Lys Arg Thr Ala Arg Arg Arg Tyr Thr Arg Arg Lys Asn Arg Ile Cys
65                  70                  75                  80 tat ctg caa gag atc ttc agc aac gag atg gcc aag gtg gac gac agc    288
Tyr Leu Gln Glu Ile Phe Ser Asn Glu Met Ala Lys Val Asp Asp Ser
                85                  90                  95 ttc ttc cac aga ctg gaa gag tcc ttc ctg gtg gaa gag gat aag aag    336
Phe Phe His Arg Leu Glu Glu Ser Phe Leu Val Glu Glu Asp Lys Lys
            100                 105                 110 cac gag cgg cac ccc atc ttc ggc aac atc gtg gac gag gtg gcc tac    384
His Glu Arg His Pro Ile Phe Gly Asn Ile Val Asp Glu Val Ala Tyr
        115                 120                 125 cac gag aag tac ccc acc atc tac cac ctg aga aag aaa ctg gtg gac    432
His Glu Lys Tyr Pro Thr Ile Tyr His Leu Arg Lys Lys Leu Val Asp
    130                 135                 140 agc acc gac aag gcc gac ctg cgg ctg atc tat ctg gcc ctg gcc cac    480
Ser Thr Asp Lys Ala Asp Leu Arg Leu Ile Tyr Leu Ala Leu Ala His
145                 150                 155                 160 atg atc aag ttc cgg ggc cac ttc ctg atc gag ggc gac ctg aac ccc    528
Met Ile Lys Phe Arg Gly His Phe Leu Ile Glu Gly Asp Leu Asn Pro
                165                 170                 175 gac aac agc gac gtg gac aag ctg ttc atc cag ctg gtg cag acc tac    576
Asp Asn Ser Asp Val Asp Lys Leu Phe Ile Gln Leu Val Gln Thr Tyr
            180                 185                 190 aac cag ctg ttc gag gaa aac ccc atc aac gcc agc ggc gtg gac gcc    624
Asn Gln Leu Phe Glu Glu Asn Pro Ile Asn Ala Ser Gly Val Asp Ala
        195                 200                 205 aag gcc atc ctg tct gcc aga ctg agc aag agc aga cgg ctg gaa aat    672
Lys Ala Ile Leu Ser Ala Arg Leu Ser Lys Ser Arg Arg Leu Glu Asn
    210                 215                 220 ctg atc gcc cag ctg ccc ggc gag aag aag aat ggc ctg ttc gga aac    720
Leu Ile Ala Gln Leu Pro Gly Glu Lys Lys Asn Gly Leu Phe Gly Asn
225                 230                 235                 240 ctg att gcc ctg agc ctg ggc ctg acc ccc aac ttc aag agc aac ttc    768
Leu Ile Ala Leu Ser Leu Gly Leu Thr Pro Asn Phe Lys Ser Asn Phe
                245                 250                 255 gac ctg gcc gag gat gcc aaa ctg cag ctg agc aag gac acc tac gac    816
Asp Leu Ala Glu Asp Ala Lys Leu Gln Leu Ser Lys Asp Thr Tyr Asp
            260                 265                 270 gac gac ctg gac aac ctg ctg gcc cag atc ggc gac cag tac gcc gac    864
Asp Asp Leu Asp Asn Leu Leu Ala Gln Ile Gly Asp Gln Tyr Ala Asp
        275                 280                 285 ctg ttt ctg gcc gcc aag aac ctg tcc gac gcc atc ctg ctg agc gac    912
```

```
                Leu Phe Leu Ala Ala Lys Asn Leu Ser Asp Ala Ile Leu Leu Ser Asp
                    290                 295                 300 atc ctg aga gtg aac acc gag atc acc aag gcc ccc ctg agc gcc tct            960
Ile Leu Arg Val Asn Thr Glu Ile Thr Lys Ala Pro Leu Ser Ala Ser
305                 310                 315                 320 atg atc aag aga tac gac gag cac cac cag gac ctg acc ctg ctg aaa           1008
Met Ile Lys Arg Tyr Asp Glu His His Gln Asp Leu Thr Leu Leu Lys
                    325                 330                 335 gct ctc gtg cgg cag cag ctg cct gag aag tac aaa gag att ttc ttc           1056
Ala Leu Val Arg Gln Gln Leu Pro Glu Lys Tyr Lys Glu Ile Phe Phe
                340                 345                 350 gac cag agc aag aac ggc tac gcc ggc tac att gac ggc gga gcc agc           1104
Asp Gln Ser Lys Asn Gly Tyr Ala Gly Tyr Ile Asp Gly Gly Ala Ser
            355                 360                 365 cag gaa gag ttc tac aag ttc atc aag ccc atc ctg gaa aag atg gac           1152
Gln Glu Glu Phe Tyr Lys Phe Ile Lys Pro Ile Leu Glu Lys Met Asp
        370                 375                 380 ggc acc gag gaa ctg ctc gtg aag ctg aac aga gag gac ctg ctg cgg           1200
Gly Thr Glu Glu Leu Leu Val Lys Leu Asn Arg Glu Asp Leu Leu Arg
385                 390                 395                 400 aag cag cgg acc ttc gac aac ggc agc atc ccc cac cag atc cac ctg           1248
Lys Gln Arg Thr Phe Asp Asn Gly Ser Ile Pro His Gln Ile His Leu
                    405                 410                 415 gga gag ctg cac gcc att ctg cgg cgg cag gaa gat ttt tac cca ttc           1296
Gly Glu Leu His Ala Ile Leu Arg Arg Gln Glu Asp Phe Tyr Pro Phe
                420                 425                 430 ctg aag gac aac cgg gaa aag atc gag aag atc ctg acc ttc cgc atc           1344
Leu Lys Asp Asn Arg Glu Lys Ile Glu Lys Ile Leu Thr Phe Arg Ile
            435                 440                 445 ccc tac tac gtg ggc cct ctg gcc agg gga aac agc aga ttc gcc tgg           1392
Pro Tyr Tyr Val Gly Pro Leu Ala Arg Gly Asn Ser Arg Phe Ala Trp
        450                 455                 460 atg acc aga aag agc gag gaa acc atc acc ccc tgg aac ttc gag gaa           1440
Met Thr Arg Lys Ser Glu Glu Thr Ile Thr Pro Trp Asn Phe Glu Glu
465                 470                 475                 480 gtg gtg gac aag ggc gct tcc gcc cag agc ttc atc gag cgg atg acc           1488
Val Val Asp Lys Gly Ala Ser Ala Gln Ser Phe Ile Glu Arg Met Thr
                    485                 490                 495 aac ttc gat aag aac ctg ccc aac gag aag gtg ctg ccc aag cac agc           1536
Asn Phe Asp Lys Asn Leu Pro Asn Glu Lys Val Leu Pro Lys His Ser
                500                 505                 510 ctg ctg tac gag tac ttc acc gtg tat aac gag ctg acc aaa gtg aaa           1584
Leu Leu Tyr Glu Tyr Phe Thr Val Tyr Asn Glu Leu Thr Lys Val Lys
            515                 520                 525 tac gtg acc gag gga atg aga aag ccc gcc ttc ctg agc ggc gag cag           1632
Tyr Val Thr Glu Gly Met Arg Lys Pro Ala Phe Leu Ser Gly Glu Gln
        530                 535                 540 aaa aag gcc atc gtg gac ctg ctg ttc aag acc aac cgg aaa gtg acc           1680
Lys Lys Ala Ile Val Asp Leu Leu Phe Lys Thr Asn Arg Lys Val Thr
545                 550                 555                 560 gtg aag cag ctg aaa gag gac tac ttc aag aaa atc gag tgc ttc gac           1728
Val Lys Gln Leu Lys Glu Asp Tyr Phe Lys Lys Ile Glu Cys Phe Asp
                    565                 570                 575 tcc gtg gaa atc tcc ggc gtg gaa gat cgg ttc aac gcc tcc ctg ggc           1776
Ser Val Glu Ile Ser Gly Val Glu Asp Arg Phe Asn Ala Ser Leu Gly
                580                 585                 590 aca tac cac gat ctg ctg aaa att atc aag gac aag gac ttc ctg gac           1824
Thr Tyr His Asp Leu Leu Lys Ile Ile Lys Asp Lys Asp Phe Leu Asp
            595                 600                 605
```

-continued

| | |
|---|---|
| aat gag gaa aac gag gac att ctg gaa gat atc gtg ctg acc ctg aca<br>Asn Glu Glu Asn Glu Asp Ile Leu Glu Asp Ile Val Leu Thr Leu Thr<br>610                           615                      620 | 1872 |
| ctg ttt gag gac aga gag atg atc gag gaa cgg ctg aaa acc tat gcc<br>Leu Phe Glu Asp Arg Glu Met Ile Glu Glu Arg Leu Lys Thr Tyr Ala<br>625                         630                         635                640 | 1920 |
| cac ctg ttc gac gac aaa gtg atg aag cag ctg aag cgg cgg aga tac<br>His Leu Phe Asp Asp Lys Val Met Lys Gln Leu Lys Arg Arg Arg Tyr<br>                        645                       650                      655 | 1968 |
| acc ggc tgg ggc agg ctg agc cgg aag ctg atc aac ggc atc cgg gac<br>Thr Gly Trp Gly Arg Leu Ser Arg Lys Leu Ile Asn Gly Ile Arg Asp<br>                  660                       665                      670 | 2016 |
| aag cag tcc ggc aag aca atc ctg gat ttc ctg aag tcc gac ggc ttc<br>Lys Gln Ser Gly Lys Thr Ile Leu Asp Phe Leu Lys Ser Asp Gly Phe<br>            675                       680                       685 | 2064 |
| gcc aac aga aac ttc atg cag ctg atc cac gac gac agc ctg acc ttt<br>Ala Asn Arg Asn Phe Met Gln Leu Ile His Asp Asp Ser Leu Thr Phe<br>690                         695                        700 | 2112 |
| aaa gag gac atc cag aaa gcc cag gtg tcc ggc cag ggc gat agc ctg<br>Lys Glu Asp Ile Gln Lys Ala Gln Val Ser Gly Gln Gly Asp Ser Leu<br>705                         710                      715                      720 | 2160 |
| cac gag cac att gcc aat ctg gcc ggc agc ccc gcc att aag aag ggc<br>His Glu His Ile Ala Asn Leu Ala Gly Ser Pro Ala Ile Lys Lys Gly<br>                       725                       730                      735 | 2208 |
| atc ctg cag aca gtg aag gtg gtg gac gag ctc gtg aaa gtg atg ggc<br>Ile Leu Gln Thr Val Lys Val Val Asp Glu Leu Val Lys Val Met Gly<br>                740                       745                      750 | 2256 |
| cgg cac aag ccc gag aac atc gtg atc gaa atg gcc aga gag aac cag<br>Arg His Lys Pro Glu Asn Ile Val Ile Glu Met Ala Arg Glu Asn Gln<br>        755                       760                       765 | 2304 |
| acc acc cag aag gga cag aag aac agc cgc gag aga atg aag cgg atc<br>Thr Thr Gln Lys Gly Gln Lys Asn Ser Arg Glu Arg Met Lys Arg Ile<br>770                         775                        780 | 2352 |
| gaa gag ggc atc aaa gag ctg ggc agc cag atc ctg aaa gaa cac ccc<br>Glu Glu Gly Ile Lys Glu Leu Gly Ser Gln Ile Leu Lys Glu His Pro<br>785                         790                        795                      800 | 2400 |
| gtg gaa aac acc cag ctg cag aac gag aag ctg tac ctg tac tac ctg<br>Val Glu Asn Thr Gln Leu Gln Asn Glu Lys Leu Tyr Leu Tyr Tyr Leu<br>                       805                       810                      815 | 2448 |
| cag aat ggg cgg gat atg tac gtg gac cag gaa ctg gac atc aac cgg<br>Gln Asn Gly Arg Asp Met Tyr Val Asp Gln Glu Leu Asp Ile Asn Arg<br>                  820                       825                      830 | 2496 |
| ctg tcc gac tac gat gtg gac cat atc gtg cct cag agc ttt ctg aag<br>Leu Ser Asp Tyr Asp Val Asp His Ile Val Pro Gln Ser Phe Leu Lys<br>            835                       840                       845 | 2544 |
| gac gac tcc atc gac aac aag gtg ctg acc aga agc gac aag aac cgg<br>Asp Asp Ser Ile Asp Asn Lys Val Leu Thr Arg Ser Asp Lys Asn Arg<br>850                         855                        860 | 2592 |
| ggc aag agc gac aac gtg ccc tcc gaa gag gtc gtg aag aag atg aag<br>Gly Lys Ser Asp Asn Val Pro Ser Glu Glu Val Val Lys Lys Met Lys<br>865                         870                        875                      880 | 2640 |
| aac tac tgg cgg cag ctg ctg aac gcc aag ctg att acc cag aga aag<br>Asn Tyr Trp Arg Gln Leu Leu Asn Ala Lys Leu Ile Thr Gln Arg Lys<br>                       885                       890                      895 | 2688 |
| ttc gac aat ctg acc aag gcc gag aga ggc ggc ctg agc gaa ctg gat<br>Phe Asp Asn Leu Thr Lys Ala Glu Arg Gly Gly Leu Ser Glu Leu Asp<br>                  900                       905                      910 | 2736 |
| aag gcc ggc ttc atc aag aga cag ctg gtg gaa acc cgg cag atc aca<br>Lys Ala Gly Phe Ile Lys Arg Gln Leu Val Glu Thr Arg Gln Ile Thr<br>            915                       920                       925 | 2784 |

-continued

```
aag cac gtg gca cag atc ctg gac tcc cgg atg aac act aag tac gac      2832
Lys His Val Ala Gln Ile Leu Asp Ser Arg Met Asn Thr Lys Tyr Asp
    930                 935                 940 gag aat gac aag ctg atc cgg gaa gtg aaa gtg atc acc ctg aag tcc      2880
Glu Asn Asp Lys Leu Ile Arg Glu Val Lys Val Ile Thr Leu Lys Ser
945                 950                 955                 960 aag ctg gtg tcc gat ttc cgg aag gat ttc cag ttt tac aaa gtg cgc      2928
Lys Leu Val Ser Asp Phe Arg Lys Asp Phe Gln Phe Tyr Lys Val Arg
                965                 970                 975 gag atc aac aac tac cac cac gcc cac gac gcc tac ctg aac gcc gtc      2976
Glu Ile Asn Asn Tyr His His Ala His Asp Ala Tyr Leu Asn Ala Val
            980                 985                 990 gtg gga acc gcc ctg atc aaa aag tac cct aag ctg gaa agc gag ttc      3024
Val Gly Thr Ala Leu Ile Lys Lys Tyr Pro Lys Leu Glu Ser Glu Phe
        995                 1000                1005 gtg tac ggc gac tac aag gtg tac gac gtg cgg aag atg atc gcc          3069
Val Tyr Gly Asp Tyr Lys Val Tyr Asp Val Arg Lys Met Ile Ala
    1010                1015                1020 aag agc gag cag gaa atc ggc aag gct acc gcc aag tac ttc ttc          3114
Lys Ser Glu Gln Glu Ile Gly Lys Ala Thr Ala Lys Tyr Phe Phe
    1025                1030                1035 tac agc aac atc atg aac ttt ttc aag acc gag att acc ctg gcc          3159
Tyr Ser Asn Ile Met Asn Phe Phe Lys Thr Glu Ile Thr Leu Ala
    1040                1045                1050 aac ggc gag atc cgg aag cgg cct ctg atc gag aca aac ggc gaa          3204
Asn Gly Glu Ile Arg Lys Arg Pro Leu Ile Glu Thr Asn Gly Glu
    1055                1060                1065 acc ggg gag atc gtg tgg gat aag ggc cgg gat ttt gcc acc gtg          3249
Thr Gly Glu Ile Val Trp Asp Lys Gly Arg Asp Phe Ala Thr Val
    1070                1075                1080 cgg aaa gtg ctg agc atg ccc caa gtg aat atc gtg aaa aag acc          3294
Arg Lys Val Leu Ser Met Pro Gln Val Asn Ile Val Lys Lys Thr
    1085                1090                1095 gag gtg cag aca ggc ggc ttc agc aaa gag tct atc cgg ccc aag          3339
Glu Val Gln Thr Gly Gly Phe Ser Lys Glu Ser Ile Arg Pro Lys
    1100                1105                1110 agg aac agc gat aag ctg atc gcc aga aag aag gac tgg gac cct          3384
Arg Asn Ser Asp Lys Leu Ile Ala Arg Lys Lys Asp Trp Asp Pro
    1115                1120                1125 aag aag tac ggc ggc ttc gtt agc ccc acc gtg gcc tat tct gtg          3429
Lys Lys Tyr Gly Gly Phe Val Ser Pro Thr Val Ala Tyr Ser Val
    1130                1135                1140 ctg gtg gtg gcc aaa gtg gaa aag ggc aag tcc aag aaa ctg aag          3474
Leu Val Val Ala Lys Val Glu Lys Gly Lys Ser Lys Lys Leu Lys
    1145                1150                1155 agt gtg aaa gag ctg ctg ggg atc acc atc atg gaa aga agc agc          3519
Ser Val Lys Glu Leu Leu Gly Ile Thr Ile Met Glu Arg Ser Ser
    1160                1165                1170 ttc gag aag aat ccc atc gac ttt ctg gaa gcc aag ggc tac aaa          3564
Phe Glu Lys Asn Pro Ile Asp Phe Leu Glu Ala Lys Gly Tyr Lys
    1175                1180                1185 gaa gtg aaa aag gac ctg atc atc aag ctg cct aag tac tcc ctg          3609
Glu Val Lys Lys Asp Leu Ile Ile Lys Leu Pro Lys Tyr Ser Leu
    1190                1195                1200 ttc gag ctg gaa aac ggc cgg aag aga atg ctg gcc tct gcc cgg          3654
Phe Glu Leu Glu Asn Gly Arg Lys Arg Met Leu Ala Ser Ala Arg
    1205                1210                1215 ttt ctg cag aag gga aac gaa ctg gcc ctg ccc tcc aaa tat gtg          3699
Phe Leu Gln Lys Gly Asn Glu Leu Ala Leu Pro Ser Lys Tyr Val
```

```
                  1220              1225              1230
aac ttc ctg tac ctg gcc agc cac tat gag aag ctg aag ggc tcc      3744
Asn Phe Leu Tyr Leu Ala Ser His Tyr Glu Lys Leu Lys Gly Ser
    1235              1240              1245 ccc gag gat aat gag cag aaa cag ctg ttt gtg gaa cag cac aag      3789
Pro Glu Asp Asn Glu Gln Lys Gln Leu Phe Val Glu Gln His Lys
1250              1255              1260 cac tac ctg gac gag atc atc gag cag atc agc gag ttc tcc aag      3834
His Tyr Leu Asp Glu Ile Ile Glu Gln Ile Ser Glu Phe Ser Lys
    1265              1270              1275 aga gtg atc ctg gcc gac gct aat ctg gac aaa gtg ctg tcc gcc      3879
Arg Val Ile Leu Ala Asp Ala Asn Leu Asp Lys Val Leu Ser Ala
1280              1285              1290 tac aac aag cac cgg gat aag ccc atc aga gag cag gcc gag aat      3924
Tyr Asn Lys His Arg Asp Lys Pro Ile Arg Glu Gln Ala Glu Asn
    1295              1300              1305 atc atc cac ctg ttt acc ctg acc aat ctg gga gcc cct cgg gcc      3969
Ile Ile His Leu Phe Thr Leu Thr Asn Leu Gly Ala Pro Arg Ala
1310              1315              1320 ttc aag tac ttt gac acc acc atc gac cgg aag gcc tac cgg agc      4014
Phe Lys Tyr Phe Asp Thr Thr Ile Asp Arg Lys Ala Tyr Arg Ser
    1325              1330              1335 acc aaa gag gtg ctg gac gcc acc ctg atc cac cag agc atc acc      4059
Thr Lys Glu Val Leu Asp Ala Thr Leu Ile His Gln Ser Ile Thr
1340              1345              1350 ggc ctg tac gag aca cgg atc gac ctg tct cag ctg gga ggc gac      4104
Gly Leu Tyr Glu Thr Arg Ile Asp Leu Ser Gln Leu Gly Gly Asp
    1355              1360              1365 taa                                                              4107

<210> SEQ ID NO 17
<211> LENGTH: 4107
<212> TYPE: DNA
<213> ORGANISM: Streptococcus pyogenes
<220> FEATURE:
<221> NAME/KEY: CDS
<222> LOCATION: (1)..(4107)

<400> SEQUENCE: 17 atg gac aag aag tac agc atc ggc ctg gac atc ggc acc aac tct gtg    48
Met Asp Lys Lys Tyr Ser Ile Gly Leu Asp Ile Gly Thr Asn Ser Val
1               5                   10                  15 ggc tgg gcc gtg atc acc gac gag tac aag gtg ccc agc aag aaa ttc    96
Gly Trp Ala Val Ile Thr Asp Glu Tyr Lys Val Pro Ser Lys Lys Phe
            20                  25                  30 aag gtg ctg ggc aac acc gac cgg cac agc atc aag aag aac ctg atc   144
Lys Val Leu Gly Asn Thr Asp Arg His Ser Ile Lys Lys Asn Leu Ile
        35                  40                  45 gga gcc ctg ctg ttc gac agc ggc gaa aca gcc gag gcc acc cgg ctg   192
Gly Ala Leu Leu Phe Asp Ser Gly Glu Thr Ala Glu Ala Thr Arg Leu
    50                  55                  60 aag aga acc gcc aga aga aga tac acc aga cgg aag aac cgg atc tgc   240
Lys Arg Thr Ala Arg Arg Arg Tyr Thr Arg Arg Lys Asn Arg Ile Cys
65                  70                  75                  80 tat ctg caa gag atc ttc agc aac gag atg gcc aag gtg gac gac agc   288
Tyr Leu Gln Glu Ile Phe Ser Asn Glu Met Ala Lys Val Asp Asp Ser
                85                  90                  95 ttc ttc cac aga ctg gaa gag tcc ttc ctg gtg gaa gag gat aag aag   336
Phe Phe His Arg Leu Glu Glu Ser Phe Leu Val Glu Glu Asp Lys Lys
            100                 105                 110
```

| | | |
|---|---|---|
| cac gag cgg cac ccc atc ttc ggc aac atc gtg gac gag gtg gcc tac<br>His Glu Arg His Pro Ile Phe Gly Asn Ile Val Asp Glu Val Ala Tyr<br>115 120 125 | | 384 |
| cac gag aag tac ccc acc atc tac cac ctg aga aag aaa ctg gtg gac<br>His Glu Lys Tyr Pro Thr Ile Tyr His Leu Arg Lys Lys Leu Val Asp<br>130 135 140 | | 432 |
| agc acc gac aag gcc gac ctg cgg ctg atc tat ctg gcc ctg gcc cac<br>Ser Thr Asp Lys Ala Asp Leu Arg Leu Ile Tyr Leu Ala Leu Ala His<br>145 150 155 160 | | 480 |
| atg atc aag ttc cgg ggc cac ttc ctg atc gag ggc gac ctg aac ccc<br>Met Ile Lys Phe Arg Gly His Phe Leu Ile Glu Gly Asp Leu Asn Pro<br>165 170 175 | | 528 |
| gac aac agc gac gtg gac aag ctg ttc atc cag ctg gtg cag acc tac<br>Asp Asn Ser Asp Val Asp Lys Leu Phe Ile Gln Leu Val Gln Thr Tyr<br>180 185 190 | | 576 |
| aac cag ctg ttc gag gaa aac ccc atc aac gcc agc ggc gtg gac gcc<br>Asn Gln Leu Phe Glu Glu Asn Pro Ile Asn Ala Ser Gly Val Asp Ala<br>195 200 205 | | 624 |
| aag gcc atc ctg tct gcc aga ctg agc aag agc aga cgg ctg gaa aat<br>Lys Ala Ile Leu Ser Ala Arg Leu Ser Lys Ser Arg Arg Leu Glu Asn<br>210 215 220 | | 672 |
| ctg atc gcc cag ctg ccc ggc gag aag aag aat ggc ctg ttc ggc aac<br>Leu Ile Ala Gln Leu Pro Gly Glu Lys Lys Asn Gly Leu Phe Gly Asn<br>225 230 235 240 | | 720 |
| ctg att gcc ctg agc ctg ggc ctg acc ccc aac ttc aag agc aac ttc<br>Leu Ile Ala Leu Ser Leu Gly Leu Thr Pro Asn Phe Lys Ser Asn Phe<br>245 250 255 | | 768 |
| gac ctg gcc gag gat gcc aaa ctg cag ctg agc aag gac acc tac gac<br>Asp Leu Ala Glu Asp Ala Lys Leu Gln Leu Ser Lys Asp Thr Tyr Asp<br>260 265 270 | | 816 |
| gac gac ctg gac aac ctg ctg gcc cag atc ggc gac cag tac gcc gac<br>Asp Asp Leu Asp Asn Leu Leu Ala Gln Ile Gly Asp Gln Tyr Ala Asp<br>275 280 285 | | 864 |
| ctg ttt ctg gcc gcc aag aac ctg tcc gac gcc atc ctg ctg agc gac<br>Leu Phe Leu Ala Ala Lys Asn Leu Ser Asp Ala Ile Leu Leu Ser Asp<br>290 295 300 | | 912 |
| atc ctg aga gtg aac acc gag atc acc aag gcc ccc ctg agc gcc tct<br>Ile Leu Arg Val Asn Thr Glu Ile Thr Lys Ala Pro Leu Ser Ala Ser<br>305 310 315 320 | | 960 |
| atg atc aag aga tac gac gag cac cac cag gac ctg acc ctg ctg aaa<br>Met Ile Lys Arg Tyr Asp Glu His His Gln Asp Leu Thr Leu Leu Lys<br>325 330 335 | | 1008 |
| gct ctc gtg cgg cag cag ctg cct gag aag tac aaa gag att ttc ttc<br>Ala Leu Val Arg Gln Gln Leu Pro Glu Lys Tyr Lys Glu Ile Phe Phe<br>340 345 350 | | 1056 |
| gac cag agc aag aac ggc tac gcc ggc tac att gac ggc gga gcc agc<br>Asp Gln Ser Lys Asn Gly Tyr Ala Gly Tyr Ile Asp Gly Gly Ala Ser<br>355 360 365 | | 1104 |
| cag gaa gag ttc tac aag ttc atc aag ccc atc ctg gaa aag atg gac<br>Gln Glu Glu Phe Tyr Lys Phe Ile Lys Pro Ile Leu Glu Lys Met Asp<br>370 375 380 | | 1152 |
| ggc acc gag gaa ctg ctc gtg aag ctg aac aga gag gac ctg ctg cgg<br>Gly Thr Glu Glu Leu Leu Val Lys Leu Asn Arg Glu Asp Leu Leu Arg<br>385 390 395 400 | | 1200 |
| aag cag cgg acc ttc gac aac ggc agc atc ccc cac cag atc cac ctg<br>Lys Gln Arg Thr Phe Asp Asn Gly Ser Ile Pro His Gln Ile His Leu<br>405 410 415 | | 1248 |
| gga gag ctg cac gcc att ctg cgg cgg cag gaa gat ttt tac cca ttc<br>Gly Glu Leu His Ala Ile Leu Arg Arg Gln Glu Asp Phe Tyr Pro Phe<br>420 425 430 | | 1296 |

```
ctg aag gac aac cgg gaa aag atc gag aag atc ctg acc ttc cgc atc    1344
Leu Lys Asp Asn Arg Glu Lys Ile Glu Lys Ile Leu Thr Phe Arg Ile
        435                 440                 445 ccc tac tac gtg ggc cct ctg gcc agg gga aac agc aga ttc gcc tgg    1392
Pro Tyr Tyr Val Gly Pro Leu Ala Arg Gly Asn Ser Arg Phe Ala Trp
    450                 455                 460 atg acc aga aag agc gag gaa acc atc acc ccc tgg aac ttc gag gaa    1440
Met Thr Arg Lys Ser Glu Glu Thr Ile Thr Pro Trp Asn Phe Glu Glu
465                 470                 475                 480 gtg gtg gac aag ggc gct tcc gcc cag agc ttc atc gag cgg atg acc    1488
Val Val Asp Lys Gly Ala Ser Ala Gln Ser Phe Ile Glu Arg Met Thr
                485                 490                 495 aac ttc gat aag aac ctg ccc aac gag aag gtg ctg ccc aag cac agc    1536
Asn Phe Asp Lys Asn Leu Pro Asn Glu Lys Val Leu Pro Lys His Ser
            500                 505                 510 ctg ctg tac gag tac ttc acc gtg tat aac gag ctg acc aaa gtg aaa    1584
Leu Leu Tyr Glu Tyr Phe Thr Val Tyr Asn Glu Leu Thr Lys Val Lys
        515                 520                 525 tac gtg acc gag gga atg aga aag ccc gcc ttc ctg agc ggc gag cag    1632
Tyr Val Thr Glu Gly Met Arg Lys Pro Ala Phe Leu Ser Gly Glu Gln
    530                 535                 540 aaa aag gcc atc gtg gac ctg ctg ttc aag acc aac cgg aaa gtg acc    1680
Lys Lys Ala Ile Val Asp Leu Leu Phe Lys Thr Asn Arg Lys Val Thr
545                 550                 555                 560 gtg aag cag ctg aaa gag gac tac ttc aag aaa atc gag tgc ttc gac    1728
Val Lys Gln Leu Lys Glu Asp Tyr Phe Lys Lys Ile Glu Cys Phe Asp
                565                 570                 575 tcc gtg gaa atc tcc ggc gtg gaa gat cgg ttc aac gcc tcc ctg ggc    1776
Ser Val Glu Ile Ser Gly Val Glu Asp Arg Phe Asn Ala Ser Leu Gly
            580                 585                 590 aca tac cac gat ctg ctg aaa att atc aag gac aag gac ttc ctg gac    1824
Thr Tyr His Asp Leu Leu Lys Ile Ile Lys Asp Lys Asp Phe Leu Asp
        595                 600                 605 aat gag gaa aac gag gac att ctg gaa gat atc gtg ctg acc ctg aca    1872
Asn Glu Glu Asn Glu Asp Ile Leu Glu Asp Ile Val Leu Thr Leu Thr
    610                 615                 620 ctg ttt gag gac aga gag atg atc gag gaa cgg ctg aaa acc tat gcc    1920
Leu Phe Glu Asp Arg Glu Met Ile Glu Glu Arg Leu Lys Thr Tyr Ala
625                 630                 635                 640 cac ctg ttc gac gac aaa gtg atg aag cag ctg aag cgg cgg aga tac    1968
His Leu Phe Asp Asp Lys Val Met Lys Gln Leu Lys Arg Arg Arg Tyr
                645                 650                 655 acc ggc tgg ggc agg ctg agc cgg aag ctg atc aac ggc atc cgg gac    2016
Thr Gly Trp Gly Arg Leu Ser Arg Lys Leu Ile Asn Gly Ile Arg Asp
            660                 665                 670 aag cag tcc ggc aag aca atc ctg gat ttc ctg aag tcc gac ggc ttc    2064
Lys Gln Ser Gly Lys Thr Ile Leu Asp Phe Leu Lys Ser Asp Gly Phe
        675                 680                 685 gcc aac aga aac ttc atg cag ctg atc cac gac gac agc ctg acc ttt    2112
Ala Asn Arg Asn Phe Met Gln Leu Ile His Asp Asp Ser Leu Thr Phe
    690                 695                 700 aaa gag gac atc cag aaa gcc cag gtg tcc ggc cag ggc gat agc ctg    2160
Lys Glu Asp Ile Gln Lys Ala Gln Val Ser Gly Gln Gly Asp Ser Leu
705                 710                 715                 720 cac gag cac att gcc aat ctg gcc ggc agc ccc gcc att aag aag ggc    2208
His Glu His Ile Ala Asn Leu Ala Gly Ser Pro Ala Ile Lys Lys Gly
                725                 730                 735 atc ctg cag aca gtg aag gtg gtg gac gag ctc gtg aaa gtg atg ggc    2256
Ile Leu Gln Thr Val Lys Val Val Asp Glu Leu Val Lys Val Met Gly
```

|  |  |  |  |  |  |  |  |  |  |  |  |  |  |  |  |
|---|---|---|---|---|---|---|---|---|---|---|---|---|---|---|---|
|  |  |  | 740 |  |  |  | 745 |  |  |  | 750 |  |  |  |  |
| cgg | cac | aag | ccc | gag | aac | atc | gtg | atc | gaa | atg | gcc | aga | gag | aac | cag | 2304 |
| Arg | His | Lys | Pro | Glu | Asn | Ile | Val | Ile | Glu | Met | Ala | Arg | Glu | Asn | Gln |  |
|  |  | 755 |  |  |  |  | 760 |  |  |  |  | 765 |  |  |  |  |
| acc | acc | cag | aag | gga | cag | aag | aac | agc | cgc | gag | aga | atg | aag | cgg | atc | 2352 |
| Thr | Thr | Gln | Lys | Gly | Gln | Lys | Asn | Ser | Arg | Glu | Arg | Met | Lys | Arg | Ile |  |
| 770 |  |  |  |  | 775 |  |  |  |  | 780 |  |  |  |  |  |  |
| gaa | gag | ggc | atc | aaa | gag | ctg | ggc | agc | cag | atc | ctg | aaa | gaa | cac | ccc | 2400 |
| Glu | Glu | Gly | Ile | Lys | Glu | Leu | Gly | Ser | Gln | Ile | Leu | Lys | Glu | His | Pro |  |
| 785 |  |  |  |  | 790 |  |  |  |  | 795 |  |  |  |  | 800 |  |
| gtg | gaa | aac | acc | cag | ctg | cag | aac | gag | aag | ctg | tac | ctg | tac | tac | ctg | 2448 |
| Val | Glu | Asn | Thr | Gln | Leu | Gln | Asn | Glu | Lys | Leu | Tyr | Leu | Tyr | Tyr | Leu |  |
|  |  |  |  | 805 |  |  |  |  | 810 |  |  |  |  | 815 |  |  |
| cag | aat | ggg | cgg | gat | atg | tac | gtg | gac | cag | gaa | ctg | gac | atc | aac | cgg | 2496 |
| Gln | Asn | Gly | Arg | Asp | Met | Tyr | Val | Asp | Gln | Glu | Leu | Asp | Ile | Asn | Arg |  |
|  |  |  | 820 |  |  |  |  | 825 |  |  |  |  | 830 |  |  |  |
| ctg | tcc | gac | tac | gat | gtg | gac | cat | atc | gtg | cct | cag | agc | ttt | ctg | aag | 2544 |
| Leu | Ser | Asp | Tyr | Asp | Val | Asp | His | Ile | Val | Pro | Gln | Ser | Phe | Leu | Lys |  |
|  |  | 835 |  |  |  |  | 840 |  |  |  |  | 845 |  |  |  |  |
| gac | gac | tcc | atc | gac | aac | aag | gtg | ctg | acc | aga | agc | gac | aag | aac | cgg | 2592 |
| Asp | Asp | Ser | Ile | Asp | Asn | Lys | Val | Leu | Thr | Arg | Ser | Asp | Lys | Asn | Arg |  |
| 850 |  |  |  |  | 855 |  |  |  |  | 860 |  |  |  |  |  |  |
| ggc | aag | agc | gac | aac | gtg | ccc | tcc | gaa | gag | gtc | gtg | aag | aag | atg | aag | 2640 |
| Gly | Lys | Ser | Asp | Asn | Val | Pro | Ser | Glu | Glu | Val | Val | Lys | Lys | Met | Lys |  |
| 865 |  |  |  |  | 870 |  |  |  |  | 875 |  |  |  |  | 880 |  |
| aac | tac | tgg | cgg | cag | ctg | ctg | aac | gcc | aag | ctg | att | acc | cag | aga | aag | 2688 |
| Asn | Tyr | Trp | Arg | Gln | Leu | Leu | Asn | Ala | Lys | Leu | Ile | Thr | Gln | Arg | Lys |  |
|  |  |  |  | 885 |  |  |  |  | 890 |  |  |  |  | 895 |  |  |
| ttc | gac | aat | ctg | acc | aag | gcc | gag | aga | ggc | ggc | ctg | agc | gaa | ctg | gat | 2736 |
| Phe | Asp | Asn | Leu | Thr | Lys | Ala | Glu | Arg | Gly | Gly | Leu | Ser | Glu | Leu | Asp |  |
|  |  |  | 900 |  |  |  |  | 905 |  |  |  |  | 910 |  |  |  |
| aag | gcc | ggc | ttc | atc | aag | aga | cag | ctg | gtg | gaa | acc | cgg | cag | atc | aca | 2784 |
| Lys | Ala | Gly | Phe | Ile | Lys | Arg | Gln | Leu | Val | Glu | Thr | Arg | Gln | Ile | Thr |  |
|  |  | 915 |  |  |  |  | 920 |  |  |  |  | 925 |  |  |  |  |
| aag | cac | gtg | gca | cag | atc | ctg | gac | tcc | cgg | atg | aac | act | aag | tac | gac | 2832 |
| Lys | His | Val | Ala | Gln | Ile | Leu | Asp | Ser | Arg | Met | Asn | Thr | Lys | Tyr | Asp |  |
| 930 |  |  |  |  | 935 |  |  |  |  | 940 |  |  |  |  |  |  |
| gag | aat | gac | aag | ctg | atc | cgg | gaa | gtg | aaa | gtg | atc | acc | ctg | aag | tcc | 2880 |
| Glu | Asn | Asp | Lys | Leu | Ile | Arg | Glu | Val | Lys | Val | Ile | Thr | Leu | Lys | Ser |  |
| 945 |  |  |  |  | 950 |  |  |  |  | 955 |  |  |  |  | 960 |  |
| aag | ctg | gtg | tcc | gat | ttc | cgg | aag | gat | ttc | cag | ttt | tac | aaa | gtg | cgc | 2928 |
| Lys | Leu | Val | Ser | Asp | Phe | Arg | Lys | Asp | Phe | Gln | Phe | Tyr | Lys | Val | Arg |  |
|  |  |  |  | 965 |  |  |  |  | 970 |  |  |  |  | 975 |  |  |
| gag | atc | aac | aac | tac | cac | cac | gcc | cac | gac | gcc | tac | ctg | aac | gcc | gtc | 2976 |
| Glu | Ile | Asn | Asn | Tyr | His | His | Ala | His | Asp | Ala | Tyr | Leu | Asn | Ala | Val |  |
|  |  |  | 980 |  |  |  |  | 985 |  |  |  |  | 990 |  |  |  |
| gtg | gga | acc | gcc | ctg | atc | aaa | aag | tac | cct | aag | ctg | gaa | agc | gag | ttc | 3024 |
| Val | Gly | Thr | Ala | Leu | Ile | Lys | Lys | Tyr | Pro | Lys | Leu | Glu | Ser | Glu | Phe |  |
|  |  | 995 |  |  |  |  | 1000 |  |  |  |  | 1005 |  |  |  |  |
| gtg | tac | ggc | gac | tac | aag | gtg | tac | gac | gtg | cgg | aag | atg | atc | gcc |  | 3069 |
| Val | Tyr | Gly | Asp | Tyr | Lys | Val | Tyr | Asp | Val | Arg | Lys | Met | Ile | Ala |  |  |
|  |  | 1010 |  |  |  |  | 1015 |  |  |  |  | 1020 |  |  |  |  |
| aag | agc | gag | cag | gaa | atc | ggc | aag | gct | acc | gcc | aag | tac | ttc | ttc |  | 3114 |
| Lys | Ser | Glu | Gln | Glu | Ile | Gly | Lys | Ala | Thr | Ala | Lys | Tyr | Phe | Phe |  |  |
|  | 1025 |  |  |  |  | 1030 |  |  |  |  | 1035 |  |  |  |  |  |
| tac | agc | aac | atc | atg | aac | ttt | ttc | aag | acc | gag | att | acc | ctg | gcc |  | 3159 |
| Tyr | Ser | Asn | Ile | Met | Asn | Phe | Phe | Lys | Thr | Glu | Ile | Thr | Leu | Ala |  |  |
|  | 1040 |  |  |  |  | 1045 |  |  |  |  | 1050 |  |  |  |  |  |
| aac | ggc | gag | atc | cgg | aag | cgg | cct | ctg | atc | gag | aca | aac | ggc | gaa |  | 3204 |

-continued

| | | | | | | | | | | | | | | |
|---|---|---|---|---|---|---|---|---|---|---|---|---|---|---|
| | Asn | Gly | Glu | Ile | Arg | Lys | Arg | Pro | Leu | Ile | Glu | Thr | Asn | Gly | Glu |
| | 1055 | | | | | 1060 | | | | | 1065 | | | | |

| acc | ggg | gag | atc | gtg | tgg | gat | aag | ggc | cgg | gat | ttt | gcc | acc | gtg | 3249 |
|---|---|---|---|---|---|---|---|---|---|---|---|---|---|---|---|
| Thr | Gly | Glu | Ile | Val | Trp | Asp | Lys | Gly | Arg | Asp | Phe | Ala | Thr | Val | |
| 1070 | | | | | 1075 | | | | | 1080 | | | | | |

| cgg | aaa | gtg | ctg | agc | atg | ccc | caa | gtg | aat | atc | gtg | aaa | aag | acc | 3294 |
|---|---|---|---|---|---|---|---|---|---|---|---|---|---|---|---|
| Arg | Lys | Val | Leu | Ser | Met | Pro | Gln | Val | Asn | Ile | Val | Lys | Lys | Thr | |
| 1085 | | | | | 1090 | | | | | 1095 | | | | | |

| gag | gtg | cag | aca | ggc | ggc | ttc | agc | aaa | gag | tct | atc | cgg | ccc | aag | 3339 |
|---|---|---|---|---|---|---|---|---|---|---|---|---|---|---|---|
| Glu | Val | Gln | Thr | Gly | Gly | Phe | Ser | Lys | Glu | Ser | Ile | Arg | Pro | Lys | |
| 1100 | | | | | 1105 | | | | | 1110 | | | | | |

| agg | aac | agc | gat | aag | ctg | atc | gcc | aga | aag | aag | gac | tgg | gac | cct | 3384 |
|---|---|---|---|---|---|---|---|---|---|---|---|---|---|---|---|
| Arg | Asn | Ser | Asp | Lys | Leu | Ile | Ala | Arg | Lys | Lys | Asp | Trp | Asp | Pro | |
| 1115 | | | | | 1120 | | | | | 1125 | | | | | |

| aag | aag | tac | ggc | ggc | ttc | gac | agc | ccc | acc | gtg | gcc | tat | tct | gtg | 3429 |
|---|---|---|---|---|---|---|---|---|---|---|---|---|---|---|---|
| Lys | Lys | Tyr | Gly | Gly | Phe | Asp | Ser | Pro | Thr | Val | Ala | Tyr | Ser | Val | |
| 1130 | | | | | 1135 | | | | | 1140 | | | | | |

| ctg | gtg | gtg | gcc | aaa | gtg | gaa | aag | ggc | aag | tcc | aag | aaa | ctg | aag | 3474 |
|---|---|---|---|---|---|---|---|---|---|---|---|---|---|---|---|
| Leu | Val | Val | Ala | Lys | Val | Glu | Lys | Gly | Lys | Ser | Lys | Lys | Leu | Lys | |
| 1145 | | | | | 1150 | | | | | 1155 | | | | | |

| agt | gtg | aaa | gag | ctg | ctg | ggg | atc | acc | atc | atg | gaa | aga | agc | agc | 3519 |
|---|---|---|---|---|---|---|---|---|---|---|---|---|---|---|---|
| Ser | Val | Lys | Glu | Leu | Leu | Gly | Ile | Thr | Ile | Met | Glu | Arg | Ser | Ser | |
| 1160 | | | | | 1165 | | | | | 1170 | | | | | |

| ttc | gag | aag | aat | ccc | atc | gac | ttt | ctg | gaa | gcc | aag | ggc | tac | aaa | 3564 |
|---|---|---|---|---|---|---|---|---|---|---|---|---|---|---|---|
| Phe | Glu | Lys | Asn | Pro | Ile | Asp | Phe | Leu | Glu | Ala | Lys | Gly | Tyr | Lys | |
| 1175 | | | | | 1180 | | | | | 1185 | | | | | |

| gaa | gtg | aaa | aag | gac | ctg | atc | atc | aag | ctg | cct | aag | tac | tcc | ctg | 3609 |
|---|---|---|---|---|---|---|---|---|---|---|---|---|---|---|---|
| Glu | Val | Lys | Lys | Asp | Leu | Ile | Ile | Lys | Leu | Pro | Lys | Tyr | Ser | Leu | |
| 1190 | | | | | 1195 | | | | | 1200 | | | | | |

| ttc | gag | ctg | gaa | aac | ggc | cgg | aag | aga | atg | ctg | gcc | tct | gcc | cgg | 3654 |
|---|---|---|---|---|---|---|---|---|---|---|---|---|---|---|---|
| Phe | Glu | Leu | Glu | Asn | Gly | Arg | Lys | Arg | Met | Leu | Ala | Ser | Ala | Arg | |
| 1205 | | | | | 1210 | | | | | 1215 | | | | | |

| tgg | ctg | cag | aag | gga | aac | gaa | ctg | gcc | ctg | ccc | tcc | aaa | tat | gtg | 3699 |
|---|---|---|---|---|---|---|---|---|---|---|---|---|---|---|---|
| Trp | Leu | Gln | Lys | Gly | Asn | Glu | Leu | Ala | Leu | Pro | Ser | Lys | Tyr | Val | |
| 1220 | | | | | 1225 | | | | | 1230 | | | | | |

| aac | ttc | ctg | tac | ctg | gcc | agc | cac | tat | gag | aag | ctg | aag | ggc | tcc | 3744 |
|---|---|---|---|---|---|---|---|---|---|---|---|---|---|---|---|
| Asn | Phe | Leu | Tyr | Leu | Ala | Ser | His | Tyr | Glu | Lys | Leu | Lys | Gly | Ser | |
| 1235 | | | | | 1240 | | | | | 1245 | | | | | |

| ccc | gag | gat | aat | gag | cag | aaa | cag | ctg | ttt | gtg | gaa | cag | cac | aag | 3789 |
|---|---|---|---|---|---|---|---|---|---|---|---|---|---|---|---|
| Pro | Glu | Asp | Asn | Glu | Gln | Lys | Gln | Leu | Phe | Val | Glu | Gln | His | Lys | |
| 1250 | | | | | 1255 | | | | | 1260 | | | | | |

| cac | tac | ctg | gac | gag | atc | atc | gag | cag | atc | agc | gag | ttc | tcc | aag | 3834 |
|---|---|---|---|---|---|---|---|---|---|---|---|---|---|---|---|
| His | Tyr | Leu | Asp | Glu | Ile | Ile | Glu | Gln | Ile | Ser | Glu | Phe | Ser | Lys | |
| 1265 | | | | | 1270 | | | | | 1275 | | | | | |

| aga | gtg | atc | ctg | gcc | gac | gct | aat | ctg | gac | aaa | gtg | ctg | tcc | gcc | 3879 |
|---|---|---|---|---|---|---|---|---|---|---|---|---|---|---|---|
| Arg | Val | Ile | Leu | Ala | Asp | Ala | Asn | Leu | Asp | Lys | Val | Leu | Ser | Ala | |
| 1280 | | | | | 1285 | | | | | 1290 | | | | | |

| tac | aac | aag | cac | cgg | gat | aag | ccc | atc | aga | gag | cag | gcc | gag | aat | 3924 |
|---|---|---|---|---|---|---|---|---|---|---|---|---|---|---|---|
| Tyr | Asn | Lys | His | Arg | Asp | Lys | Pro | Ile | Arg | Glu | Gln | Ala | Glu | Asn | |
| 1295 | | | | | 1300 | | | | | 1305 | | | | | |

| atc | atc | cac | ctg | ttt | acc | ctg | acc | aat | ctg | gga | gcc | cct | cgg | gcc | 3969 |
|---|---|---|---|---|---|---|---|---|---|---|---|---|---|---|---|
| Ile | Ile | His | Leu | Phe | Thr | Leu | Thr | Asn | Leu | Gly | Ala | Pro | Arg | Ala | |
| 1310 | | | | | 1315 | | | | | 1320 | | | | | |

| ttc | aag | tac | ttt | gac | acc | acc | atc | gac | cgg | aag | gcc | tac | cgg | agc | 4014 |
|---|---|---|---|---|---|---|---|---|---|---|---|---|---|---|---|
| Phe | Lys | Tyr | Phe | Asp | Thr | Thr | Ile | Asp | Arg | Lys | Ala | Tyr | Arg | Ser | |
| 1325 | | | | | 1330 | | | | | 1335 | | | | | |

| acc | aaa | gag | gtg | ctg | gac | gcc | acc | ctg | atc | cac | cag | agc | atc | acc | 4059 |
|---|---|---|---|---|---|---|---|---|---|---|---|---|---|---|---|
| Thr | Lys | Glu | Val | Leu | Asp | Ala | Thr | Leu | Ile | His | Gln | Ser | Ile | Thr | |
| 1340 | | | | | 1345 | | | | | 1350 | | | | | |

-continued

| | | |
|---|---|---|
| ggc ctg tac gag aca cgg atc gac ctg tct cag ctg gga ggc gac<br>Gly Leu Tyr Glu Thr Arg Ile Asp Leu Ser Gln Leu Gly Gly Asp<br>     1355                        1360                       1365 | | 4104 |
| taa | | 4107 |

<210> SEQ ID NO 18
<211> LENGTH: 4107
<212> TYPE: DNA
<213> ORGANISM: Streptococcus pyogenes
<220> FEATURE:
<221> NAME/KEY: CDS
<222> LOCATION: (1)..(4107)

<400> SEQUENCE: 18

| | |
|---|---|
| atg gac aag aag tac agc atc ggc ctg gac atc ggc acc aac tct gtg<br>Met Asp Lys Lys Tyr Ser Ile Gly Leu Asp Ile Gly Thr Asn Ser Val<br>1                 5                   10                15 | 48 |
| ggc tgg gcc gtg atc acc gac gag tac aag gtg ccc agc aag aaa ttc<br>Gly Trp Ala Val Ile Thr Asp Glu Tyr Lys Val Pro Ser Lys Lys Phe<br>                20                   25                  30 | 96 |
| aag gtg ctg ggc aac acc gac cgg cac agc atc aag aag aac ctg atc<br>Lys Val Leu Gly Asn Thr Asp Arg His Ser Ile Lys Lys Asn Leu Ile<br>          35                     40                  45 | 144 |
| gga gcc ctg ctg ttc gac agc ggc gaa aca gcc gag gcc acc cgg ctg<br>Gly Ala Leu Leu Phe Asp Ser Gly Glu Thr Ala Glu Ala Thr Arg Leu<br>50                55                    60 | 192 |
| aag aga acc gcc aga aga aga tac acc aga cgg aag aac cgg atc tgc<br>Lys Arg Thr Ala Arg Arg Arg Tyr Thr Arg Arg Lys Asn Arg Ile Cys<br>65                70                     75                80 | 240 |
| tat ctg caa gag atc ttc agc aac gag atg gcc aag gtg gac gac agc<br>Tyr Leu Gln Glu Ile Phe Ser Asn Glu Met Ala Lys Val Asp Asp Ser<br>                       85                   90                95 | 288 |
| ttc ttc cac aga ctg gaa gag tcc ttc ctg gtg gaa gag gat aag aag<br>Phe Phe His Arg Leu Glu Glu Ser Phe Leu Val Glu Glu Asp Lys Lys<br>                100                 105                110 | 336 |
| cac gag cgg cac ccc atc ttc ggc aac atc gtg gac gag gtg gcc tac<br>His Glu Arg His Pro Ile Phe Gly Asn Ile Val Asp Glu Val Ala Tyr<br>          115                     120                125 | 384 |
| cac gag aag tac ccc acc atc tac cac ctg aga aag aaa ctg gtg gac<br>His Glu Lys Tyr Pro Thr Ile Tyr His Leu Arg Lys Lys Leu Val Asp<br>130                 135                 140 | 432 |
| agc acc gac aag gcc gac ctg cgg ctg atc tat ctg gcc ctg gcc cac<br>Ser Thr Asp Lys Ala Asp Leu Arg Leu Ile Tyr Leu Ala Leu Ala His<br>145                150                 155                160 | 480 |
| atg atc aag ttc cgg ggc cac ttc ctg atc gag ggc gac ctg aac ccc<br>Met Ile Lys Phe Arg Gly His Phe Leu Ile Glu Gly Asp Leu Asn Pro<br>                165                 170                175 | 528 |
| gac aac agc gac gtg gac aag ctg ttc atc cag ctg gtg cag acc tac<br>Asp Asn Ser Asp Val Asp Lys Leu Phe Ile Gln Leu Val Gln Thr Tyr<br>               180                 185                190 | 576 |
| aac cag ctg ttc gag gaa aac ccc atc aac gcc agc ggc gtg gac gcc<br>Asn Gln Leu Phe Glu Glu Asn Pro Ile Asn Ala Ser Gly Val Asp Ala<br>         195                     200                205 | 624 |
| aag gcc atc ctg tct gcc aga ctg agc aag agc aga cgg ctg gaa aat<br>Lys Ala Ile Leu Ser Ala Arg Leu Ser Lys Ser Arg Arg Leu Glu Asn<br>210                215                220 | 672 |
| ctg atc gcc cag ctg ccc ggc gag aag aag aat ggc ctg ttc gga aac<br>Leu Ile Ala Gln Leu Pro Gly Glu Lys Lys Asn Gly Leu Phe Gly Asn<br>225                230                 235                240 | 720 |
| ctg att gcc ctg agc ctg ggc ctg acc ccc aac ttc aag agc aac ttc<br>Leu Ile Ala Leu Ser Leu Gly Leu Thr Pro Asn Phe Lys Ser Asn Phe | 768 |

```
                245                 250                 255
gac ctg gcc gag gat gcc aaa ctg cag ctg agc aag gac acc tac gac      816
Asp Leu Ala Glu Asp Ala Lys Leu Gln Leu Ser Lys Asp Thr Tyr Asp
            260                 265                 270 gac gac ctg gac aac ctg ctg gcc cag atc ggc gac cag tac gcc gac      864
Asp Asp Leu Asp Asn Leu Leu Ala Gln Ile Gly Asp Gln Tyr Ala Asp
        275                 280                 285 ctg ttt ctg gcc gcc aag aac ctg tcc gac gcc atc ctg ctg agc gac      912
Leu Phe Leu Ala Ala Lys Asn Leu Ser Asp Ala Ile Leu Leu Ser Asp
    290                 295                 300 atc ctg aga gtg aac acc gag atc acc aag gcc ccc ctg agc gcc tct      960
Ile Leu Arg Val Asn Thr Glu Ile Thr Lys Ala Pro Leu Ser Ala Ser
305                 310                 315                 320 atg atc aag aga tac gac gag cac cac cag gac ctg acc ctg ctg aaa     1008
Met Ile Lys Arg Tyr Asp Glu His His Gln Asp Leu Thr Leu Leu Lys
                325                 330                 335 gct ctc gtg cgg cag cag ctg cct gag aag tac aaa gag att ttc ttc     1056
Ala Leu Val Arg Gln Gln Leu Pro Glu Lys Tyr Lys Glu Ile Phe Phe
            340                 345                 350 gac cag agc aag aac ggc tac gcc ggc tac att gac ggc gga gcc agc     1104
Asp Gln Ser Lys Asn Gly Tyr Ala Gly Tyr Ile Asp Gly Gly Ala Ser
        355                 360                 365 cag gaa gag ttc tac aag ttc atc aag ccc atc ctg gaa aag atg gac     1152
Gln Glu Glu Phe Tyr Lys Phe Ile Lys Pro Ile Leu Glu Lys Met Asp
    370                 375                 380 ggc acc gag gaa ctg ctc gtg aag ctg aac aga gag gac ctg ctg cgg     1200
Gly Thr Glu Glu Leu Leu Val Lys Leu Asn Arg Glu Asp Leu Leu Arg
385                 390                 395                 400 aag cag cgg acc ttc gac aac ggc agc atc ccc cac cag atc cac ctg     1248
Lys Gln Arg Thr Phe Asp Asn Gly Ser Ile Pro His Gln Ile His Leu
                405                 410                 415 gga gag ctg cac gcc att ctg cgg cgg cag gaa gat ttt tac cca ttc     1296
Gly Glu Leu His Ala Ile Leu Arg Arg Gln Glu Asp Phe Tyr Pro Phe
            420                 425                 430 ctg aag gac aac cgg gaa aag atc gag aag atc ctg acc ttc cgc atc     1344
Leu Lys Asp Asn Arg Glu Lys Ile Glu Lys Ile Leu Thr Phe Arg Ile
        435                 440                 445 ccc tac tac gtg ggc cct ctg gcc agg gga aac agc aga ttc gcc tgg     1392
Pro Tyr Tyr Val Gly Pro Leu Ala Arg Gly Asn Ser Arg Phe Ala Trp
    450                 455                 460 atg acc aga aag agc gag gaa acc atc acc ccc tgg aac ttc gag gaa     1440
Met Thr Arg Lys Ser Glu Glu Thr Ile Thr Pro Trp Asn Phe Glu Glu
465                 470                 475                 480 gtg gtg gac aag ggc gct tcc gcc cag agc ttc atc gag cgg atg acc     1488
Val Val Asp Lys Gly Ala Ser Ala Gln Ser Phe Ile Glu Arg Met Thr
                485                 490                 495 aac ttc gat aag aac ctg ccc aac gag aag gtg ctg ccc aag cac agc     1536
Asn Phe Asp Lys Asn Leu Pro Asn Glu Lys Val Leu Pro Lys His Ser
            500                 505                 510 ctg ctg tac gag tac ttc acc gtg tat aac gag ctg acc aaa gtg aaa     1584
Leu Leu Tyr Glu Tyr Phe Thr Val Tyr Asn Glu Leu Thr Lys Val Lys
        515                 520                 525 tac gtg acc gag gga atg aga aag ccc gcc ttc ctg agc ggc gag cag     1632
Tyr Val Thr Glu Gly Met Arg Lys Pro Ala Phe Leu Ser Gly Glu Gln
    530                 535                 540 aaa aag gcc atc gtg gac ctg ctg ttc aag acc aac cgg aaa gtg acc     1680
Lys Lys Ala Ile Val Asp Leu Leu Phe Lys Thr Asn Arg Lys Val Thr
545                 550                 555                 560 gtg aag cag ctg aaa gag gac tac ttc aag aaa atc gag tgc ttc gac     1728
```

```
                Val Lys Gln Leu Lys Glu Asp Tyr Phe Lys Lys Ile Glu Cys Phe Asp
                                565                 570                 575 tcc gtg gaa atc tcc ggc gtg gaa gat cgg ttc aac gcc tcc ctg ggc        1776
Ser Val Glu Ile Ser Gly Val Glu Asp Arg Phe Asn Ala Ser Leu Gly
            580                 585                 590 aca tac cac gat ctg ctg aaa att atc aag gac aag gac ttc ctg gac        1824
Thr Tyr His Asp Leu Leu Lys Ile Ile Lys Asp Lys Asp Phe Leu Asp
            595                 600                 605 aat gag gaa aac gag gac att ctg gaa gat atc gtg ctg acc ctg aca        1872
Asn Glu Glu Asn Glu Asp Ile Leu Glu Asp Ile Val Leu Thr Leu Thr
610                 615                 620 ctg ttt gag gac aga gag atg atc gag gaa cgg ctg aaa acc tat gcc        1920
Leu Phe Glu Asp Arg Glu Met Ile Glu Glu Arg Leu Lys Thr Tyr Ala
625                 630                 635                 640 cac ctg ttc gac gac aaa gtg atg aag cag ctg aag cgg cgg aga tac        1968
His Leu Phe Asp Asp Lys Val Met Lys Gln Leu Lys Arg Arg Arg Tyr
            645                 650                 655 acc ggc tgg ggc agg ctg agc cgg aag ctg atc aac ggc atc cgg gac        2016
Thr Gly Trp Gly Arg Leu Ser Arg Lys Leu Ile Asn Gly Ile Arg Asp
            660                 665                 670 aag cag tcc ggc aag aca atc ctg gat ttc ctg aag tcc gac ggc ttc        2064
Lys Gln Ser Gly Lys Thr Ile Leu Asp Phe Leu Lys Ser Asp Gly Phe
            675                 680                 685 gcc aac aga aac ttc atg cag ctg atc cac gac gac agc ctg acc ttt        2112
Ala Asn Arg Asn Phe Met Gln Leu Ile His Asp Asp Ser Leu Thr Phe
690                 695                 700 aaa gag gac atc cag aaa gcc cag gtg tcc ggc cag ggc gat agc ctg        2160
Lys Glu Asp Ile Gln Lys Ala Gln Val Ser Gly Gln Gly Asp Ser Leu
705                 710                 715                 720 cac gag cac att gcc aat ctg gcc ggc agc ccc gcc att aag aag ggc        2208
His Glu His Ile Ala Asn Leu Ala Gly Ser Pro Ala Ile Lys Lys Gly
            725                 730                 735 atc ctg cag aca gtg aag gtg gtg gac gag ctc gtg aaa gtg atg ggc        2256
Ile Leu Gln Thr Val Lys Val Val Asp Glu Leu Val Lys Val Met Gly
            740                 745                 750 cgg cac aag ccc gag aac atc gtg atc gaa atg gcc aga gag aac cag        2304
Arg His Lys Pro Glu Asn Ile Val Ile Glu Met Ala Arg Glu Asn Gln
            755                 760                 765 acc acc cag aag gga cag aag aac agc cgc gag aga atg aag cgg atc        2352
Thr Thr Gln Lys Gly Gln Lys Asn Ser Arg Glu Arg Met Lys Arg Ile
770                 775                 780 gaa gag ggc atc aaa gag ctg ggc agc cag atc ctg aaa gaa cac ccc        2400
Glu Glu Gly Ile Lys Glu Leu Gly Ser Gln Ile Leu Lys Glu His Pro
785                 790                 795                 800 gtg gaa aac acc cag ctg cag aac gag aag ctg tac ctg tac tac ctg        2448
Val Glu Asn Thr Gln Leu Gln Asn Glu Lys Leu Tyr Leu Tyr Tyr Leu
            805                 810                 815 cag aat ggg cgg gat atg tac gtg gac cag gaa ctg gac atc aac cgg        2496
Gln Asn Gly Arg Asp Met Tyr Val Asp Gln Glu Leu Asp Ile Asn Arg
            820                 825                 830 ctg tcc gac tac gat gtg gac cat atc gtg cct cag agc ttt ctg aag        2544
Leu Ser Asp Tyr Asp Val Asp His Ile Val Pro Gln Ser Phe Leu Lys
            835                 840                 845 gac gac tcc atc gac aac aag gtg ctg acc aga agc gac aag aac cgg        2592
Asp Asp Ser Ile Asp Asn Lys Val Leu Thr Arg Ser Asp Lys Asn Arg
850                 855                 860 ggc aag agc gac aac gtg ccc tcc gaa gag gtc gtg aag aag atg aag        2640
Gly Lys Ser Asp Asn Val Pro Ser Glu Glu Val Val Lys Lys Met Lys
865                 870                 875                 880
```

|  |  |  |  |  |  |  |  |  |  |  |  |  |  |  |  |
|---|---|---|---|---|---|---|---|---|---|---|---|---|---|---|---|
| aac | tac | tgg | cgg | cag | ctg | ctg | aac | gcc | aag | ctg | att | acc | cag | aga | aag |
| Asn | Tyr | Trp | Arg | Gln | Leu | Leu | Asn | Ala | Lys | Leu | Ile | Thr | Gln | Arg | Lys |
|  |  |  |  | 885 |  |  |  | 890 |  |  |  |  | 895 |  |  |

2688

|  |  |  |  |  |  |  |  |  |  |  |  |  |  |  |  |
|---|---|---|---|---|---|---|---|---|---|---|---|---|---|---|---|
| ttc | gac | aat | ctg | acc | aag | gcc | gag | aga | ggc | ggc | ctg | agc | gaa | ctg | gat |
| Phe | Asp | Asn | Leu | Thr | Lys | Ala | Glu | Arg | Gly | Gly | Leu | Ser | Glu | Leu | Asp |
|  |  |  | 900 |  |  |  |  | 905 |  |  |  |  | 910 |  |  |

2736

|  |  |  |  |  |  |  |  |  |  |  |  |  |  |  |  |
|---|---|---|---|---|---|---|---|---|---|---|---|---|---|---|---|
| aag | gcc | ggc | ttc | atc | aag | aga | cag | ctg | gtg | gaa | acc | cgg | cag | atc | aca |
| Lys | Ala | Gly | Phe | Ile | Lys | Arg | Gln | Leu | Val | Glu | Thr | Arg | Gln | Ile | Thr |
|  |  |  | 915 |  |  |  |  | 920 |  |  |  |  | 925 |  |  |

2784

|  |  |  |  |  |  |  |  |  |  |  |  |  |  |  |  |
|---|---|---|---|---|---|---|---|---|---|---|---|---|---|---|---|
| aag | cac | gtg | gca | cag | atc | ctg | gac | tcc | cgg | atg | aac | act | aag | tac | gac |
| Lys | His | Val | Ala | Gln | Ile | Leu | Asp | Ser | Arg | Met | Asn | Thr | Lys | Tyr | Asp |
|  |  |  | 930 |  |  |  |  | 935 |  |  |  |  | 940 |  |  |

2832

|  |  |  |  |  |  |  |  |  |  |  |  |  |  |  |  |
|---|---|---|---|---|---|---|---|---|---|---|---|---|---|---|---|
| gag | aat | gac | aag | ctg | atc | cgg | gaa | gtg | aaa | gtg | atc | acc | ctg | aag | tcc |
| Glu | Asn | Asp | Lys | Leu | Ile | Arg | Glu | Val | Lys | Val | Ile | Thr | Leu | Lys | Ser |
| 945 |  |  |  | 950 |  |  |  |  | 955 |  |  |  |  |  | 960 |

2880

|  |  |  |  |  |  |  |  |  |  |  |  |  |  |  |  |
|---|---|---|---|---|---|---|---|---|---|---|---|---|---|---|---|
| aag | ctg | gtg | tcc | gat | ttc | cgg | aag | gat | ttc | cag | ttt | tac | aaa | gtg | cgc |
| Lys | Leu | Val | Ser | Asp | Phe | Arg | Lys | Asp | Phe | Gln | Phe | Tyr | Lys | Val | Arg |
|  |  |  |  | 965 |  |  |  |  | 970 |  |  |  |  | 975 |  |

2928

|  |  |  |  |  |  |  |  |  |  |  |  |  |  |  |  |
|---|---|---|---|---|---|---|---|---|---|---|---|---|---|---|---|
| gag | atc | aac | aac | tac | cac | cac | gcc | cac | gac | gcc | tac | ctg | aac | gcc | gtc |
| Glu | Ile | Asn | Asn | Tyr | His | His | Ala | His | Asp | Ala | Tyr | Leu | Asn | Ala | Val |
|  |  |  | 980 |  |  |  |  | 985 |  |  |  |  | 990 |  |  |

2976

|  |  |  |  |  |  |  |  |  |  |  |  |  |  |
|---|---|---|---|---|---|---|---|---|---|---|---|---|---|
| gtg | gga | acc | gcc | ctg | atc | aaa | aag | tac | cct | aag | ctg | gaa | agc | gag | ttc |
| Val | Gly | Thr | Ala | Leu | Ile | Lys | Lys | Tyr | Pro | Lys | Leu | Glu | Ser | Glu | Phe |
|  |  |  | 995 |  |  |  | 1000 |  |  |  |  | 1005 |  |  |

3024

|  |  |  |  |  |  |  |  |  |  |  |  |  |  |
|---|---|---|---|---|---|---|---|---|---|---|---|---|---|
| gtg | tac | ggc | gac | tac | aag | gtg | tac | gac | gtg | cgg | aag | atg | atc | gcc |
| Val | Tyr | Gly | Asp | Tyr | Lys | Val | Tyr | Asp | Val | Arg | Lys | Met | Ile | Ala |
|  |  | 1010 |  |  |  |  | 1015 |  |  |  |  | 1020 |  |  |

3069

|  |  |  |  |  |  |  |  |  |  |  |  |  |  |  |
|---|---|---|---|---|---|---|---|---|---|---|---|---|---|---|
| aag | agc | gag | cag | gaa | atc | ggc | aag | gct | acc | gcc | aag | tac | ttc | ttc |
| Lys | Ser | Glu | Gln | Glu | Ile | Gly | Lys | Ala | Thr | Ala | Lys | Tyr | Phe | Phe |
|  | 1025 |  |  |  |  | 1030 |  |  |  |  | 1035 |  |  |  |

3114

|  |  |  |  |  |  |  |  |  |  |  |  |  |  |  |
|---|---|---|---|---|---|---|---|---|---|---|---|---|---|---|
| tac | agc | aac | atc | atg | aac | ttt | ttc | aag | acc | gag | att | acc | ctg | gcc |
| Tyr | Ser | Asn | Ile | Met | Asn | Phe | Phe | Lys | Thr | Glu | Ile | Thr | Leu | Ala |
|  | 1040 |  |  |  |  | 1045 |  |  |  |  | 1050 |  |  |  |

3159

|  |  |  |  |  |  |  |  |  |  |  |  |  |  |  |
|---|---|---|---|---|---|---|---|---|---|---|---|---|---|---|
| aac | ggc | gag | atc | cgg | aag | cgg | cct | ctg | atc | gag | aca | aac | ggc | gaa |
| Asn | Gly | Glu | Ile | Arg | Lys | Arg | Pro | Leu | Ile | Glu | Thr | Asn | Gly | Glu |
| 1055 |  |  |  |  | 1060 |  |  |  |  | 1065 |  |  |  |  |

3204

|  |  |  |  |  |  |  |  |  |  |  |  |  |  |  |
|---|---|---|---|---|---|---|---|---|---|---|---|---|---|---|
| acc | ggg | gag | atc | gtg | tgg | gat | aag | ggc | cgg | gat | ttt | gcc | acc | gtg |
| Thr | Gly | Glu | Ile | Val | Trp | Asp | Lys | Gly | Arg | Asp | Phe | Ala | Thr | Val |
| 1070 |  |  |  |  | 1075 |  |  |  |  | 1080 |  |  |  |  |

3249

|  |  |  |  |  |  |  |  |  |  |  |  |  |  |  |
|---|---|---|---|---|---|---|---|---|---|---|---|---|---|---|
| cgg | aaa | gtg | ctg | agc | atg | ccc | caa | gtg | aat | atc | gtg | aaa | aag | acc |
| Arg | Lys | Val | Leu | Ser | Met | Pro | Gln | Val | Asn | Ile | Val | Lys | Lys | Thr |
|  | 1085 |  |  |  |  | 1090 |  |  |  |  | 1095 |  |  |  |

3294

|  |  |  |  |  |  |  |  |  |  |  |  |  |  |  |
|---|---|---|---|---|---|---|---|---|---|---|---|---|---|---|
| gag | gtg | cag | aca | ggc | ggc | ttc | agc | aaa | gag | tct | atc | cgg | ccc | aag |
| Glu | Val | Gln | Thr | Gly | Gly | Phe | Ser | Lys | Glu | Ser | Ile | Arg | Pro | Lys |
|  | 1100 |  |  |  |  | 1105 |  |  |  |  | 1110 |  |  |  |

3339

|  |  |  |  |  |  |  |  |  |  |  |  |  |  |  |
|---|---|---|---|---|---|---|---|---|---|---|---|---|---|---|
| agg | aac | agc | gat | aag | ctg | atc | gcc | aga | aag | aag | gac | tgg | gac | cct |
| Arg | Asn | Ser | Asp | Lys | Leu | Ile | Ala | Arg | Lys | Lys | Asp | Trp | Asp | Pro |
|  | 1115 |  |  |  |  | 1120 |  |  |  |  | 1125 |  |  |  |

3384

|  |  |  |  |  |  |  |  |  |  |  |  |  |  |  |
|---|---|---|---|---|---|---|---|---|---|---|---|---|---|---|
| aag | aag | tac | ggc | ggc | ttc | gtt | agc | ccc | acc | gtg | gcc | tat | tct | gtg |
| Lys | Lys | Tyr | Gly | Gly | Phe | Val | Ser | Pro | Thr | Val | Ala | Tyr | Ser | Val |
|  | 1130 |  |  |  |  | 1135 |  |  |  |  | 1140 |  |  |  |

3429

|  |  |  |  |  |  |  |  |  |  |  |  |  |  |  |
|---|---|---|---|---|---|---|---|---|---|---|---|---|---|---|
| ctg | gtg | gtg | gcc | aaa | gtg | gaa | aag | ggc | aag | tcc | aag | aaa | ctg | aag |
| Leu | Val | Val | Ala | Lys | Val | Glu | Lys | Gly | Lys | Ser | Lys | Lys | Leu | Lys |
|  | 1145 |  |  |  |  | 1150 |  |  |  |  | 1155 |  |  |  |

3474

|  |  |  |  |  |  |  |  |  |  |  |  |  |  |  |
|---|---|---|---|---|---|---|---|---|---|---|---|---|---|---|
| agt | gtg | aaa | gag | ctg | ctg | ggg | atc | acc | atc | atg | gaa | aga | agc | agc |
| Ser | Val | Lys | Glu | Leu | Leu | Gly | Ile | Thr | Ile | Met | Glu | Arg | Ser | Ser |
| 1160 |  |  |  |  | 1165 |  |  |  |  | 1170 |  |  |  |  |

3519

|  |  |  |  |  |  |  |  |  |  |  |  |  |  |  |
|---|---|---|---|---|---|---|---|---|---|---|---|---|---|---|
| ttc | gag | aag | aat | ccc | atc | gac | ttt | ctg | gaa | gcc | aag | ggc | tac | aaa |
| Phe | Glu | Lys | Asn | Pro | Ile | Asp | Phe | Leu | Glu | Ala | Lys | Gly | Tyr | Lys |
| 1175 |  |  |  |  | 1180 |  |  |  |  | 1185 |  |  |  |  |

3564

```
gaa gtg aaa aag gac ctg atc atc aag ctg cct aag tac tcc ctg     3609
Glu Val Lys Lys Asp Leu Ile Ile Lys Leu Pro Lys Tyr Ser Leu
    1190            1195                1200 ttc gag ctg gaa aac ggc cgg aag aga atg ctg gcc tct gcc cgg     3654
Phe Glu Leu Glu Asn Gly Arg Lys Arg Met Leu Ala Ser Ala Arg
1205            1210                1215 ttc ctg cag aag gga aac gaa ctg gcc ctg ccc tcc aaa tat gtg     3699
Phe Leu Gln Lys Gly Asn Glu Leu Ala Leu Pro Ser Lys Tyr Val
        1220            1225                1230 aac ttc ctg tac ctg gcc agc cac tat gag aag ctg aag ggc tcc     3744
Asn Phe Leu Tyr Leu Ala Ser His Tyr Glu Lys Leu Lys Gly Ser
    1235            1240                1245 ccc gag gat aat gag cag aaa cag ctg ttt gtg gaa cag cac aag     3789
Pro Glu Asp Asn Glu Gln Lys Gln Leu Phe Val Glu Gln His Lys
1250            1255                1260 cac tac ctg gac gag atc atc gag cag atc agc gag ttc tcc aag     3834
His Tyr Leu Asp Glu Ile Ile Glu Gln Ile Ser Glu Phe Ser Lys
        1265            1270                1275 aga gtg atc ctg gcc gac gct aat ctg gac aaa gtg ctg tcc gcc     3879
Arg Val Ile Leu Ala Asp Ala Asn Leu Asp Lys Val Leu Ser Ala
    1280            1285                1290 tac aac aag cac cgg gat aag ccc atc aga gag cag gcc gag aat     3924
Tyr Asn Lys His Arg Asp Lys Pro Ile Arg Glu Gln Ala Glu Asn
1295            1300                1305 atc atc cac ctg ttt acc ctg acc aat ctg gga gcc cct cgg gcc     3969
Ile Ile His Leu Phe Thr Leu Thr Asn Leu Gly Ala Pro Arg Ala
        1310            1315                1320 ttc aag tac ttt gac acc acc atc gac cgg aag gcc tac cgg agc     4014
Phe Lys Tyr Phe Asp Thr Thr Ile Asp Arg Lys Ala Tyr Arg Ser
    1325            1330                1335 acc aaa gag gtg ctg gac gcc acc ctg atc cac cag agc atc acc     4059
Thr Lys Glu Val Leu Asp Ala Thr Leu Ile His Gln Ser Ile Thr
1340            1345                1350 ggc ctg tac gag aca cgg atc gac ctg tct cag ctg gga ggc gac     4104
Gly Leu Tyr Glu Thr Arg Ile Asp Leu Ser Gln Leu Gly Gly Asp
        1355            1360                1365 taa                                                              4107

<210> SEQ ID NO 19
<211> LENGTH: 81
<212> TYPE: RNA
<213> ORGANISM: Artificial Sequence
<220> FEATURE:
<223> OTHER INFORMATION: Synthetic Sequence - guide RNA

<400> SEQUENCE: 19
ggaaauuagg ugcgcuuggc guuuuagagc uagaaauagc aaguuaaaau aaggcuaguc     60
cguuaucaac uugaaaaagu g                                               81

<210> SEQ ID NO 20
<211> LENGTH: 23
<212> TYPE: DNA
<213> ORGANISM: Artificial Sequence
<220> FEATURE:
<223> OTHER INFORMATION: Synthetic Sequence - target DNA

<400> SEQUENCE: 20
ggaaattagg tgcgcttggc tgg                                             23
```